(12) United States Patent
Allen et al.

(10) Patent No.: US 10,435,686 B2
(45) Date of Patent: Oct. 8, 2019

(54) PLANT MICRORNAS AND METHODS OF USE THEREOF

(71) Applicant: Monsanto Technology LLC, St. Louis, MO (US)

(72) Inventors: Edwards M. Allen, O'Fallon, MO (US); Barry S. Goldman, St. Louis, MO (US); Liang Guo, St. Louis, MO (US); Sara E. Heisel, Labadie, MO (US); Shihshieh Huang, Woodland, CA (US); Sergey I. Ivashuta, Ballwin, MO (US); David K. Kovalic, Clayton, MO (US); Elysia K. Krieger, Kirkwood, MO (US); James K. Roberts, Chesterfield, MO (US); Yuanji Zhang, Weldon Spring, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 14/567,786

(22) Filed: Dec. 11, 2014

(65) Prior Publication Data
US 2015/0166993 A1    Jun. 18, 2015

Related U.S. Application Data

(63) Continuation of application No. 11/974,469, filed on Oct. 12, 2007, now Pat. No. 8,946,511.

(60) Provisional application No. 60/969,195, filed on Aug. 31, 2007, provisional application No. 60/908,826, filed on Mar. 29, 2007, provisional application No. 60/851,187, filed on Oct. 12, 2006.

(51) Int. Cl.
*C12N 15/113* (2010.01)
*C12N 15/82* (2006.01)

(52) U.S. Cl.
CPC ........ *C12N 15/113* (2013.01); *C12N 15/8216* (2013.01); *C12N 15/8218* (2013.01); *C12N 15/8238* (2013.01); *C12N 15/8261* (2013.01); *C12N 15/8271* (2013.01); *C12N 15/8273* (2013.01); *C12N 15/8279* (2013.01); *C12N 15/8286* (2013.01); *C12N 2310/141* (2013.01); *C12N 2320/50* (2013.01); *Y02A 40/146* (2018.01); *Y02A 40/162* (2018.01)

(58) Field of Classification Search
CPC .................................................. C12N 15/113
USPC ....................................................... 800/285
See application file for complete search history.

(56) References Cited

U.S. PATENT DOCUMENTS

| | | |
|---|---|---|
| 4,735,649 A | 5/1988 | Dhingra |
| 5,004,863 A | 4/1991 | Umbeck |
| 5,015,580 A | 5/1991 | Christou et al. |
| 5,107,065 A | 4/1992 | Shewmaker et al. |
| 5,159,135 A | 10/1992 | Umbeck |
| 5,190,931 A | 3/1993 | Inouye |
| 5,208,149 A | 5/1993 | Inouye |
| 5,272,065 A | 12/1993 | Inouye et al. |
| 5,283,184 A | 2/1994 | Jorgensen et al. |
| 5,416,011 A | 5/1995 | Hinchee et al. |
| 5,453,566 A | 9/1995 | Shewmaker et al. |
| 5,463,174 A | 10/1995 | Moloney et al. |
| 5,500,365 A | 3/1996 | Fischhoff et al. |
| 5,518,908 A | 5/1996 | Corbin et al. |
| 5,538,880 A | 7/1996 | Lundquist et al. |
| 5,550,318 A | 8/1996 | Adams et al. |
| 5,569,834 A | 10/1996 | Hinchee et al. |
| 5,591,616 A | 1/1997 | Hiei et al. |
| 5,593,874 A | 1/1997 | Brown et al. |
| 5,633,435 A | 5/1997 | Barry et al. |
| 5,750,848 A | 5/1998 | Krüger et al. |
| 5,759,829 A | 6/1998 | Shewmaker et al. |
| 5,763,245 A | 6/1998 | Greenplate et al. |
| 5,773,691 A | 6/1998 | Falco et al. |
| 5,780,708 A | 7/1998 | Lundquist et al. |
| 5,824,877 A | 10/1998 | Hinchee et al. |
| 5,837,848 A | 11/1998 | Ely et al. |
| 5,859,347 A | 1/1999 | Brown et al. |
| 5,888,732 A | 3/1999 | Hartley et al. |
| 5,908,779 A | 6/1999 | Carmichael et al. |

(Continued)

FOREIGN PATENT DOCUMENTS

| | | |
|---|---|---|
| WO | WO 91/11524 A1 | 8/1991 |
| WO | WO 95/06128 A2 | 3/1995 |

(Continued)

OTHER PUBLICATIONS

Sweetlove et al. 1996, Biochem. J. 320:493-498.*
Achard et al., "Modulation of floral development by a gibberellin-regulated microRNA," *Development*, 131:3357-3365 (2004).
Adang et al., "The reconstruction and expression of a *Bacillus thuringiensis* cryIIIA gene in protoplasts and potato plants," *Plant Mol. Biol.*, 21:1131-1145 (1993).
Allen et al., "Evolution of microRNA genes by inverted duplication of target gene sequences in *Arabidopsis thaliana*," *Nature Genetics*, 36(12):1282-1290 (2004).
Allen et al., "microRNA-Directed Phasing during *Trans*-Acting siRNA Biogenesis in Plants," *Cell*, 121:207-221 (2005).

(Continued)

*Primary Examiner* — Li Zheng
(74) *Attorney, Agent, or Firm* — Amanda Carmany-Rampey; David R. Marsh; Arnold & Porter Kaye Scholer LLP

(57) ABSTRACT

This invention discloses novel microRNAs and their precursors, and recombinant DNA constructs including such novel miRNAs, miRNA precursors, miRNA promoters, and miRNA recognition sites corresponding to the miRNAs. Included are novel miRNA and miRNA precursors that exhibit nutrient-responsive expression. Also disclosed are miRNA decoy sequences. Further provided are non-natural transgenic plant cells, plants, and seeds containing in their genome a recombinant DNA construct of this invention and methods of controlling gene expression using recombinant DNA constructs of this invention.

11 Claims, 24 Drawing Sheets

Specification includes a Sequence Listing.

(56) References Cited

U.S. PATENT DOCUMENTS

| | | |
|---|---|---|
| 5,981,840 A | 11/1999 | Zhao et al. |
| 6,046,382 A | 4/2000 | Mariani |
| 6,072,110 A | 6/2000 | Henson |
| 6,084,089 A | 7/2000 | Mine et al. |
| 6,118,047 A | 9/2000 | Anderson et al. |
| 6,140,078 A | 10/2000 | Sanders et al. |
| 6,153,812 A | 11/2000 | Fry et al. |
| 6,160,208 A | 12/2000 | Lundquist et al. |
| 6,194,636 B1 | 2/2001 | McElroy et al. |
| 6,207,879 B1 | 3/2001 | McElroy et al. |
| 6,232,526 B1 | 5/2001 | McElroy et al. |
| 6,252,138 B1 | 6/2001 | Karimi et al. |
| 6,255,564 B1 | 7/2001 | Fabijanski |
| 6,265,167 B1 | 7/2001 | Carmichael et al. |
| 6,277,608 B1 | 8/2001 | Hartley et al. |
| 6,288,312 B1 | 9/2001 | Christou et al. |
| 6,294,714 B1 | 9/2001 | Matsunaga et al. |
| 6,372,965 B1 | 4/2002 | Lightner et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,384,304 B1 | 7/2002 | Quandt |
| 6,423,885 B1 | 7/2002 | Waterhouse |
| 6,426,446 B1 | 7/2002 | McElroy et al. |
| 6,426,448 B1 | 7/2002 | Booth, Jr. et al. |
| 6,429,357 B1 | 8/2002 | McElroy et al. |
| 6,433,252 B1 | 8/2002 | Kriz et al. |
| 6,437,217 B1 | 8/2002 | McElroy et al. |
| 6,458,559 B1 | 10/2002 | Shi et al. |
| 6,459,019 B1 | 10/2002 | Falco et al. |
| 6,506,559 B1 | 1/2003 | Fire et al. |
| 6,583,338 B2 | 6/2003 | McElroy et al. |
| 6,646,186 B1 | 11/2003 | Steine |
| 6,759,575 B2 | 7/2004 | Michiels et al. |
| 6,762,344 B1 | 7/2004 | Spencer |
| 6,872,872 B1 | 3/2005 | Lightner et al. |
| 6,949,379 B2 | 9/2005 | Ramachandra |
| 6,953,835 B2 | 10/2005 | Fischhoff et al. |
| 7,071,380 B1 | 7/2006 | Lough et al. |
| 7,786,350 B2 | 8/2010 | Allen et al. |
| 8,030,473 B2 | 10/2011 | Carrington et al. |
| 8,217,227 B2 | 7/2012 | Allen |
| 8,476,422 B2 | 7/2013 | Carrington et al. |
| 8,816,061 B2 | 8/2014 | Carrington et al. |
| 2002/0058340 A1 | 5/2002 | Clemente |
| 2002/0133852 A1 | 9/2002 | Hauge et al. |
| 2002/0166132 A1 | 11/2002 | Scherman et al. |
| 2002/0178467 A1* | 11/2002 | Dehesh .......... C12N 9/16 800/279 |
| 2003/0005491 A1 | 1/2003 | Hauge et al. |
| 2003/0049612 A1 | 3/2003 | Echt et al. |
| 2003/0056242 A1 | 3/2003 | Falco |
| 2003/0165894 A1 | 9/2003 | Waterhouse et al. |
| 2003/0167537 A1 | 9/2003 | Jiang |
| 2004/0031072 A1 | 2/2004 | La Rosa et al. |
| 2004/0031073 A1 | 2/2004 | Schmulling et al. |
| 2004/0053411 A1 | 3/2004 | Cullen et al. |
| 2004/0098761 A1 | 5/2004 | Trick et al. |
| 2004/0106566 A1 | 6/2004 | Lin et al. |
| 2004/0115642 A1 | 6/2004 | Fu |
| 2004/0123347 A1 | 6/2004 | Hinchey et al. |
| 2004/0126845 A1 | 7/2004 | Eenennaam et al. |
| 2004/0216189 A1 | 10/2004 | Houmard et al. |
| 2004/0244075 A1 | 12/2004 | Cal et al. |
| 2004/0253604 A1 | 12/2004 | Lin et al. |
| 2004/0268441 A1 | 12/2004 | Vance et al. |
| 2005/0037988 A1 | 2/2005 | Zamore et al. |
| 2005/0053951 A1 | 3/2005 | Breaker |
| 2005/0070016 A1 | 3/2005 | Liu |
| 2005/0120415 A1 | 6/2005 | Aukerman |
| 2005/0138689 A1 | 6/2005 | Aukerman |
| 2005/0144669 A1 | 6/2005 | Reinhart et al. |
| 2005/0150013 A1 | 7/2005 | Hawkes |
| 2006/0021087 A1 | 1/2006 | Baum et al. |
| 2006/0200878 A1 | 9/2006 | Lutfiyya et al. |
| 2006/0236427 A1 | 10/2006 | Chiang et al. |
| 2007/0011775 A1 | 1/2007 | Allen et al. |
| 2007/0083947 A1 | 4/2007 | Huang et al. |
| 2007/0083949 A1 | 4/2007 | Huang et al. |
| 2007/0083950 A1 | 4/2007 | Huang et al. |
| 2007/0083951 A1 | 4/2007 | Huang et al. |
| 2007/0083952 A1 | 4/2007 | Huang et al. |
| 2007/0089184 A1 | 4/2007 | Huang et al. |
| 2007/0089185 A1 | 4/2007 | Huang et al. |
| 2007/0089186 A1 | 4/2007 | Huang et al. |
| 2007/0089187 A1 | 4/2007 | Huang et al. |
| 2007/0089188 A1 | 4/2007 | Huang et al. |
| 2007/0089189 A1 | 4/2007 | Huang et al. |
| 2007/0089190 A1 | 4/2007 | Huang et al. |
| 2007/0089191 A1 | 4/2007 | Huang et al. |
| 2007/0089192 A1 | 4/2007 | Huang et al. |
| 2007/0089193 A1 | 4/2007 | Huang et al. |
| 2007/0089194 A1 | 4/2007 | Huang et al. |
| 2007/0089196 A1 | 4/2007 | Huang et al. |
| 2007/0094748 A1 | 4/2007 | Huang et al. |
| 2007/0118917 A1 | 5/2007 | Huang et al. |
| 2007/0118918 A1 | 5/2007 | Huang et al. |
| 2007/0130653 A1 | 6/2007 | Baulcombe et al. |
| 2007/0199095 A1 | 8/2007 | Allen et al. |
| 2007/0271630 A1 | 11/2007 | Boukharov et al. |
| 2007/0300329 A1 | 12/2007 | Allen |
| 2008/0229456 A1 | 9/2008 | Huang et al. |
| 2009/0013434 A1 | 1/2009 | Huang et al. |
| 2009/0068159 A1 | 3/2009 | Baum et al. |
| 2009/0235388 A1 | 9/2009 | Allen |
| 2009/0293148 A1 | 11/2009 | Ren et al. |
| 2010/0192237 A1 | 7/2010 | Ren et al. |
| 2012/0167258 A1 | 6/2012 | Allen |
| 2013/0007908 A1 | 1/2013 | Huang et al. |
| 2013/0074213 A1 | 3/2013 | Allen |
| 2013/0263325 A1 | 10/2013 | Carrington et al. |
| 2014/0234967 A1 | 8/2014 | Carrington et al. |
| 2014/0373196 A1 | 12/2014 | Carrington et al. |

FOREIGN PATENT DOCUMENTS

| | | |
|---|---|---|
| WO | WO 98/43993 A2 | 10/1998 |
| WO | WO 1990/046396 | 9/1999 |
| WO | WO 02/057471 A2 | 7/2002 |
| WO | WO 02/062129 A2 | 8/2002 |
| WO | WO 2004/009779 A2 | 1/2004 |
| WO | WO 2004/046321 A2 | 6/2004 |
| WO | WO 2004/071426 A2 | 8/2004 |
| WO | WO 2004/078841 A1 | 9/2004 |
| WO | WO 2005/007829 A2 | 1/2005 |
| WO | WO 2005/110068 A2 | 11/2005 |
| WO | WO 2006/073727 A2 | 7/2006 |
| WO | WO 2006/074400 A2 | 7/2006 |
| WO | WO 2006/105436 A2 | 10/2006 |
| WO | WO 2006/138638 A1 | 12/2006 |
| WO | WO 2007/011479 A2 | 1/2007 |
| WO | WO 2007/039454 A1 | 4/2007 |
| WO | WO 2007/047016 A3 | 4/2007 |
| WO | WO 2008/045460 A2 | 4/2008 |
| WO | WO 2009/003078 A3 | 12/2008 |

OTHER PUBLICATIONS

Altschul et al., "Basic Local Alignment Search Tool," *J. Mol. Biol.*, 215:403-410 (1990).

Altschul et al., "Gapped BLAST and PSI-BLAST: a new generation of protein database search programs," *Nucleic Acids Research*, 25(17):3389-3402 (1997).

Alvarez et al., "Endogenous and Synthetic MicroRNAs Stimulate Simultaneous, Efficient, and Localized Regulation of Multiple Targets in Diverse Species," *PlantCell*, 18:1134-1151 (2006).

Ambros et al., "A uniform system for microRNA annotation," *RNA*, 9:277-279 (2003), Amendment After Final and Before Appeal Under §1.116 filed Jul. 5, 2012 in U.S. Appl. No. 11/768,264.

Amendment After Final Under 37 CFR §1.116 filed Oct. 1, 2013, in U.S. Appl. No. 12/665,338.

(56) References Cited

OTHER PUBLICATIONS

Amendment and Response to Non-Final Action filed Jul. 20, 2012, in U.S. Appl. No. 12/089,891.
Amendment and Response to Non-Final Office Action filed Apr. 6, 2011, in U.S. Appl. No. 11/768,264.
Amendment and Response to Office Action filed Apr. 1, 2013, in U.S. Appl. No. 12/665,338.
Amendment and Response to Second Non-Final Office Action filed Dec. 20, 2011, in U.S. Appl. No. 11/768,264.
Armstrong et al., "Factors affecting PEG-mediated stable transformation of maize protoplasts," *The Plant Cell Rep.*, 9:335-339 (1990).
Aslanidis et al., "Ligation-independent cloning of PCR products (LIC-POR)," *Nucleic Acids Research*, 18(20):6069-6074 (1990).
Aukerman et al., "Regulation of Flowering Time and Floral Organ Identity by a MicroRNA and Its APETALA2-Like Target Genes," *The Plant Cell*, 15:2730-2741 (2003).
Aung et al., "pho2, a Phosphate Overaccumulator, is Caused by a Nonsense Mutation in a MicroRNA399 Target Gene," *Plant Physiology*, 3(141):1000-1011 (2006).
Axtell et al., "A two-hit trigger for siRNA biogenesis in plants," *Cell*, 127:565-577 (2006).
Baker et al., "The *early extra petalsl* Mutant Uncovers a Role for MicroRNA miR164c in Regulating Petal Number in *Arabidopsis*," *Curr. Biol.*, 15:303-315 (2005).
Bari et al., "PHO2, MicroRNA399, and PHR1 Define a Phosphate-Signaling Pathway in Plants," *Plant Physiology*, 141:988-999 (2006).
Barrick et al., "New RNA motifs suggest an expanded scope for riboswitches in bacterial genetic control," *Proc. Natl. Acad. Sci. USA*, 101(17):6421-6426 (2004).
Bartel et al., "MicroRNAs: At the Root of Plant Development?" *Plant Physiol.*, 132:709-717 (2003).
Bartel, "MicroRNAs: Genomics, Biogenesis, Mechanism, and Function," *Cell*, 116:281-297 (2004).
Bayer et al., "Programmable ligand-controlled riboregulators of eukaryotic gene expression," *Nature Biotechnol.*, 23(3):337-343 (2005).
Becker et al., "Fertile transgenic wheat from microprojectile bombardment of scutellar tissue," *The Plant Journal*, 5(2):299-307 (1994).
Belfort et al., "Prokaryotic introns and inteins: a panoply of form and function," *J. Bacteriol.*, 177(14):3897-3903 (1995).
Benfey et al., "The CaMV 35S Enhancer Contains at Least Two Domains Which Can Confer Different Developmental and Tissue-Specific Expression Patterns," *EMBO J*, 8(8):2195-2202 (1989).
Benfey et al., "The Cauliflower Mosaic Virus 35S Promoter: Combinatorial Regulation of Transcription in Plants," *Science*, 250:959-966 (1990).
Berkhout et al., "The interplay between virus infection and the cellular RNA interference machinery," *FEBS*, 580:2896-2902 (2006).
Boutros et al., "Genome-Wide RNAi Analysis of Growth and Viability in *Drosophila* Cells," *Science*, 303:832-835 (2004).
Brodersen et al., "The diversity of RNA silencing pathways in plants," *Trends Genetics*, 22:268-280 (2006).
Buckingham, "The Major World of microRNAs," *Nature Horizon Symposia*, 1-3 (2003).
Burke et al., "Recombination, RNA evolution, and bifunctional RNA molecules isolated through chimeric SELEX," *RNA*, 4:1165-1175 (1998).
Bytebier et al, "T-DNA organization in tumor cultures and transgenic plants of the monocotyledon *Asparagus officinalis*," *Proc. Natl. Acad. Sci. U.S.A.*, 84:5345-5349 (1987).
Cai et al., "Kaposi's sarcoma-associated herpesvirus expresses an array of viral microRNAs in latently infected cells," *PNAS*, 102:5570-5575 (2005).
Callis et al., "Introns increase gene expression in cultured maize cells," *Genes Dev.*, 1:1183-1200 (1987).
Chen et al., "Expression of CP4 EPSPS in microspores and tapetum cells of cotton (*Gossypium hirsutum*) is critical for male reproductive development in response to late-stage glyphosate applications," *Plant Biotechnology Journal*, 4:477-487 (2006).
Chen, "A MicroRNA as a Translational Repressor of APETALA2 in *Arabidopsis* Flower Development," *Science*, 303:2022-2025 (2004).
Cheng et al., "Production of fertile transgenic peanut (*Arachis hypogaea* L.) plants using *Agrobacterium tumefaciens*," *Plant Cell Reports*, 15:653-657 (1996).
Chiou et al., "Regulation of Phosphate Homeostasis by MicroRNA in *Arabidopsis*," *The Plant Cell*, 18:412-421 (2006).
Chuang et al., "Specific and heritable genetic interference by double-stranded RNA in *Arabidopsis thaliana*," *PNAS*, 9799):4985-4990 (2000).
Clancy et al., "Splicing of the Maize Sh1 First Intron Is Essential for Enhancement of Gene Expression, and a T-Rich Motif Increases Expression without Affecting Splicing," *Plant Physiol.*, 130:918-929 (2002).
Communication pursuant to Article 94(3) EPC dated Aug. 17, 2010, as received in European Patent Application No. 05857084.7.
Communication Pursuant to Article 94(3) EPC dated Aug. 5, 2010, as received in European Patent Application No. 06815113.3.
Communication pursuant to Article 94(3) EPC dated Feb. 21, 2012, as received in European Patent Application No. 05857084.7.
Communication Pursuant to Article 94(3) EPC dated Feb. 7, 2012, as received in European Patent Application No. 07874082.6.
Communication Pursuant to Article 94(3) EPC dated Nov. 11, 2011, as received in European Patent Application No. 06815113.3.
Communication Pursuant to Article 94(3) EPC dated Nov. 12, 2012, as received in European Patent Application No. 06815113.3.
Communication Pursuant to Article 94(3) EPC dated Nov. 16, 2010, as received in European Patent Application No. 07874082.6.
Communication Pursuant to Article 94(3) EPC dated Oct. 2, 2013, as received in European Patent Application No. 07874082.6.
Daniel et al., "Denaturation of Either *Manduca sexta* Aminopeptidase N or *Bacillus thuringiensis* Cry1A Toxins Exposes Binding Epitopes Hidden under Nondenaturing Conditions," *Appl. Env. Microbiol.*, 68(5):2106-2112 (2002).
Davidson et al., "Engineering regulatory RNAs," *TRENDS in Biotechnology*, 23(3):109-112 (2005).
Davis et al., "Isolation of high-affinity GTP aptamers from partially structured RNA libraries," *Proc. Natl. Acad. Sci. USA*, 99(18):11616-11621 (2002).
De Amicis et al., "Intercodon dincleotides affect codon choice in plant genes," *Nucleic Acid Research*, 28(17):3339-3346 (2000).
De Framond, "MINI-Ti: A New Vector Strategy for Plant Genetic Engineering," *Nature Biotechnology*, 1:262-269 (1983).
Decision of Rejection dated Jul. 3, 2013, as received in Chinese Patent Application No. 2007800457886.
Decision of Rejection dated May 6, 2013, as received in Chinese Patent Application No. 200680046237.7, and an English language translation thereof.
Denti et al., "Short interfering RNAs specific for potato spindle tuber viroid are found in the cytoplasm but not in the nucleus," *The Plant Journal*, 37:762-769 (2004).
Di Giusto et al., "Construction, Stability, and Activity of Multivalent Circular Anticoagulant Aptamers," *The Journal of Biological Chemistry*, 279(45):46483-46489 (2004).
Donnelly et al., "Analysis of the aphthovirus 2A/2B polyprotein 'cleavage' mechanism indicates not a proteolytic reaction, but a novel translational effect : a putative ribosomal 'skip'," *Journal of General Virology*, 82:1013-1025 (2001).
Donnelly et al., "The 'cleavage' activities of foot-and-mouth disease virus 2A site-directed mutants and naturally occurring '2A-like'sequences," *Journal of General Virology*, 82:1027-1041 (2001).
Du et al., "A systematic analysis of the silencing effects of an active siRNA at all single-nucleotide mismatched target sites," *Nucleic Acids Research*, 33(5):1671-1677 (2005).
Dugas et al., "MicroRNA regulation of gene expression in plants," *Current Opinion in Plant Biology*, 7:512-520 (2004).
Ebert et al., "MicroRNA Sponges: Competitive Inhibitors of Small RNAs in Mammalian Cells," *Nature Methods*, 4(9):721-726 (2007).
Eckstein, "Small non-coding RNAs as magic bullets," *Trends Biochem. Sci.*, 30(8):445-452 (2005).

(56) References Cited

OTHER PUBLICATIONS

Ellington et al., "In vitro selection of RNA molecules that bind specific ligands," *Nature*, 346:818-822 (1990).
Ellington et al., "Selection in vitro of single-stranded DNA molecules that fold into specific ligand-binding structures," *Nature*, 355:850-852 (1992).
Erdmann et al., "The non-coding RNAs as riboregulators," *Nucleic Acids Res.*, 29(1):189-193 (2001).
Esteban et al., "Kinetic Mechanism of the Hairpin Ribozyme," *J. Biol. Chem.*, 272(21):13629-13639 (1997).
Eulberg et al., "Development of an automated in vitro selection protocol to obtain RNA-based aptamers: identification of a biostable substance P antagonist," *Nucleic Acids Res.*, 33(4):e45 (2005).
Examiner's First Report dated Aug. 5, 2010, as received in Australian Patent Application No. 2006302969.
Examiner's First Report dated Feb. 17, 2010, as received in Australian Patent Application No. 2005323166.
Examiner's Report No. 2 dated Aug. 4, 2011, as received in Australian Patent Application No. 2006302969.
Examiner's Report No. 2 dated Jul. 18, 2011, as received in Australian Patent Application No. 2005323166.
Extended European Search Report dated Dec. 2, 2008, as received in European Patent Application No. 05857084.7.
Extended European Search Report dated Feb. 4, 2010, as received in European Patent Application No. 07874082.6.
Extended European Search Report dated Jul. 29, 2009, as received in European Patent Application No. 06815113.3.
Extended European Search Report dated Jul. 5, 2013, as received in European Patent Application No. 12192660.4.
Extended European Search Report dated Jun. 11, 2014, as received in European Patent Application No. 14167086.
Extended European Search Report dated Oct. 21, 2013, as received in European Patent Application No. 12192660.4.
Final Office Action dated Jan. 31, 2012, as received in U.S. Appl. No. 11/768,264.
Final Office Action dated Jul. 1, 2013, as received in U.S. Appl. No. 12/665,338.
Final Office Action dated Mar. 11, 2010, as received in U.S. Appl. No. 11/524,564.
Final Office Action dated Mar. 29, 2011, as received in U.S. Appl. No. 12/089,891.
First Examination Report dated Feb. 20, 2014, as received in Indian Patent Application No. 2497/CHENP/2009.
First Examination Report dated Jul. 11, 2013, as received in Indian Patent Application No. 1852/CHENP/2008.
First Office Action dated Apr. 18, 2012, as received in Chinese Patent Application No. 2007800457886.
First Office Action dated Oct. 12, 2010, as received in Chinese Patent Application No. 200680046237.7, and an English language translation thereof.
Franco-Zorilla et al., "Target Mimicry Provides a New Mechanism for Regulation of MicroRNA Activity," *Nature Genetics*, 39(8):1033-1037 (2007).
Fu et al., "Quality assessment of maize assembled genomic islands (MAGIs) and large-scale experimental verification of predicted genes," *PNAS*, 102(34):12282-12287 (2005).
Fujii et al., "MiRNA involved in phosphate starvation response in *Arabidopsis*," *Current Bio.*, 17(22):2038-2043 (2005).
Gandikota et al., "The MiRNA 156/157 recognition element in the 3' UTR of the *Arabidopsis* SBP box gene SPL3 prevents early flowering by translational inhibition in seedlings," *Plant J.*, 49:683-693 (2007).
Geiger et al., "RNA aptamers that bind $_L$-arginine with submicromolar dissociation constants and high enantioselectivity," *Nucleic Acids Res.*, 24(6):1029-1036 (1996).
Gill et al., "Identification, Isolation, and Cloning of a *Bacillus thuringiensis* CryIAc Toxin-binding Protein from the Midgut of the Lepidopteran Insect *Heliothis virescens*," *J. Biol. Chem.*, 270:27277-27282 (1995).
Gitlin et al., "Poliovirus escape from RNA interference: short interfering RNA-target recognition and implications for therapeutic approaches," *Virology*, 79:1027-1035 (2004).
Gomez et al., "Mapping the Epitope in Cadherin-like Receptors Involved in *Bacillus thuringiensis* Cry1A Toxin Interaction Using Phage Display," *J. Biol. Chem.*, 276:28906-28912 (2001).
Gottesman, "Micros for microbes: non-coding regulatory RNAs in bacteria," *Trends Genet.*, 21(7):399-404 (2005).
Graber et al. "In silico detection of control signals: mRNA 3'-end-processing sequences in diverse species," *Proc. Natl. Acad. Sci. USA*, 96(24):14055-14060 (1999).
Green, "Control of mRNA Stability in Higher Plants," *Plant Physiol.*, 102:1065-1070 (1993).
Griffiths-Jones et al., "Rfam: an RNA family database," *Nucleic Acids Research*, 31(1):439-441 (2003).
Griffiths-Jones et al., "Rfam: annotating non-coding RNAs in complete genomes," *Nucleic Acids Res.*, 33:121-124 (2005).
Griffiths-Jones, "The microRNA Registry," *Nucleic Acids Res.*, 32:D109-D111 (2004).
Gustafson et al., "ASRP: the *Arabdopsis* Small RNA Project Database," *Nucleic Acids Res.*, 33:D637-D640 (2005).
Hamilton et al., "A transgene with repeated DNA causes high frequency, post-transcriptional suppression of ACC-oxidase gene expression in tomato," *Plant J.*, 15(6):737-746 (1998).
Hanawa et al., "Phytoalexins from *Pinus strobus* bark infected with pinewood nematode, *Bursaphelenchus xylophilus*," *Phytochemistry*, 57:223-228 (2001).
Hartings et al., "The b-32 protein from maize endosperm: characterization of genomic sequences encoding two alternative central domains," *Plant Mol. Biol.*, 14:1031-1040 (1990).
Hasegawa et al, "In vitro analysis of transcription initiation and termination from the Lhcb1 gene family in *Nicotiana sylvestris*: detection of transcription termination sites," *Plant J.*, 33:1063-1072 (2003).
Hjalt et al., "Bulged-out nucleotides in an antisense RNA are required for rapid target RNA binding in vitro and inhibition in vivo." *Nucl. Acids Res.* 23(4):580-587 (1995).
Hjalt et al., "Bulged-out nucleotides protect an antisense RNA from RNAse III cleavage," *Nucl. Acids Res.* 23(4):571-579 (1995).
Hoekema et al., "A binary plant vector strategy based on separation of vir- and T-region of the *Agrobacterium tumefaciens* Ti-plasmid," *Nature*, 303:179-180 (1983).
Hofacker et al., "Fast Folding and Comparison of RNA Secondary Structures," *Monatsh. f. Chemie*, 125:167-188 (1994).
Homann et al., "Combinatorial selection of high affinity RNA ligands to live African trypanosomes," *Nucleic Acids Res.*, 27(9):2006-2014 (1999).
Hooykaas et al., "*Agrobacterium* and plant genetic engineering," *Plant Mol. Biol.*, 19:15-38 (1992).
Horstmann et al. "Quantitative promoter analysis in *Physcomitrella patens*: a set of plant vectors activating gene expression within three orders of magnitude," *BMC Biotechnol.*, 4:13 (2004).
Hua et al., "Binding Analyses of *Bacillus thuringiensis* Cry δ-Endotoxins Using Brush Border Membrane Vesicles of *Ostrinia nubilalis*," *Applied and Environmental Microbiology*, 67(2):872-879 (2001).
Huang et al., "Evolution of aptamers with a new specificity and new secondary structures from an ATP aptamer," *RNA*, 9:1456-1463 (2003).
Huang et al., "Improving Nutritional Quality of Maize Proteins by Expressing Sense and Antisense Zein Genen," *J. Agric. Food Chem.*, 52:1958-1964 (2004).
International Preliminary Report on Patentability (Chapter I) dated Apr. 15, 2009, as received in International Application No. PCT/US2007/021987.
International Preliminary Report on Patentability (Chapter II) dated May 2, 2013, as received in International Application No. PCT/US2007/021987.
International Preliminary Report on Patentability (Chapter II) dated Sep. 6, 2007, as received in International Patent Application No. PCT/US2005/045517.
International Search Report and Written Opinion dated Mar. 27, 2009, as received in International Application No. PCT/US2008/068276.

(56) References Cited

OTHER PUBLICATIONS

International Search Report and Written Opinion dated May 2, 2007, as received in International Patent Application No. PCT/US2005/045517.
International Search Report and Written Opinion dated Oct. 19, 2007, in International Patent Application No. PCT/US2006/036847.
International Search Report dated Mar. 16, 2009, as received in International Application No. PCT/US2007/021987.
International Search Report dated Sep. 28, 2007, as received in International Patent Application No. PCT/US2006/023039.
Isaacs et al., "Engineered riboregulators enable post-transcriptional control of gene expression," Nature Biotechnology, 22(7):841-847 (2004).
Jenison et al., "High-Resolution Molecular Discrimination by RNA," Science, 263:1425-1429 (1994).
Jones-Rhoades et al., "MicroRNAs and their regulatory roles in plants," Annual Review, 57:19-53 (2006).
Jones-Rhoades et al., "Computational Identification of Plant MicroRNAs and Their Targets, Including a Stress-Induced miRNA," Molecular Cell, 14:787-799 (2004).
Juarez et al., "microRNA-mediated repression of rolled leaf1 specifies maize leaf polarity," Nature, 428:84-88 (2004).
Jurat-Fuentes et al., "Importance of Cry1 δ-Endotoxin Domain II Loops for Binding Specificity in Heliothis virescens (L.)," Appl. Env. Microbiol., 67(1):323-329 (2001).
Kagaya et al., "The Promoter from the Rice Nuclear Gene Encoding Chloroplast Aldolase Confers Mesophyll-Specific and Light-Regulated Expression in Transgenic Tobacco," Mol. Gen. Genet, 248:668-674 (1995).
Kasschau et al., "P1/HC-Pro, a Viral Suppressor of RNA Silencing, Interferes with Arabidopsis Development and miRNA Function," Developmental Cell, 4:205-217 (2003).
Kettenberger et al., "Structure of an RNA polymerase II-RNA inhibitor complex elucidates transcription regulation by noncoding RNAs," Nature Struc. Mol. Biol., 13(1):44-48 (2006).
Khvorova et al., "Functional siRNAs and miRNAs Exhibit Strand Bias," Cell, 115:209-216 (2003).
Kidner et al., "Spatially restricted microRNA directs leaf polarity through ARGONAUTE1," Nature, 428:81-84 (2004).
Kim, "MicroRNA Biogenesis: Coordinated Cropping and Dicing," Nature Reviews | Molecular Cell Biology, 6:376-385 (2005).
Knight et al., "Molecular Cloning of an Insect Aminopeptidase N That Serves as a Receptor for Bacillus thuringiensis CryIA(c) Toxin," J. Biol. Chem., 270(3):17765-17770 (1995).
Kubodera et al., "Thiamine-regulated gene expression of Aspergillus oryzae thiA requires splicing of the intron containing a riboswitch-like domain in the 5'-UTR," FEBS Lett, 555:516-520 (2003).
Lau et al., "An Abundant Class of Tiny RNAs with Probable Regulatory Roles in Caenorhabditis elegans," Science, 294:858-862 (2001).
Lauter et al., "microRNA172 down-regulates glossy15 to promote vegetative phase change in maize," Proc. Natl. Acad. Sci. USA, 102:9412-9417 (2005).
Lee et al., "Aptamer Database," Nucleic Acids Research, 32:D95-D100 (2004).
Lee et al., "MicroRNA maturation: stepwise processing and subcellular localization," The EMBO Journal, 21(17):4663-4670 (2002).
Lin et al., "A novel RNA splicing-mediated gene silencing mechanism potential for genome evolution," Biochem. Biophys. Res. Comm., 310:754-760 (2003).
Lin et al., "Asymmetry of intronic pre-miRNA structures in functional RISC assembly," Gene, 356:32-38 (2005).
Liu et al., "A collection of 10,096 indica rice full-length cDNAs reveals highly expressed sequence divergence between Oryza sativa indica and japonica subspecies," Plant Mol. Biol., 65:403-415 (2007).
Liu et al., "Oryza sativa (indica cultivar-group) cDNA clone:OSIGCFA005E15, full insert sequence," Genbank Accession No. CT833344, (2006).

Llave et al. "Endogenous and Silencing-Associated Small RNAs in Plants," The Plant Cell, 14:1605-1619 (2002).
Llave et al., "Cleavage of Scarecrow-like mRNA Targets Directed by a Class of Arabidopsis miRNA," Science, 297:2053-2056 (2002).
Lu et al. "RNA silencing in plants by the expression of siRNA duplexes," Nucleic Acids Res., 32(21):e171 (2004).
Lund et al., "Nuclear Export of MicroRNA Precursors," Science, 303:95-98 (2004).
Ma et al., "Intrinsic direct repeats generate consistent post-transcriptional gene silencing in tobacco," The Plant Journal, 31(1):37-49 (2002).
Mallory et al., "Functions of microRNAs and related small RNAs in plants," NatureGenetics, 38:31-36 (2006).
Mallory et al., "MicroRNA control of PHABULOSA in leaf development: importance of pairing to the microRNA 5' region," EMBO Journal, 23:3356-3364 (2004).
Mallory et al., "MicroRNA Regulation of NAC-Domain Targets Is Required for Proper Formation and Separation of Adjacent Embryonic, Vegetative, and Floral Organs," Current Biology, 14:1035-1046 (2004).
Mallory et al., "MicroRNA-Directed Regulation of Arabidopsis Auxin Response Factor17 is Essential for Proper Development and Modulates Expression of Early Auxin Response Genes," The Plant Cell, 17:1360-1375 (2005).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews | Molecular Cell Biology, 5:451-463 (2004).
Mansoor et al., "Engineering novel traits in plants through RNA interference," Trends Plant Sci., 11(11):559-565 (2006).
Margulies et al., "Genome sequencing in microfabricated high-density picolitre reactors," Nature, 437:376-380 (2005).
Martienssen, "Maintenance of heterochromatin by RNA interference of tandem repeats," Nat. Genet., 35(3):213-214 (2003).
Mas, "Circadian clock signaling in Arabidopsis thaliana: from gene expression to physiology and development," International Journal of Developmental Biology, 49:491-500 (2005).
Mascarenhas et al., Intron-mediated enhancement of heterologous gene expression in maize, Plant Mol. Biol., 15:913-920 (1990).
Masoud et al., "Constitutive expression of an inducible β-1,3-glucanase in alfalfa reduces disease severity caused by the oomycete pathogen Phytophthora megasperma f. sp medicaginis, but does not reduce disease severity of chitin-containing fungi," Transgenic Research, 5:313-323 (1996).
Matzke et al., "RNAi-Mediated Pathways in the Nucleus," Nat. Rev. Genet., 6:24-35 (2005).
McElroy et al., "Isolation of an Efficient Actin Promoter for Use in Rice Transformation," The Plant Cell, 2:163-171 (1990).
MeGraw et al., "MicroRNA promoter element discovery in Arabidopsis," RNA Society, 12:1612-1619 (2006).
Millar et al., "Plant and animal microRNAs: similarities and differences," Funct. Integr. Genomics, 5:129-135 (2005).
Millar et al., "The Arabidopsis GAMYB-Like Genes, MYB33 and MYB6S, Are MicroRNA-Regulated Genes That Redundantly Facilitate Anther Development," The Plant Cell, 17:705-721 (2005).
Morris et al., "Slowing Down the Ras Lane: miRNAs as Tumor Suppressors?" Science's STKE, 297:pe41 (2005).
Murchison et al., "miRNAs on the move: miRNA biogenesis and the RNAi machinery," Current Opinion in Cell Biology, 16:223-229 (2004).
Murphy et al., "An improved method for the in vitro evolution of aptamers and applications in protein detection and purification," Nucleic Acids Res., 31(18):e110 (2003).
Najafi-Shoushtari et al., "Competitive regulation of modular allosteric aptazymes by a small molecule and oligonucleotide effector," RNA, 11:1514-1520 (2005).
Najafi-Shoushtari et al., "Sensing complex regulatory networks by conformationally controlled hairpin ribozymes," Nucleic Acids Res., 32(10):3212-3219 (2004).
Newman et al., "DST Sequences, Highly Conserved among Plant SAUR Genes, Target Reporter Transcripts for Rapid Decay in Tobacco," The Plant Cell, 5:701-714 (1993).

(56) References Cited

OTHER PUBLICATIONS

Non-Final Office Action dated Apr. 20, 2012, as received in U.S. Appl. No. No. 12/089,891.
Non-Final Office Action dated Dec. 6, 2010, as received in U.S. Appl. No. 11/768,264.
Non-Final Office Action dated Jan. 2, 2013, as received in U.S. Appl. No. 12/665,338.
Non-Final Office Action dated Jul. 1, 2009, as received in U.S. Appl. No. 11/524,564.
Non-Final Office Action dated Jul. 29, 2010, as received in U.S. Appl. No. 12/089,891.
Non-Final Office Action dated Jun. 22, 2011, as received in U.S. Appl. No. 11/768,264.
Non-Final Office Action dated Nov. 28, 2008, as received in U.S. Appl. No. 11/303,745.
Notice of Acceptance dated Sep. 6, 2012, as received in Australian Patent Application No. 2007352460.
Notification of Transmittal of International Preliminary Report on Patentability dated Oct. 23, 2007, as received in International Application No. PCT/US2005/045517.
O'Donnell et al., "c-Myc-regulated microRNAs modulate E2F1 expression," *Nature*, 435:839-843 (2005).
Office Action dated Aug. 23, 2010, as received in Argentine Patent Application No. P 06 01 04495.
Office Action dated Feb. 13, 2012, as received in Canadian Patent Application No. 2,625,031.
Office Action dated Jan. 17, 2011, as received in Mexican Patent Application No. MX/a/2008/004873.
Office Action dated Jul. 8, 2010, as received in Canadian Patent Application No. 2,625,031.
Office Action dated Jun. 16, 2013, as received in Argentine Patent Application No. P 06 01 04495.
Office Action dated Jun. 28, 2011, as received in Eurasian Patent Application No. 200801074/28, and an English language translation thereof.
Office Action dated Mar. 18, 2010, as received in Eurasian Patent Application No. 200801074/28, and an English language translation thereof.
Office Action dated Mar. 26, 2013, as received in Canadian Patent Application No. 2,625,031.
Office Action dated Oct. 12, 2010, as received in Ukrainian Patent Application No. a 2008 06024, and an English language translation thereof.
Ohme-Takagi et al., "The effect of sequences with high AU content on mRNA stability in tobacco," *Proc. Natl. Acad. Sci. USA*, 90:11811-11815 (1993).
Palatnik et al., "Control of leaf morphogenesis by microRNAs," *Nature*, 425:257-263 (2003).
Papp et al., "Evidence for Nuclear Processing of Plant Micro RNA and Short Interfering RNA Precursors," *Plant Physiol.*, 132:1382-1390 (2003).
Parizotto et al., "In vivo investigation of the transcription, processing, endonucleolytic activity, and functional relevance of the spatial distribution of a plant miRNA," *Genes Dev.*, 18:2237-2242 (2004).
Park et al., "Carpel Factory, a Dicer Homolog, and HEN1, a Novel Protein, Act in microRNA Metabolism in *Arabidopsis thaliana*," *Current Biology*, 12:1484-1495 (2002).
Patent Examination Report No. 1 dated Jul. 16, 2012, as received in Australian Patent Application No. 2007352460.
Peng et al., "A mutation in NLA, which encodes a RING-type ubiquitin ligase, disrupts the adaptability of *Arabidopsis* to nitrogen limitation," *Plant J.*, 50:320-337 (2007).
Plummer et al., "In vitro selection of RNA aptamers against a composite small molecule-protein surface," *Nucleic Acids Res.*, 33(17):5602-5610 (2005).
Preliminary Amendment filed Dec. 9, 2009, in U.S. Appl. No. 12/089,891.
Proudfoot, "New perspectives on connecting messenger RNA 3' end formation to transcription," *Curr. Opin. Cell Biol.*, 16:272-278 (2004).

Rashtchian et al., "Uracil DNA Glycosylase-Mediated Cloning of Polymerase Chain Reaction-Amplified DNA: Application to Genomic and cDNA Cloning," *Analytical Biochemistry*, 206:91-97 (1992).
Record of Interview, Preliminary Amendment, and Supplemental Response to Restriction Requirement filed Apr. 24, 2009, in U.S. Appl. No. 11/524,564.
Reinhart et al., "MicroRNAs in plants," *Genes Dev.*, 16:1616-1626 (2002 ).
Response to Notice of Non-Compliant Reply and Amendment filed Feb. 14, 2011, in U.S. Appl. No. 12/089,891.
Response to Notice to File Corrected Application Papers filed Sep. 25, 2012, in U.S. Appl. No. 12/089,891.
Response to Office Action and Amendment filed Dec. 1, 2009, in U.S. Appl. No. 11/524,564.
Response to Restriction Requirement filed Apr. 10, 2009, in U.S. Appl. No. 11/524,564.
Reynolds et al., "Rational siRNA design for RNA interference," *Nature Biotechnol.*, 22(3):326-330 (2004).
Rhoades et al., "Prediction of Plant MicroRNA Targets," *Cell*, 110:513-520 (2002).
Rice et al., "EMBOSS: The European Molecular Biology Open Software Suite," *Trends Genet.*, 16(6):276-277 (2000).
Rodionov et al., "Regulation of lysine biosynthesis and transport genes in bacteria: yet another RNA riboswitch?" *Nucleic Acids Res.*, 31(23):6748-6757 (2003).
Rombauts et al., "Computational Approaches to Identify Promoters and cis-Regulatory Elements in Plant Genomes," *Plant Physiology*, 132(3):1162-1176 (2003).
Saez et al., "Identification of ligands and coligands for the ecdysone-regulated gene switch," *Proc. Natl. Acad. Sci. USA*, 97(26):14512-14517 (2000).
Samakoglu et al., "A genetic strategy to treat sickle cell anemia by coregulating globin transgene expression and RNA interference," *Nature Biotechnology*, 24(1):89-94 (2006).
Schmidt et al., "Application of locked nucleic acids to improve aptamer in vivo stability and targeting function," *Nucleic Acids Res.*, 32(19):5757-5765 (2004).
Schwab et al., "Specific effects of microRNAs on the plant transcriptome," *DevCell.*, B:517-527 (2005).
Second Office Action dated Jan. 11, 2013, as received in Chinese Patent Application No. 2007800457886.
Second Office Action dated Mar. 19, 2012, as received in Chinese Patent Application No. 200680046237.7, and an English language translation thereof.
Second Office Action dated Oct. 19, 2010, as received in Mexican Patent Application No. MX/a/2008/004873.
Second Preliminary Amendment filed Aug. 2, 2010, in U.S. Appl. No. 12/089,891.
Sheen, "Metabolic Repression of Transcription in Higher Plants," *The Plant Cell*, 2:1027-1038 (1990).
Shi et al., "RNA aptamers as effective protein antagonists in a multicellular organism," *Proc. Natl. Acad. Sci. USA*, 96:10033-10038 (1999).
Sijen et al., "RNA-Mediated Virus Resistance: Role of Repeated Transgenes and Delineation of Targeted Regions," *The Plant Cell*, 8:2277-2294 (1996).
Staple et al., "Pseudoknots: RNA Structures with Diverse Functions," *PLoS Biology*, 3(6):0956-0959 (2005).
Subramanian et al., "Novel and nodulation-regulated microRNAs in soybean roots," *BMC Genomics*, 9:160 (2008).
Sudarsan et al. "An mRNA structure in bacteria that controls gene expression by binding lysine," *Genes Dev.*, 17:2688-2697 (2003).
Sudarsan et al., "Metabolite-binding RNA domains are present in the genes of eukaryotes," *RNA*, 9:644-647 (2003).
Sun et al., "A Highly Efficient Transformation Protocol for Micro-Tom, a Model Cultivar for Tomato Functional Genomics," *Plant Cell Physiol.*, 47:426-431 (2006).
Sunkar et al., "Novel and Stress-Regulated MicroRNAs and Other Small RNAs from *Arabidopsis*," *The Plant Cell*, 16:2001-2019 (2004).
Tang, "siRNA and miRNA: an insight into RISCs," *TRENDS in Biochemical Sciences*, 30(2):106-114 (2005).

(56) References Cited

OTHER PUBLICATIONS

Technical Examination Report dated Apr. 11, 2010, as received in Egyptian Patent Application No. 2008040601.
Technical Examination Report dated Aug. 1, 2011, as received in Egyptian Patent Application No. 2008040601.
Technical Examination Report dated Dec. 4, 2010, as received in Egyptian Patent Application No. 2008040601.
Technical Examination Report dated Jan. 14, 2012, as received in Egyptian Patent Application No. 2008040601.
Templeton et al., "A Renaissance of Metabolite Sensing and Signaling: From Modular Domains to Riboswitches," *The Plant Cell*, 16:2252-2257 (2004).
Third Office Action dated Nov. 16, 2012, as received in Chinese Patent Application No. 200680046237.7, and an English language translation thereof.
Thomas et al., "Selective Targeting and Inhibition of Yeast RNA Polymerase II by RNA Apatamers," *J. Biol. Chem.*, 272(44):27980-27986 (1997).
Ticconi et al., "Short on phosphate: plant surveillance and countermeasures," *TRENDS in Plant Science*, 9(11):548-555 (2004).
Tomari et al., "MicroRNA Biogenesis: Drosha Can't Cut It without a Partner," *Current Biology*, 15(2):R61-64 (2005).
Tomari et al., "Perspective: machines for RNAi," *Genes & Dev.*, 19:517-529 (2005).
Toriyama et al., "Transgenic Rice Plants After Direct Gene Transfer Into Protoplasts," *Bio/Technology*, 6:1072-1074 (1988).
Tuerk et al., "Systematic Evolution of Ligands by Exponential Enrichment: RNA Ligands to Bacteriophage T4 DNA Polymerase," *Science*, 249:505-510 (1990).
Ulmasov et al. "Activation and repression of transcription by auxin-response factors," *Proc. Natl. Acad. Sci. USA*, 96:5844-5849 (1999).
Urwin et al., "Ingestion of Double-stranded RNA by Preparasitic Juvenile Cyst Nematodes Leads to RNA Interference," *Mol. Plant Microbe Interactions*, 15(8):747-752 (2002).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vasil et al., "Increased Gene Expression by the First Intron of Maize *Shrunken*-1 Locus in Grass Species," *Plant Physiol.*, 91:1575-1579 (1989).
Vaucheret, "MicroRNA-Dependent Trans-Acting siRNA Production," *Science STKE*, (300):pe43 (2005).
Vettore et al., "The libraries that made SUCEST," *Genetics and Molecular Biology*, 24:1-7 (2001).
Wan et al., "Generation of Large Numbers of Independently Transformed Fertile Barley Plants," *Plant Physiol.*, 104:37-48 (1994).
Wang et al., "Characterization of cis-acting elements regulating transcription from the promoter of a constitutively active rice actin gene," *Mol. Cell Biol.*, 12(8):3399-3406 (1992).
Wang et al., "Control of Root Cap Formation by MicroRNA-Targeted Auxin Response Factors in *Arabidopsis*," *The Plant Cell*, 17:2204-2216 (2005).
Wang et al., "Structure and Expression Profile of the *Arabidopsis PHO1* Gene Family Indicates a Broad Role in Inorganic Phosphate Homeostasis," *Plant Physiology*, 135:400-411 (2004).

Weill et al., "Selection and evolution of NTP-specific aptamers," *Nucleic Acids Res.*, 32(17):5045-5058 (2004).
Wesley et al., "Construct design for efficient, effective and high-throughput gene silencing in plants," *The Plant Journal*, 27(6):581-590 (2001).
Williams et al., "Regulation of *Arabidopsis* shoot apical meristem and lateral organ formation by microRNA miR166g and its AtHD-ZIP target genes," *Development*, 132:3657-36 (2005).
Winkler et al., "Thiamine derivatives bind messenger RNAs directly to regulate bacterial gene expression," *Nature*, 419:952-956 (2002).
Written Opinion dated Apr. 12, 2009, as received in International Application No. PCT/US2007/021987.
Written Opinion dated Sep. 28, 2007, as received in International Patent Application No. PCT/US2006/023039.
Wu et al., "Temporal regulation of Shoot Development in *Arabidopsis thaliana* by Mir156 and Its Target SPL3," *Development*,133(18):3539-3547 (2006).
Xie et al., "Dicer-Like 4 functions in trans-acting small interfering RNA biogenesis and vegetative phase change in *Arabidopsis thaliana*," *Proc. Natl. Acad. Sci. USA*, 102(36):12984-12989 (2005).
Xie et al., "Expression of *Arabidopsis MIRNA* Genes," *Plant Physiology*, 138:2145-2154 (2005).
Xie et al., "Genetic and Functional Diversification of Small RNA Pathways in Plants," *PLoS Biol.*, 2(5):0642-0652 (2004).
Yamasaki et al., "Regulation of Copper Homeostasis by Micro-RNA in *Arabidopsis*," *The Journal of Biological Chemistry*, 282(22):16369-16378 (2007).
Yao et al. "Cloning and characterization of *Arabidopsis* homologues of the animal CstF complex that regulates 3' mRNA cleavage and polyadenylation," *J. Exp. Bot.*, 53(378):2277-2278 (2002).
Ying et al., "Intron-derived micro-RNAs-fine tuning of gene functions," *Gene*, 342:25-28 (2004).
Ying et al., "Intronic microRNAs," *Biochemical and Biophysical Research Communications*, 326:515-520 (2005).
Yoshikawa et al. "A pathway for the biogenesis of trans-acting siRNAs in *Arabidopsis*," *Genes Dev.*, 19:2164-2175 (2005).
Yoshimatsu et al., "Control of Gene Expression by Artificial Introns in *Saccharomyces cerevisiae*," *Science*, 244:1346-1348 (1989).
Zhang et al., "Plant microRNA: A small reg. mol. with big impact," *Development Biology*, 289:3-16 (2006).
Zhang et al., "DEG: a database of essential genes," *Nucleic Acids Research*, 32:D271-D272 (2004).
Zhang et al., "MicroRNAs and Their Regulatory Roles in Animals and Plants," *Journal of Cellular Physiology*, 210:279-289 (2007).
Zhang et al., "Transgenic rice plants produced by electroporation-mediated plasmid uptake into protoplasts," *The Plant Cell Rep.*, 7:379-384 (1988).
Zhang, "miRU: an automated plant miRNA target prediction server," *Nucleic Acids Research*, 33:W701-W704 (2005).
Zhuang et al., "*Heliothis virescens* and *Manduca sexta* Lipid Rafts Are Involved in Cry1A Toxin Binding to the Midgut Epithelium and Subsequent Pore Formation," *The Journal of Biological Chemistry*, 277(16):13863-13872 (2002).
Zilberman et al. "ARGONAUTE4 Control of Locus-Specific siRNA Accumulation and DNA and Histone Methylation," *Science*, 299:716-719 (2003).
Zuker, "Mfold web server for nucleic acid folding and hybridization prediction," *Nucleic Acids Res.*, 31(13):3406-3415 (2003).

\* cited by examiner

FIGURE 2
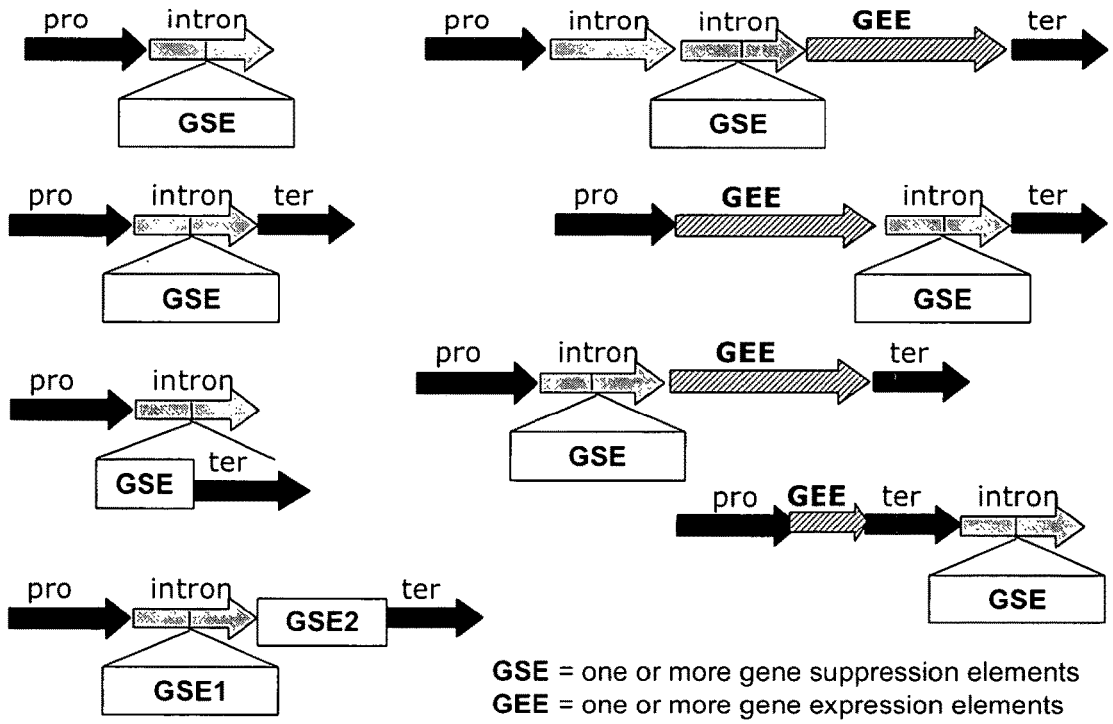
A
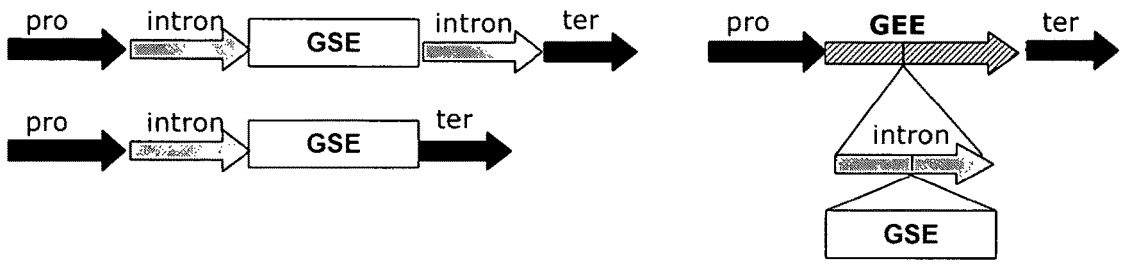
B

FIGURE 7

```
CUGU                         GCU         AUGGAUUGGUGCAUGCAUGG
    UUUGUUGGUGGUCAUUUAACCAUGCAU   UCGAUCG                    A        A
    |||||:||:|||||||:||||||||||:  ||||||:                    U
    AAACGACUACCAGUAGAUUGGUACGUG   ACGCGGU                    U   SEQ ID NO. 3936
GUAC                         ACU         GUACGUAGUGUGAUACGUUA        (Zea mays)

CUGU      C                C    A   CCUGGAGAUUGGAGAAUAAUUGA            B
    UUUGUUG UGGUCAUCUAGCUAC CGUGC UG                        C
    |||||:|| ||||||||||:|:||  |||||  ::                      G   SEQ ID NO. 1763
    AAACGAC ACCAGUAGAUUGGUG GCACG GU                        A   (Oryza sativa)
GAAC      U                C    G  UCUCGGUUAUUCGGCUGACGACGU -C U    U U           U A    C AU        UCC
UGCAA    CC UGAA G GUUUGUUGAU G UAUCUA AC GUUGAUCA  U        C
|||||    || ||||  |||||||||||  ||||||  ||  |||||||  U   SEQ ID NO. 8743
ACGUU   GG GCUU C CAAACAACUA C GUAGAU UG UAGCUAGU G      (Arabidopsis thaliana)
     UU U   U U           C A    U GU        UGU
```

```
         1            10           21           miRMON18:
         ↓            ↓            ↓            rice (SEQ ID NO. 393)
                                                maize (SEQ ID NO. 3227)
5'-UUAGAUGACCAUCAGCAAACA-3'                     soybean (SEQ ID NO. 8742)

|||||||||||||||  |||||

5'-UUAGAUGACCAUCAACAAACU-3'
         ↑            ↑            ↑            miR827:
         1            10           21           Arabidopsis thaliana
                                                (SEQ ID NO. 8744)
```

D

FIGURE 8
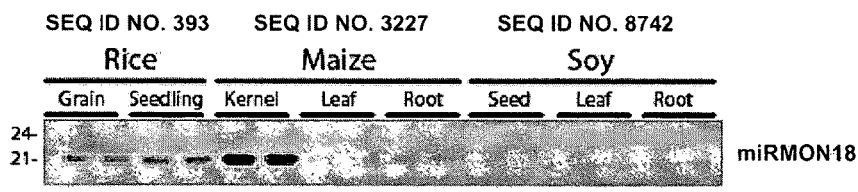
A
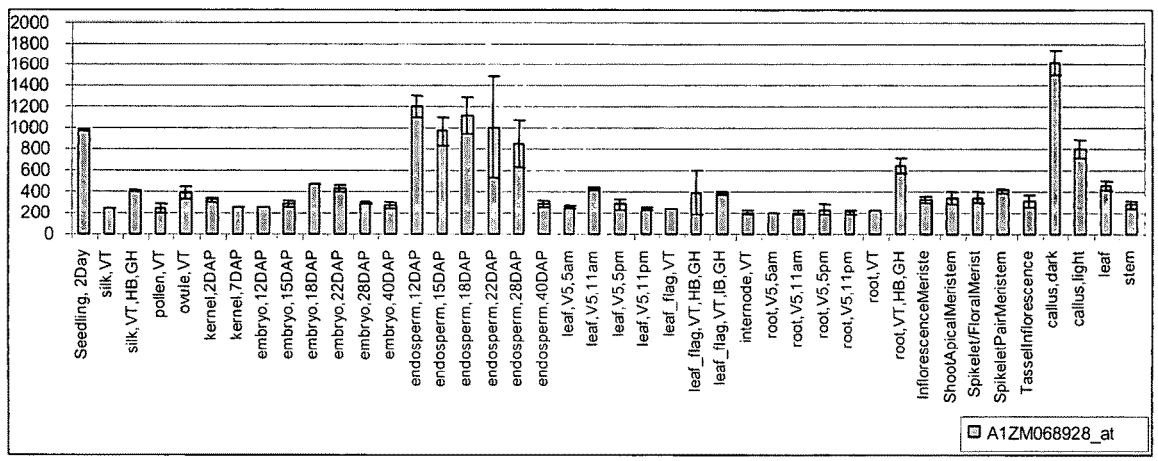
B

FIGURE 9
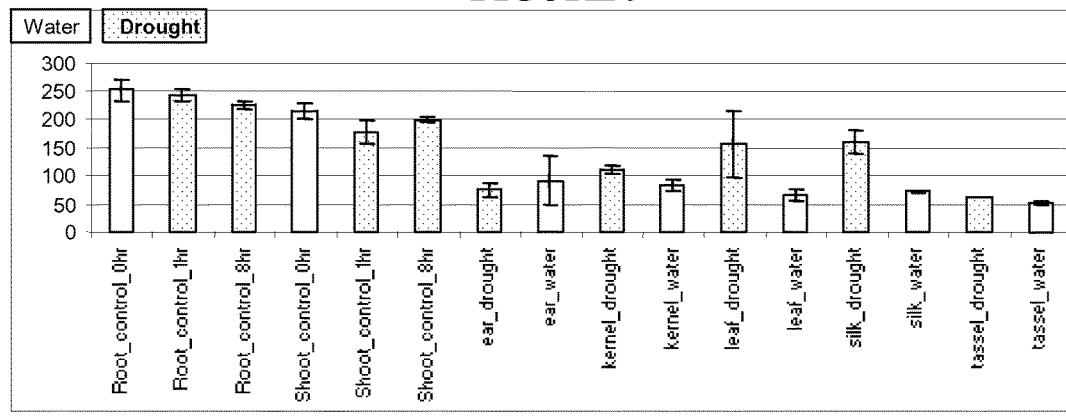
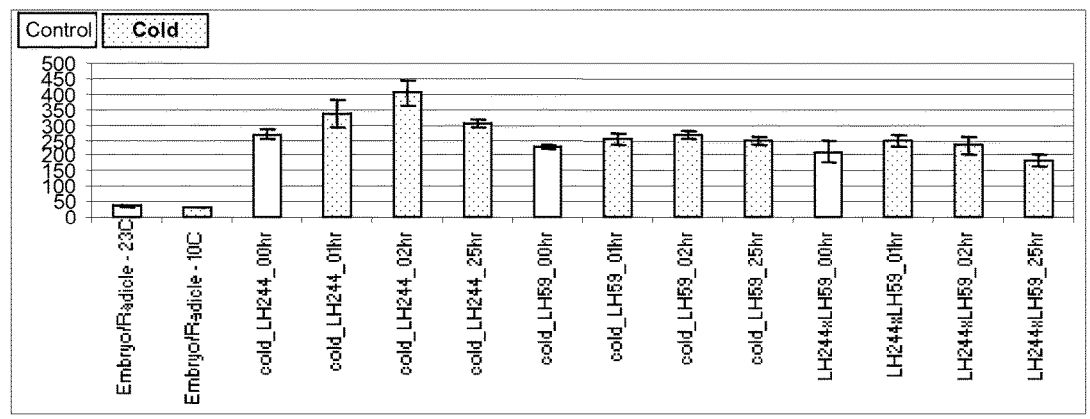
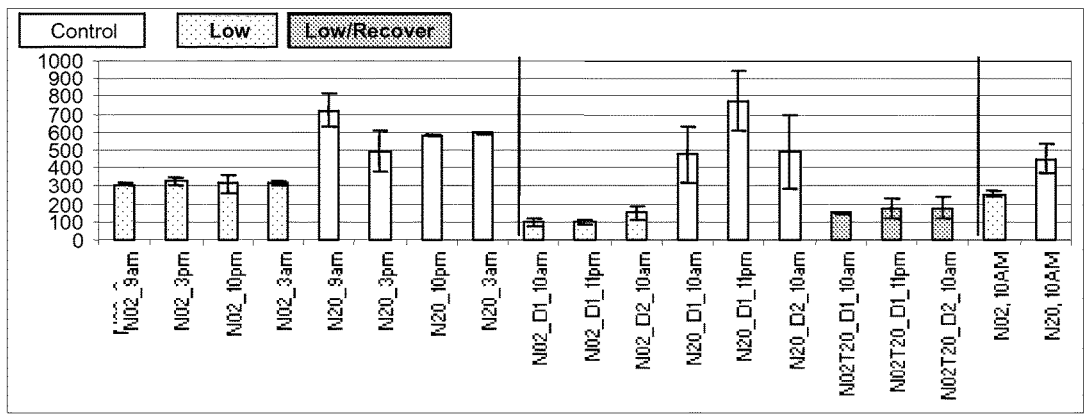

FIGURE 10
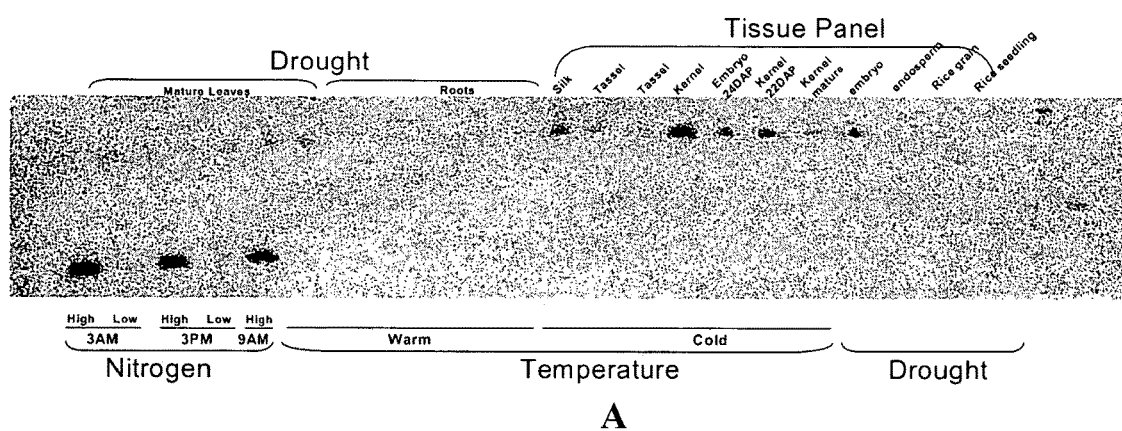
A
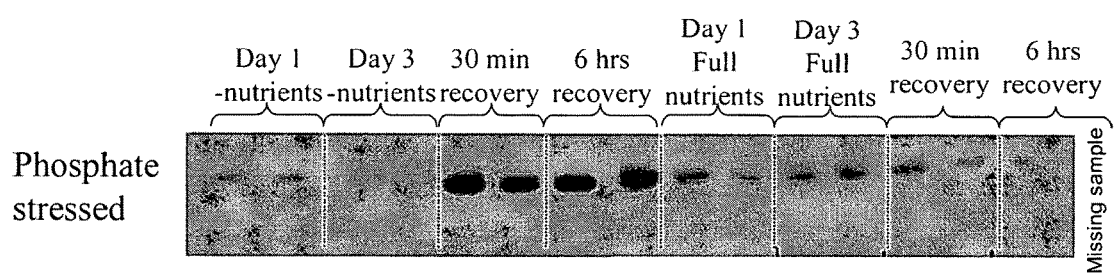
B

FIGURE 11

| | | |
|---|---|---|
| SPX_MFS_126116193_plus_est_sti | (SEQ ID NO. 8766) | ---------------------------------------------- |
| fs_SPX_MFS_126116193_plus_est | (SEQ ID NO. 8765) | MVNFGKKLMADQIPEWKGYYINYKLMKKKVKQYGQQLQQGEKDRRRVLKD |
| SPX_MFS_118200525_cdna.pep | (SEQ ID NO. 8761) | MVNFGKKLMADQIPEWKGYYINYKLMKKKVKQYGQQLQQGEKDRRRVLKD |
| SPX_MFS_118200525_2_pep | (SEQ ID NO. 8763) | ---------------------------------------------- |
| SPX_MFS_117961287_cdna.pep | (SEQ ID NO. 8757) | MVNFGKKLMADQVDEWKGYYINYKLMKKMLKQYVQQTQHDEKDREQVLKD |
| SPX_MFS_117961287_2_cdna.pep | (SEQ ID NO. 8759) | ---------------------------------------------- |
| | | |
| SPX_MFS_126116193_plus_est_sti | (SEQ ID NO. 8766) | ---------------------------------------------- |
| fs_SPX_MFS_126116193_plus_est | (SEQ ID NO. 8765) | FSKMLDDQIEKIALFLLEQQGMLASRIEELGKQRAILQDQPDISGIAELR |
| SPX_MFS_118200525_cdna.pep | (SEQ ID NO. 8761) | FSKMLDDQIEKIVLFLLEQQGLLASRIEKLGKQRAILQEQPDISGIAELR |
| SPX_MFS_118200525_2_pep | (SEQ ID NO. 8763) | ---------------------------------------------- |
| SPX_MFS_117961287_cdna.pep | (SEQ ID NO. 8757) | FSRFLDDQIERIVLFLLQQQGHLASRIEKLAEKRTALLEEYDISQVYQLH |
| SPX_MFS_117961287_2_cdna.pep | (SEQ ID NO. 8759) | ---------------------------------------------- |
| | | |
| SPX_MFS_126116193_plus_est_sti | (SEQ ID NO. 8766) | ---------------------------------------------- |
| fs_SPX_MFS_126116193_plus_est | (SEQ ID NO. 8765) | EAYREVGIDLIKLLKFVDLNATGIRKILKKFDKRFGYRFTDYVTSRSNH |
| SPX_MFS_118200525_cdna.pep | (SEQ ID NO. 8761) | EAYREVGINLIKLLKFVDLNATGIRKILKKFDKRFGYRFTDYVTSRSNH |
| SPX_MFS_118200525_2_pep | (SEQ ID NO. 8763) | ---------------------------------------------- |
| SPX_MFS_117961287_cdna.pep | (SEQ ID NO. 8757) | DAYREVGLDLIKLLRFVDVNATGIRKILKKFDKRFGYKFTDYVTTRANH |
| SPX_MFS_117961287_2_cdna.pep | (SEQ ID NO. 8759) | ---------------------------------------------- |
| | | |
| SPX_MFS_126116193_plus_est_sti | (SEQ ID NO. 8766) | ---------------------------------------------- |
| fs_SPX_MFS_126116193_plus_est | (SEQ ID NO. 8765) | PYSQLQQVFKHVGVGAVVGALSRNLAELQERQGSYLSIYDQPSSALKDPI |
| SPX_MFS_118200525_cdna.pep | (SEQ ID NO. 8761) | PYSQLQQVFKHVGVGAVVGALSRNLAELQERQGSYLSIYDQPSSALKDPI |
| SPX_MFS_118200525_2_pep | (SEQ ID NO. 8763) | ---------------------------------------------- |
| SPX_MFS_117961287_cdna.pep | (SEQ ID NO. 8757) | PYSQLQQVFKQVGIVAVVGALSRNLEYLQHHEGSFVSIYDRPAVTLKDPI |
| SPX_MFS_117961287_2_cdna.pep | (SEQ ID NO. 8759) | ---------------------------------------------- |
| | | |
| SPX_MFS_126116193_plus_est_sti | (SEQ ID NO. 8766) | ---------------------------------------------- |
| fs_SPX_MFS_126116193_plus_est | (SEQ ID NO. 8765) | IDMINSPVDKLTRSTNFLRFLGQHALIVDEESPSTAGEEIEDQKYHFMS |
| SPX_MFS_118200525_cdna.pep | (SEQ ID NO. 8761) | IDMINSSVDKLTRSTNFLRFLGQHAMIVDEESPSTAGEEIEDQKYHFMS |
| SPX_MFS_118200525_2_pep | (SEQ ID NO. 8763) | ---------------------------------------------- |
| SPX_MFS_117961287_cdna.pep | (SEQ ID NO. 8757) | IDQVNHAVQKLTHATNFMQFLGQHALIVQEDAES-ESEDLVGDQSYHFMS |
| SPX_MFS_117961287_2_cdna.pep | (SEQ ID NO. 8759) | ---------------------------------------------- |

FIGURE 11 (continued)

```
SPX_MFS_126116193_plus_est_sti  (SEQ ID NO. 8766)  ------------------------------
fs_SPX_MFS_126116193_plus_est_  (SEQ ID NO. 8765)  LMLNLVNTFLYMVNTYIIVP----------
SPX_MFS_118200525_cdna.pep      (SEQ ID NO. 8761)  LMLNLVNTFLYMVNTYIIVPTADDYSVSLGAASTVCGVVIGSMTVAQIFS
SPX_MFS_118200525_2_pep         (SEQ ID NO. 8763)  ------------------------------
SPX_MFS_117961287_cdna.pep      (SEQ ID NO. 8757)  ------------------------------
SPX_MFS_117961287_2_cdna.pep    (SEQ ID NO. 8759)  LVLNLVNTFLYMVNTYIIVPTADDYAVSLGAAATVCGIIIGSMAVAQVFS SPX_MFS_126116193_plus_est_sti  (SEQ ID NO. 8766)  ------------------------MTIQ
fs_SPX_MFS_126116193_plus_est_  (SEQ ID NO. 8765)  ---------------------TADDYX
SPX_MFS_118200525_cdna.pep      (SEQ ID NO. 8761)  SIYFSAWSNKSYFKPLVFSSIVLFLGNICYAMAYDMKSLTVLIIGRLLCG
SPX_MFS_118200525_2_pep         (SEQ ID NO. 8763)  ---------------------
SPX_MFS_117961287_cdna.pep      (SEQ ID NO. 8757)  ---------------------
SPX_MFS_117961287_2_cdna.pep    (SEQ ID NO. 8759)  SVYFSAWSNKSYFKPLVFSSIMLFLGNLLYALAYDLNSLIVLLTGRLLCG ----MCR SPX_MFS_126116193_plus_est_sti  (SEQ ID NO. 8766)  MGSARAVNRRYISDCVPARIRMQASAGFVSASALGMACGPALAGLLQWKF
fs_SPX_MFS_126116193_plus_est_  (SEQ ID NO. 8765)  MGSARAVNRRYISDCVPARIRMQASAGFVSASALGMACGPALAGLLQWKF
SPX_MFS_118200525_cdna.pep      (SEQ ID NO. 8761)  MGSARAVNRRYISDCVPARIRMQASAGFVSASALGMACGPALAGLLQWKF
SPX_MFS_118200525_2_pep         (SEQ ID NO. 8763)  MGSARAVNRRYISDCVPARIRMQASAGFVSASALGMACGPALAGLLQWKF
SPX_MFS_117961287_cdna.pep      (SEQ ID NO. 8757)  LGSARAVNRRYISDCVPLKMRLQASAGFVSASALGMACGPALAGFLQIKF
SPX_MFS_117961287_2_cdna.pep    (SEQ ID NO. 8759)  LGSARAVNRRYISDCVPLKMRLQASAGFVSASALGMACGPALAGFLQIKF
                                                   :.************  : :***************************:**

SPX_MFS_126116193_plus_est_sti  (SEQ ID NO. 8766)  KIYMVTFNQSTLPGWVMAVAWLLYLIWLWVSFKEPNRATEVNEAPQNPAS
fs_SPX_MFS_126116193_plus_est_  (SEQ ID NO. 8765)  KIYMVTFNQSTLPGWVMAVAWLLYLIWLWVSFKEPNRATEVNEAPQNPAS
SPX_MFS_118200525_cdna.pep      (SEQ ID NO. 8761)  KVYMVTFNQSTLPGWVMAVAWLLYLIWLWFSFKEPNRATEVNEAPQNPAS
SPX_MFS_118200525_2_pep         (SEQ ID NO. 8763)  KVYMVTFNQSTLPGWVMAVAWLLYLIWLWFSFKEPNRATEVNEAPQNPAS
SPX_MFS_117961287_cdna.pep      (SEQ ID NO. 8757)  KIYSLSFNQSTLPGWVMCISWLIYLLWIMLTFKEPEHFTKTLVNEQPSES
SPX_MFS_117961287_2_cdna.pep    (SEQ ID NO. 8759)  KIYSLSFNQSTLPGWVMCISWLIYLLWIMLTFKEPEHFTKTLVNEQPSES
                                                   *:* ::************** :* **:****.:**** . **  .  *

SPX_MFS_126116193_plus_est_sti  (SEQ ID NO. 8766)  GQTVDIGQVENGLAQPLLMDSVDKQNEDEDEEVDESEEAADDSRKPATSI
fs_SPX_MFS_126116193_plus_est_  (SEQ ID NO. 8765)  GQTVDIGQVENGLAQPLLMDSVDKQNEDEDEEVDESEEAADDSRKPATSI
SPX_MFS_118200525_cdna.pep      (SEQ ID NO. 8761)  GQTVDIGRLENGIAQPLLKDSVDKQNEDEDE-VDDIEETADDSRKPATSI
SPX_MFS_118200525_2_pep         (SEQ ID NO. 8763)  GQTVDIGRLENGIAQPLLKDSVDKQNEDEDE-VDDIEETADDSRKPATSI
SPX_MFS_117961287_cdna.pep      (SEQ ID NO. 8757)  GRQGNS-NLEAGLAEPLLQG-IERRQDENSEVNDDTEVESESSHEPATSI
SPX_MFS_117961287_2_cdna.pep    (SEQ ID NO. 8759)  GRQGNS-NLEAGLAEPLLQG-IERRQDENSEVNDDTEVESESSHEPATSI
                                                   *:  . .:* :****       : . :*   .* ******
```

FIGURE 11 (continued)

| | | |
|---|---|---|
| SPX_MFS_126116193_plus_est_sti | (SEQ ID NO. 8766) | GSAYRLLTPSVKVQLLIYFMLKYAMEILLSESSVITNHYFSWNTSAVAIF |
| fs_SPX_MFS_126116193_plus_est_ | (SEQ ID NO. 8765) | GSAYRLLTPSVKVQLLIYFMLKYAMEILLSESSVITNHYFSWNTSAVAIF |
| SPX_MFS_118200525_cdna.pep | (SEQ ID NO. 8761) | GSAYRLLTPSVKVQLLIYFMLKYAMEILLSESSVITNHYFSWNTSAVAIF |
| SPX_MFS_118200525_2_pep | (SEQ ID NO. 8763) | GSAYRLLTPSVKVQLLIYFMLKYAMEILLSESSVITNHYFSWNTSAVAIF |
| SPX_MFS_117961287_cdna.pep | (SEQ ID NO. 8757) | ASAYRLLTPSVKAQLLIYFMLKYAMEILLSESSVVTTYYFSWSTSAVAIF |
| SPX_MFS_117961287_2_cdna.pep | (SEQ ID NO. 8759) | ASAYRLLTPSVKAQLLIYFMLKYAMEILLSESSVVTTYYFSWSTSAVAIF |
| | | .****..************** ::..*.***** |

| | | |
|---|---|---|
| SPX_MFS_126116193_plus_est_sti | (SEQ ID NO. 8766) | LAILGLTVLPVNAVVGTYISNMFEDRQLLMVSQITLLVGIIFSFKVTSTY |
| fs_SPX_MFS_126116193_plus_est_ | (SEQ ID NO. 8765) | LAILGLTVLPVNAVVGTYISNMFEDRQLLMVSQITLLVGIIFSFKVTSTY |
| SPX_MFS_118200525_cdna.pep | (SEQ ID NO. 8761) | LAILGLTVLPVNAVVGTYISNMFEDRQLLMVSQITLLVGIIFSFKVTSTY |
| SPX_MFS_118200525_2_pep | (SEQ ID NO. 8763) | LAILGLTVLPVNAVVGTYISNMFEDRQLLMVSQITLLVGIIFSFKVTSTY |
| SPX_MFS_117961287_cdna.pep | (SEQ ID NO. 8757) | LAILGLTVLPVNAIVGSYVTNLFEDRQILLASEVMVLIGIIMSFCFTPHY |
| SPX_MFS_117961287_2_cdna.pep | (SEQ ID NO. 8759) | LAILGLTVLPVNAIVGSYVTNLFEDRQILLASEVMVLIGIIMSFCFTPHY |
| | | ***********:.*::*:*****:::.*:*::**:* .*. * |

| | | |
|---|---|---|
| SPX_MFS_126116193_plus_est_sti | (SEQ ID NO. 8766) | SVVQYVVSALVTFVSAEVLEGVNLSLLSSVMSSRLSRGTYNGLLSTEAG |
| fs_SPX_MFS_126116193_plus_est_ | (SEQ ID NO. 8765) | SVVQYVVSALVTFVSAEVLEGVNLSLLSSVMSSRLSRGTYNGLLSTEAG |
| SPX_MFS_118200525_cdna.pep | (SEQ ID NO. 8761) | YVVQYVVSALVTFVSAEVLEGVNLSLLSSVMSSRLSRGTYNGLLSTEAG |
| SPX_MFS_118200525_2_pep | (SEQ ID NO. 8763) | YVVQYVVSALVTFVSAEVLEGVNLSLLSSVMSSRLSRGTYNGLLSTEAG |
| SPX_MFS_117961287_cdna.pep | (SEQ ID NO. 8757) | SIPQYVLSAFITFVFAEVLEGVNLSLLSRVMSSRLSRGTYNGLLSTEAG |
| SPX_MFS_117961287_2_cdna.pep | (SEQ ID NO. 8759) | SIPQYVLSAFITFVFAEVLEGVNLSLLSRVMSSRLSRGTYNGLLSTEAG |
| | | : :::: :**************************** |

| | | |
|---|---|---|
| SPX_MFS_126116193_plus_est_sti | (SEQ ID NO. 8766) | TLARVVADCTITAAGYLGVGKLLNVTLLPSLVICVASIACTFLTYNSLF |
| fs_SPX_MFS_126116193_plus_est_ | (SEQ ID NO. 8765) | TLARVVADCTITAAGYLGVGKLLNVTLLPSLVICVASIACTFLTYNSLF |
| SPX_MFS_118200525_cdna.pep | (SEQ ID NO. 8761) | TLARVVADCTITAAGYLGVGKLLNVTLLPSLVICVASIACTFLTYNSLF |
| SPX_MFS_118200525_2_pep | (SEQ ID NO. 8763) | TLARVVADCTITAAGYLGVGKLLNVTLLPSLVICVASIACTFLTYNSLF |
| SPX_MFS_117961287_cdna.pep | (SEQ ID NO. 8757) | TLARVVADATITAAGYLGTDLLLNVTLLPSLVICIVSIAAALYTYNNLY |
| SPX_MFS_117961287_2_cdna.pep | (SEQ ID NO. 8759) | TLARVVADATITAAGYLGTDLLLNVTLLPSLVICIVSIAAALYTYNNLY |
| | | ******.**** .:********:.*:: *.**.*: |

FIGURE 13 ctgcagcccactgctcctccacggcgtggatcttctccaacgcggcattcacgttcgcgcgtatgcgat
ggaggggaaactaggcggaagaaggcattggtggcggcattggatttctggacggcttcggaaaggagt
ggcgtgggaggtcaccgtgtggacgaacatgtggttgggctacgtggggtgggcacggaggtggacta
gtggtggaagacagcgagctcgtcggcgagggaggttggaactgggacgcggtagccgataccctgcgc
acggcccggtagcaagaaatggcaagggaaggatgcggcacacggtgaagtgatggaccgggtctgcac
atttatggcccccaggaagcaagggaacgacccccggcaaactcctaggcgagagaagcggtccagccac
aaccacccaaggaagaagacccggcctgagcagtaaaacaataccggaggaggaacacaagaaggtaga
gcaccaacacccaacttggtgatgctcgccaacaccaccatcgctctcatccaagaaaggtacgatcaa
gattaatcccttagattagtctaggaccctttacttcatcgaggttagattggattggccttctagagt
tttactaatggcattggagccaacctaagaaccctagattccctaatccaacaagttagagtcaagaat
gtctctcgacccataattaagaacccacatagggatttaaagaggtagaagaagagcagtaggggagcg
agtggtagccctaacccaaacacccagaattagcagaaaggggttcgagttaggtaaccctaacactaa
atccccaataactcagaggaaggagatggaccgtagagggactcaagttagattaaactaaccctaatt
cccaagttaaggaaaagatcactcggggaggggggttaggggtgttaaatcctaccccaatccccaaa
tcattagaaagggaaacaacatagaggaccttcagttaggtaaccctaacccttaatcccaaatcatca
aaaggaactgaggacaaccctaaattccaaccttccagaaccttacaaggggctcaggatggagatcca
aagccccaaagcacaggtcctgaacatcgagacaaattagggttttgaaccctaaatccttccccaaat
catataaagaaatgtaccaaggcggccggagagtgcaaattgtttttatagagacaactatcctttct
acgtgccactgtaactctattaaatctatttgtacagtatgttgtaaattccaatcatctcagaaaaca
tatttatagagagacgtctctcatttctagtcccctctataaatctcatttctaggaacagttacaatg
tgtttggtttgaggttaaagtgggatgagtcagggcgacaccgtctcctcattttttgggatcatgc
cgccatcaaaattactacggggtttatctcgcccctacgtgactctcatccaaatattattagaactat
ggtcgtcctatttatccctccatatatctaaccaaacacacccggccagccacctatacaaatcat
ttatttacagtaaggacgactggcctacacgagacaaggccgccgtctcttagatcttaggtgctgttt
ggttcacatatttataacgcaatgggtaactgataacgttaaatcatgtttgttttagtccaaccgtaa
tcagataccacactaaaaattgataccagcctattcaaatttgttaccgccagtaatcgagcgtaaact
attaccattaccatttgcgttacatttcttgaaccaaacaacaccttagttcgtagcagtggatcaaac
gccggtttcatccgattgctattccccaattataataaatctccatcgtggtcaacattaaaaaaaaaa
ctccgtcgaccctagtactgctactcgctagaattttattttgtcttctagacgagttactgatgtttg
cttgctggcccatctaatccgcaggagaattgaagaagcaagcgctgttgtcctgtcacacagctagct
cggtccctctatcattgttgaatggtttattcccggggaatatgccctcgctcctctggcatcatccgc
agcatatatcctccgtctcgtcttccacctcggATCAGGTAGGCGCGGCGCGGACCGCAACACGCCAGC
TTTCTTGCTCTTGTCTCTAAGCAGCAGCAGCTTCCTGTCTCTCCAGCCACCATTCCATTCTCGCTCCTT
GGTAATGAGGCTGGCTAGCCAGCTAATGCAGCTCCGAACCTGTTTTGTTGGTGGTCATTTAACCATGCA
TGCTTCGATCGATGGATTGGTGCATGCATGGATTATTGCATAGTGTGATGCATGTGGCGCATCAGTGCA
TGGTTAGATGACCATCAGCAAACATGTTCTTGAGGCATGCAAGTTCTCTAGCTACACATATCAGAGATC
GATCACCACTGCGGCGCCATGGCTACTTAATTGAAATGGAGGTTTGCATTTCTCCGAACCCGGATGTCG
TGATTCTGCTTCCGTTCTTGATCCAGGATCTTCCGGTCTTGTTCCCACCATTACTTTCCTTAGGAAACT
GGAATGGTTTCAACCTTAATTTGTTTATGTGTGTGTGCACATGCAGCGTGTGTTTCATATGGAGATCGG
TGCACTCACCTTGTAGCTTTAGCTTGCATCCCCTTCGCTAACAGAGAGTAAGATATCTTAGTCCTCTCG
CCATCTCTCTAAACATATACGTATCA Zm-miRMON18 (SEQ ID NO. 8800)

FIGURE 15
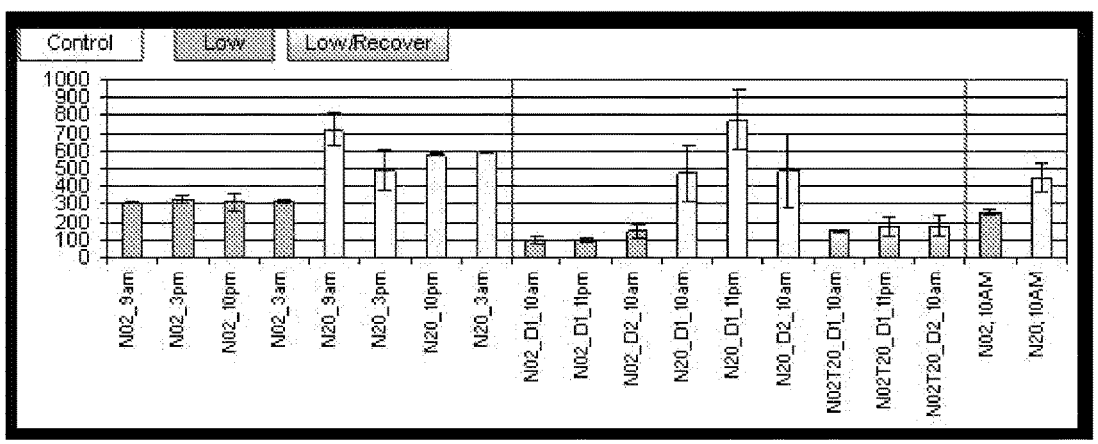
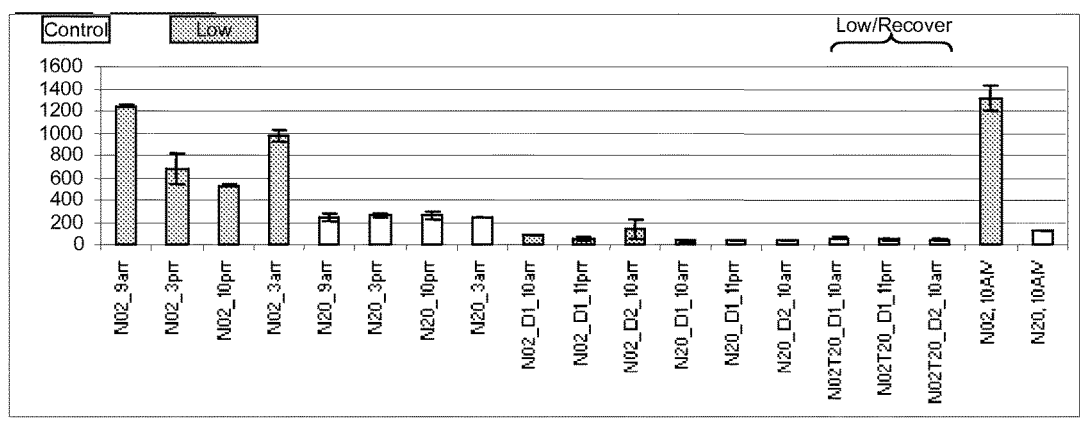

FIGURE 17
miRNA gene: MRT4577_22484C.8 (Hairpin length = 105) fold-back structure of SEQ ID NO. 8816
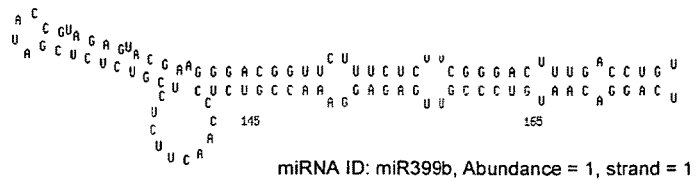
miRNA ID: miR399b, Abundance = 1, strand = 1
miRNA gene: MRT4577_22487C.6 (Hairpin length = 195) fold-back structure of SEQ ID NO. 8818
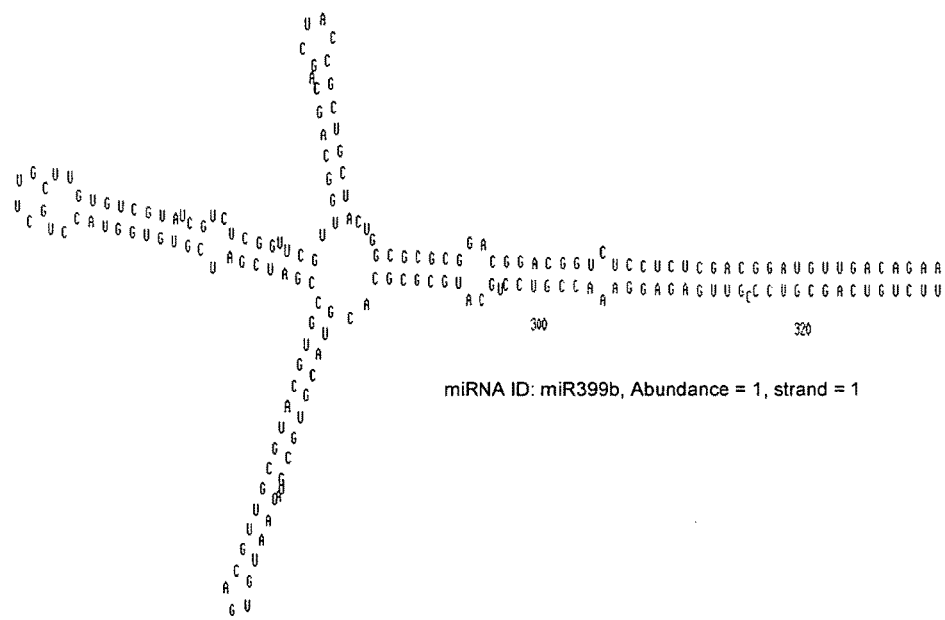
miRNA ID: miR399b, Abundance = 1, strand = 1
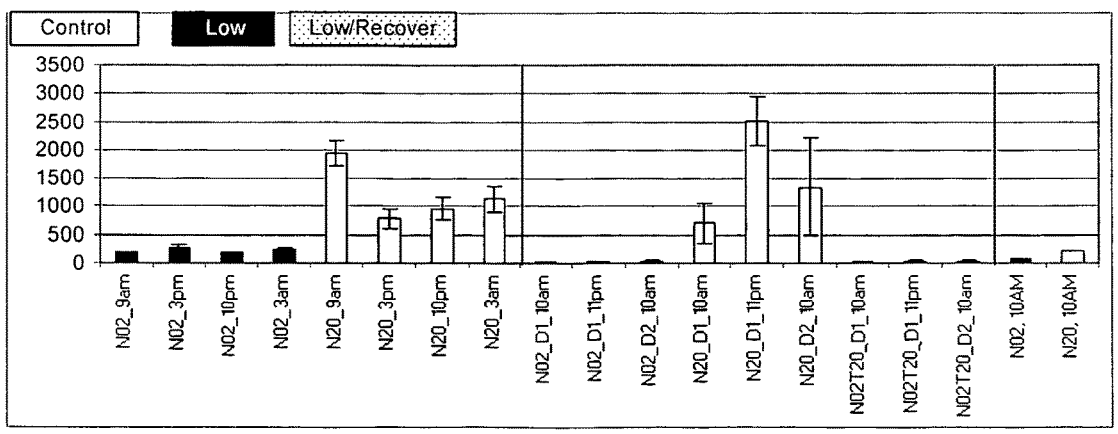
B

FIGURE 18

FIGURE 19
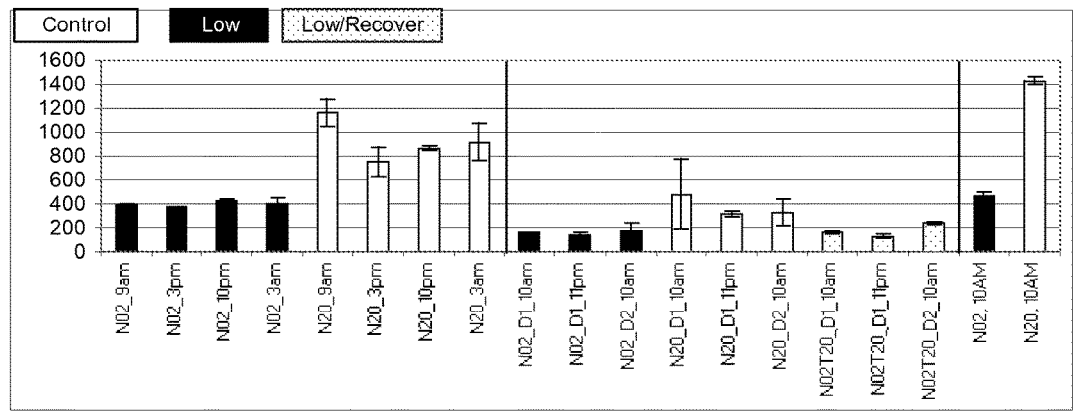
A
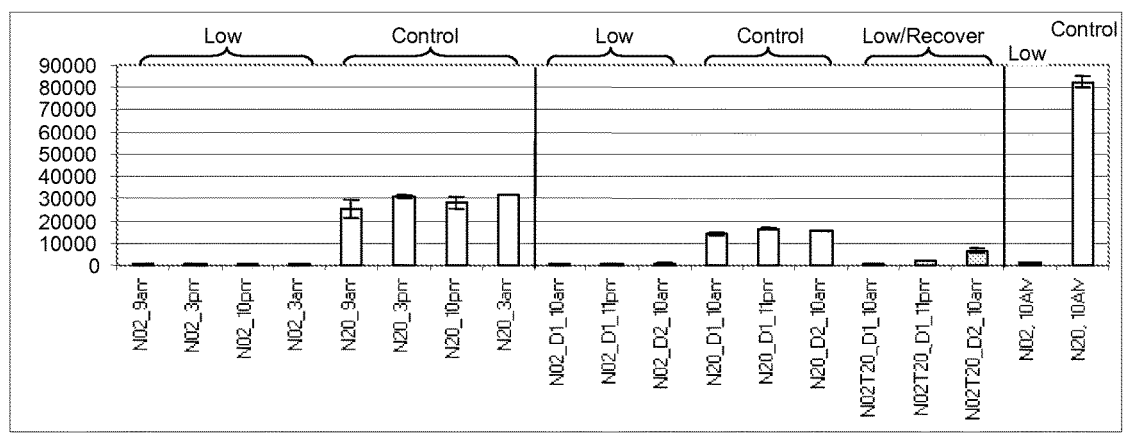
B
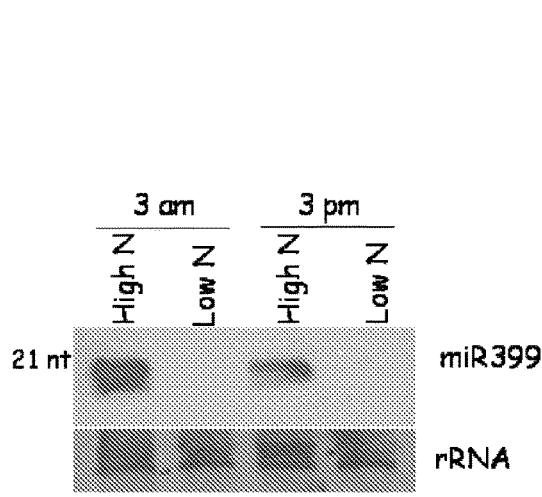 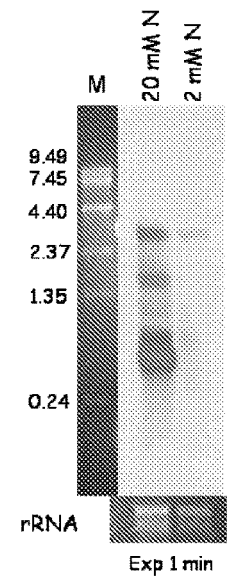
C                    D

FIGURE 20
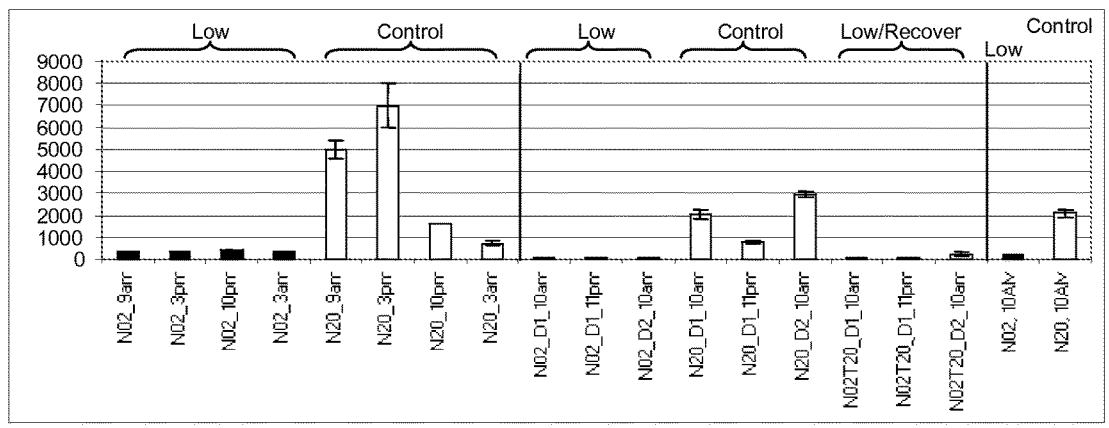
A
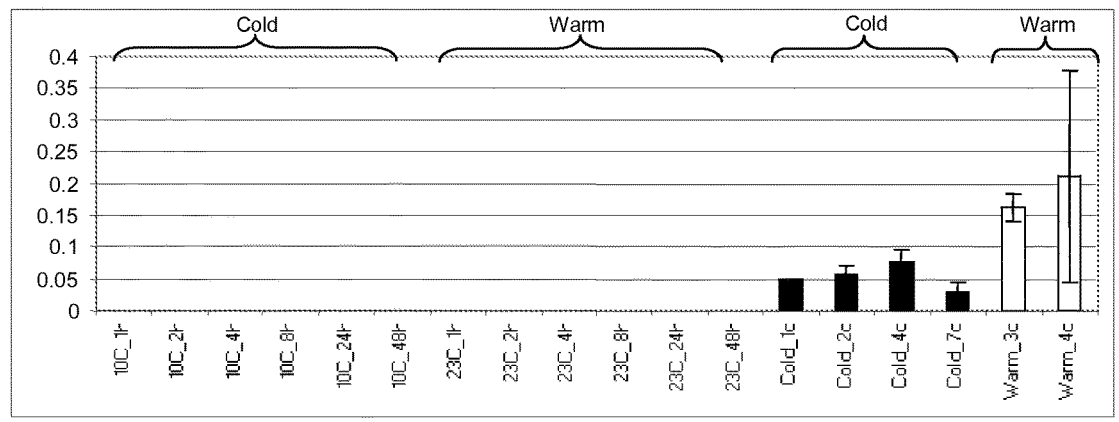
B
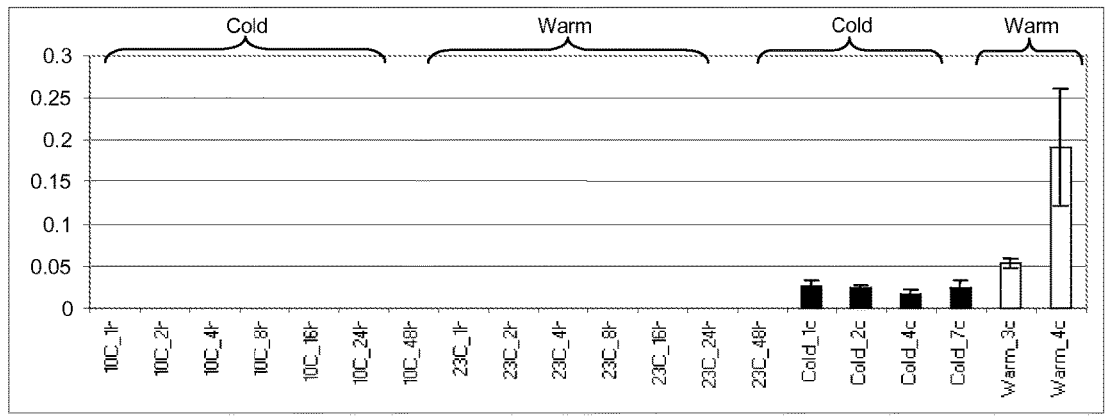
C

FIGURE 21
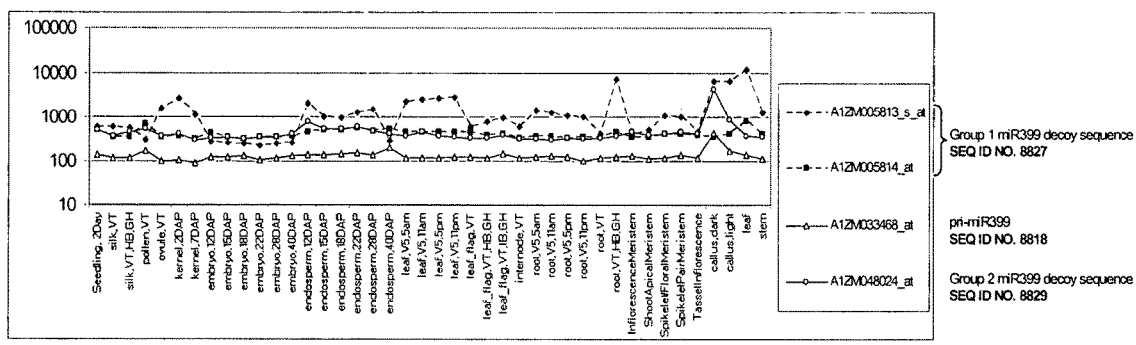
A
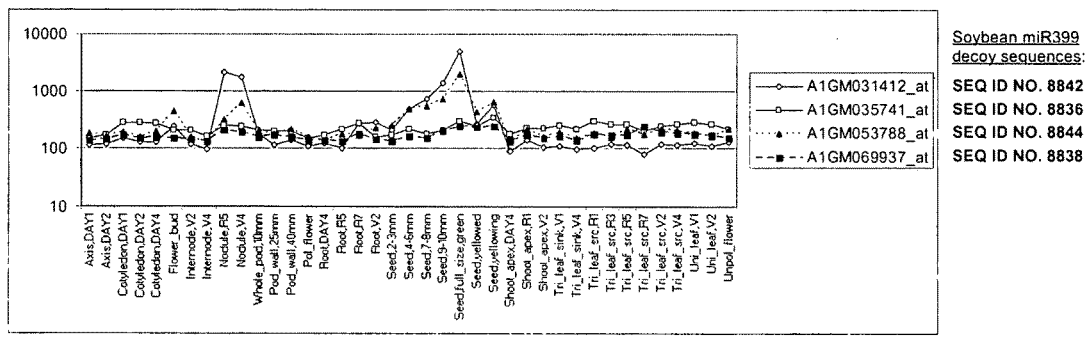
B

FIGURE 22
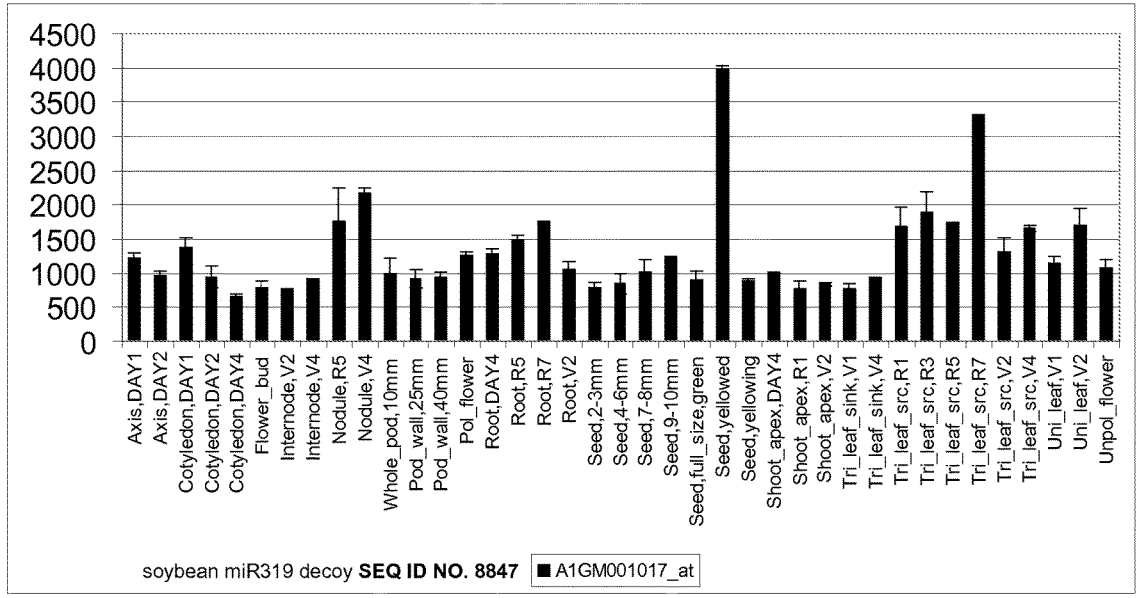
A
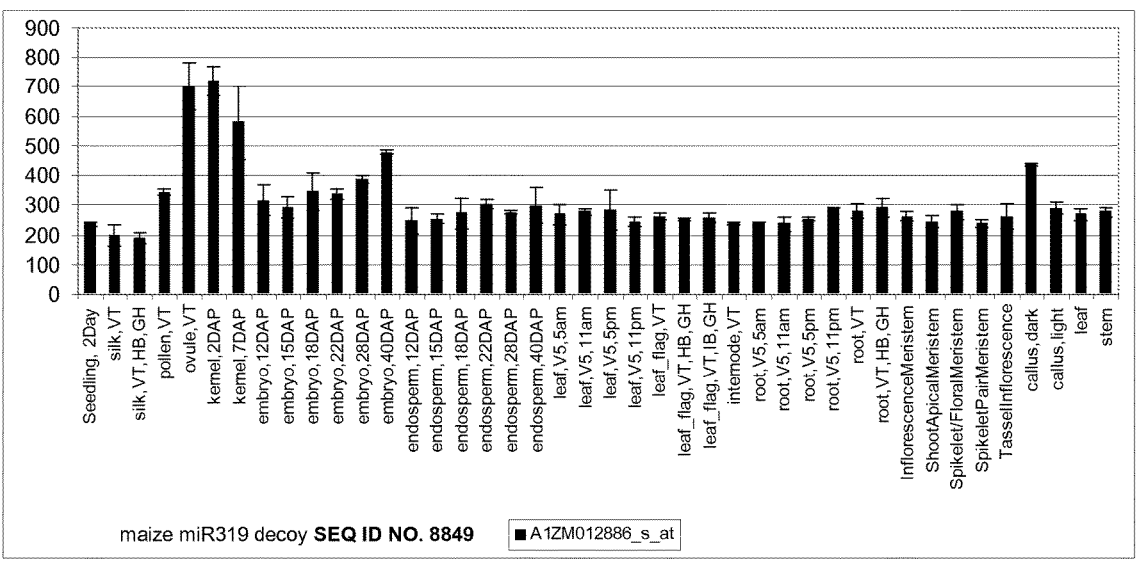
B

PLANT MICRORNAS AND METHODS OF USE THEREOF

CROSS-REFERENCE TO RELATED APPLICATIONS AND INCORPORATION OF SEQUENCE LISTINGS

This application is a continuation of U.S. patent application Ser. No. 11/974,469, filed on Oct. 12, 2007, which claims priority to U.S. Provisional Patent Application No. 60/851,187, filed on Oct. 12, 2006, U.S. Provisional Patent Application No. 60/908,826, filed Mar. 29, 2007, and U.S. Provisional Patent Application No. 60/969,195, filed Aug. 31, 2007, all of which are incorporated by reference in their entirety herein. A computer readable form of the Sequence Listing is filed with this application by electronic submission and is incorporated into this application by reference in its entirety. The Sequence Listing is contained in the file created on Dec. 9, 2014, having the file name P34154US04_SL.txt, and is 2,265,088 bytes in size (as measured in the MS-Windows® operating system).

FIELD OF THE INVENTION

This invention discloses novel microRNAs and microRNA precursors, recombinant DNA constructs including such novel miRNAs, miRNA precursors, and miRNA recognition sites corresponding to the miRNAs. Included are novel miRNA and miRNA precursors that exhibit abiotic-stress-responsive expression. Further provided are miRNA decoy sequences, non-natural transgenic plant cells, plants, and seeds containing in their genome a recombinant DNA construct of this invention, and methods of controlling gene expression using recombinant DNA constructs of this invention.

BACKGROUND OF THE INVENTION

Several cellular pathways involved in RNA-mediated gene suppression have been described, each distinguished by a characteristic pathway and specific components. See, for example, the reviews by Brodersen and Voinnet (2006), *Trends Genetics*, 22:268-280, and Tomari and Zamore (2005) *Genes & Dev.*, 19:517-529. The siRNA pathway involves the non-phased cleavage of a double-stranded RNA ("RNA duplex") to small interfering RNAs (siRNAs). The microRNA pathway involves microRNAs (miRNAs), non-protein coding RNAs generally of between about 19 to about 25 nucleotides (commonly about 20-24 nucleotides in plants) that guide cleavage in trans of target transcripts, negatively regulating the expression of genes involved in various regulation and development pathways. Plant miRNAs have been defined by a set of characteristics including a stem-loop precursor that is processed by DCL1 to a single specific ~21-nucleotide miRNA, expression of a single pair of miRNA and miRNA* species from the RNA duplex with two-nucleotide 3' overhangs, and silencing of specific targets in trans. See Bartel (2004) *Cell*, 116:281-297; Kim (2005) *Nature Rev. Mol. Cell Biol.*, 6:376-385; Jones-Rhoades et al. (2006) *Annu. Rev. Plant Biol.*, 57:19-53; Ambros et al. (2003) RNA, 9:277-279. In the trans-acting siRNA (ta-siRNA) pathway, miRNAs serve to guide in-phase processing of siRNA primary transcripts in a process that requires an RNA-dependent RNA polymerase for production of an RNA duplex; trans-acting siRNAs are defined by lack of secondary structure, an miRNA target site that initiates production of double-stranded RNA, requirements of DCL4 and an RNA-dependent RNA polymerase (RDR6), and production of multiple perfectly phased ~21-nucleotide small RNAs with perfectly matched duplexes with two-nucleotide 3' overhangs (see Allen et al. (2005) *Cell*, 121: 207-221).

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways (Bartel (2004) *Cell*, 116:281-297). In some cases, miRNAs serve to guide in-phase processing of siRNA primary transcripts (see Allen et al. (2005) *Cell*, 121:207-221).

Some microRNA genes (MIR genes) have been identified and made publicly available in a database ('miRBase", available on line at microrna.sanger.ac.uk/sequences). The applicants have disclosed novel MIR genes, mature miRNAs, and miRNA recognition sites in U.S. patent application Ser. No. 11/303,745, filed 15 Dec. 2005, which are incorporated by reference herein. Additional MIR genes and mature miRNAs are also described in U.S. Patent Application Publications 2005/0120415 and 2005/144669A1, which are incorporated by reference herein. MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) *Nature Rev. Mol. Cell Biol.*, 6:376-385. Transcription of MIR genes can be, at least in some cases, under promotional control of a MIR gene's own promoter. MIR gene transcription is probably generally mediated by RNA polymerase II (see, e.g., Aukerman. and Sakai (2003) *Plant Cell*, 15:2730-2741; Parizotto et al. (2004) *Genes Dev.*, 18:2237-2242), and therefore could be amenable to gene silencing approaches that have been used in other polymerase II-transcribed genes. The primary transcript (which can be polycistronic) is termed a "pri-miRNA", a miRNA precursor molecule that can be quite large (several kilobases) and contains one or more local double-stranded or "hairpin" regions as well as the usual 5' "cap" and polyadenylated tail of an mRNA. See, for example, FIG. 1 in Kim (2005) *Nature Rev. Mol. Cell Biol.*, 6:376-385.

In plant cells, microRNA precursor molecules are believed to be largely processed in the nucleus. The pri-miRNA is processed to a shorter miRNA precursor molecule that also includes a stem-loop or fold-back structure and is termed the "pre-miRNA". In plants, miRNAs and siRNAs are formed by distinct DICER-like (DCL) enzymes, and in *Arabidopsis* a nuclear DCL enzyme (DCL1) is believed to be required for mature miRNA formation; see, for example, Ambros et al. (2003) *RNA*, 9:277-279, and Xie et al. (2004) *PLoS Biol.*, 2:642-652. Additional reviews on microRNA biogenesis and function are found, for example, in Bartel (2004) *Cell*, 116:281-297; Murchison and Hannon (2004) *Curr. Opin. Cell Biol.*, 16:223-229; and Dugas and Bartel (2004) *Curr. Opin. Plant Biol.*, 7:512-520. MicroRNAs can thus be described in terms of RNA (e.g., RNA sequence of a mature miRNA or a miRNA precursor RNA molecule), or in terms of DNA (e.g., DNA sequence corresponding to a mature miRNA RNA sequence or DNA sequence encoding a MIR gene or fragment of a MIR gene or a miRNA precursor).

MIR gene families are estimated to account for 1% of at least some genomes and capable of influencing or regulating expression of about a third of all genes (see, e.g., Tomari et al. (2005) *Curr. Biol.*, 15:R61-64; G. Tang (2005) *Trends Biochem. Sci.*, 30:106-14; Kim (2005) *Nature Rev. Mol. Cell Biol.*, 6:376-385). Because miRNAs are important regulatory elements in eukaryotes, including animals and plants, transgenic suppression of miRNAs could, for example, lead to the understanding of important biological processes or allow the manipulation of certain pathways (e.g., regulation of cellular differentiation, proliferation, and apoptosis) useful, for example, in biotechnological applications. See, for example, O'Donnell et al. (2005) *Nature*, 435:839-843; Cai et al. (2005) *Proc. Natl. Acad. Sci. USA*, 102:5570-5575; Morris and McManus (2005) *Sci. STKE*, pe41 (stke-.sciencemag.org/cgi/reprint/sigtrans;2005/297/pe41.pdf). MicroRNA (MIR) genes have identifying characteristics, including conservation among plant species, a stable foldback structure, and processing of a specific miRNA/miRNA* duplex by Dicer-like enzymes (Ambros et al. (2003) *RNA*, 9:277-279). These characteristics have been used to identify miRNAs and their corresponding genes in plants (Xie et al. (2005) *Plant Physiol.*, 138:2145-2154; Jones-Rhoades and Bartel (2004) *Mol. Cell*, 14:787-799; Reinhart et al. (2002) *Genes Dev.*, 16:1616-1626; Sunkar and Zhu (2004) *Plant Cell*, 16:2001-2019). Publicly available microRNA genes are catalogued at miRBase (Griffiths-Jones et al. (2003) *Nucleic Acids Res.*, 31:439-441).

MiRNAs are expressed in very specific cell types in *Arabidopsis* (see, for example, Kidner and Martienssen (2004) *Nature*, 428:81-84, Millar and Gubler (2005) *Plant Cell*, 17:705-721). Suppression can be limited to a side, edge, or other division between cell types, and is believed to be required for proper cell type patterning and specification (see, e.g., Palatnik et al. (2003) *Nature*, 425:257-263). Suppression of a GFP reporter gene containing an endogenous miR171 recognition site was found to limit expression to specific cells in transgenic *Arabidopsis* (Parizotto et al. (2004) *Genes Dev.*, 18:2237-2242). Recognition sites of miRNAs have been validated in all regions of an mRNA, including the 5' untranslated region, coding region, and 3' untranslated region, indicating that the position of the miRNA target site relative to the coding sequence may not necessarily affect suppression (see, e.g., Jones-Rhoades and Bartel (2004). *Mol. Cell*, 14:787-799, Rhoades et al. (2002) *Cell*, 110:513-520, Allen et al. (2004) *Nat. Genet.*, 36:1282-1290, Sunkar and Zhu (2004) *Plant Cell*, 16:2001-2019).

The mature miRNAs disclosed herein are processed from MIR genes that generally belong to canonical families conserved across distantly related plant species. These MIR genes and their encoded mature miRNAs are also useful, e.g., for modifying developmental pathways, e.g., by affecting cell differentiation or morphogenesis (see, for example, Palatnik et al. (2003) *Nature*, 425:257-263; Mallory et al. (2004) *Curr. Biol.*, 14:1035-1046), to serve as sequence sources for engineered (non-naturally occurring) miRNAs that are designed to silence sequences other than the transcripts targeted by the naturally occurring miRNA sequence (see, for example, Parizotto et al. (2004) *Genes Dev.*, 18:2237-2242; also see U.S. Patent Application Publications 2004/3411A1 and 2005/0120415, incorporated by reference herein), and to stabilize dsRNA. A MIR gene itself (or its native 5' or 3' untranslated regions, or its native promoter or other elements involved in its transcription) is useful as a target gene for gene suppression (e.g., by methods of the present invention), where suppression of the miRNA encoded by the MIR gene is desired. Promoters of MIR genes can have very specific expression patterns (e.g., cell-specific, tissue-specific, or temporally specific), and thus are useful in recombinant constructs to induce such specific transcription of a DNA sequence to which they are operably linked.

This invention provides novel microRNAs and microRNA precursors identified from plants (including crop plants such as maize, rice, and soybean), as well as recombinant DNA constructs including such novel miRNAs, miRNA precursors, miRNA recognition sites, miRNA decoy sequences, and miRNA promoters corresponding to the miRNAs. Also disclosed and claimed are non-natural transgenic plant cells, plants, and seeds containing in their genome a recombinant DNA construct of this invention. Further provided are methods of gene suppression using recombinant DNA constructs of this invention and methods of providing transgenic plants with desired phenotypes, especially transgenic plants exhibiting increased yield (relative to non-transgenic plants) under abiotic stress conditions including drought, nutrient deficiency, and cold or heat stress.

SUMMARY OF THE INVENTION

In one aspect, this invention provides a recombinant DNA construct including at least one transcribable DNA element for modulating the expression of at least one target gene, wherein the at least one transcribable DNA element is selected from the group consisting of: (a) a DNA element that transcribes to an miRNA precursor with the fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the miRNA precursor includes a contiguous segment of at least 90% of the nucleotides of the maize, rice, or soybean miRNA precursor sequence; (b) a DNA element that transcribes to an engineered miRNA precursor derived from the fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the engineered miRNA precursor includes a modified mature miRNA; (c) a DNA element that is located within or adjacent to a transgene transcription unit and that is transcribed to RNA including a miRNA recognition site recognized by a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or by a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819; and (d) a DNA element for suppressing expression of an endogenous miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819.

Another aspect of this invention provides a non-natural transgenic plant cell including any of the recombinant DNA constructs of this invention. Further provided is a non-natural transgenic plant containing the non-natural transgenic plant cell of this invention, including plants of any developmental stage, and including a regenerated plant prepared from the non-natural transgenic plant cells disclosed herein, or a progeny plant (which can be an inbred or hybrid progeny plant) of the regenerated plant, or seed of such a non-natural transgenic plant. Also provided and claimed is a transgenic seed having in its genome any of the recombinant DNA constructs provided by this invention.

In a further aspect, this invention provides a method of effecting gene suppression, including the steps of: (a) providing a non-natural transgenic plant including a regenerated plant prepared from a non-natural transgenic plant cell of this invention, or a progeny plant of the regenerated plant; and (b) transcribing the recombinant DNA construct in the non-natural transgenic plant; wherein the transcribing produces RNA that is capable of suppressing the at least one target gene in the non-natural transgenic plant, and whereby the at least one target gene is suppressed relative to its expression in the absence of transcription of the recombinant DNA construct.

In yet another aspect, this invention provides a method of concurrently effecting gene suppression of at least one target gene and gene expression of at least one gene of interest, including the steps of: (a) providing a non-natural transgenic plant including a regenerated plant prepared from the non-natural transgenic plant cell of this invention, or a progeny plant of the regenerated plant, wherein the recombinant DNA construct further includes a gene expression element for expressing the at least one gene of interest; and (b) transcribing the recombinant DNA construct in the non-natural transgenic plant, wherein, when the recombinant DNA construct is transcribed in the non-natural transgenic plant, transcribed RNA that is capable of suppressing the at least one target gene and transcribed RNA encoding the at least one gene of interest are produced, whereby the at least one target gene is suppressed relative to its expression in the absence of transcription of the recombinant DNA construct and the at least one gene of interest is concurrently expressed.

In a further aspect, this invention provides a recombinant DNA construct including a synthetic miRNA-unresponsive transgene sequence that is unresponsive to a given mature miRNA, wherein the synthetic miRNA-unresponsive transgene sequence is: (a) derived from a natively miRNA-responsive sequence by deletion or modification of all native miRNA recognition sites recognized by the given mature miRNA within the natively miRNA-responsive sequence, and (b) is not recognized by the given mature miRNA.

In another aspect, this invention provides a recombinant DNA construct including a promoter of a miRNA that exhibits an expression pattern that is responsive to abiotic stress, for example, a promoter of a miRNA that exhibits an expression pattern characterized by suppression of the miRNA under nutrient stress, a promoter of a miRNA that exhibits an expression pattern characterized by suppression of the miRNA under water stress, or a promoter of a miRNA that exhibits an expression pattern characterized by suppression of the miRNA under temperature stress.

In still a further aspect, this invention provides a recombinant DNA construct that is transcribed to an RNA transcript including at least one miRNA decoy sequence that is recognized and bound by an endogenous mature miRNA but not cleaved; included are transgenic plant cells, plants, and seeds having this construct in their genome, and methods of use of this construct. Related aspects of this invention include recombinant DNA constructs and methods for suppression of endogenous miRNA decoy sequences. Also disclosed are analogous decoy sequences that recognize and bind to other small RNAs (ta-siRNAs, nat-siRNAs, and phased small RNAs) but are not cleaved, thus reducing the activity of the small RNA.

Other specific embodiments of the invention are disclosed in the following detailed description.

BRIEF DESCRIPTION OF THE DRAWINGS

FIGS. 2 and 3 depict non-limiting examples of DNA elements for suppressing expression of a target gene, e.g., an endogenous miRNA, as described in Example 3.

FIG. 7 depicts the fold-back structures of miRNA precursors from different plants, as described in Example 6. Panel A depicts the fold-back structure of a miRMON18 precursor from maize (SEQ ID NO. 3936), Panel B depicts the fold-back structure of a miRMON18 precursor from rice (SEQ ID NO. 1763), and Panel C depicts the fold-back structure of a miR827 precursor from *Arabidopsis thaliana* (SEQ ID NO. 8743). Panel D depicts a comparison of miR827 (SEQ ID NO. 8744) and miRMON18 (SEQ ID NO. 393, SEQ ID NO. 3227, or SEQ ID NO. 8742), with numbered arrows indicating positions 1, 10, and 21 of the mature miRNA; the nucleotide at position 10 is also underlined.

FIG. 8 depicts expression patterns of miRMON18 as determined by Northern blots of the mature miRMON18 21-mer (Panel A) and transcription profiling of the miRMON18 precursor (Panel B), as described in Example 6.

FIG. 9 depicts analysis of expression of the maize miRMON18 precursor (SEQ ID NO. 3936) in maize tissues from plants grown under water-deficient (drought) (Panel A), cold (Panel B), and nitrogen-deficient conditions (Panel C), as described in Example 6.

FIG. 10 depicts results of northern blots of small RNAs in maize (*Zea mays* var. LH244), showing enhanced miRMON18 expression in maize endosperm and kernel, and strong miRMON18 suppression in leaves induced by nitrogen deficiency (Panel A), and strong miRMON18 expression in leaf tissue under phosphate-sufficient conditions and miRMON18 suppression under phosphate-deficient conditions (Panel B), as described in Example 6.

FIG. 11 depicts a multiple sequence alignment of novel maize miRMON18 target genes containing the maize SPX domain (indicated by underlined sequence, where present) and the maize MFS domain (indicated by sequence in bold text), as described in Example 7.

FIG. 13 depicts a miRMON18 genomic sequence (SEQ ID NO. 8800), as described in Example 8. This shows the miRMON18 transcript in upper-case text at nucleotides 2173-2788 a miRMON18 promoter element in lower-case text at nucleotides 211-2172, a leader element in lower-case text at nucleotides 2173-2308, a canonical TATA box (ending 25 nucleotides upstream of the transcription start site) in underlined lower-case text at nucleotides 2144-2147, the mature miRMON18 as underlined upper-case text at nucleotides 2419-2439, and the miRMON18* as underlined upper-case text at nucleotides 2322-2341.

FIG. 15 depicts the inverse correlation between the miRMON18 precursor (Panel A) and a miRMON18 target (Panel B), as described in Example 9. Panel B shows that the maize sequence MRT4577_36529C (SEQ ID NO. 8788), exhibited higher expression levels under nitrogen-deficient conditions than under nitrogen-sufficient conditions, i.e., an expression pattern opposite to that of the miRMON18 precursor as shown in Panel A.

FIG. 17 depicts the fold-back structures of maize miR399 precursors (Panel A) and results of transcriptional profiling experiments (Panel B), which demonstrate that the Zm-miR399 pri-miRNA is suppressed under nitrogen-deficient conditions (black bars) and is expressed under nitrogen-sufficient conditions (white bars), as described in Example 11.

FIG. 18 depicts alignment of the maize cDNA sequences of the miR399 decoy sequences, with the consensus sequence given as SEQ ID NO. 8834, and reveals at least two groups of genes containing miR399 decoy sequences, as described in Example 11.

FIG. 19 depicts experiments comparing expression of maize miR399 decoy sequences and miR399 precursors as described in Example 11. Panel A shows a transcription profile of group 1 miR399 decoy gene MRT4577_47862C.7 (SEQ ID NO. 8827) and Panel B shows a transcription profile of group 2 miR399 decoy gene MRT4577_36567C.8 (SEQ ID NO. 8829), indicating that these miR399 decoy sequences are down-regulated by nitrogen deficiency. These results were verified by northern blots measuring expression of the mature miR399 (Panel C) and of the miR399 decoy sequence MRT4577_47862C.7 (SEQ ID NO. 8827) (Panel D).

FIG. 20 depicts transcription profiling experiments comparing expression of maize endogenous miR399 decoy cDNA sequences and the corresponding maize miR399 precursors under different temperature conditions, as described in Example 11. Group 2 miR399 decoy gene MRT4577_36567C.8 (SEQ ID NO. 8829) exhibited at least ten-fold or greater higher expression during nitrogen-sufficient conditions in maize leaf, especially during daylight hours (Panel A). This same gene exhibited at least a two-fold down-regulation in root (Panel B) and in shoot (Panel C) after extended exposure to cold.

FIG. 21 depicts expression of endogenous miR399 decoy cDNA sequences in different tissues in both maize and soybean, as described in Example 11. Panel A depicts expression levels of the group 1 maize miR399 decoy sequence SEQ ID NO. 8827 (MRT4577_47862C, represented by probes A1ZMO05814_at and A1ZMO05813_s_at), and the group 2 maize miR399 decoy sequence SEQ ID NO. 8829 (MRT4577_36567C, represented by probe A1ZM048024_at), as well as of the maize pri-miR399 sequence SEQ ID NO. 8818 (MRT4577_22487C.6 represented by probe A1ZM033468_at). Panel B depicts expression levels of the soybean miR399 decoy sequences SEQ ID NO. 8842 (MRT3847_217257C.2, represented by probe A1GM031412_at), SEQ ID NO. 8844 (MRT3847_236871C.2, represented by probe A1GM053788_at), SEQ ID NO. 8836 (MRT3847_238967C.1, represented by probe A1GM035741_at), and SEQ ID NO. 8838 (MRT3847_241832C.1, represented by probe A1GM069937_at).

FIG. 22 depicts transcription profiling data in various soybean tissues of the soybean endogenous miR319 decoy SEQ ID NO. 8847 (MRT3847_41831C.6, represented by probe A1GM001017 at) (Panel A) and transcription profiling data in various maize tissues of the maize endogenous miR319 decoy SEQ ID NO. 8849 (MRT4577_577703C.1, represented by probe A1ZMO12886_s_at) (Panel B), as described in Example 11.

DETAILED DESCRIPTION OF THE INVENTION

Figure 1:
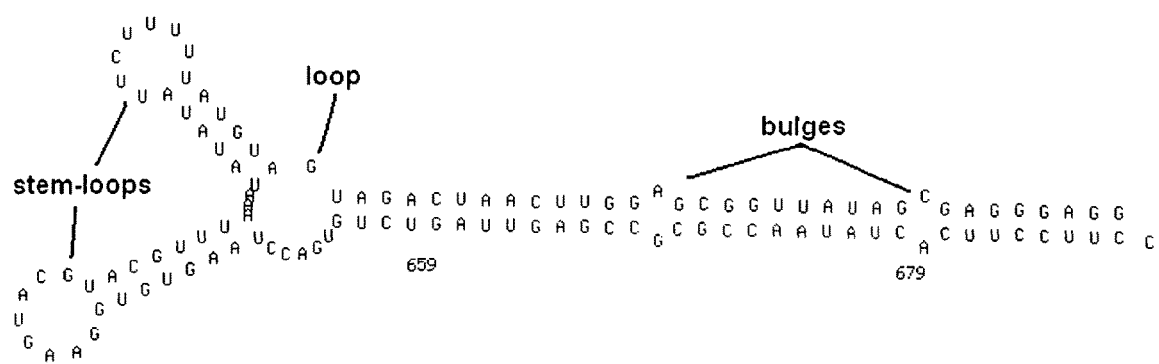
FIG. 1 depicts a non-limiting example of a fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, more specifically, the fold-back structure of the miRNA precursor sequence having SEQ ID NO. 1136, which includes two short stem-loops, a loop, and two bulges. The miRNA precursor is processed in planta to a mature miRNA (in this particular example, to the mature miRNA having SEQ ID NO. 32).

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

Recombinant DNA Constructs

This invention provides a recombinant DNA construct including at least one transcribable DNA element for modulating the expression of at least one target gene, wherein the at least one transcribable DNA element is selected from the group consisting of: (a) a DNA element that transcribes to an miRNA precursor with the fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the miRNA precursor includes a contiguous segment of at least 90% of the nucleotides of the maize, rice, or soybean miRNA precursor sequence; (b) a DNA element that transcribes to an engineered miRNA precursor derived from the fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the engineered miRNA precursor includes a modified mature miRNA; (c) a DNA element that is located within or adjacent to a transgene transcription unit and that is transcribed to RNA including a miRNA recognition site recognized by a mature miRNA selected from a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or by a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819; and (d) a DNA element for suppressing expression of an endogenous miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819. Target genes, the expression of which can be modulated by use of a recombinant DNA construct of this invention, are described under the heading "Target Genes". Embodiments and utilities of the at least one transcribable DNA element are described below.

(A) Expression of a Native miRNA under Non-native Conditions.

In one embodiment of the recombinant DNA construct, the at least one transcribable DNA element for modulating the expression of at least one target gene includes a DNA element that transcribes to an miRNA precursor with the fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the miRNA precursor includes a contiguous segment of at least 90% of the nucleotides of the maize, rice, or soybean miRNA precursor sequence. In preferred embodiments, the at least one target gene is an endogenous gene of a plant, and expression of the recombinant DNA construct in the plant results in suppression of the at least one target gene. By "miRNA precursor" is meant a transcribed RNA that is larger than a mature miRNA processed from the miRNA precursor, and that typically can be predicted to form a fold-back structure containing non-perfectly complementary double-stranded RNA regions. See Bartel (2004) *Cell*, 116:281-297; Kim (2005) *Nature Rev. Mol. Cell Biol.*, 6:376-385; Jones-Rhoades et al. (2006) *Annu. Rev. Plant Biol.*, 57:19-53; Ambros et al. (2003) *RNA*, 9:277-279. Examples of microRNA precursors include, but are not limited to, the primary miRNA transcript (pri-miRNA) as well as the pre-miRNA that is natively derived from a pri-miRNA; miRNA precursors also include non-natural RNA sequences that are predicted to form a fold-back structure containing non-perfectly complementary double-stranded RNA regions and are processed in vivo, generally by one or more cleavage steps, to a mature miRNA. By "miRNA precursor sequence" is meant an RNA sequence that includes at least the nucleotides of the miRNA precursor but that may include additional nucleotides (such that the miRNA precursor includes a contiguous segment of at least 90% of the nucleotides of the maize, rice, or soybean miRNA precursor sequence). Each miRNA precursor itself forms a fold-back structure that is identical or near-identical to the fold-back structure that is formed by at least part of the corresponding miRNA precursor sequence.

In these embodiments, the miRNA precursor need not include all of the nucleotides contained in a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, but preferably includes a contiguous segment of at least 80%, or at least 85%, or at least 90%, or at least 95%, or at least 97%, or at least 98%, or at least 99% of the nucleotides of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819.

In preferred embodiments, the at least one target gene is an endogenous gene of a plant, and thus expression of the recombinant DNA construct in the plant results in suppression of the at least one target gene. Transcription of the recombinant DNA construct in a transgenic plant cell modulates the expression of any gene (endogenous genes or transgenes) that contains a sequence ("miRNA recognition site") that is substantially complementary to and recognized by the mature miRNA encoded by the miRNA precursor. Generally, transcription of the recombinant DNA construct results in suppression of an endogenous gene that contains a miRNA recognition site that is recognized by the mature miRNA encoded by the miRNA precursor. In preferred embodiments, the recombinant DNA construct further includes a promoter other than the native promoter of the miRNA sequence. This permits expression of the mature miRNA under spatial or temporal or inducible conditions under which it would not natively be expressed. For example, the recombinant DNA construct can be designed to include a constitutive promoter and thus constitutively express a mature miRNA that is natively expressed (i.e., when expressed in the form of the endogenous miRNA precursor under the control of the native promoter) only under dark conditions. Promoters that are useful with this recombinant DNA construct are described under the heading "Promoters".

In one non-limiting example, the recombinant DNA construct includes a transcribable DNA element for modulating the expression of at least one target gene, wherein the at least one transcribable DNA element includes a DNA element that transcribes to an miRNA precursor that is a contiguous segment consisting of about 90% of the nucleotides of the maize miRNA precursor sequence having SEQ ID NO. 1136, and that is predicted to have a fold-back structure that is substantially the same (that is, having areas of double-stranded RNA stems and single-stranded loops or bulges in the same or approximately the same location) as the fold-back structure of the miRNA precursor sequence having SEQ ID NO. 1136. The fold-back structure of the miRNA precursor sequence having SEQ ID NO. 1136 includes about 118 nucleotides, with two short stem-loops projecting from a loop at the closed end of the fold-back structure, and two small bulges within the main double-stranded "stem" of the fold-back structure (FIG. 1). The mature miRNA processed in planta from a miRNA precursor that is a contiguous segment consisting of about 90% of the nucleotides of the maize miRNA precursor sequence having SEQ ID NO. 1136 is preferably identical to that encoded by the fold-back structure of the miRNA precursor sequence having SEQ ID NO. 1136, i.e., the mature miRNA having SEQ ID NO. 32. Transcription of this recombinant DNA construct preferably results in suppression of at least one endogenous gene that contains a miRNA recognition site that is recognized by the mature miRNA having SEQ ID NO. 32. While the maize miRNA precursor sequence having SEQ ID NO. 1136 is natively expressed in kernel tissue but not in leaf (see Table 2), the recombinant DNA construct can further include a promoter other than the native promoter of the miRNA s precursor sequence having SEQ ID NO. 1136, e.g., a constitutive promoter, to allow transcription of a mature miRNA having SEQ ID NO. 32 in tissues in addition to kernel tissue.

(B) Expression of an Engineered Mature miRNA.

In another embodiment of the recombinant DNA construct, the at least one transcribable DNA element for modulating the expression of at least one target gene includes a DNA element that transcribes to an engineered miRNA precursor derived from the fold-back structure of a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the engineered miRNA precursor includes a modified mature miRNA. In preferred embodiments, the at least one target gene is an endogenous gene of a plant or an endogenous gene of a pest or pathogen of the plant, and expression of the recombinant DNA construct in the plant results in suppression of the at least one target gene. By "engineered" is meant that nucleotides are changed (substituted, deleted, or added) in a native miRNA precursor sequence such a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, thereby resulting in an engineered miRNA precursor having substantially the same the fold-back structure as the native miRNA precursor sequence, but wherein the mature miRNA that is processed from the engineered miRNA precursor has a modified sequence (i.e., different from that of the native mature miRNA) that is designed to suppress a target gene different from the target genes natively suppressed by the native miRNA precursor sequence.

One general, non-limiting method for determining nucleotide changes in the native miRNA precursor sequence to produce the engineered miRNA precursor, useful in making a recombinant DNA construct of this invention, includes the steps:

(a) Selecting a unique target sequence of at least 18 nucleotides specific to the target gene, e.g. by using sequence alignment tools such as BLAST (see, for example, Altschul et al. (1990) *J. Mol. Biol.*, 215:403-410; Altschul et al. (1997) *Nucleic Acids Res.*, 25:3389-3402), for example, of both maize cDNA and genomic DNA databases, to identify target transcript orthologues and any potential matches to unrelated genes, thereby avoiding unintentional silencing of non-target sequences.

(b) Analyzing the target gene for undesirable sequences (e.g., matches to sequences from non-target species, especially animals), and score each potential 19-mer segment for GC content, Reynolds score (see Reynolds et al. (2004) *Nature Biotechnol.*, 22:326-330), and functional asymmetry characterized by a negative difference in free energy ("ΔΔG") (see Khvorova et al. (2003) *Cell*, 115:209-216). Preferably 19-mers are selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Preferably multiple (3 or more) 19-mers are selected for testing.

(c) Determining the reverse complement of the selected 19-mers to use in making a modified mature miRNA; the additional nucleotide at position 20 is preferably matched to the selected target sequence, and the nucleotide at position 21 is preferably chosen to be unpaired to prevent spreading of silencing on the target transcript.

(d) Testing the engineered miRNA precursor, for example, in an *Agrobacterium* mediated transient *Nicotiana benthamiana* assay for modified mature miRNA expression and target repression.

and (e) Cloning the most effective engineered miRNA precursor into a construct for stable transformation of maize (see the sections under the headings "Making and Using Recombinant DNA Constructs" and "Making and Using Non-natural Transgenic plant Cells and Non-natural Transgenic Plants").

(C) Expression of a Transgene and a miRNA Recognition Site.

In another embodiment of the recombinant DNA construct, the recombinant DNA construct further includes a transgene transcription unit, wherein the at least one transcribable DNA element for modulating the expression of at least one target gene includes a DNA element that is located within or adjacent to the transgene transcription unit and that is transcribed to RNA including a miRNA recognition site recognized by a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, and the at least one target gene includes the transgene encoded by the transgene transcription unit, and wherein expression of the recombinant DNA construct in a plant results in expression of the transgene in cells of the plant wherein the mature miRNA is not natively expressed. Preferred embodiments of miRNA recognition sites are those predicted to be recognized by at least one mature miRNA selected from a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or by at least one mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819. Prediction of a recognition site is achieved using methods known in the art, such as sequence complementarity rules as described by Zhang (2005) *Nucleic Acids Res.*, 33:W701-704 and by Rhoades et al. (2002) *Cell*, 110:513-520.

Prediction of a miRNA recognition site permits identification and validation of endogenous genes regulated by miRNAs from a natively expressed miRNA precursor; this is useful, e.g., to eliminate or modify a miRNA recognition site in an endogenous gene in order to decouple expression of that gene from regulation by the endogenous miRNA that natively regulates expression of the gene. For example, the number of mispairs involving bases at positions 2 to 13 (in a miRNA recognition site having contiguous 21 nucleotides) can be increased to prevent recognition and cleavage by the miRNA.

These recombinant DNA constructs are particularly useful for in planta expression of the transgene under a specific spatial, temporal, or inducible pattern without the need of a promoter having that specific expression pattern. These recombinant DNA constructs allow, for example, the restricted expression of a gene transcribed by a constitutive promoter or a promoter with expression beyond the desired cell or tissue type(s). Restricted expression may be spatially or temporally restricted, e.g., restricted to specific tissues or cell types or files, or to specific developmental, reproductive, growth, or seasonal stages. Where a miRNA is expressed under particular conditions (e.g., under biotic stress such as crowding, allelopathic interactions or pest or pathogen infestation, or abiotic stress such as heat or cold stress, drought stress, nutrient stress, heavy metal or salt stress), the corresponding miRNA recognition site can be used for conditionally specific suppression, i.e., to suppress a transgene under the particular condition. In a non-limiting example, a recombinant DNA construct of this invention that encodes (a) a transgene under the control of a constitutive promoter and (b) a miRNA recognition site recognized by a mature miRNA that is specifically expressed only under conditions of water stress, can be used for expression of the transgene in a plant under non-water-stress conditions. In another non-limiting example, a recombinant DNA construct of this invention that encodes (a) a transgene expressing an insecticidal protein under the control of a promoter specifically inducible by wounding, and (b) a miRNA recognition site recognized by a mature miRNA that is expressed in tissues other than root, can be used for limited expression of the insecticidal protein in plant roots under conditions when the plant is wounded by an insect pest.

The transgene transcription unit includes at least a transgene, and optionally additional sequence such as, but not limited to, a promoter, a promoter enhancer, a terminator, messenger RNA stabilizing or destabilizing sequence (see, e.g., Newman et al. (1993) *Plant Cell*, 5:701-714; Green (1993) *Plant Physiol.*, 102:1065-1070; and Ohme-Takagi et al. (1993) *Proc. Natl. Acad. Sci. USA*, 90:11811-11815), sequence for localization or transport of the transgene transcript to a specific locale (e.g., mitochondrion, plastid, nucleolus, peroxisome, endoplasmic reticulum, etc.), or other sequence related to the desired processing of the transgene. The transgene encoded by the transgene transcription unit can include any one or more genes of interest, including coding sequence, non-coding sequence, or both. Genes of interest can include any of the genes listed under "Target Genes", preferred examples of which include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

(D) Suppression of an Endogenous or Native miRNA.

In yet another embodiment of the recombinant DNA construct, the at least one transcribable DNA element for modulating the expression of at least one target gene includes a DNA element for suppressing expression of an endogenous miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819. In preferred embodiments, the at least one target gene is an endogenous gene of a plant, and expression of the endogenous gene is suppressed in cells of the plant where native expression of the endogenous miRNA occurs, and thus expression of the recombinant DNA construct in the cells results in expression of the endogenous gene in the cells.

The DNA element for suppressing expression includes at least one of:

(a) DNA that includes at least one anti-sense DNA segment that is anti-sense to at least one segment of the target gene;

(b) DNA that includes multiple copies of at least one anti-sense DNA segment that is anti-sense to at least one segment of the target gene;

(c) DNA that includes at least one sense DNA segment that is at least one segment of the target gene;

(d) DNA that includes multiple copies of at least one sense DNA segment that is at least one segment of the target gene;

(e) DNA that transcribes to RNA for suppressing the target gene by forming double-stranded RNA and includes at least one anti-sense DNA segment that is anti-sense to at least one segment of the target gene and at least one sense DNA segment that is at least one segment of the target gene;

(f) DNA that transcribes to RNA for suppressing the target gene by forming a single double-stranded RNA and includes multiple serial anti-sense DNA segments that are anti-sense to at least one segment of the target gene and multiple serial sense DNA segments that are at least one segment of the target gene;

(g) DNA that transcribes to RNA for suppressing the target gene by forming multiple double strands of RNA and includes multiple anti-sense DNA segments that are anti-sense to at least one segment of the target gene and multiple sense DNA segments that are at least one segment of the target gene, and wherein the multiple anti-sense DNA segments and the multiple sense DNA segments are arranged in a series of inverted repeats;

(h) DNA that includes nucleotides derived from a plant miRNA;

(i) DNA that includes nucleotides of a siRNA;

(j) DNA that transcribes to an RNA aptamer capable of binding to a ligand; and (k) DNA that transcribes to an RNA aptamer capable of binding to a ligand, and DNA that transcribes to regulatory RNA capable of regulating expression of the target gene, wherein the regulation is dependent on the conformation of the regulatory RNA, and the conformation of the regulatory RNA is allosterically affected by the binding state of the RNA aptamer.

Figure 3:
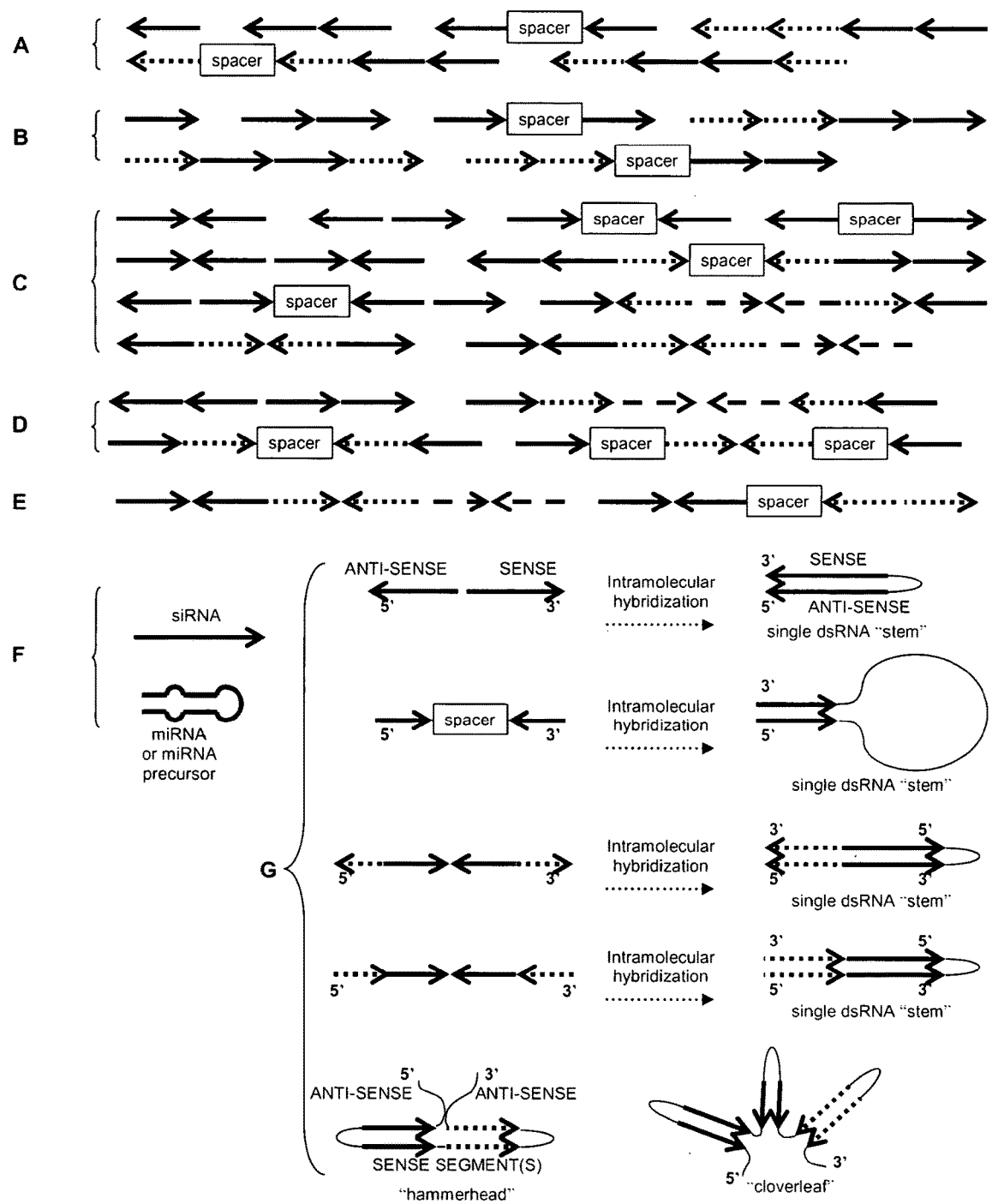

DNA elements for suppressing expression are described further in Example 3 and depicted in FIGS. 2 and 3.

In some embodiments, the recombinant DNA construct includes DNA designed to be transcribed to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity. In one example, the spacer is transcribed to a stabilizing loop that links the first and second series of contiguous RNA segments (see, for example, Di Giusto and King (2004) *J. Biol. Chem.*, 279:46483-46489). In another example, the recombinant DNA construct includes DNA that transcribes to RNA including an RNA aptamer (e.g., an aptamer that binds to a cell-specific ligand) that allows cell- or tissue-specific targetting of the recombinant RNA duplex.

The recombinant DNA construct is made by commonly used techniques, such as those described under the heading "Making and Using Recombinant DNA Constructs" and illustrated in the working Examples. The recombinant DNA construct is particularly useful for making non-natural transgenic plant cells, non-natural transgenic plants, and transgenic seeds as discussed below under "Transgenic Plant Cells and Transgenic Plants".

The effects of a miRNA on its target gene can be controlled by alternative methods described in detail below under "MicroRNA Decoy Sequences".

Target Genes

The recombinant DNA construct of this invention can be designed to suppress any target gene or genes. The target gene can be translatable (coding) sequence, or can be non-coding sequence (such as non-coding regulatory sequence), or both, and can include at least one gene selected from the group consisting of a eukaryotic target gene, a non-eukaryotic target gene, a microRNA precursor DNA sequence, and a microRNA promoter. The target gene can be native (endogenous) to the cell (e.g., a cell of a plant or animal) in which the recombinant DNA construct is transcribed, or can be native to a pest or pathogen of the plant or animal in which the recombinant DNA construct is transcribed. The target gene can be an exogenous gene, such as a transgene in a plant. A target gene can be a native gene targeted for suppression, with or without concurrent expression of an exogenous transgene, for example, by including a gene expression element in the recombinant DNA construct, or in a separate recombinant DNA construct. For example, it can be desirable to replace a native gene with an exogenous transgene homologue.

The target gene can include a single gene or part of a single gene that is targeted for suppression, or can include, for example, multiple consecutive segments of a target gene, multiple non-consecutive segments of a target gene, multiple alleles of a target gene, or multiple target genes from one or more species. A target gene can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans.

In one embodiment, the target gene is exogenous to the plant in which the recombinant DNA construct is to be transcribed, but endogenous to a pest or pathogen (e.g., viruses, bacteria, fungi, oomycetes, and invertebrates such as insects, nematodes, and molluscs) of the plant. The target gene can include multiple target genes, or multiple segments of one or more genes. In one preferred embodiment, the target gene or genes is a gene or genes of an invertebrate pest or pathogen of the plant. These embodiments are particularly useful in providing non-natural transgenic plants having resistance to one or more plant pests or pathogens, for example, resistance to a nematode such as soybean cyst nematode or root knot nematode or to a pest insect.

The target gene can be translatable (coding) sequence, or can be non-coding sequence (such as non-coding regulatory sequence), or both. Non-limiting examples of a target gene include non-translatable (non-coding) sequence, such as, but not limited to, 5' untranslated regions, promoters, enhancers, or other non-coding transcriptional regions, 3' untranslated regions, terminators, and introns. Target genes include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) *Nucleic Acids Res.*, 29:189-193; Gottesman (2005) *Trends Genet.*, 21:399-404; Griffiths-Jones et al. (2005) *Nucleic Acids Res.*, 33:121-124). One specific example of a target gene includes a microRNA recognition site (that is, the site on an RNA strand to which a mature miRNA binds and induces cleavage). Another specific example of a target gene includes a microRNA precursor sequence native to a pest or pathogen of the non-natural transgenic plant, that is, the primary transcript encoding a microRNA, or the RNA intermediates processed from this primary transcript (e.g., a nuclear-limited pri-miRNA or a pre-miRNA which can be exported from the nucleus into the cytoplasm). See, for example, Lee et al. (2002) *EMBO Journal*, 21:4663-4670; Reinhart et al. (2002) *Genes & Dev.*, 16:161611626; Lund et al. (2004) *Science*, 303:95-98; and Millar and Waterhouse (2005) *Funct. Integr. Genomics*, 5:129-135. Target genes can also include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

In many preferred embodiments, the target gene is an essential gene of a plant pest or pathogen. Essential genes include genes that are required for development of the pest or pathogen to a fertile reproductive adult. Essential genes include genes that, when silenced or suppressed, result in the death of the organism (as an adult or at any developmental stage, including gametes) or in the organism's inability to successfully reproduce (e. g., sterility in a male or female parent or lethality to the zygote, embryo, or larva). A description of nematode essential genes is found, e. g., in Kemphues, K. "Essential Genes" (Dec. 24, 2005), WormBook, ed. The *C. elegans* Research Community, WormBook, doi/10.1895/wormbook.1.57.1, available on line at wormbook.org. Non-limiting examples of nematode essential genes include major sperm protein, RNA polymerase II, and chitin synthase (see, e. g., U. S. Patent Application Publication US20040098761 A1); additional soybean cyst nematode essential genes are provided in U. S. patent application Ser. No. 11/360,355, filed 23 Feb. 2006, incorporated by reference herein. A description of insect genes is publicly available at the *Drosophila genome* database (available on line at flybase.bio.indiana.edu/). The majority of predicted *Drosophila* genes have been analyzed for function by a cell culture-based RNA interference screen, resulting in 438 essential genes being identified; see Boutros et al. (2004) *Science*, 303:832-835, and supporting material available on line at sciencemag.org/cgi/content/full/303/5659/832/DC1. A description of bacterial and fungal essential genes is provided in the Database of Essential Genes ("DEG", available on line at tubic.tju.edu.cn/deg/); see Zhang et al. (2004) *Nucleic Acids Res.*, 32:D271-D272.

Plant pest invertebrates include, but are not limited to, pest nematodes, pest molluscs (slugs and snails), and pest insects. Plant pathogens of interest include fungi, oomycetes, bacteria (e. g., the bacteria that cause leaf spotting, fireblight, crown gall, and bacterial wilt), mollicutes, and viruses (e. g., the viruses that cause mosaics, vein banding, flecking, spotting, or abnormal growth). See also G. N. Agrios, "Plant Pathology" (Fourth Edition), Academic Press, San Diego, 1997, 635 pp., for descriptions of fungi, bacteria, mollicutes (including mycoplasmas and spiroplasmas), viruses, nematodes, parasitic higher plants, and flagellate protozoans, all of which are plant pests or pathogens of interest. See also the continually updated compilation of plant pests and pathogens and the diseases caused by such on the American Phytopathological Society's "Common Names of Plant Diseases", compiled by the Committee on Standardization of Common Names for Plant Diseases of The American Phytopathological Society, 1978-2005, available online at apsnet.org/online/common/top.asp.

Non-limiting examples of fungal plant pathogens of particular interest include, e.g., the fungi that cause powdery mildew, rust, leaf spot and blight, damping-off, root rot, crown rot, cotton boll rot, stem canker, twig canker, vascular wilt, smut, or mold, including, but not limited to, *Fusarium* spp., *Phakospora* spp., *Rhizoctonia* spp., *Aspergillus* spp., *Gibberella* spp., *Pyricularia* spp., and *Alternaria* spp. Specific examples of fungal plant pathogens include *Phakospora pachirhizi* (Asian soybean rust), *Puccinia sorghi* (corn common rust), *Puccinia polysora* (corn Southern rust), *Fusarium oxysporum* and other *Fusarium* spp., *Alternaria* spp., *Penicillium* spp., *Rhizoctonia solani, Exserohilum turcicum* (Northern corn leaf blight), *Bipolaris maydis* (Southern corn leaf blight), *Ustilago maydis* (corn smut), *Fusarium graminearum* (*Gibberella zeae*), *Fusarium verticilliodes* (*Gibberella moniliformis*), *F. proliferatum* (*G. fujikuroi* var. *intermedia*), *F. subglutinans* (*G. subglutinans*), *Diplodia maydis, Sporisorium holci-sorghi, Colletotrichum graminicola, Setosphaeria turcica, Aureobasidium zeae, Sclerotinia sclerotiorum*, and the numerous fungal species provided in Tables 4 and 5 of U.S. Pat. No. 6,194,636, which is incorporated in its entirety by reference herein. Non-limiting examples of plant pathogens include pathogens previously classified as fungi but more recently classified as oomycetes. Specific examples of oomycete plant pathogens of particular interest include members of the genus *Pythium* (e.g., *Pythium aphanidermatum*) and *Phytophthora* (e.g., *Phytophthora infestans, Phytophthora sojae,*) and organisms that cause downy mildew (e.g., *Peronospora farinosa*).

Non-limiting examples of bacterial pathogens include the mycoplasmas that cause yellows disease and spiroplasmas such as *Spiroplasma kunkelii*, which causes corn stunt, eubacteria such as *Pseudomonas avenae, Pseudomonas andropogonis, Erwinia stewartii, Pseudomonas syringae* pv. *syringae, Xylella fastidiosa*, and the numerous bacterial species listed in Table 3 of U.S. Pat. No. 6,194,636, which is incorporated in its entirety by reference herein.

Non-limiting examples of viral plant pathogens of particular interest include maize dwarf mosaic virus (MDMV), sugarcane mosaic virus (SCMV, formerly MDMV strain B), wheat streak mosaic virus (WSMV), maize chlorotic dwarf virus (MCDV), barley yellow dwarf virus (BYDV), banana bunchy top virus (BBTV), and the numerous viruses listed in Table 2 of U.S. Pat. No. 6,194,636, which is incorporated in its entirety by reference herein.

Non-limiting examples of invertebrate pests include cyst nematodes *Heterodera* spp. especially soybean cyst nematode *Heterodera glycines*, root knot nematodes *Meloidogyne* spp., lance nematodes *Hoplolaimus* spp., stunt nematodes *Tylenchorhynchus* spp., spiral nematodes *Helicotylenchus* spp., lesion nematodes *Pratylenchus* spp., ring nematodes *Criconema* spp., foliar nematodes *Aphelenchus* spp. or *Aphelenchoides* spp., corn rootworms, *Lygus* spp., aphids and similar sap-sucking insects such as phylloxera (*Daktulosphaira vitifoliae*), corn borers, cutworms, armyworms, leafhoppers, Japanese beetles, grasshoppers, and other pest coleopterans, dipterans, and lepidopterans. Specific examples of invertebrate pests include pests capable of infesting the root systems of crop plants, e.g., northern corn rootworm (*Diabrotica barberi*), southern corn rootworm (*Diabrotica undecimpunctata*), Western corn rootworm (*Diabrotica virgifera*), corn root aphid (*Anuraphis maidiradicis*), black cutworm (*Agrotis ipsilon*), glassy cutworm (*Crymodes devastator*), dingy cutworm (*Feltia ducens*), claybacked cutworm (*Agrotis gladiaria*), wireworm (*Melanotus* spp., *Aeolus mellillus*), wheat wireworm (*Aeolus mancus*), sand wireworm (*Horistonotus uhlerii*), maize billbug (*Sphenophorus maidis*), timothy billbug (*Sphenophorus zeae*), bluegrass billbug (*Sphenophorus parvulus*), southern corn billbug (*Sphenophorus callosus*), white grubs (*Phyllophaga* spp.), seedcorn maggot (*Delia platura*), grape colaspis (*Colaspis brunnea*), seedcorn beetle (*Stenolophus lecontei*), and slender seedcorn beetle (*Clivinia impressifrons*), as well as the parasitic nematodes listed in Table 6 of U.S. Pat. No. 6,194,636, which is incorporated in its entirety by reference herein.

Invertebrate pests of particular interest, especially in but not limited to southern hemisphere regions (including South and Central America) include aphids, corn rootworms, *spodoptera*, noctuideae, potato beetle, *Lygus* spp., any hemipteran, homopteran, or heteropteran, any lepidopteran, any coleopteran, nematodes, cutworms, earworms, armyworms, borers, leaf rollers, and others. Arthropod pests specifically encompassed by this invention include various cutworm species including cutworm (*Agrotis repleta*), black cutworm (*Agrotis ipsilon*), cutworm (*Anicla ignicans*), granulate cutworm (*Feltia subterranea*),"gusano aspero" (*Agrotis malefida*); Mediterranean flour moth (*Anagasta kuehniella*), square-necked grain beetle (*Cathartus quadricollis*), flea beetle (*Chaetocnema* spp), rice moth (*Corcyra cephalonica*), corn rootworm or "vaquita de San Antonio" (*Diabotica speciosa*), sugarcane borer (*Diatraea saccharalis*), lesser cornstalk borer (*Elasmopalpus lignosellus*), brown stink bug (*Euschistus* spp.), corn earworm (*Helicoverpa zea*), flat grain beetle (*Laemophloeus minutus*), grass looper moth (*Mocis latipes*), sawtoothed grain beetle (*Oryzaephilus surinamensis*), meal moth (*Pyralis farinalis*), Indian meal moth (*Plodia interpunctella*), corn leaf aphid (*Rhopalosiphum maidis*), brown burrowing bug or "chinche subterranea" (*Scaptocoris castanea*), greenbug (*Schizaphis graminum*), grain weevil (*Sitophilus zeamais*), Angoumois grain moth (*Sitotroga cerealella*), fall armyworm (*Spodoptera frugiperda*), cadelle beetle (*Tenebroides mauritanicus*), two-spotted spider mite (*Tetranychus urticae*), red flour beetle (*Triboleum castaneum*), cotton leafworm (*Alabama argillacea*), boll weevil (*Anthonomus grandis*), cotton aphid (*Aphis gossypii*), sweet potato whitefly (*Bemisia tabaci*), various *thrips* species (*Frankliniella* spp.), cotton earworm (*Helicoverpa zea*), "oruga bolillera" (e.g., *Helicoverpa geletopoeon*), tobacco budworm (*Heliothis virescens*), stinkbug (*Nezara viridula*), pink bollworm (*Pectinophora gossypiella*), beet armyworm (*Spodoptera exigua*), spider mites (*Tetranychus* spp.), onion thrips (*Thrips tabaci*), greenhouse whitefly (*Trialeurodes vaporarium*), velvetbean caterpillar (*Anticarsia gemmatalis*), spotted maize beetle or "astilo moteado" (*Astylus atromaculatus*),"oruga de la alfalfa" (*Colias lesbia*),"chinche macron" or "chinche de los cuernos" (*Dichelops furcatus*),"alquiche chico" (*Edessa miditabunda*), blister beetles (*Epicauta* spp.), "barrenador del brote" (*Epinotia aporema*),"oruga verde del yuyo colorado" (*Loxostege bifidalis*), rootknot nematodes (*Meloidogyne* spp.), "oruga cuarteadora" (*Mocis repanda*), southern green stink bug (*Nezara viridula*), "chinche de la alfalfa" (*Piezodorus guildinii*), green cloverworm (*Plathypena scabra*), soybean looper (*Pseudoplusia includens*), looper moth "isoca medidora del girasol" (*Rachiplusia nu*), yellow woolybear (*Spilosoma virginica*), yellowstriped armyworm (*Spodoptera ornithogalli*), various root weevils (family Curculionidae), various wireworms (family Elateridae), and various white grubs (family Scarabaeidae). Nematode pests specifically encompassed by this invention include nematode pests of maize (*Belonolaimus* spp., *Trichodorus* spp., *Longidorus* spp., *Dolichodorus* spp., *Anguina* spp., *Pratylenchus* spp., *Meloidogyne* spp., *Heterodera* spp.), soybean (*Heterodera glycines, Meloidogyne* spp., *Belonolaimus* spp.), bananas (*Radopholus similis, Meloidogyne* spp., *Helicotylenchus* spp.), sugarcane (*Heterodera sacchari, Pratylenchus* spp., *Meloidogyne* spp.), oranges (*Tylenchulus* spp., *Radopholus* spp., *Belonolaimus* spp., *Pratylenchus* spp., *Xiphinema* spp.), coffee (*Meloidogyne* spp., *Pratylenchus* spp.), coconut palm (*Bursaphelenchus* spp.), tomatoes (*Meloidogyne* spp., *Belonolaimus* spp., *Nacobbus* spp.), grapes (*Meloidogyne* spp., *Xiphinema* spp., *Tylenchulus* spp., *Criconemella* spp.), lemon and lime (*Tylenchulus* spp., *Radopholus* spp., *Belonolaimus* spp., *Pratylenchus* spp., *Xiphinema* spp.), cacao (*Meloidogyne* spp., *Rotylenchulus reniformis*), pineapple (*Meloidogyne* spp., *Pratylenchus* spp., *Rotylenchulus reniformis*), papaya (*Meloidogyne* spp., *Rotylenchulus reniformis*), grapefruit (*Tylenchulus* spp., *Radopholus* spp. *Belonolaimus* spp., *Pratylenchus* spp., *Xiphinema* spp., and broad beans (*Meloidogyne* spp.).

Target genes from pests can include invertebrate genes for major sperm protein, alpha tubulin, beta tubulin, vacuolar ATPase, glyceraldehyde-3-phosphate dehydrogenase, RNA polymerase II, chitin synthase, cytochromes, miRNAs, miRNA precursor molecules, miRNA promoters, as well as other genes such as those disclosed in U.S. Patent Application Publication 2006/0021087 A1, PCT Patent Application PCT/US05/11816, and in Table II of U.S. Patent Application Publication 2004/0098761 A1, which are incorporated by reference herein. Target genes from pathogens can include genes for viral translation initiation factors, viral replicases, miRNAs, miRNA precursor molecules, fungal tubulin, fungal vacuolar ATPase, fungal chitin synthase, fungal MAP kinases, fungal Pacl Tyr/Thr phosphatase, enzymes involved in nutrient transport (e.g., amino acid transporters or sugar transporters), enzymes involved in fungal cell wall biosynthesis, cutinases, melanin biosynthetic enzymes, polygalacturonases, pectinases, pectin lyases, cellulases, proteases, genes that interact with plant avirulence genes, and other genes involved in invasion and replication of the pathogen in the infected plant. Thus, a target gene need not be endogenous to the plant in which the recombinant DNA construct is transcribed. A recombinant DNA construct of this invention can be transcribed in a plant and used to suppress a gene of a pathogen or pest that may infest the plant.

Specific, non-limiting examples of suitable target genes also include amino acid catabolic genes (such as, but not limited to, the maize LKR/SDH gene encoding lysineketoglutarate reductase (LKR) and saccharopine dehydrogenase (SDH), and its homologues), maize zein genes, genes involved in fatty acid synthesis (e.g., plant microsomal fatty acid desaturases and plant acyl-ACP thioesterases, such as, but not limited to, those disclosed in U.S. Pat. Nos. 6,426, 448, 6,372,965, and 6,872,872), genes involved in multistep biosynthesis pathways, where it may be of interest to regulate the level of one or more intermediates, such as genes encoding enzymes for polyhydroxyalkanoate biosynthesis (see, for example, U.S. Pat. No. 5,750,848); and genes encoding cell-cycle control proteins, such as proteins with cyclin-dependent kinase (CDK) inhibitor-like activity (see, for example, genes disclosed in International Patent Application Publication Number WO 05007829A2). Target genes can include genes encoding undesirable proteins (e.g., allergens or toxins) or the enzymes for the biosynthesis of undesirable compounds (e.g., undesirable flavor or odor components). Thus, one embodiment of the invention is a non-natural transgenic plant or tissue of such a plant that is improved by the suppression of allergenic proteins or toxins, e.g., a peanut, soybean, or wheat kernel with decreased allergenicity. Target genes can include genes involved in fruit ripening, such as polygalacturonase. Target genes can include genes where expression is preferably limited to a particular cell or tissue or developmental stage, or where expression is preferably transient, that is to say, where constitutive or general suppression, or suppression that spreads through many tissues, is not necessarily desired. Thus, other examples of suitable target genes include genes encoding proteins that, when expressed in transgenic plants, make the transgenic plants resistant to pests or pathogens (see, for example, genes for cholesterol oxidase as disclosed in U.S. Pat. No. 5,763,245); genes where expression is pest- or pathogen-induced; and genes which can induce or restore fertility (see, for example, the barstar/barnase genes described in U.S. Pat. No. 6,759,575); all the patents cited in this paragraph are incorporated by reference in their entirety herein.

The recombinant DNA construct can be designed to be more specifically suppress the target gene, for example, by designing the recombinant DNA construct to encode a mature miRNA to include regions substantially non-identical (or non-complementary) to a non-target gene sequence. Non-target genes can include any gene not intended to be silenced or suppressed, either in a plant containing the recombinant DNA construct or in organisms that may come into contact with the recombinant DNA construct. A non-target gene sequence can include any sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, domestic or wild mammals, and even humans).

In one embodiment, the target gene is a gene endogenous to a given species, such as a given plant (such as, but not limited to, agriculturally or commercially important plants, including monocots and dicots), and the non-target gene can be, e.g., a gene of a non-target species, such as another plant species or a gene of a virus, fungus, bacterium, invertebrate, or vertebrate, even a human. One non-limiting example is where the recombinant DNA construct is designed to suppress a target gene that is a gene endogenous to a single species (e.g., Western corn rootworm, *Diabrotica virgifera virgifera* LeConte) but to not suppress a non-target gene such as genes from related, even closely related, species (e.g., Northern corn rootworm, *Diabrotica barberi* Smith and Lawrence, or Southern corn rootworm, *Diabrotica undecimpunctata*).

In other embodiments (e.g., where it is desirable to suppress a target gene across multiple species), it may be desirable to design the recombinant DNA construct to suppress a target gene sequence common to the multiple species in which the target gene is to be silenced. Thus, an RNA duplex can be selected to be specific for one taxon (for example, specific to a genus, family, or even a larger taxon such as a phylum, e.g., arthropoda) but not for other taxa (e.g., plants or vertebrates or mammals). In one non-limiting example of this embodiment, a recombinant DNA construct for gene silencing can be selected so as to target pathogenic fungi (e.g., a *Fusarium* spp.) but not target any gene sequence from beneficial fungi.

In another non-limiting example of this embodiment, a recombinant DNA construct for gene silencing in corn rootworm can be selected to be specific to all members of the genus *Diabrotica*. In a further example of this embodiment, such a *Diabrotica*-targeted recombinant DNA construct can be selected so as to not target any gene sequence from beneficial coleopterans (for example, predatory coccinellid beetles, commonly known as ladybugs or ladybirds) or other beneficial insect species.

The required degree of specificity of a recombinant DNA construct of this invention for silencing a target gene depends on various factors. Factors can include the size and nucleic acid sequence of a mature microRNA encoded by the recombinant DNA construct, and the relative importance of decreasing such a mature miRNA's potential to suppress non-target genes. In a non-limiting example, where such a mature miRNA is expected to be 21 base pairs in size, one particularly preferred embodiment includes DNA encoding a mature miRNA for silencing a target gene wherein the mature miRNA includes sequence that is substantially non-identical to a non-target gene sequence, such as fewer than 18, or fewer than 17, or fewer than 16, or fewer than 15 matches out of 21 contiguous nucleotides of a non-target gene sequence.

In some embodiments, it may be desirable to design the recombinant DNA construct for silencing a target gene to include regions predicted to not generate undesirable polypeptides, for example, by screening the recombinant DNA construct for sequences that may encode known undesirable polypeptides or close homologues of these. Undesirable polypeptides include, but are not limited to, polypeptides homologous to known allergenic polypeptides and polypeptides homologous to known polypeptide toxins. Publicly available sequences encoding such undesirable potentially allergenic peptides are available, for example, the Food Allergy Research and Resource Program (FARRP) allergen database (available at allergenonline.com) or the Biotechnology Information for Food Safety Databases (available at iit.edu/~sgendel/fa.htm) (see also, for example, Gendel (1998) *Adv. Food Nutr. Res.*, 42:63-92). Undesirable sequences can also include, for example, those polypeptide sequences annotated as known toxins or as potential or known allergens and contained in publicly available databases such as GenBank, EMBL, SwissProt, and others, which are searchable by the Entrez system (ncbi.nih.gov/Entrez). Non-limiting examples of undesirable, potentially allergenic peptide sequences include glycinin from soybean, oleosin and agglutinin from peanut, glutenins from wheat, casein, lactalbumin, and lactoglobulin from bovine milk, and tropomyosin from various shellfish (allergenonline.com). Non-limiting examples of undesirable, potentially toxic peptides include tetanus toxin tetA from *Clostridium tetani*, diarrheal toxins from *Staphylococcus aureus*, and venoms such as conotoxins from *Conus* spp. and neurotoxins from arthropods and reptiles (ncbi.nih.gov/Entrez).

In one non-limiting example, the recombinant DNA construct is screened to eliminate those transcribable sequences encoding polypeptides with perfect homology to a known allergen or toxin over 8 contiguous amino acids, or with at least 35% identity over at least 80 amino acids; such screens can be performed on any and all possible reading frames in both directions, on potential open reading frames that begin with AUG (ATG in the corresponding DNA), or on all possible reading frames, regardless of whether they start with an AUG (or ATG) or not. When a "hit" or match is made, that is, when a sequence that encodes a potential polypeptide with perfect homology to a known allergen or toxin over 8 contiguous amino acids (or at least about 35% identity over at least about 80 amino acids), is identified, the nucleic acid sequences corresponding to the hit can be avoided, eliminated, or modified when selecting sequences to be used in an RNA for silencing a target gene. In one embodiment the recombinant DNA construct is designed so no potential open reading frame that begins with AUG (ATG in the corresponding DNA) is included.

Avoiding, elimination of, or modification of, an undesired sequence can be achieved by any of a number of methods known to those skilled in the art. In some cases, the result can be novel sequences that are believed to not exist naturally. For example, avoiding certain sequences can be accomplished by joining together "clean" sequences into novel chimeric sequences to be used in the RHA duplex.

Applicants recognize that in some microRNA-mediated gene silencing, it is possible for imperfectly matching miRNA sequences to be effective at gene silencing. For example, it has been shown that mismatches near the center of a miRNA complementary site has stronger effects on the miRNA's gene silencing than do more distally located mismatches. See, for example, FIG. 4 in Mallory et al. (2004) *EMBO J.*, 23:3356-3364. In another example, it has been reported that, both the position of a mismatched base pair and the identity of the nucleotides forming the mismatch influence the ability of a given siRNA to silence a target gene, and that adenine-cytosine mismatches, in addition to the G:U wobble base pair, were well tolerated (see Du et al. (2005) *Nucleic Acids Res.*, 33:1671-1677). Thus, a given strand of the recombinant DNA construct need not always have 100% sequence identity with the intended target gene, but generally would preferably have substantial sequence identity with the intended target gene, such as about 95%, about 90%, about 85%, or about 80% sequence identity with the intended target gene. Described in terms of complementarity, one strand of the recombinant DNA construct is preferably designed to have substantial complementarity to the intended target (e.g., a target messenger RNA or target non-coding RNA), such as about 95%, about 90%, about 85%, or about 80% complementarity to the intended target. In a non-limiting example, in the case of a recombinant DNA construct encoding a mature miRNA of 21 nucleotides, the encoded mature miRNA is designed to be is substantially but not perfectly complementary to 21 contiguous nucleotides of a target RNA; preferably the nucleotide at position 21 is unpaired with the corresponding position in the target RNA to prevent transitivity.

One skilled in the art would be capable of judging the importance given to screening for regions predicted to be more highly specific to the target gene or predicted to not generate undesirable polypeptides, relative to the importance given to other criteria, such as, but not limited to, the percent sequence identity with the intended target gene or the predicted gene silencing efficiency of a given sequence. For example, a recombinant DNA construct of this invention that encodes a mature miRNA may be designed to be active across several species, and therefore one skilled in the art can determine that it is more important to include in the recombinant DNA construct DNA encoding a mature miRNA that is specific to the several species of interest, but less important to screen for regions predicted to have higher gene silencing efficiency or for regions predicted to generate undesirable polypeptides.

Promoters

Generally, the recombinant DNA construct of this invention includes a promoter, functional in a plant cell, and operably linked to the transcribable DNA element. In various embodiments, the promoter is selected from the group consisting of a constitutive promoter, a spatially specific promoter, a temporally specific promoter, a developmentally specific promoter, and an inducible promoter.

Non-constitutive promoters suitable for use with the recombinant DNA constructs of the invention include spatially specific promoters, temporally specific promoters, and inducible promoters. Spatially specific promoters can include organelle-, cell-, tissue-, or organ-specific promoters (e.g., a plastid-specific, a root-specific, a pollen-specific, or a seed-specific promoter for suppressing expression of the first target RNA in plastids, roots, pollen, or seeds, respectively). In many cases a seed-specific, embryo-specific, aleurone-specific, or endosperm-specific promoter is especially useful. Temporally specific promoters can include promoters that tend to promote expression during certain developmental stages in a plant's growth cycle, or during different times of day or night, or at different seasons in a year. Inducible promoters include promoters induced by chemicals or by environmental conditions such as, but not limited to, biotic or abiotic stress (e.g., water deficit or drought, heat, cold, high or low nutrient or salt levels, high or low light levels, or pest or pathogen infection). An expression-specific promoter can also include promoters that are generally constitutively expressed but at differing degrees or "strengths" of expression, including promoters commonly regarded as "strong promoters" or as "weak promoters".

Promoters of particular interest include the following non-limiting examples: an opaline synthase promoter isolated from T-DNA of *Agrobacterium*; a cauliflower mosaic virus 35S promoter; enhanced promoter elements or chimeric promoter elements such as an enhanced cauliflower mosaic virus (CaMV) 35S promoter linked to an enhancer element (an intron from heat shock protein 70 of *Zea mays*); root specific promoters such as those disclosed in U.S. Pat. Nos. 5,837,848; 6,437,217 and 6,426,446; a maize L3 oleosin promoter disclosed in U.S. Pat. No. 6,433,252; a promoter for a plant nuclear gene encoding a plastid-localized aldolase disclosed in U.S. Patent Application Publication 2004/0216189; cold-inducible promoters disclosed in U.S. Pat. No. 6,084,089; salt-inducible promoters disclosed in U.S. Pat. No. 6,140,078; light-inducible promoters disclosed in U.S. Pat. No. 6,294,714; pathogen-inducible promoters disclosed in U.S. Pat. No. 6,252,138; and water deficit-inducible promoters disclosed in U.S. Patent Application Publication 2004/0123347 A1. All of the above-described patents and patent publications disclosing promoters and their use, especially in recombinant DNA constructs functional in plants are incorporated herein by reference.

The promoter element can include nucleic acid sequences that are not naturally occurring promoters or promoter elements or homologues thereof but that can regulate expression of a gene. Examples of such "gene independent" regulatory sequences include naturally occurring or artificially designed RNA sequences that include a ligand-binding region or aptamer and a regulatory region (which can be cis-acting). See, for example, Isaacs et al. (2004) *Nat. Biotechnol.*, 22:841-847, Bayer and Smolke (2005) *Nature Biotechnol.*, 23:337-343, Mandal and Breaker (2004) *Nature Rev. Mol. Cell Biol.*, 5:451-463, Davidson and Ellington (2005) *Trends Biotechnol.*, 23:109-112, Winkler et al. (2002) *Nature*, 419:952-956, Sudarsan et al. (2003) *RNA*, 9:644-647, and Mandal and Breaker (2004) *Nature Struct. Mol. Biol.*, 11:29-35. Such "riboregulators" can be selected or designed for specific spatial or temporal specificity, for example, to regulate translation of the exogenous gene only in the presence (or absence) of a given concentration of the appropriate ligand.

Making and Using Recombinant DNA Constructs

The recombinant DNA constructs of this invention are made by any method suitable to the intended application, taking into account, for example, the type of expression desired and convenience of use in the plant in which the construct is to be transcribed. General methods for making and using DNA constructs and vectors are well known in the art and described in detail in, for example, handbooks and laboratory manuals including Sambrook and Russell, "Molecular Cloning: A Laboratory Manual" (third edition), Cold Spring Harbor Laboratory Press, NY, 2001. An example of useful technology for building DNA constructs and vectors for transformation is disclosed in U.S. Patent Application Publication 2004/0115642 A1, incorporated herein by reference. DNA constructs can also be built using the GATEWAY™ cloning technology (available from Invitrogen Life Technologies, Carlsbad, Calif.), which uses the site-specific recombinase LR cloning reaction of the Integrase/att system from bacteriophage lambda vector construction, instead of restriction endonucleases and ligases. The LR cloning reaction is disclosed in U.S. Pat. Nos. 5,888,732 and 6,277,608, and in U.S. Patent Application Publications 2001/283529, 2001/282319 and 2002/0007051, all of which are incorporated herein by reference. The GATEWAY™ Cloning Technology Instruction Manual, which is also supplied by Invitrogen, provides concise directions for routine cloning of any desired DNA into a vector comprising operable plant expression elements. Another alternative vector fabrication method employs ligation-independent cloning as disclosed by Aslandis et al. (1990) *Nucleic Acids Res.*, 18:6069-6074 and Rashtchian et al. (1992) *Biochem.*, 206:91-97, where a DNA fragment with single-stranded 5' and 3' ends is ligated into a desired vector which can then be amplified in vivo.

In certain embodiments, the DNA sequence of the recombinant DNA construct includes sequence that has been codon-optimized for the plant in which the recombinant DNA construct is to be expressed. For example, a recombinant DNA construct to be expressed in a plant can have all or parts of its sequence (e.g., the first gene suppression element or the gene expression element) codon-optimized for expression in a plant by methods known in the art. See, e.g., U.S. Pat. No. 5,500,365, incorporated by reference, for a description of codon-optimization for plants; see also De Amicis and Marchetti (2000) *Nucleic Acid Res.*, 28:3339-3346.

Transgenic Plant Cells and Plants

Another aspect of this invention provides a non-natural transgenic plant cell including any of the recombinant DNA constructs of this invention, as described above under the heading "Recombinant DNA Constructs". Further provided is a non-natural transgenic plant containing the non-natural transgenic plant cell of this invention. The non-natural transgenic plant of this invention includes plants of any developmental stage, and includes a regenerated plant prepared from the transgenic plant cells disclosed herein, or a progeny plant (which can be an inbred or hybrid progeny plant) of the regenerated plant, or seed of such a transgenic plant. Also provided and claimed is a transgenic seed having in its genome any of the recombinant DNA constructs provided by this invention. The non-natural transgenic plant cells, non-natural transgenic plants, and transgenic seeds of this invention are made by methods well-known in the art, as described below under the heading "Making and Using Non-natural Transgenic Plant Cells and Non-natural Transgenic Plants".

The non-natural transgenic plant cell can include an isolated plant cell (e.g., individual plant cells or cells grown in or on an artificial culture medium), or can include a plant cell in undifferentiated tissue (e.g., callus or any aggregation of plant cells). The non-natural transgenic plant cell can include a plant cell in at least one differentiated tissue selected from the group consisting of leaf (e.g., petiole and blade), root, stem (e.g., tuber, rhizome, stolon, bulb, and corm) stalk (e.g., xylem, phloem), wood, seed, fruit (e.g., nut, grain, fleshy fruits), and flower (e.g., stamen, filament, anther, pollen, carpel, pistil, ovary, ovules).

The non-natural transgenic plant cell or non-natural transgenic plant of the invention can be any suitable plant cell or plant of interest. Both transiently transformed and stably transformed plant cells are encompassed by this invention. Stably transformed transgenic plants are particularly preferred. In many preferred embodiments, the non-natural transgenic plant is a fertile transgenic plant from which seed can be harvested, and the invention further claims transgenic seed of such transgenic plants, wherein the seed preferably also contains the recombinant construct of this invention.

Making and Using Non-natural Transgenic Plant Cells and Non-natural Transgenic Plants Where a recombinant DNA construct of this invention is used to produce a non-natural transgenic plant cell, non-natural transgenic plant, or transgenic seed of this invention, transformation can include any of the well-known and demonstrated methods and compositions. Suitable methods for plant transformation include virtually any method by which DNA can be introduced into a cell, such as by direct delivery of DNA (e.g., by PEG-mediated transformation of protoplasts, by electroporation, by agitation with silicon carbide fibers, and by acceleration of DNA coated particles), by *Agrobacterium*-mediated transformation, by viral or other vectors, etc. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize), all of which are incorporated by reference.

Another preferred method of plant transformation is *Agrobacterium*-mediated transformation. In one preferred embodiment, the non-natural transgenic plant cell of this invention is obtained by transformation by means of *Agrobacterium* containing a binary Ti plasmid system, wherein the *Agrobacterium* carries a first Ti plasmid and a second, chimeric plasmid containing at least one T-DNA border of a wild-type Ti plasmid, a promoter functional in the transformed plant cell and operably linked to a gene suppression construct of the invention. See, for example, the binary system described in U.S. Pat. No. 5,159,135, incorporated by reference. Also see De Framond (1983) *Biotechnology*, 1:262-269; and Hoekema et al., (1983) *Nature*, 303:179. In such a binary system, the smaller plasmid, containing the T-DNA border or borders, can be conveniently constructed and manipulated in a suitable alternative host, such as *E. coli*, and then transferred into *Agrobacterium*.

Detailed procedures for *Agrobacterium*-mediated transformation of plants, especially crop plants, include, for example, procedures disclosed in U.S. Pat. Nos. 5,004,863, 5,159,135, and 5,518,908 (cotton); U.S. Pat. Nos. 5,416,011, 5,569,834, 5,824,877 and 6,384,301 (soy); U.S. Pat. No. 5,591,616 and U.S. Pat. No. 5,981,840 (maize); U.S. Pat. No. 5,463,174 (brassicas), and in U.S. Patent Application Publication 2004/0244075 (maize), all of which are incorporated by reference. Similar methods have been reported for many plant species, both dicots and monocots, including, among others, peanut (Cheng et al. (1996) *Plant Cell Rep.*, 15: 653); asparagus (Bytebier et al. (1987) *Proc. Natl. Acad. Sci. U.S.A.*, 84:5345); barley (Wan and Lemaux (1994) *Plant Physiol.*, 104:37); rice (Toriyama et al. (1988) *Bio/Technology*, 6:10; Zhang et al. (1988) *Plant Cell Rep.*, 7:379; wheat (Vasil et al. (1992) *Bio/Technology*, 10:667; Becker et al. (1994) *Plant J.*, 5:299), alfalfa (Masoud et al. (1996) *Transgen. Res.*, 5:313); and tomato (Sun et al. (2006) *Plant Cell Physiol.*, 47:426-431). See also a description of vectors, transformation methods, and production of transformed *Arabidopsis thaliana* plants where transcription factors are constitutively expressed by a CaMV35S promoter, in U.S. Patent Application Publication 2003/0167537 A1, incorporated by reference. Transgenic plant cells and transgenic plants can also be obtained by transformation with other vectors, such as, but not limited to, viral vectors (e.g., tobacco etch potyvirus (TEV), barley stripe mosaic virus (BSMV), and the viruses referenced in Edwardson and Christie, "The Potyvirus Group: Monograph No. 16, 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol, e.g., bacterial infection (e.g., with *Agrobacterium* as described above), binary bacterial artificial chromosome constructs, direct delivery of DNA (e.g., via PEG-mediated transformation, desiccation/inhibition-mediated DNA uptake, electroporation, agitation with silicon carbide fibers, and microprojectile bombardment). It would be clear to one of ordinary skill in the art that various transformation methodologies can be used and modified for production of stable transgenic plants from any number of plant species of interest.

Transformation methods to provide transgenic plant cells and transgenic plants containing stably integrated recombinant DNA are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos or parts of embryos, and gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making non-natural transgenic plants of this invention (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, which are incorporated by reference. Transgenic plants include transgenic plant tissue or parts, such as transgenic rootstock or transgenic graft or scion material, which can be used in combination with non-transgenic plant tissue or parts.

In general transformation practice, DNA is introduced into only a small percentage of target cells in any one transformation experiment. Marker genes are generally used to provide an efficient system for identification of those cells that are stably transformed by receiving and integrating a transgenic DNA construct into their genomes. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the recombinant DNA. Commonly used selective marker genes include those conferring resistance to antibiotics such as kanamycin or paromomycin (nptll), hygromycin B (aph IV) and gentamycin (aac3 and aacC4) or resistance to herbicides such as glufosinate (bar or pat) and glyphosate (EPSPS). Examples of useful selective marker genes and selection agents are illustrated in U.S. Pat. Nos. 5,550,318, 5,633,435, 5,780,708, and 6,118,047, all of which are incorporated by reference. Screenable markers or reporters, such as markers that provide an ability to visually identify transformants can also be employed. Non-limiting examples of useful screenable markers include, for example, a gene expressing a protein that produces a detectable color by acting on a chromogenic substrate (e.g., beta-glucuronidase (GUS) (uidA) or luciferase (luc)) or that itself is detectable, such as green fluorescent protein (GFP) (gfp) or an immunogenic molecule. Those of skill in the art will recognize that many other useful markers or reporters are available for use.

Detecting or measuring the resulting change in expression of the target gene (or concurrent expression of a gene of interest) obtained by transcription of the recombinant construct in the non-natural transgenic plant of the invention can be achieved by any suitable methods, including protein detection methods (e.g., western blots, ELISAs, and other immunochemical methods), measurements of enzymatic activity, or nucleic acid detection methods (e.g., Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

Other suitable methods for detecting or measuring the resulting change in expression of the target gene (or concurrent expression of a gene of interest) obtained by transcription of the recombinant DNA in the non-natural transgenic plant of the invention include measurement of any other trait that is a direct or proxy indication of expression of the target gene (or concurrent expression of a gene of interest) in the transgenic plant in which the recombinant DNA is transcribed, relative to one in which the recombinant DNA is not transcribed, e.g., gross or microscopic morphological traits, growth rates, yield, reproductive or recruitment rates, resistance to pests or pathogens, or resistance to biotic or abiotic stress (e.g., water deficit stress, salt stress, nutrient stress, heat or cold stress). Such methods can use direct measurements of a phenotypic trait or proxy assays (e.g., in plants, these assays include plant part assays such as leaf or root assays to determine tolerance of abiotic stress).

The recombinant DNA constructs of the invention can be stacked with other recombinant DNA for imparting additional traits (e.g., in the case of transformed plants, traits including herbicide resistance, pest resistance, cold germination tolerance, water deficit tolerance, and the like) for example, by expressing or suppressing other genes. Constructs for coordinated decrease and increase of gene expression are disclosed in U.S. Patent Application Publication 2004/0126845 A1, incorporated by reference.

Seeds of transgenic, fertile plants can be harvested and used to grow progeny generations, including hybrid generations, of non-natural transgenic plants of this invention that include the recombinant DNA construct in their genome. Thus, in addition to direct transformation of a plant with a recombinant DNA construct, non-natural transgenic plants of the invention can be prepared by crossing a first plant having the recombinant DNA with a second plant lacking the construct. For example, the recombinant DNA can be introduced into a plant line that is amenable to transformation to produce a non-natural transgenic plant, which can be crossed with a second plant line to introgress the recombinant DNA into the resulting progeny. A non-natural transgenic plant of the invention with one recombinant DNA (effecting change in expression of a target gene) can be crossed with a plant line having other recombinant DNA that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s).

Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA Progeny plants carrying DNA for both parental traits can be crossed back into the female parent line multiple times, e.g., usually 6 to 8 generations, to produce a progeny plant with substantially the same genotype as one original transgenic parental line but for the recombinant DNA of the other transgenic parental line.

Yet another aspect of the invention is a non-natural transgenic plant grown from the transgenic seed of the invention. This invention contemplates non-natural transgenic plants grown directly from transgenic seed containing the recombinant DNA as well as progeny generations of plants, including inbred or hybrid plant lines, made by crossing a transgenic plant grown directly from transgenic seed to a second plant not grown from the same transgenic seed.

Crossing can include, for example, the following steps:
(a) plant seeds of the first parent plant (e.g., non-transgenic or a transgenic) and a second parent plant that is transgenic according to the invention;
(b) grow the seeds of the first and second parent plants into plants that bear flowers;
(c) pollinate a flower from the first parent with pollen from the second parent; and
(d) harvest seeds produced on the parent plant bearing the fertilized flower.

It is often desirable to introgress recombinant DNA into elite varieties, e.g., by backcrossing, to transfer a specific desirable trait from one source to an inbred or other plant that lacks that trait. This can be accomplished, for example, by first crossing a superior inbred ("A") (recurrent parent) to a donor inbred ("B") (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent "B", and then the selected progeny are mated back to the superior recurrent parent "A". After five or more backcross generations with selection for the desired trait, the progeny are hemizygous for loci controlling the characteristic being transferred, but are like the superior parent for most or almost all other genes. The last backcross generation would be selfed to give progeny which are pure breeding for the gene(s) being transferred, i.e., one or more transformation events.

Through a series of breeding manipulations, a selected DNA construct can be moved from one line into an entirely different line without the need for further recombinant manipulation. One can thus produce inbred plants which are true breeding for one or more DNA constructs. By crossing different inbred plants, one can produce a large number of different hybrids with different combinations of DNA constructs. In this way, plants can be produced which have the desirable agronomic properties frequently associated with hybrids ("hybrid vigor"), as well as the desirable characteristics imparted by one or more DNA constructs.

Genetic markers can be used to assist in the introgression of one or more DNA constructs of the invention from one genetic background into another. Marker assisted selection offers advantages relative to conventional breeding in that it can be used to avoid errors caused by phenotypic variations. Further, genetic markers can provide data regarding the relative degree of elite germplasm in the individual progeny of a particular cross. For example, when a plant with a desired trait which otherwise has a non-agronomically desirable genetic background is crossed to an elite parent, genetic markers can be used to select progeny which not only possess the trait of interest, but also have a relatively large proportion of the desired germplasm. In this way, the number of generations required to introgress one or more traits into a particular genetic background is minimized. The usefulness of marker assisted selection in breeding non-natural transgenic plants of the current invention, as well as types of useful molecular markers, such as but not limited to SSRs and SNPs, are discussed in PCT Application Publication WO 02/062129 and U.S. Patent Application Publications Numbers 2002/0133852, 2003/0049612, and 2003/0005491, each of which is incorporated by reference in their entirety.

In certain non-natural transgenic plant cells and non-natural transgenic plants of the invention, it may be desirable to concurrently express (or suppress) a gene of interest while also regulating expression of a target gene. Thus, in some embodiments, the non-natural transgenic plant contains recombinant DNA further including a gene expression (or suppression) element for expressing at least one gene of interest, and regulation of expression of a target gene is preferably effected with concurrent expression (or suppression) of the at least one gene of interest in the transgenic plant.

Thus, as described herein, the non-natural transgenic plant cells or non-natural transgenic plants of the invention can be obtained by use of any appropriate transient or stable, integrative or non-integrative transformation method known in the art or presently disclosed. The recombinant DNA constructs can be transcribed in any plant cell or tissue or in a whole plant of any developmental stage. Transgenic plants can be derived from any monocot or dicot plant, such as, but not limited to, plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Preferred dicot plants include, but are not limited to, canola, broccoli, cabbage, carrot, cauliflower, Chinese cabbage, cucumber, dry beans, eggplant, fennel, garden beans, gourds, lettuces, melons, okra, peas, peppers, pumpkin, radishes, spinach, squash, watermelon, cotton, potato, quinoa, amaranth, buckwheat, safflower, soybean, sugarbeet, and sunflower. Preferred monocots include, but are not limited to, wheat, oat, barley, maize (including sweet corn and other varieties), rye, triticale, rice, ornamental and forage grasses, sorghum, millet, onions, leeks, and sugarcane, more preferably maize, wheat, and rice.

The ultimate goal in plant transformation is to produce plants which are useful to man. In this respect, non-natural transgenic plants of the invention can be used for virtually any purpose deemed of value to the grower or to the consumer. For example, one may wish to harvest the transgenic plant itself, or harvest transgenic seed of the transgenic plant for planting purposes, or products can be made from the transgenic plant or its seed such as oil, starch, ethanol or other fermentation products, animal feed or human food, pharmaceuticals, and various industrial products. For example, maize is used extensively in the food and feed industries, as well as in industrial applications. Further discussion of the uses of maize can be found, for example, in U.S. Pat. Nos. 6,194,636, 6,207,879, 6,232,526, 6,426,446, 6,429,357, 6,433,252, 6,437,217, and 6,583,338, incorporated by reference, and PCT Publications WO 95/06128 and WO 02/057471. Thus, this invention also provides commodity products produced from a transgenic plant cell, plant, or seed of this invention, including, but not limited to, harvested leaves, roots, shoots, tubers, stems, fruits, seeds, or other parts of a plant, meals, oils, extracts, fermentation or digestion products, crushed or whole grains or seeds of a plant, or any food or non-food product including such commodity products produced from a transgenic plant cell, plant, or seed of this invention. The detection of one or more of nucleic acid sequences of the recombinant DNA constructs of this invention in one or more commodity or commodity products contemplated herein is de facto evidence that the commodity or commodity product contains or is derived from a transgenic plant cell, plant, or seed of this invention.

In preferred embodiments, the non-natural transgenic plant prepared from the non-natural transgenic plant cell of this invention, i.e, a transgenic plant having in its genome a recombinant DNA construct of this invention has at least one additional altered trait, relative to a plant lacking the recombinant DNA construct, selected from the group of traits consisting of:
  (a) improved abiotic stress tolerance;
  (b) improved biotic stress tolerance;
  (c) modified primary metabolite composition;
  (d) modified secondary metabolite composition;
  (e) modified trace element, carotenoid, or vitamin composition;
  (f) improved yield;
  (g) improved ability to use nitrogen or other nutrients;
  (h) modified agronomic characteristics;
  (i) modified growth or reproductive characteristics; and
  (j) improved harvest, storage, or processing quality.

In particularly preferred embodiments, the non-natural transgenic plant is characterized by: improved tolerance of abiotic stress (e.g., tolerance of water deficit or drought, heat, cold, non-optimal nutrient or salt levels, non-optimal light levels) or of biotic stress (e.g., crowding, allelopathy, or wounding); by a modified primary metabolite (e.g., fatty acid, oil, amino acid, protein, sugar, or carbohydrate) composition; a modified secondary metabolite (e.g., alkaloids, terpenoids, polyketides, non-ribosomal peptides, and secondary metabolites of mixed biosynthetic origin) composition; a modified trace element (e.g., iron, zinc), carotenoid (e.g., beta-carotene, lycopene, lutein, zeaxanthin, or other carotenoids and xanthophylls), or vitamin (e.g., tocopherols) composition; improved yield (e.g., improved yield under non-stress conditions or improved yield under biotic or abiotic stress); improved ability to use nitrogen or other nutrients; modified agronomic characteristics (e.g., delayed ripening; delayed senescence; earlier or later maturity; improved shade tolerance; improved resistance to root or stalk lodging; improved resistance to "green snap" of stems; modified photoperiod response); modified growth or reproductive characteristics (e.g., intentional dwarfing; intentional male sterility, useful, e.g., in improved hybridization procedures; improved vegetative growth rate; improved germination; improved male or female fertility); improved harvest, storage, or processing quality (e.g., improved resistance to pests during storage, improved resistance to breakage, improved appeal to consumers); or any combination of these traits.

In one preferred embodiment, transgenic seed, or seed produced by the non-natural transgenic plant, has modified primary metabolite (e.g., fatty acid, oil, amino acid, protein, sugar, or carbohydrate) composition, a modified secondary metabolite (e.g., alkaloids, terpenoids, polyketides, non-ribosomal peptides, and secondary metabolites of mixed biosynthetic origin) composition, a modified trace element (e.g., iron, zinc), carotenoid (e.g., beta-carotene, lycopene, lutein, zeaxanthin, or other carotenoids and xanthophylls), or vitamin (e.g., tocopherols,) composition, an improved harvest, storage, or processing quality, or a combination of these. For example, it can be desirable to modify the amino acid (e.g., lysine, methionine, tryptophan, or total protein), oil (e.g., fatty acid composition or total oil), carbohydrate (e.g., simple sugars or starches), trace element, carotenoid, or vitamin content of seeds of crop plants (e.g., canola, cotton, safflower, soybean, sugarbeet, sunflower, wheat, maize, or rice), preferably in combination with improved seed harvest, storage, or processing quality, and thus provide improved seed for use in animal feeds or human foods. In another instance, it can be desirable to change levels of native components of the transgenic plant or seed of a transgenic plant, for example, to decrease levels of proteins with low levels of lysine, methionine, or tryptophan, or to increase the levels of a desired amino acid or fatty acid, or to decrease levels of an allergenic protein or glycoprotein (e.g., peanut allergens including ara h 1, wheat allergens including gliadins and glutenins, soybean allergens including P34 allergen, globulins, glycinins, and conglycinins) or of a toxic metabolite (e.g., cyanogenic glycosides in cassava, *solanum* alkaloids in members of the Solanaceae).

Methods of Gene Suppression

A further aspect of this invention provides a method of effecting gene suppression, including the steps of: (a) providing a non-natural transgenic plant including a regenerated plant prepared from a non-natural transgenic plant cell of this invention, or a progeny plant of the regenerated plant (as described above under the heading "Transgenic Plant Cells and Plants"); and (b) transcribing the recombinant DNA construct in the non-natural transgenic plant; wherein the transcribing produces RNA that is capable of suppressing the at least one target gene in the non-natural transgenic plant, and whereby the at least one target gene is suppressed relative to its expression in the absence of transcription of the recombinant DNA construct.

The at least one target gene is at least one gene selected from the group consisting of a gene native to the transgenic plant, a transgene in the transgenic plant, and a gene native to a viral, a bacterial, a fungal, or an invertebrate pest or pathogen of the transgenic plant. Suitable target genes are described above under the heading "Target Genes". In some embodiments, the at least one target gene is a single target gene. In other embodiments, the at least one target gene is multiple target genes. Suppression of a target gene includes non-specific suppression, e.g., constitutive expression, as well as specific expression, e.g., spatially specific, temporally specific, developmentally specific, or inducible gene suppression. Specificity of suppression of the at least one target gene is achieved by techniques known to those skilled in the art, such as by selecting a promoter having the desired specific expression pattern, or by selecting a microRNA recognition site that is recognized by a mature miRNA having the desired specific expression pattern.

Transcription of the recombinant DNA construct is carried out by means known in the art. In some embodiments, transcription is constitutive or non-specific, e.g., under the control of a constitutive promoter. In other embodiments, transcription occurs under specific spatial, temporal, or inducible conditions. For example, the recombinant DNA construct can include a spatially, temporally, or inducible specific promoter. In another example, the recombinant DNA construct can include a riboswitch (DNA that transcribes to an RNA aptamer capable of binding to a ligand, and DNA that transcribes to regulatory RNA capable of regulating expression of the target gene, wherein the regulation is dependent on the conformation of the regulatory RNA, and the conformation of the regulatory RNA is allosterically affected by the binding state of the RNA aptamer) thereby allowing transcription of the recombinant DNA construct to be controlled by the binding state of the RNA aptamer and thus the presence (or absence) of the ligand.

This invention further provides a method of concurrently effecting gene suppression of at least one target gene and gene expression of at least one gene of interest, including the steps of: (a) providing a non-natural transgenic plant including a regenerated plant prepared from the non-natural transgenic plant cell of this invention, or a progeny plant of the regenerated plant (as described above under the heading "Transgenic Plant Cells and Plants"), wherein the recombinant DNA construct further includes a gene expression element for expressing the at least one gene of interest; and (b) transcribing the recombinant DNA construct in the non-natural transgenic plant, wherein, when the recombinant DNA construct is transcribed in the non-natural transgenic plant, transcribed RNA that is capable of suppressing the at least one target gene and transcribed RNA encoding the at least one gene of interest are produced, whereby the at least one target gene is suppressed relative to its expression in the absence of transcription of the recombinant DNA construct and the at least one gene of interest is concurrently expressed.

A gene of interest can include any coding or non-coding sequence from any species (including, but not limited to, non-eukaryotes such as bacteria, and viruses; fungi; plants, including monocots and dicots, such as crop plants, ornamental plants, and non-domesticated or wild plants; invertebrates such as arthropods, annelids, nematodes, and molluscs; and vertebrates such as amphibians, fish, birds, and mammals. Non-limiting examples of a non-coding sequence to be expressed by a gene expression element include, but not limited to, 5' untranslated regions, promoters, enhancers, or other non-coding transcriptional regions, 3' untranslated regions, terminators, intron, microRNAs, microRNA precursor DNA sequences, small interfering RNAs, RNA components of ribosomes or ribozymes, small nucleolar RNAs, RNA aptamers capable of binding to a ligand, and other non-coding RNAs. Non-limiting examples of a gene of interest further include, but are not limited to, translatable (coding) sequence, such as genes encoding transcription factors and genes encoding enzymes involved in the biosynthesis or catabolism of molecules of interest (such as amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). A gene of interest can be a gene native to the cell (e.g., a plant cell) in which the recombinant DNA construct of the invention is to be transcribed, or can be a non-native gene. A gene of interest can be a marker gene, for example, a selectable marker gene encoding antibiotic, antifungal, or herbicide resistance, or a marker gene encoding an easily detectable trait (e.g., in a plant cell, phytoene synthase or other genes imparting a particular pigment to the plant), or a gene encoding a detectable molecule, such as a fluorescent protein, luciferase, or a unique polypeptide or nucleic acid "tag" detectable by protein or nucleic acid detection methods, respectively). Selectable markers are genes of interest of particular utility in identifying successful processing of constructs of the invention. Genes of interest include those genes also described above as target genes, under the heading "Target Genes".

The gene of interest to be expressed by the gene expression element can include at least one gene selected from the group consisting of a eukaryotic target gene, a non-eukaryotic target gene, and a microRNA precursor DNA sequence. The gene of interest can include a single gene or multiple genes (such as multiple copies of a single gene, multiple alleles of a single gene, or multiple genes including genes from multiple species). In one embodiment, the gene expression element can include self-hydrolyzing peptide sequences, e.g., located between multiple sequences coding for one or more polypeptides (see, for example, the 2A and "2A-like" self-cleaving sequences from various species, including viruses, trypanosomes, and bacteria, disclosed by Donnelly et al. (2001), *J. Gen. Virol.*, 82:1027-1041). In another embodiment, the gene expression element can include ribosomal "skip" sequences, e.g., located between multiple sequences coding for one or more polypeptides (see, for example, the aphthovirus foot-and-mouth disease virus (FMDV) 2A ribosomal "skip" sequences disclosed by Donnelly et al. (2001), *J. Gen. Virol.*, 82:1013-1025).

Abiotic-Stress-Responsive MiRNAs

A further aspect of this invention is directed to miRNAs that exhibit an expression pattern that is responsive to abiotic stress, for example, a miRNA that exhibits an expression pattern characterized by regulation of the miRNA by nutrient stress, a miRNA that exhibits an expression pattern characterized by regulation of the miRNA by water stress, or a miRNA that exhibits an expression pattern characterized by regulation of the miRNA by temperature stress.

Examples 6-11 describe a novel miRNA that was identified in crop plants and assigned the trivial name miR-MON18, which exhibits an expression pattern characterized by suppression of the miRNA under nutrient stress (i.e., nitrogen deficiency, phosphate deficiency, or both nitrogen and phosphate deficiency). The mature miRMON18 is a 21-nucleotide miRNA with the sequence UUAGAUGAC-CAUCAGCAAACA and was cloned from rice (SEQ ID NO. 393), maize (SEQ ID NO. 3227), and soybean (SEQ ID NO. 8742) small RNA libraries. Precursor sequences were identified in rice (SEQ ID NO. 1763) and in maize (SEQ ID NO. 3936).

Recombinant DNA constructs of this invention are described in detail under the heading "Recombinant DNA Constructs" above and are useful with any of the miRNAs disclosed herein, for example, a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819. The description of recombinant DNA constructs of this invention also applies generally to embodiments of this invention that are more specifically directed to a miR-NAs having a particular expression pattern, such as a nutrient-stress-responsive plant miRNA (e.g., miRMON18 and other miRNAs described in the Examples) as described in this section. The following description is directed to miRMON18 but is also applicable to other miRNAs regulated by abiotic stress, especially a miRNAs that exhibits an expression pattern characterized by suppression of the miRNA under nutrient stress, a miRNA that exhibits an expression pattern characterized by suppression of the miRNA under water stress, or a miRNA that exhibits an expression pattern characterized by suppression of the miRNA under temperature stress; non-limiting examples of miRNAs regulated by abiotic stress include miR399 and miR319.

Thus, this invention provides a recombinant DNA construct including at least one transcribable DNA element for modulating the expression of at least one target gene, wherein the at least one transcribable DNA element is selected from the group consisting of: (a) a DNA element that transcribes to an miRNA precursor with the fold-back structure of a miRMON18 precursor sequence selected from SEQ ID NO. 1763 and SEQ ID NO. 3936 and is processed to a mature miRMON18 miRNA having the sequence of UUAGAUGACCAUCAGCAAACA (SEQ ID NO. 393, SEQ ID NO. 3227, or SEQ ID NO. 8742); (b) a DNA element that transcribes to an engineered miRNA precursor derived from the fold-back structure of a miRMON18 precursor sequence selected from SEQ ID NO. 1763 and SEQ ID NO. 3936, wherein the engineered miRNA precursor includes a modified mature miRMON18 miRNA; (c) a DNA element that is located within or adjacent to a transgene transcription unit and that is transcribed to RNA including a miRNA recognition site recognized by a mature miRNA derived from a miRMON18 precursor sequence selected from SEQ ID NO. 1763 and SEQ ID NO. 3936; and (d) a DNA element for suppressing expression of an endogenous miRNA derived from a miRMON18 precursor sequence selected from SEQ ID NO. 1763 and SEQ ID NO. 3936. These embodiments directed to miRMON18 are described in more detail below.

(A) Expression of a Native miRMON18 under Non-native Conditions.

This invention provides a recombinant DNA construct including at least one transcribable DNA element for modulating the expression of at least one target gene, wherein the at least one transcribable DNA element includes a DNA element that transcribes to a miRNA precursor with the fold-back structure of a miRMON18 precursor sequence selected from SEQ ID NO. 1763 and SEQ ID NO. 3936 and is processed to a mature miRMON18 miRNA having the sequence of SEQ ID NO. 393, SEQ ID NO. 3227, or SEQ ID NO. 8742, and the at least one target gene is an endogenous gene of a plant, and wherein expression of the recombinant DNA construct in the plant results in suppression of the at least one target gene. In one preferred embodiment, the miRNA precursor includes a contiguous segment of at least 90% of the nucleotides of the miRMON18 precursor sequence. Such constructs are especially useful for expression of miRMON18 in an expression pattern other than the native miRMON18 expression pattern (e.g., in different tissues, at different times, or at different levels of expression).

The miRMON18 precursor need not include all of the nucleotides contained in a miRMON18 precursor sequence selected from SEQ ID NO. 1763 and SEQ ID NO. 3936, but preferably includes a contiguous segment of at least 80%, or at least 85%, or at least 90%, or at least 95%, or at least 97%, or at least 98%, or at least 99% of the nucleotides of a miRMON18 precursor sequence selected from SEQ ID NO. 1763 and SEQ ID NO. 3936. In a preferred embodiment, the miRNA precursor includes a contiguous segment of at least 90% of the nucleotides of a miRMON18 precursor sequence selected from SEQ ID NO. 1763 and SEQ ID NO. 3936. Regardless of the specific nucleotide sequence employed, the miRMON18 precursor forms a fold-back structure that is identical or near-identical to the fold-back structure formed by amiRMON18 precursor sequence selected from SEQ ID NO. 1763 and SEQ ID NO. 3936 and is processed in vivo by one or more steps to a mature miRMON18 miRNA having the sequence of SEQ ID NO. 393, SEQ ID NO. 3227, or SEQ ID NO. 8742.

In preferred embodiments, the at least one target gene is an endogenous gene of a plant that includes at least one miRMON18 recognition site (target site), and expression of the recombinant DNA construct in the plant results in suppression of the at least one target gene. In preferred embodiments, the at least one target gene is an endogenous gene of a plant, and thus expression of the recombinant DNA construct in the plant results in suppression of the at least one target gene. In preferred embodiments, the recombinant DNA construct further includes a promoter other than a native miRMON18 promoter. This permits expression of the mature miRMON18 miRNA under spatial or temporal or inducible conditions under which it would not natively be expressed. For example, the recombinant DNA construct can be designed to include a constitutive promoter and thus constitutively express a mature miRMON18 that has an expression pattern characterized by suppression of the miRNA under nutrient stress (i.e., nitrogen deficiency, phosphate deficiency, or both nitrogen and phosphate deficiency); this would result in constitutive suppression of the miRMON18 target gene. In another example, the recombinant DNA construct can be designed to include an inducible root-specific promoter and thus express a mature miRMON18 in root upon induction; this would result in suppression of the miRMON18 target gene in root tissue upon induction. Promoters that are useful with this recombinant DNA construct are described under the heading "Promoters".

(B) Expression of an Engineered Mature miRNA Derived from miRMON18.

In another embodiment, the recombinant DNA construct includes at least one transcribable DNA element for modulating the expression of at least one target gene, wherein the at least one transcribable DNA element for modulating the expression of at least one target gene includes a DNA element that transcribes to an engineered miRNA precursor derived from the fold-back structure of a miRMON18 precursor sequence selected from SEQ ID NO. 1763 and SEQ ID NO. 3936, wherein the engineered miRNA precursor includes a modified mature miRMON18 miRNA, wherein the at least one target gene is an endogenous gene of a plant or an endogenous gene of a pest or pathogen of the plant, and wherein expression of the recombinant DNA construct in the plant results in suppression of the at least one target gene.

In preferred embodiments, the at least one target gene is an endogenous gene of a plant or an endogenous gene of a pest or pathogen of the plant, and expression of the recombinant DNA construct in the plant results in suppression of the at least one target gene. Suitable target genes are described above under the heading "Target Genes". By "engineered" is meant that nucleotides are changed (substituted, deleted, or added) in a native miRMON18 precursor sequence selected from SEQ ID NO. 1763 and SEQ ID NO. 3936, thereby resulting in an engineered miRNA precursor having substantially the same the fold-back structure as the native miRMON18 precursor sequence, but wherein the mature miRNA that is processed from the engineered miRMON18 precursor has a modified sequence (i.e., different from that of the native mature miRMON18) that is designed to suppress a target gene different from the target genes natively suppressed by the native miRMON18 precursor sequence. A general, non-limiting method for determining nucleotide changes in the native miRMON18 precursor sequence to produce the engineered miRNA precursor is described above under the heading "Expression of an engineered mature miRNA".

(C) Expression of a Transgene and a miRMON18 Recognition Site.

In another embodiment, the recombinant DNA construct includes at least one transcribable DNA element for modulating the expression of at least one target gene, and further includes a transgene transcription unit, wherein the at least one transcribable DNA element for modulating the expression of at least one target gene includes a DNA element that is located within or adjacent to the transgene transcription unit and that is transcribed to RNA including a miRNA recognition site recognized by a mature miRMON18 miRNA having the sequence of SEQ ID NO. 393, SEQ ID NO. 3227, or SEQ ID NO. 8742 or by a mature miRMON18 miRNA derived from a miRMON18 precursor sequence selected from SEQ ID NO. 1763 and SEQ ID NO. 3936, and the at least one target gene includes the transgene encoded by the transgene transcription unit, and wherein expression of the recombinant DNA construct in a plant results in expression of the transgene in cells of the plant wherein the mature miRMON18 miRNA is not natively expressed. Prediction of a miRMON18 recognition site is achieved using methods known in the art, such as sequence complementarity rules as described by Zhang (2005) *Nucleic Acids Res.*, 33:W701-704 and by Rhoades et al. (2002) *Cell,* 110:513-520; non-limiting examples of miRMON18 recognition sites are provided in the working Examples below.

Prediction of a miRMON18 recognition site permits identification and validation of endogenous genes regulated by a mature miRMON18 from a natively expressed miRMON18 precursor; this is useful, e.g., to eliminate or modify a miRMON18 recognition site in an endogenous gene in order to decouple expression of that gene from regulation by the endogenous miRMON18 that natively regulates expression of the gene. In one embodiment, the number of mismatches (especially those corresponding to positions 2 to 13 of the mature miRMON18) between a miRMON18 recognition site and a mature miRMON18 can be increased to prevent recognition and cleavage by an endogenous miRMON18.

These recombinant DNA constructs are particularly useful for in planta expression of the transgene to be restricted according to the endogenous expression of miRMON18, that is, the transgene is expressed when miRMON18 is suppressed, such as under nutrient stress (i.e., nitrogen deficiency, phosphate deficiency, or both nitrogen and phosphate deficiency). Expression of the transgene can be further controlled by use of an appropriate promoter. In a non-limiting example, a recombinant DNA construct of this invention that encodes (a) a transgene under the control of a root-specific promoter and (b) a miRNA recognition site recognized by a mature miRMON18 that is specifically suppressed only under conditions of nitrogen (or phosphate) deficiency is used for expression of the transgene in roots of a plant under nitrogen-deficient (or phosphate-deficient) conditions.

The transgene transcription unit includes at least a transgene, and optionally additional sequence such as, but not limited to, a promoter, a promoter enhancer, a terminator, messenger RNA stabilizing or destabilizing sequence (see, e.g., Newman et al. (1993) *Plant Cell,* 5:701-714; Green (1993) *Plant Physiol.,* 102:1065-1070; and Ohme-Takagi et al. (1993) *Proc. Natl. Acad. Sci. USA,* 90:11811-11815), sequence for localization or transport of the transgene transcript to a specific locale (e.g., mitochondrion, plastid, nucleolus, peroxisome, endoplasmic reticulum, etc.), or other sequence related to the desired processing of the transgene. The transgene encoded by the transgene transcription unit can include any one or more genes of interest, including coding sequence, non-coding sequence, or both. Genes of interest can include any of the genes listed under "Target Genes", preferred examples of which include translatable (coding) sequence for genes encoding transcription factors and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin).

(D) Suppression of an Endogenous or Native miRMON18.

In another embodiment, the recombinant DNA construct includes at least one transcribable DNA element for modulating the expression of at least one target gene, wherein the at least one transcribable DNA element includes a DNA element for suppressing expression of an endogenous mature miRMON18 miRNA derived from a miRMON18 precursor sequence selected from SEQ ID NO. 1763 and SEQ ID NO. 3936, wherein the at least one target gene is an endogenous gene of a plant, and wherein expression of the endogenous gene is suppressed in cells of the plant where native expression of the endogenous mature miRMON18 miRNA occurs, and wherein expression of the recombinant DNA construct in the cells results in expression of the endogenous gene in the cells. Such constructs are especially useful for suppression of a native or endogenous miRMON18 and thus for permitting expression of genes that have one or more miRMON18 recognition sites. In preferred embodiments, the at least one target gene is an endogenous gene of a plant and includes one or more miRMON18 recognition sites, and expression of the endogenous gene is suppressed in cells of the plant where native expression of the mature miRMON18 occurs, and thus expression of the recombinant DNA construct in the cells results in expression of the endogenous target gene in the cells.

The DNA element for suppressing expression includes at least one of:

(a) DNA that includes at least one anti-sense DNA segment that is anti-sense to at least one segment of the target gene;

(b) DNA that includes multiple copies of at least one anti-sense DNA segment that is anti-sense to at least one segment of the target gene;

(c) DNA that includes at least one sense DNA segment that is at least one segment of the target gene;

(d) DNA that includes multiple copies of at least one sense DNA segment that is at least one segment of the target gene;
(e) DNA that transcribes to RNA for suppressing the target gene by forming double-stranded RNA and includes at least one anti-sense DNA segment that is anti-sense to at least one segment of the target gene and at least one sense DNA segment that is at least one segment of the target gene;
(f) DNA that transcribes to RNA for suppressing the target gene by forming a single double-stranded RNA and includes multiple serial anti-sense DNA segments that are anti-sense to at least one segment of the target gene and multiple serial sense DNA segments that are at least one segment of the target gene;
(g) DNA that transcribes to RNA for suppressing the target gene by forming multiple double strands of RNA and includes multiple anti-sense DNA segments that are anti-sense to at least one segment of the target gene and multiple sense DNA segments that are at least one segment of the target gene, and wherein the multiple anti-sense DNA segments and the multiple sense DNA segments are arranged in a series of inverted repeats;
(h) DNA that includes nucleotides derived from a plant miRNA;
(i) DNA that includes nucleotides of a siRNA;
(j) DNA that transcribes to an RNA aptamer capable of binding to a ligand; and
(k) DNA that transcribes to an RNA aptamer capable of binding to a ligand, and DNA that transcribes to regulatory RNA capable of regulating expression of the target gene, wherein the regulation is dependent on the conformation of the regulatory RNA, and the conformation of the regulatory RNA is allosterically affected by the binding state of the RNA aptamer.

DNA elements for suppressing expression are described further in Example 3 and depicted in FIGS. 2 and 3. The effects of a miRNA on its target gene can also be controlled by alternative methods described in detail below under "MicroRNA Decoy Sequences".

In some embodiments, the recombinant DNA construct includes DNA designed to be transcribed to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity. In one example, the spacer is transcribed to a stabilizing loop that links the first and second series of contiguous RNA segments (see, for example, Di Giusto and King (2004) *J. Biol. Chem.*, 279:46483-46489). In another example, the recombinant DNA construct includes DNA that transcribes to RNA including an RNA aptamer (e.g., an aptamer that binds to a cell-specific ligand) that allows cell- or tissue-specific targetting of the recombinant RNA duplex.

(E) miRNA-unresponsive Transgenes, Including miRMON18-unresponsive Transgenes.

Also disclosed and claimed is a recombinant DNA construct including a synthetic miRNA-unresponsive transgene sequence that is unresponsive to a given mature miRNA, wherein the synthetic miRNA-unresponsive transgene sequence is: (a) derived from a natively miRNA-responsive sequence by deletion or modification of all native miRNA recognition sites recognized by the given mature miRNA within the natively miRNA-responsive sequence, and (b) is not recognized by the given mature miRNA. Non-limiting embodiments include a recombinant DNA construct including a synthetic miRNA-unresponsive transgene sequence that is unresponsive to a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or unresponsive to a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819, wherein the synthetic miRNA-unresponsive transgene sequence is: (a) derived from a natively miRNA-responsive sequence by deletion or modification of all native miRNA recognition sites recognized by the given mature miRNA within the natively miRNA-responsive sequence, and (b) is not recognized by the given mature miRNA. Prediction of a recognition site is achieved using methods known in the art, such as sequence complementarity rules as described by Zhang (2005) *Nucleic Acids Res.*, 33:W701-704 and by Rhoades et al. (2002) *Cell*, 110:513-520.

One non-limiting preferred embodiment is a recombinant DNA construct including a synthetic miRMON18-unresponsive transgene sequence, wherein the synthetic miRMON18-unresponsive transgene sequence is: (a) derived from a natively miRMON18-responsive sequence by deletion or modification of all native miRMON18 miRNA recognition sites (that is to say, deletion or modification of any recognition site that is recognized by a mature miRMON18 miRNA having the sequence of SEQ ID NO. 393, SEQ ID NO. 3227, or SEQ ID NO. 8742 or by a mature miRMON18 miRNA derived from a miRMON18 precursor sequence selected from SEQ ID NO. 1763 and SEQ ID NO. 3936) within the natively miRMON18-responsive sequence, and (b) is not recognized by a mature miRMON18 miRNA.

(F) Abiotic-stress-responsive miRNA Promoters, Including miRMON18 Promoters.

Also disclosed and claimed is a recombinant DNA construct including a promoter of a miRNA that exhibits an expression pattern characterized by regulation by abiotic stress, for example, a promoter of a miRNA that exhibits an expression pattern characterized by regulation of the miRNA by nutrient stress, a promoter of a miRNA that exhibits an expression pattern characterized by regulation of the miRNA by water stress, or a promoter of a miRNA that exhibits an expression pattern characterized by regulation of the miRNA by temperature stress. Preferred embodiments include a recombinant DNA construct including a promoter of a miRNA that exhibits an expression pattern characterized by regulation of the miRNA by nutrient stress, wherein the nutrient stress comprises at least one nutrient deficiency selected from the group consisting of nitrogen deficiency and phosphate deficiency. In one embodiment, the promoter is that of a miRNA that is suppressed by nitrogen deficiency. In another embodiment, the promoter is that of a miRNA that is suppressed by inorganic phosphate deficiency. In yet another embodiment, the promoter is that of a miRNA that is suppressed by the co-occurrence of nitrogen and phosphate deficiency. In further embodiments, the promoter is that of a miRNA that is upregulated by by nitrogen deficiency or by phosphate deficiency.

Particularly preferred embodiments include a recombinant DNA construct including a promoter of a miRNA that exhibits an expression pattern characterized by suppression of the miRNA under nutrient stress, wherein the nutrient stress comprises at least one nutrient deficiency selected from the group consisting of nitrogen deficiency and phosphate deficiency, and wherein the promoter includes at least one of: (a) the promoter of a maize miRNA that exhibits in leaf tissue strong expression under nitrogen-sufficient conditions and suppression under nitrogen-deficient conditions; (b) the promoter of a maize miRNA that exhibits in leaf tissue strong expression under phosphate-sufficient conditions and suppression under phosphate-deficient conditions; (c) a miRMON18 promoter having the sequence of SEQ ID NO. 8804; (d) a fragment of at least about 50 contiguous nucleotides having at least 85% identity to a segment of SEQ ID NO. 8804. Also preferred are embodiments wherein the promoter is operably linked to at least one of: (a) a gene suppression element, and (b) a gene expression element; preferably, these embodiments are useful for expressing the recombinant DNA construct in a plant Non-limiting examples include the promoter having the sequence of nucleotides 211-2172 of SEQ ID NO. 8800; a fragment of at least about 50, at least about 100, at least about 150, at least about 200, at least about 300, at least about 400, or at least 500 contiguous nucleotides having at least 85%, at least 90%, at least 95%, or at least 98% identity to nucleotides 211-2172 of SEQ ID NO. 8800, wherein the fragment has promoter activity in at least one plant tissue that is characterized by strong expression under nitrogen-sufficient conditions and suppression under nitrogen-deficient conditions or strong expression under phosphate-sufficient conditions and suppression under phosphate-deficient conditions; and a fragment of at least about 50, at least about 100, at least about 150, at least about 200, at least about 300, at least about 400, or at least 500 contiguous nucleotides having at least 85%, at least 90%, at least 95%, or at least 98% identity to SEQ ID NO. 8804, wherein the fragment has promoter activity in at least one plant tissue that is characterized by strong expression under nitrogen-sufficient conditions and suppression under nitrogen-deficient conditions or strong expression under phosphate-sufficient conditions and suppression under phosphate-deficient conditions.

(G) Abiotic-stress-responsive Transgenic Plant Cells and Plants

Further disclosed and claimed is a non-natural transgenic plant cell including any of the recombinant DNA constructs disclosed under this heading ("Abiotic-Stress-Responsive miRNAs"). One preferred embodiment includes a non-natural transgenic plant prepared from a non-natural transgenic plant cell including a recombinant DNA construct including at least one transcribable DNA element for modulating the expression of at least one target gene, wherein the at least one transcribable DNA element includes a DNA element that transcribes to an miRNA precursor with the fold-back structure of a miRMON18 precursor sequence selected from SEQ ID NO. 1763, SEQ ID NO. 3936, and SEQ ID NO. 8800, wherein the miRNA precursor includes a contiguous segment of at least 90% of the nucleotides of the miRMON18 precursor sequence and is processed to a mature miRMON18 miRNA having the sequence of UUAGAUGACCAUCAGCAAACA (SEQ ID NO. 393, SEQ ID NO. 3227, or SEQ ID NO. 8742) and the at least one target gene is an endogenous gene of a plant and includes an SPX domain, and wherein expression of the recombinant DNA construct in the plant results in suppression of the at least one target gene; generally the recombinant DNA construct further includes a promoter other than the native miRMON18 promoter to drive expression of the mature miRMON18.

Another preferred embodiment includes a non-natural transgenic plant prepared from a non-natural transgenic plant cell including a recombinant DNA construct including at least one transcribable DNA element for modulating the expression of at least one target gene, wherein the at least one transcribable DNA element includes a DNA element for suppressing expression of an endogenous mature miRMON18 miRNA derived from a miRMON18 precursor sequence selected from SEQ ID NO. 1763, SEQ ID NO. 3936, and SEQ ID NO. 8800, the at least one target gene is an endogenous gene of a plant and includes an SPX domain, and expression of the endogenous gene is suppressed in cells of the plant where native expression of the endogenous mature miRMON18 miRNA occurs, and wherein expression of the recombinant DNA construct in the cells results in expression of the endogenous gene in the cells. Suitable DNA elements for suppressing expression of an endogenous mature miRMON18 miRNA are described above under the heading "Suppression of an endogenous or native miRMON18".

MicroRNA Decoy Sequences

Plant microRNAs regulate their target genes by recognizing and binding to a near-perfectly complementary sequence (miRNA recognition site) in the target transcript, followed by cleavage of the transcript by RNase III enzymes such as Ago1. In plants, certain mismatches between a given miRNA recognition site and the corresponding mature miRNA are not tolerated, particularly mismatched nucleotides at positions 10 and 11 of the mature miRNA. Positions within the mature miRNA are given in the 5' to 3' direction; for clarity, FIG. 7D depicts examples of miRNAs, miR827 (SEQ ID NO. 8744) and miRMON18 (SEQ ID NO. 393, SEQ ID NO. 3227, or SEQ ID NO. 8742), with numbered arrows indicating positions 1, 10, and 21 of the mature miRNA; the nucleotide at position 10 is also underlined. Perfect complementarity between a given miRNA recognition site and the corresponding mature miRNA is usually required at positions 10 and 11 of the mature miRNA. See, for example, Franco-Zorrilla et al. (2007) *Nature Genetics*, 39:1033-1037; and Axtell et al. (2006) *Cell*, 127:565-577.

This characteristic of plant miRNAs was exploited to arrive at rules for predicting a "microRNA decoy sequence", i.e., a sequence that can be recognized and bound by an endogenous mature miRNA resulting in base-pairing between the miRNA decoy sequence and the endogenous mature miRNA, thereby forming a cleavage-resistant RNA duplex that is not cleaved because of the presence of mismatches between the miRNA decoy sequence and the mature miRNA. Mismatches include canonical mismatches (e.g., G-A, C-U, C-A) as well as G::U wobble pairs and indels (nucleotide insertions or deletions). In general, these rules define (1) mismatches that are required, and (2) mismatches that are permitted but not required.

Required mismatches include: (a) at least 1 mismatch between the miRNA decoy sequence and the endogenous mature miRNA at positions 9, 10, or 11 of the endogenous mature miRNA, or alternatively, (b) 1, 2, 3, 4, or 5 insertions (i.e., extra nucleotides) at a position in the miRNA decoy sequence corresponding to positions 9, 10, or 11 of the endogenous mature miRNA. In preferred embodiments, there exists either (a) at least 1 mismatch between the miRNA decoy sequence and the endogenous mature miRNA at positions 10 and/or 11 of the endogenous mature miRNA, or (b) at least 1 insertion at a position in the miRNA decoy sequence corresponding to positions 10 and/or 11 of the endogenous mature miRNA.

Mismatches that are permitted, but not required, include: (a) 0, 1, or 2 mismatches between the miRNA decoy sequence and the endogenous mature miRNA at positions 1, 2, 3, 4, 5, 6, 7, 8, and 9 of the endogenous mature miRNA, and (b) 0, 1, 2, or 3 mismatches between the miRNA decoy sequence and the endogenous mature miRNA at positions 12 through the last position of the endogenous mature miRNA (i.e., at position 21 of a 21-nucleotide mature miRNA), wherein each of the mismatches at positions 12 through the last position of the endogenous mature miRNA is adjacent to at least one complementary base-pair (i.e., so that there is not more than 2 contiguous mismatches at positions 12 through the last position of the endogenous mature miRNA). In preferred embodiments, there exist no mismatches (i.e., there are all complementary base-pairs) at positions 1, 2, 3, 4, 5, 6, 7, and 8 of the endogenous mature miRNA.

The miRNA decoy sequence can be of any length as long as it is recognized and bound by an endogenous mature miRNA to form a cleavage-resistant RNA duplex. In preferred embodiments, the miRNA decoy sequence includes between about 18 to about 36 nucleotides. Specifically claimed embodiments include miRNA decoy sequences of 18, 19, 20, 21, 22, 23, 24, 25, 26, 27, 28, 29, 30, and 31 nucleotides. In non-limiting examples, a miRNA decoy sequence (for a 21-nucleotide mature miRNA) having a required mismatch consisting of a 4-nucleotide insertion at position 10 of the mature miRNA and a permitted mismatch consisting of a 1-nucleotide insertion at position 20 of the mature miRNA has a total of 26 nucleotides; a miRNA decoy sequence (for a 25-nucleotide mature miRNA) having a required mismatch consisting of a 5-nucleotide insertion at position 11 of the mature miRNA and permitted mismatches consisting of a canonical mismatch at position 20 of the mature miRNA and 1-nucleotide insertion at position 23 of the mature miRNA will have a total of 31 nucleotides.

Thus, one embodiment of this invention includes a recombinant DNA construct that is transcribed to an RNA transcript including at least one miRNA decoy sequence that is recognized and bound by an endogenous mature miRNA but not cleaved (e.g., not cleaved by Argonaute or an AGO-like protein), wherein the endogenous miRNA is at least one miRNA selected from (a) mature miRNA selected from a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or (b) a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819; and the miRNA decoy sequence includes an RNA sequence of between about 19 to about 36 contiguous RNA nucleotides, wherein the miRNA decoy sequence is recognized and bound by the endogenous mature miRNA, resulting in base-pairing between the miRNA decoy sequence and the endogenous mature miRNA, thereby forming a cleavage-resistant RNA duplex including: (a) at least one mismatch between said miRNA decoy sequence and said endogenous mature miRNA at positions 9, 10, or 11 of said endogenous mature miRNA, or at least one insertion at a position in said miRNA decoy sequence corresponding to positions 10-11 of said endogenous mature miRNA, (b) 0, 1, or 2 mismatches between said miRNA decoy sequence and said endogenous mature miRNA at positions 1, 2, 3, 4, 5, 6, 7, 8, and 9 of said endogenous mature miRNA, and (c) 0, 1, 2, or 3 mismatches between said miRNA decoy sequence and said endogenous mature miRNA at positions 12 through the last position of said endogenous mature miRNA, wherein each of said mismatches at positions 12 through the last position of said endogenous mature miRNA is adjacent to at least one complementary base-pair.

Recombinant DNA constructs of this invention include at least one miRNA decoy sequence, and can include multiple miRNA decoy sequences (either multiple copies of a single miRNA decoy sequence, or copies of different miRNA decoy sequences, or a combination of both). In one example, multiple copies of a miRNA decoy sequence are arranged in tandem in a recombinant DNA construct designed to decrease the activity of the corresponding mature miRNA. In another example, the activity of different mature miRNAs is decreased by expressing a single chimeric recombinant DNA construct that transcribes to multiple different miRNA decoy sequences. Expression of miRNA decoy sequences can be driven by various promoters, including, but not limited to, tissue-specific, cell-specific, temporally specific, inducible, or constitutive promoters, for example, any of the promoters described under the heading "Promoters". The miRNA decoy sequences can be located in various positions in a transcript. In a recombinant DNA construct that is intended to also transcribe to coding sequence, non-coding sequence (e.g., a miRNA), or both, the miRNA decoy sequence is preferably located in an intron or after the polyadenylation signal, to permit normal transcription of the coding sequence, non-coding sequence, or both.

In further embodiments of this invention, analogous decoy sequences are used to regulate the activity of other small RNAs involved in double-stranded RNA-mediated gene suppression, including trans-acting small interfering RNAs (ta-siRNAs), natural anti-sense transcript siRNAs (nat-siRNAs), and phased small RNAs (as described in U.S. patent application Ser. No. 11/897,611, filed 31 Aug. 2007, which is incorporated by reference herein). These analogous ta-siRNA decoy sequences, nat-siRNAs decoy sequences, and phased small RNA decoy sequences are predicted using essentially the same rules as those for predicting miRNA decoy sequences, and have utilities similar to those of the miRNA decoy sequences.

The miRNA decoy sequence can be a naturally-occurring sequence or an artificial sequence. In one embodiment, the at least one miRNA decoy sequence includes a naturally occurring miRNA decoy sequence, for example, an endogenous miRNA decoy sequence identified by bioinformatics. In another embodiment the at least one miRNA decoy sequence includes a synthetic miRNA decoy sequence, for example, one that is designed ab initio to bind to a given mature miRNA to form a cleavage-resistant RNA duplex.

Thus, one embodiment of this invention is a recombinant DNA construct that is transcribed to an RNA transcript including at least one miRMON18 decoy sequence that is recognized and bound by an endogenous mature miRMON18 but not cleaved (e.g., not cleaved by Argonaute or an AGO-like protein), wherein the endogenous miRMON18 is at least one selected from (a) a mature miRMON18, or (b) a mature miRNA derived from a plant miRMON18 precursor sequence; and the miRMON18 decoy sequence includes an RNA sequence of between about 19 to about 36 contiguous RNA nucleotides, wherein the miRMON18 decoy sequence is recognized and bound by the endogenous mature miRMON18, resulting in base-pairing between the miRMON18 decoy sequence and the endogenous mature miRMON18, thereby forming a cleavage-resistant RNA duplex including: (a) at least one mismatch between the miRMON18 decoy sequence and the endogenous mature miRMON18 at positions 9, 10, or 11 of the endogenous mature miRMON18, or at least one insertion at a position in the miRMON18 decoy sequence corresponding to positions 10-11 of the endogenous mature miRMON18, (b) 0, 1, or 2 mismatches between the miRMON18 decoy sequence and the endogenous mature miRMON18 at positions 1, 2, 3, 4, 5, 6, 7, 8, and 9 of the endogenous mature miRMON18, and (c) 0, 1, 2, or 3 mismatches between the miRMON18 decoy sequence and the endogenous mature miRMON18 at positions 12 through the last position of the endogenous mature miRMON18, wherein each of the mismatches at positions 12 through the last position of the endogenous mature miRMON18 is adjacent to at least one complementary base-pair; and wherein the at least one miRMON18 decoy sequence is recognized and bound but not cleaved by a mature miRMON18 miRNA. In preferred embodiments, the mature miRMON18 has the sequence of SEQ ID NO. 393, SEQ ID NO. 3227, or SEQ ID NO. 874, or is a mature miRNA derived from a miRMON18 precursor sequence selected from SEQ ID NO. 1763 and SEQ ID NO. 3936. Further provided by this invention is a method of providing a non-natural transgenic crop plant having improved yield under at least one nutrient deficiency selected from nitrogen deficiency and phosphate deficiency, including expressing in the non-natural transgenic crop plant a recombinant DNA construct that is transcribed to an RNA transcript including at least one miRMON18 decoy sequence.

Another embodiment of this invention is a recombinant DNA construct that is transcribed to an RNA transcript including at least one miR399 decoy sequence that is recognized and bound by an endogenous mature miR399 but not cleaved (e.g., not cleaved by Argonaute or an AGO-like protein), wherein the endogenous miR399 is at least one selected from (a) a mature miR399, or (b) a mature miRNA derived from a miR399 precursor sequence selected from SEQ ID NOS. 8816-8819; and the miR399 decoy sequence includes an RNA sequence of between about 19 to about 36 contiguous RNA nucleotides, wherein the miR399 decoy sequence is recognized and bound by the endogenous mature miR399, resulting in base-pairing between the miR399 decoy sequence and the endogenous mature miR399, thereby forming a cleavage-resistant RNA duplex including: (a) at least one mismatch between the miR399 decoy sequence and the endogenous mature miR399 at positions 9, 10, or 11 of the endogenous mature miR399, or at least one insertion at a position in the miR399 decoy sequence corresponding to positions 10-11 of the endogenous mature miR399, (b) 0, 1, or 2 mismatches between the miR399 decoy sequence and the endogenous mature miR399 at positions 1, 2, 3, 4, 5, 6, 7, 8, and 9 of the endogenous mature miR399, and (c) 0, 1, 2, or 3 mismatches between the miR399 decoy sequence and the endogenous mature miR399 at positions 12 through the last position of the endogenous mature miR399, wherein each of the mismatches at positions 12 through the last position of the endogenous mature miR399 is adjacent to at least one complementary base-pair; and wherein the at least one miR399 decoy sequence is recognized and bound but not cleaved by a mature miR399. In preferred embodiments, the mature miR399 has the sequence of SEQ ID NOS. 8812-8815 or is a mature miRNA derived from a miR399 precursor sequence selected from SEQ ID NOS. 8816-8819. Further provided by this invention is a method of providing a non-natural transgenic crop plant having improved yield under at least one nutrient deficiency selected from nitrogen deficiency and phosphate deficiency, including expressing in the non-natural transgenic crop plant a recombinant DNA construct that is transcribed to an RNA transcript including at least one miR399 decoy sequence.

Yet another embodiment of this invention is suppression of an endogenous miRNA decoy sequence, for example, by means of a gene suppression element (such as those described under the header "DNA element for suppressing expression"), especially driven by a cell- or tissue-specific or an inducible promoter.

Any of these recombinant DNA constructs described herein can be made by commonly used techniques, such as those described under the heading "Making and Using Recombinant DNA Constructs" and illustrated in the working Examples. The recombinant DNA constructs are particularly useful for making non-natural transgenic plant cells, non-natural transgenic plants, and transgenic seeds as discussed below under "Transgenic Plant Cells and Transgenic Plants".

Recombinant DNA constructs including a miRNA decoy sequence are useful for providing unique expression patterns for a synthetic miRNA that is engineered to suppress an endogenous gene; this is especially desirable for preventing adverse phenotypes caused by undesirable expression of the synthetic miRNA in certain tissues. For example, the synthetic miRNA can be used to suppress the endogenous gene only in specific tissues of a plant, e.g., by expression in the plant of a recombinant DNA construct including (a) a constitutive promoter driving expression of the synthetic miRNA, and (b) a tissue-specific promoter driving expression of a miRNA decoy sequence designed to sequester the synthetic miRNA.

Further provided by this invention are methods useful in providing improved crop plants. One aspect of this invention includes a method of providing a non-natural transgenic crop plant having at least one altered trait including expressing in the non-natural transgenic crop plant a recombinant DNA construct that is transcribed to an RNA transcript including at least one miRNA decoy sequence that is recognized and bound by an endogenous mature miRNA but not cleaved (e.g., not cleaved by Argonaute or an AGO-like protein), wherein the endogenous miRNA is at least one miRNA selected from (a) a mature miRNA selected from a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or (b) a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819; and the miRNA decoy sequence includes an RNA sequence of between about 19 to about 36 contiguous RNA nucleotides, wherein the miRNA decoy sequence is recognized and bound by the endogenous mature miRNA, resulting in base-pairing between the miRNA decoy sequence and the endogenous mature miRNA, thereby forming a cleavage-resistant RNA duplex including: (a) at least one mismatch between said miRNA decoy sequence and said endogenous mature miRNA at positions 9, 10, or 11 of said endogenous mature miRNA, or at least one insertion at a position in said miRNA decoy sequence corresponding to positions 10-11 of said endogenous mature miRNA, (b) 0, 1, or 2 mismatches between said miRNA decoy sequence and said endogenous mature miRNA at positions 1, 2, 3, 4, 5, 6, 7, 8, and 9 of said endogenous mature miRNA, and (c) 0, 1, 2, or 3 mismatches between said miRNA decoy sequence and said endogenous mature miRNA at positions 12 through the last position of said endogenous mature miRNA, wherein each of said mismatches at positions 12 through the last position of said endogenous mature miRNA is adjacent to at least one complementary base-pair, thereby resulting in the non-natural transgenic crop plant exhibiting at least one altered trait, relative to a crop plant not expressing the recombinant DNA construct, selected from the group of traits consisting of:
  (i) improved abiotic stress tolerance;
  (ii) improved biotic stress tolerance;
  (iii) improved resistance to a pest or pathogen of the plant;
  (iv) modified primary metabolite composition;
  (v) modified secondary metabolite composition;
  (vi) modified trace element, carotenoid, or vitamin composition;
  (vii) improved yield;
  (viii) improved ability to use nitrogen or other nutrients;
  (ix) modified agronomic characteristics;
  (x) modified growth or reproductive characteristics; and
  (xi) improved harvest, storage, or processing quality.

In another aspect, this invention provides a method of providing a non-natural transgenic crop plant having at least one altered trait including suppressing in the non-natural transgenic crop plant at least one endogenous miRNA decoy sequence that is recognized and bound by an endogenous mature miRNA but not cleaved (e.g., not cleaved by Argonaute or an AGO-like protein), wherein the endogenous miRNA is at least one miRNA selected from (a) a mature miRNA selected from a mature miRNA selected from SEQ ID NOS. 1-1035, SEQ ID NOS. 2730-3921, SEQ ID NOS. 5498-6683, SEQ ID NOS. 8409-8560, SEQ ID NO 8742, SEQ ID NO. 8744, SEQ ID NOS. 8812-8815, SEQ ID NO. 8845, and SEQ ID NO. 8850, or (b) a mature miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819; and the miRNA decoy sequence includes an RNA sequence of between about 19 to about 36 contiguous RNA nucleotides, wherein the miRNA decoy sequence is recognized and bound by the endogenous mature miRNA, resulting in base-pairing between the miRNA decoy sequence and the endogenous mature miRNA, thereby forming a cleavage-resistant RNA duplex including: (a) at least one mismatch between said miRNA decoy sequence and said endogenous mature miRNA at positions 9, 10, or 11 of said endogenous mature miRNA, or at least one insertion at a position in said miRNA decoy sequence corresponding to positions 10-11 of said endogenous mature miRNA, (b) 0, 1, or 2 mismatches between said miRNA decoy sequence and said endogenous mature miRNA at positions 1, 2, 3, 4, 5, 6, 7, 8, and 9 of said endogenous mature miRNA, and (c) 0, 1, 2, or 3 mismatches between said miRNA decoy sequence and said endogenous mature miRNA at positions 12 through the last position of said endogenous mature miRNA, wherein each of said mismatches at positions 12 through the last position of said endogenous mature miRNA is adjacent to at least one complementary base-pair; thereby resulting in the non-natural transgenic crop plant exhibiting at least one altered trait, relative to a crop plant not expressing the recombinant DNA construct, selected from the group of traits consisting of:
  (i) improved abiotic stress tolerance;
  (ii) improved biotic stress tolerance;
  (iii) improved resistance to a pest or pathogen of the plant;
  (iv) modified primary metabolite composition;
  (v) modified secondary metabolite composition;
  (vi) modified trace element, carotenoid, or vitamin composition;
  (vii) improved yield;
  (viii) improved ability to use nitrogen or other nutrients;
  (ix) modified agronomic characteristics;
  (x) modified growth or reproductive characteristics; and
  (xi) improved harvest, storage, or processing quality.

Suppression of the at least one endogenous miRNA decoy sequence is achieved by any means, including expression in the non-natural transgenic crop plant a gene suppression element (e.g., such as the DNA elements for suppressing expression described under the heading "Suppression of an endogenous or native miRNA"), or by any other means of gene suppression.

In one non-limiting example, a transgenic plant overexpresses under conditions of nutrient sufficiency at least one miRNA decoy sequence for a miRNA that is natively expressed at high levels under conditions of nutrient sufficiency and at low levels under conditions of nutrient deficiency, thereby resulting in improved performance or yield under nutrient deficiency and improved nutrient utilization by the plant. For example, miRMON18 and miR399 are expressed at low levels during nitrogen- or phosphate-deficient conditions, and at high levels under nitrogen- and phosphate-sufficient conditions, and thus their native target genes are suppressed during nitrogen- or phosphate-deficient conditions and expressed at relatively higher levels under nitrogen- and phosphate-sufficient conditions; this results in improved nitrogen and/or phosphate utilization by the transgenic plant. Thus, a transgenic plant overexpressing a recombinant DNA construct including at least one miRMON18 decoy sequence (or at least one miR399 decoy sequence) results in a higher level of expression of the miRMON18 native target genes (or of the miR399 native target genes) during nitrogen- and phosphate-sufficient conditions, relative to a plant in which the recombinant DNA construct is not expressed. In a non-limiting example, a transgenic plant overexpressing a recombinant DNA construct including at least one miRMON18 decoy sequence is expected to accumulate relatively higher levels of the native miRMON18 targets (e.g., genes containing an SPX domain, such as the genes depicted in FIG. 12, as described in Examples 7, 9, and 10).

EXAMPLES

Example 1

This example describes non-limiting embodiments of methods for identifying crop plant (rice and maize) microRNAs and their precursor (foldback) structures, useful in making recombinant DNA constructs of this invention. Several small (19 to 25 nucleotide) RNA libraries were cloned from mature rice (*Oryza sativa* cv. Nipponbare) mature grain (3 replicates) and seedling and from corn (maize, *Zea mays*) leaf and kernel (39 days after pollination) by high-throughput sequencing (Margulies et al. (2005) *Nature*, 437:376-380). The sequences thus obtained were used for miRNA prediction in rice genomic and maize genomic sequences, respectively, employing a set of rules derived from previously characterized miRNAs, followed by manual inspection to eliminate poorly predicted foldback structures. Small RNAs that matched perfectly to annotated tRNA, rRNA, transposon/retrotransposon and other known repeats, and chloroplast or mitochondria genomes were excluded from the analysis.

The Institute for Genomic Research's rice genome annotation version 4.0 (publicly available at tigr.org) was used to predict two flanking genomic segments of ~310 nucleotides in which a given small RNA was located near the left or right terminus of the segment (thus giving either a sequence consisting of 280 nucleotides plus the small RNA plus 10 nucleotides, or a sequence consisting of 10 nucleotides plus the small RNA plus 280 nucleotides. The foldback structure of each segment thus obtained was predicted using the RNAfold program in the Vienna package as described by Hofacker et al. (1994) *Monatsh. f Chemie*, 125:167-188. To facilitate the structure prediction, each small RNA was assigned a pseudo-abundance of 2.

The structures were filtered based on characteristics of validated miRNA precursors modified from those derived by Jones-Rhoades et al. (2006) *Annu. Rev. Plant. Biol.*, 57:19-53. For rice miRNAs, the filtering requirements included: (1) the small RNA must be located wholly within one arm of the predicted foldback (stem-loop) structure; (2) the small RNA and its counterpart segment in the opposite arm must have nucleotide sequences of at least 75% complementarity to each other; and (3) the small RNA and its counterpart, when forming the imperfect duplex, must not contain a symmetric bulge larger than 3 nucleotides or an asymmetric bulge larger than 2 nucleotides. The predicted structures satisfying the above criteria were further filtered by selecting (1) only small RNAs of length of 20 or 21 nucleotides and having a uracil as the 5' terminal base; or (2) the small RNA that were sequenced at least 10 times. Final filtering steps included: (1) selecting small RNAs with fewer than 23 perfect matches to the genome to remove repetitive elements, and (2) the segment used for the prediction could not include small RNAs from the minus strand. In cases where multiple overlapping small RNAs were identified, the most abundant member of the cluster was chosen as the representative sequence.

In the case of maize miRNA prediction, the prediction/filtering procedures were modified from those used for the rice miRNAs, since a complete maize genome is not yet available. Small RNAs from the maize leaf and kernel libraries were analyzed independently to facilitate use of small RNA abundances for miRNA prediction. Small RNAs were mapped to Maize Assembled Gene Islands (MAGI version 4), a publicly available, assembled corn genomic sequence dataset as described by Fu et al. (2005), *Proc. Natl. Acad. Sci. USA*, 102:12282-12287. Sequences with small RNAs arising from both plus and minus strands were excluded. MicroRNA foldback structures were predicted and filtered using the same requirements as for rice, and were further manually inspected to eliminate structures with large (>100 nucleotide) or highly unpaired loop regions. Previously characterized miRNAs excluded by filters were used as an indicator of false negatives.

A total of 260676 unique small RNAs from rice in the size range of 19-25 nucleotides were analyzed for putative novel miRNAs. After filtering and manual inspection, 840 small RNAs corresponding to 1072 loci, were identified as novel rice miRNAs. Of the 27 known miRNA families present in the miRNA database "miRBase" (available at microrna.sanger.ac.uk/sequences/) and in the original unique sequence set 22 families were captured after filtering. The false negatives rate of 18.5% percent estimated based on characterized miRNAs (miRBase) indicate that the majority of miRNAs were captured by this approach. From a total of 126691 small RNAs from corn kernel, 116 novel maize miRNAs corresponding to 281 loci in the MAGI version 4.0 corn genomic sequence were identified; similarly, from a total of 53103 small RNAs from corn leaf, 79 novel maize miRNAs corresponding to 302 loci were identified. The rice and maize miRNAs and their corresponding miRNA precursor sequences, as well as the nucleotide position of the mature miRNA in each miRNA precursor sequence, are referred to by their respective sequence identification number in Table 1 as follows: corn kernel miRNAs (SEQ ID NOS. 1-116), corn leaf miRNAs (SEQ ID NOS. 117-195), rice miRNAs (SEQ ID NOS. 196-1035), corn kernel miRNA precursor sequences (SEQ ID NOS. 1036-1316), corn leaf miRNA precursor sequences (SEQ ID NOS. 1317-1618), and rice miRNA precursor sequences (SEQ ID NOS. 1619-2690). The total of 174 predicted novel maize miRNAs (representing 528 genomic loci) included 9 miRNA orthologues that were identical to known miRNAs previously identified in species other than corn; these are listed in Table 2.

TABLE 1

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 1 | 1067 | 11 | 31 |
| 1 | 1236 | 166 | 186 |
| 1 | 1269 | 166 | 186 |
| 2 | 1251 | 172 | 192 |
| 3 | 1115 | 167 | 187 |
| 4 | 1240 | 11 | 31 |
| 5 | 1262 | 100 | 120 |
| 6 | 1074 | 11 | 31 |
| 6 | 1229 | 11 | 31 |
| 6 | 1234 | 11 | 31 |
| 6 | 1235 | 76 | 96 |
| 6 | 1274 | 11 | 31 |
| 6 | 1275 | 11 | 31 |
| 6 | 1276 | 11 | 31 |
| 6 | 1277 | 11 | 31 |
| 6 | 1278 | 11 | 31 |
| 6 | 1279 | 76 | 96 |
| 6 | 1280 | 76 | 96 |
| 6 | 1281 | 11 | 31 |
| 6 | 1282 | 11 | 31 |
| 6 | 1283 | 11 | 31 |
| 6 | 1284 | 11 | 31 |
| 6 | 1285 | 76 | 96 |
| 6 | 1286 | 11 | 31 |
| 6 | 1287 | 11 | 31 |
| 6 | 1288 | 11 | 31 |
| 6 | 1289 | 11 | 31 |
| 7 | 1205 | 70 | 90 |
| 7 | 1221 | 116 | 136 |
| 8 | 1041 | 11 | 31 |
| 8 | 1196 | 78 | 98 |
| 9 | 1110 | 92 | 113 |
| 9 | 1182 | 79 | 100 |
| 9 | 1255 | 11 | 32 |
| 10 | 1106 | 64 | 84 |
| 11 | 1194 | 64 | 84 |
| 12 | 1048 | 74 | 94 |
| 12 | 1257 | 11 | 31 |
| 12 | 1266 | 74 | 94 |
| 12 | 1267 | 74 | 94 |
| 13 | 1059 | 72 | 92 |
| 13 | 1068 | 11 | 31 |
| 13 | 1237 | 11 | 31 |
| 14 | 1226 | 11 | 31 |
| 14 | 1249 | 69 | 89 |
| 15 | 1066 | 11 | 31 |
| 15 | 1233 | 11 | 31 |
| 15 | 1256 | 11 | 31 |
| 15 | 1260 | 11 | 31 |
| 15 | 1265 | 115 | 135 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 15 | 1308 | 11 | 31 |
| 16 | 1129 | 128 | 146 |
| 16 | 1199 | 11 | 29 |
| 17 | 1040 | 45 | 68 |
| 17 | 1246 | 11 | 34 |
| 17 | 1247 | 45 | 68 |
| 18 | 1131 | 104 | 127 |
| 19 | 1119 | 142 | 162 |
| 19 | 1166 | 11 | 31 |
| 19 | 1169 | 143 | 163 |
| 19 | 1172 | 69 | 89 |
| 19 | 1175 | 11 | 31 |
| 19 | 1177 | 143 | 163 |
| 19 | 1180 | 11 | 31 |
| 19 | 1186 | 11 | 31 |
| 20 | 1087 | 230 | 251 |
| 20 | 1258 | 11 | 32 |
| 21 | 1046 | 11 | 31 |
| 21 | 1157 | 63 | 83 |
| 21 | 1216 | 73 | 93 |
| 22 | 1254 | 102 | 122 |
| 23 | 1261 | 11 | 30 |
| 24 | 1125 | 70 | 90 |
| 24 | 1314 | 11 | 31 |
| 24 | 1315 | 11 | 31 |
| 25 | 1161 | 11 | 31 |
| 26 | 1124 | 11 | 31 |
| 27 | 1198 | 77 | 96 |
| 28 | 1309 | 74 | 94 |
| 29 | 1114 | 11 | 29 |
| 29 | 1232 | 11 | 29 |
| 30 | 1192 | 70 | 91 |
| 31 | 1077 | 72 | 92 |
| 32 | 1136 | 88 | 108 |
| 33 | 1054 | 38 | 58 |
| 34 | 1053 | 11 | 31 |
| 34 | 1096 | 11 | 31 |
| 34 | 1292 | 84 | 104 |
| 34 | 1307 | 84 | 104 |
| 34 | 1313 | 85 | 105 |
| 35 | 1063 | 11 | 31 |
| 35 | 1214 | 11 | 31 |
| 36 | 1156 | 11 | 31 |
| 37 | 1055 | 11 | 30 |
| 38 | 1291 | 83 | 103 |
| 39 | 1116 | 11 | 31 |
| 39 | 1138 | 11 | 31 |
| 40 | 1201 | 82 | 102 |
| 41 | 1065 | 65 | 85 |
| 41 | 1070 | 11 | 31 |
| 41 | 1088 | 65 | 85 |
| 41 | 1113 | 11 | 31 |
| 41 | 1154 | 11 | 31 |
| 41 | 1163 | 11 | 31 |
| 41 | 1173 | 63 | 83 |
| 42 | 1310 | 11 | 31 |
| 43 | 1122 | 105 | 125 |
| 44 | 1159 | 86 | 106 |
| 45 | 1081 | 11 | 31 |
| 46 | 1104 | 11 | 31 |
| 47 | 1108 | 11 | 31 |
| 48 | 1057 | 11 | 31 |
| 48 | 1162 | 185 | 205 |
| 49 | 1112 | 127 | 147 |
| 49 | 1130 | 11 | 31 |
| 49 | 1144 | 11 | 31 |
| 49 | 1145 | 11 | 31 |
| 49 | 1168 | 11 | 31 |
| 49 | 1195 | 115 | 135 |
| 49 | 1211 | 122 | 142 |
| 49 | 1215 | 11 | 31 |
| 49 | 1217 | 127 | 147 |
| 49 | 1219 | 11 | 31 |
| 50 | 1056 | 11 | 30 |
| 51 | 1036 | 60 | 80 |
| 51 | 1089 | 11 | 31 |
| 52 | 1143 | 64 | 84 |
| 53 | 1060 | 36 | 56 |
| 54 | 1058 | 206 | 226 |
| 54 | 1064 | 199 | 219 |
| 54 | 1128 | 199 | 219 |
| 54 | 1224 | 197 | 217 |
| 54 | 1242 | 200 | 220 |
| 54 | 1272 | 11 | 31 |
| 54 | 1312 | 11 | 31 |
| 55 | 1141 | 70 | 90 |
| 56 | 1061 | 11 | 30 |
| 57 | 1183 | 114 | 134 |
| 58 | 1140 | 132 | 152 |
| 59 | 1126 | 11 | 31 |
| 60 | 1181 | 11 | 31 |
| 61 | 1204 | 47 | 67 |
| 62 | 1037 | 89 | 109 |
| 62 | 1071 | 11 | 31 |
| 62 | 1146 | 11 | 31 |
| 62 | 1148 | 11 | 31 |
| 62 | 1270 | 11 | 31 |
| 63 | 1227 | 11 | 31 |
| 63 | 1231 | 11 | 31 |
| 63 | 1243 | 11 | 31 |
| 63 | 1295 | 151 | 171 |
| 63 | 1296 | 151 | 171 |
| 63 | 1297 | 151 | 171 |
| 63 | 1298 | 151 | 171 |
| 63 | 1299 | 11 | 31 |
| 63 | 1300 | 11 | 31 |
| 63 | 1301 | 151 | 171 |
| 63 | 1302 | 11 | 31 |
| 63 | 1303 | 11 | 31 |
| 63 | 1304 | 152 | 172 |
| 63 | 1305 | 11 | 31 |
| 64 | 1038 | 101 | 120 |
| 64 | 1084 | 11 | 30 |
| 64 | 1127 | 11 | 30 |
| 64 | 1133 | 11 | 30 |
| 64 | 1147 | 101 | 120 |
| 64 | 1160 | 11 | 30 |
| 64 | 1170 | 183 | 202 |
| 64 | 1171 | 11 | 30 |
| 64 | 1185 | 11 | 30 |
| 64 | 1190 | 11 | 30 |
| 64 | 1193 | 11 | 30 |
| 64 | 1206 | 11 | 30 |
| 64 | 1208 | 11 | 30 |
| 64 | 1244 | 11 | 30 |
| 64 | 1245 | 11 | 30 |
| 64 | 1253 | 11 | 30 |
| 64 | 1259 | 11 | 30 |
| 64 | 1268 | 183 | 202 |
| 65 | 1098 | 241 | 261 |
| 65 | 1189 | 241 | 261 |
| 66 | 1045 | 11 | 31 |
| 66 | 1252 | 133 | 153 |
| 67 | 1094 | 71 | 91 |
| 68 | 1152 | 11 | 31 |
| 68 | 1158 | 11 | 31 |
| 68 | 1203 | 11 | 31 |
| 69 | 1097 | 43 | 63 |
| 70 | 1103 | 11 | 31 |
| 71 | 1239 | 41 | 61 |
| 72 | 1044 | 11 | 31 |
| 73 | 1271 | 44 | 64 |
| 74 | 1042 | 76 | 96 |
| 75 | 1230 | 11 | 31 |
| 76 | 1149 | 11 | 31 |
| 77 | 1218 | 11 | 30 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 78 | 1073 | 141 | 161 |
| 79 | 1047 | 11 | 31 |
| 80 | 1293 | 82 | 101 |
| 81 | 1080 | 11 | 31 |
| 82 | 1316 | 11 | 31 |
| 83 | 1118 | 11 | 31 |
| 84 | 1050 | 11 | 31 |
| 85 | 1072 | 115 | 135 |
| 86 | 1085 | 31 | 51 |
| 86 | 1241 | 31 | 51 |
| 87 | 1187 | 11 | 31 |
| 87 | 1197 | 11 | 31 |
| 87 | 1207 | 39 | 59 |
| 87 | 1213 | 38 | 58 |
| 88 | 1117 | 91 | 111 |
| 89 | 1101 | 47 | 67 |
| 90 | 1174 | 155 | 174 |
| 91 | 1209 | 149 | 169 |
| 91 | 1273 | 149 | 169 |
| 92 | 1039 | 11 | 31 |
| 92 | 1228 | 55 | 75 |
| 92 | 1238 | 55 | 75 |
| 92 | 1250 | 55 | 75 |
| 93 | 1099 | 11 | 30 |
| 94 | 1132 | 145 | 165 |
| 94 | 1139 | 140 | 160 |
| 94 | 1167 | 11 | 31 |
| 95 | 1052 | 11 | 31 |
| 96 | 1049 | 11 | 30 |
| 96 | 1105 | 11 | 30 |
| 97 | 1051 | 66 | 85 |
| 97 | 1100 | 136 | 155 |
| 98 | 1164 | 11 | 31 |
| 99 | 1086 | 73 | 93 |
| 99 | 1093 | 11 | 31 |
| 99 | 1294 | 70 | 90 |
| 100 | 1109 | 83 | 103 |
| 100 | 1111 | 11 | 31 |
| 100 | 1137 | 11 | 31 |
| 100 | 1151 | 11 | 31 |
| 100 | 1179 | 36 | 56 |
| 100 | 1184 | 11 | 31 |
| 100 | 1210 | 11 | 31 |
| 100 | 1222 | 72 | 92 |
| 101 | 1043 | 35 | 55 |
| 102 | 1311 | 67 | 87 |
| 103 | 1082 | 11 | 31 |
| 103 | 1120 | 11 | 31 |
| 103 | 1165 | 147 | 167 |
| 103 | 1178 | 147 | 167 |
| 103 | 1220 | 11 | 31 |
| 104 | 1076 | 131 | 151 |
| 104 | 1083 | 131 | 151 |
| 105 | 1102 | 11 | 31 |
| 105 | 1212 | 11 | 31 |
| 105 | 1225 | 11 | 31 |
| 106 | 1306 | 11 | 31 |
| 107 | 1062 | 11 | 30 |
| 107 | 1075 | 11 | 30 |
| 107 | 1091 | 75 | 94 |
| 107 | 1121 | 11 | 30 |
| 107 | 1134 | 11 | 30 |
| 107 | 1142 | 11 | 30 |
| 107 | 1176 | 75 | 94 |
| 107 | 1191 | 76 | 95 |
| 107 | 1200 | 76 | 95 |
| 107 | 1248 | 73 | 92 |
| 107 | 1263 | 76 | 95 |
| 108 | 1078 | 11 | 31 |
| 109 | 1135 | 75 | 95 |
| 110 | 1153 | 11 | 31 |
| 111 | 1150 | 110 | 130 |
| 112 | 1123 | 11 | 30 |
| 113 | 1202 | 73 | 93 |
| 114 | 1223 | 144 | 164 |
| 115 | 1069 | 11 | 31 |
| 115 | 1079 | 11 | 31 |
| 115 | 1092 | 11 | 31 |
| 115 | 1290 | 11 | 31 |
| 116 | 1090 | 11 | 31 |
| 116 | 1095 | 182 | 202 |
| 116 | 1107 | 11 | 31 |
| 116 | 1155 | 193 | 213 |
| 116 | 1188 | 198 | 218 |
| 116 | 1264 | 199 | 219 |
| 117 | 1366 | 11 | 31 |
| 117 | 1538 | 166 | 186 |
| 117 | 1578 | 166 | 186 |
| 118 | 1557 | 172 | 192 |
| 119 | 1397 | 167 | 187 |
| 120 | 1449 | 213 | 233 |
| 120 | 1540 | 11 | 31 |
| 121 | 1572 | 100 | 120 |
| 122 | 1507 | 189 | 208 |
| 123 | 1369 | 11 | 31 |
| 123 | 1534 | 11 | 31 |
| 123 | 1536 | 11 | 31 |
| 123 | 1537 | 76 | 96 |
| 123 | 1583 | 11 | 31 |
| 123 | 1584 | 11 | 31 |
| 123 | 1585 | 11 | 31 |
| 123 | 1586 | 11 | 31 |
| 123 | 1587 | 11 | 31 |
| 123 | 1588 | 11 | 31 |
| 123 | 1589 | 76 | 96 |
| 123 | 1590 | 76 | 96 |
| 123 | 1591 | 11 | 31 |
| 123 | 1592 | 11 | 31 |
| 123 | 1593 | 11 | 31 |
| 123 | 1594 | 11 | 31 |
| 123 | 1595 | 76 | 96 |
| 123 | 1596 | 11 | 31 |
| 123 | 1597 | 11 | 31 |
| 123 | 1598 | 11 | 31 |
| 123 | 1599 | 11 | 31 |
| 124 | 1505 | 70 | 90 |
| 124 | 1522 | 116 | 136 |
| 125 | 1324 | 11 | 31 |
| 125 | 1484 | 78 | 98 |
| 126 | 1466 | 79 | 100 |
| 126 | 1560 | 11 | 32 |
| 127 | 1389 | 64 | 84 |
| 127 | 1401 | 11 | 31 |
| 128 | 1482 | 64 | 84 |
| 129 | 1337 | 74 | 94 |
| 129 | 1565 | 11 | 31 |
| 129 | 1576 | 74 | 94 |
| 129 | 1577 | 74 | 94 |
| 130 | 1559 | 11 | 31 |
| 131 | 1532 | 11 | 31 |
| 131 | 1554 | 69 | 89 |
| 132 | 1365 | 11 | 31 |
| 132 | 1535 | 11 | 31 |
| 132 | 1562 | 11 | 31 |
| 132 | 1568 | 11 | 31 |
| 132 | 1575 | 115 | 135 |
| 132 | 1612 | 11 | 31 |
| 133 | 1451 | 156 | 176 |
| 133 | 1519 | 107 | 127 |
| 134 | 1413 | 128 | 146 |
| 134 | 1500 | 11 | 29 |
| 135 | 1406 | 232 | 252 |
| 136 | 1489 | 80 | 102 |
| 137 | 1543 | 11 | 31 |
| 138 | 1558 | 102 | 122 |
| 139 | 1549 | 56 | 75 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 140 | 1571 | 11 | 30 |
| 141 | 1462 | 11 | 31 |
| 142 | 1514 | 11 | 31 |
| 143 | 1613 | 74 | 94 |
| 144 | 1611 | 68 | 88 |
| 145 | 1418 | 11 | 31 |
| 145 | 1459 | 11 | 31 |
| 145 | 1460 | 11 | 31 |
| 146 | 1479 | 70 | 91 |
| 147 | 1320 | 11 | 31 |
| 147 | 1380 | 11 | 31 |
| 147 | 1381 | 11 | 31 |
| 147 | 1382 | 11 | 31 |
| 147 | 1383 | 11 | 31 |
| 147 | 1384 | 11 | 31 |
| 147 | 1385 | 11 | 31 |
| 147 | 1409 | 97 | 117 |
| 147 | 1411 | 100 | 120 |
| 147 | 1417 | 102 | 122 |
| 147 | 1422 | 11 | 31 |
| 147 | 1456 | 11 | 31 |
| 147 | 1483 | 11 | 31 |
| 147 | 1493 | 100 | 120 |
| 147 | 1502 | 11 | 31 |
| 147 | 1517 | 100 | 120 |
| 147 | 1545 | 11 | 31 |
| 147 | 1550 | 11 | 31 |
| 147 | 1561 | 11 | 31 |
| 147 | 1564 | 11 | 31 |
| 147 | 1566 | 11 | 31 |
| 147 | 1569 | 11 | 31 |
| 148 | 1372 | 72 | 92 |
| 149 | 1424 | 74 | 95 |
| 149 | 1616 | 11 | 32 |
| 150 | 1457 | 152 | 175 |
| 150 | 1513 | 152 | 175 |
| 150 | 1515 | 152 | 175 |
| 151 | 1398 | 11 | 31 |
| 151 | 1442 | 11 | 31 |
| 151 | 1469 | 11 | 31 |
| 151 | 1506 | 11 | 31 |
| 151 | 1520 | 191 | 211 |
| 151 | 1551 | 190 | 210 |
| 151 | 1581 | 192 | 212 |
| 152 | 1504 | 99 | 119 |
| 153 | 1503 | 82 | 102 |
| 154 | 1410 | 38 | 58 |
| 155 | 1487 | 200 | 220 |
| 156 | 1386 | 11 | 31 |
| 156 | 1396 | 43 | 63 |
| 156 | 1546 | 11 | 31 |
| 156 | 1563 | 11 | 31 |
| 156 | 1601 | 11 | 31 |
| 157 | 1360 | 91 | 110 |
| 157 | 1400 | 95 | 114 |
| 157 | 1415 | 95 | 114 |
| 157 | 1425 | 11 | 30 |
| 157 | 1426 | 92 | 111 |
| 157 | 1453 | 11 | 30 |
| 157 | 1474 | 127 | 146 |
| 157 | 1480 | 56 | 75 |
| 157 | 1527 | 91 | 110 |
| 157 | 1552 | 11 | 30 |
| 157 | 1570 | 57 | 76 |
| 157 | 1618 | 58 | 77 |
| 158 | 1394 | 11 | 31 |
| 159 | 1421 | 11 | 30 |
| 159 | 1450 | 207 | 226 |
| 159 | 1495 | 11 | 30 |
| 160 | 1423 | 202 | 222 |
| 160 | 1529 | 11 | 31 |
| 160 | 1533 | 199 | 219 |
| 161 | 1447 | 11 | 31 |
| 161 | 1555 | 11 | 31 |
| 162 | 1336 | 11 | 30 |
| 162 | 1579 | 11 | 30 |
| 163 | 1454 | 133 | 153 |
| 164 | 1553 | 11 | 31 |
| 165 | 1343 | 11 | 31 |
| 165 | 1353 | 11 | 31 |
| 165 | 1468 | 168 | 188 |
| 165 | 1475 | 113 | 133 |
| 165 | 1512 | 113 | 133 |
| 165 | 1547 | 107 | 127 |
| 166 | 1432 | 128 | 148 |
| 166 | 1548 | 128 | 148 |
| 167 | 1350 | 11 | 30 |
| 168 | 1405 | 72 | 91 |
| 169 | 1429 | 38 | 58 |
| 170 | 1376 | 198 | 218 |
| 170 | 1416 | 11 | 31 |
| 170 | 1440 | 11 | 31 |
| 170 | 1465 | 199 | 219 |
| 170 | 1614 | 11 | 31 |
| 171 | 1420 | 138 | 158 |
| 172 | 1317 | 67 | 87 |
| 172 | 1326 | 67 | 87 |
| 172 | 1333 | 67 | 87 |
| 172 | 1338 | 67 | 87 |
| 172 | 1339 | 68 | 88 |
| 172 | 1340 | 67 | 87 |
| 172 | 1341 | 67 | 87 |
| 172 | 1344 | 67 | 87 |
| 172 | 1346 | 68 | 88 |
| 172 | 1348 | 67 | 87 |
| 172 | 1352 | 67 | 87 |
| 172 | 1431 | 68 | 88 |
| 172 | 1437 | 67 | 87 |
| 172 | 1448 | 67 | 87 |
| 172 | 1458 | 68 | 88 |
| 172 | 1477 | 68 | 88 |
| 173 | 1582 | 36 | 56 |
| 174 | 1322 | 136 | 156 |
| 174 | 1330 | 9 | 29 |
| 174 | 1349 | 11 | 31 |
| 174 | 1355 | 136 | 156 |
| 174 | 1399 | 137 | 157 |
| 174 | 1491 | 136 | 156 |
| 174 | 1508 | 136 | 156 |
| 174 | 1509 | 11 | 31 |
| 175 | 1615 | 11 | 31 |
| 176 | 1392 | 117 | 136 |
| 176 | 1438 | 43 | 62 |
| 176 | 1464 | 11 | 30 |
| 176 | 1490 | 11 | 30 |
| 176 | 1492 | 43 | 62 |
| 176 | 1498 | 11 | 30 |
| 176 | 1499 | 43 | 62 |
| 176 | 1510 | 11 | 30 |
| 177 | 1371 | 11 | 31 |
| 178 | 1358 | 75 | 95 |
| 178 | 1364 | 59 | 79 |
| 178 | 1390 | 11 | 31 |
| 178 | 1393 | 75 | 95 |
| 178 | 1395 | 11 | 31 |
| 178 | 1408 | 71 | 91 |
| 178 | 1428 | 57 | 77 |
| 178 | 1434 | 11 | 31 |
| 178 | 1436 | 75 | 95 |
| 178 | 1443 | 75 | 95 |
| 178 | 1455 | 56 | 76 |
| 178 | 1461 | 75 | 95 |
| 178 | 1463 | 75 | 95 |
| 178 | 1467 | 75 | 95 |
| 178 | 1470 | 75 | 95 |
| 178 | 1476 | 11 | 31 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 178 | 1485 | 11 | 31 |
| 178 | 1488 | 11 | 31 |
| 178 | 1496 | 11 | 31 |
| 178 | 1516 | 11 | 31 |
| 178 | 1518 | 11 | 31 |
| 178 | 1523 | 75 | 95 |
| 178 | 1525 | 75 | 95 |
| 178 | 1528 | 11 | 31 |
| 178 | 1531 | 10 | 30 |
| 178 | 1542 | 11 | 31 |
| 178 | 1544 | 11 | 31 |
| 178 | 1556 | 11 | 31 |
| 178 | 1567 | 11 | 31 |
| 178 | 1573 | 11 | 31 |
| 178 | 1574 | 75 | 95 |
| 179 | 1435 | 55 | 75 |
| 180 | 1402 | 113 | 133 |
| 180 | 1441 | 11 | 31 |
| 180 | 1521 | 103 | 123 |
| 180 | 1617 | 105 | 125 |
| 181 | 1329 | 33 | 53 |
| 182 | 1334 | 11 | 31 |
| 182 | 1345 | 211 | 231 |
| 182 | 1347 | 11 | 31 |
| 183 | 1452 | 36 | 56 |
| 184 | 1407 | 144 | 164 |
| 185 | 1404 | 11 | 31 |
| 185 | 1412 | 11 | 31 |
| 185 | 1419 | 11 | 31 |
| 185 | 1481 | 11 | 31 |
| 185 | 1494 | 11 | 31 |
| 185 | 1524 | 11 | 31 |
| 185 | 1526 | 11 | 31 |
| 186 | 1478 | 11 | 31 |
| 186 | 1511 | 11 | 31 |
| 186 | 1539 | 11 | 31 |
| 187 | 1430 | 112 | 132 |
| 187 | 1439 | 241 | 261 |
| 188 | 1342 | 11 | 31 |
| 188 | 1541 | 11 | 31 |
| 189 | 1367 | 11 | 31 |
| 189 | 1391 | 63 | 83 |
| 189 | 1414 | 11 | 31 |
| 189 | 1427 | 11 | 31 |
| 189 | 1530 | 11 | 31 |
| 189 | 1602 | 11 | 31 |
| 189 | 1603 | 11 | 31 |
| 189 | 1604 | 11 | 31 |
| 189 | 1605 | 10 | 30 |
| 189 | 1606 | 11 | 31 |
| 189 | 1607 | 11 | 31 |
| 189 | 1608 | 11 | 31 |
| 189 | 1609 | 11 | 31 |
| 189 | 1610 | 11 | 31 |
| 190 | 1403 | 11 | 31 |
| 190 | 1471 | 11 | 31 |
| 190 | 1497 | 11 | 31 |
| 191 | 1318 | 72 | 92 |
| 191 | 1319 | 72 | 92 |
| 191 | 1321 | 11 | 31 |
| 191 | 1325 | 11 | 31 |
| 191 | 1327 | 11 | 31 |
| 191 | 1328 | 11 | 31 |
| 191 | 1331 | 72 | 92 |
| 191 | 1332 | 72 | 92 |
| 191 | 1335 | 72 | 92 |
| 191 | 1351 | 11 | 31 |
| 191 | 1357 | 11 | 31 |
| 191 | 1359 | 75 | 95 |
| 191 | 1361 | 72 | 92 |
| 191 | 1362 | 11 | 31 |
| 191 | 1363 | 72 | 92 |
| 191 | 1368 | 11 | 31 |
| 191 | 1370 | 72 | 92 |
| 191 | 1373 | 72 | 92 |
| 191 | 1374 | 72 | 92 |
| 191 | 1375 | 11 | 31 |
| 191 | 1377 | 11 | 31 |
| 191 | 1378 | 72 | 92 |
| 191 | 1379 | 72 | 92 |
| 192 | 1356 | 11 | 31 |
| 193 | 1323 | 77 | 97 |
| 193 | 1354 | 11 | 31 |
| 193 | 1387 | 11 | 31 |
| 193 | 1388 | 11 | 31 |
| 193 | 1433 | 112 | 132 |
| 193 | 1444 | 11 | 31 |
| 193 | 1445 | 11 | 31 |
| 193 | 1446 | 11 | 31 |
| 193 | 1473 | 77 | 97 |
| 193 | 1486 | 11 | 31 |
| 193 | 1501 | 11 | 31 |
| 193 | 1580 | 75 | 95 |
| 194 | 1472 | 33 | 53 |
| 195 | 1600 | 63 | 83 |
| 196 | 1663 | 281 | 299 |
| 197 | 2542 | 11 | 31 |
| 198 | 2532 | 11 | 31 |
| 199 | 1977 | 66 | 86 |
| 200 | 1946 | 11 | 30 |
| 201 | 2365 | 11 | 31 |
| 202 | 1735 | 34 | 53 |
| 203 | 2046 | 64 | 84 |
| 204 | 1746 | 281 | 301 |
| 205 | 1778 | 11 | 31 |
| 206 | 2189 | 45 | 64 |
| 207 | 2549 | 11 | 31 |
| 208 | 2597 | 11 | 31 |
| 209 | 2519 | 195 | 214 |
| 210 | 1829 | 257 | 277 |
| 211 | 2291 | 241 | 260 |
| 212 | 1938 | 11 | 30 |
| 212 | 1994 | 11 | 30 |
| 213 | 2056 | 144 | 164 |
| 213 | 2265 | 137 | 157 |
| 214 | 1950 | 264 | 283 |
| 214 | 2039 | 225 | 244 |
| 214 | 2148 | 225 | 244 |
| 214 | 2358 | 225 | 244 |
| 214 | 2491 | 209 | 228 |
| 215 | 2116 | 194 | 213 |
| 216 | 2273 | 258 | 278 |
| 217 | 1631 | 252 | 270 |
| 218 | 1679 | 11 | 31 |
| 219 | 2304 | 11 | 30 |
| 220 | 2071 | 85 | 105 |
| 221 | 1813 | 281 | 301 |
| 222 | 2604 | 201 | 220 |
| 223 | 2054 | 11 | 30 |
| 224 | 2653 | 124 | 147 |
| 225 | 1761 | 134 | 153 |
| 226 | 2554 | 11 | 29 |
| 227 | 1713 | 259 | 277 |
| 228 | 2557 | 11 | 31 |
| 229 | 1860 | 11 | 31 |
| 229 | 1922 | 41 | 61 |
| 230 | 2582 | 11 | 31 |
| 231 | 2309 | 104 | 122 |
| 232 | 1913 | 11 | 31 |
| 233 | 1747 | 11 | 31 |
| 234 | 1644 | 11 | 30 |
| 235 | 2174 | 11 | 31 |
| 236 | 2017 | 100 | 120 |
| 236 | 2120 | 98 | 118 |
| 237 | 2010 | 113 | 132 |
| 238 | 2528 | 11 | 31 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 239 | 2417 | 11 | 30 |
| 240 | 1802 | 112 | 130 |
| 240 | 2299 | 200 | 218 |
| 240 | 2591 | 243 | 261 |
| 240 | 2592 | 11 | 29 |
| 241 | 1643 | 11 | 30 |
| 241 | 2122 | 11 | 30 |
| 241 | 2280 | 11 | 30 |
| 242 | 2489 | 11 | 30 |
| 243 | 2074 | 274 | 294 |
| 244 | 1890 | 266 | 285 |
| 245 | 2139 | 193 | 216 |
| 246 | 1892 | 80 | 100 |
| 247 | 1861 | 55 | 77 |
| 248 | 2676 | 11 | 30 |
| 249 | 2681 | 272 | 291 |
| 249 | 2682 | 11 | 30 |
| 250 | 2005 | 73 | 93 |
| 250 | 2092 | 73 | 93 |
| 250 | 2406 | 52 | 72 |
| 251 | 2202 | 11 | 29 |
| 252 | 1919 | 239 | 258 |
| 253 | 2409 | 248 | 271 |
| 254 | 1926 | 11 | 31 |
| 255 | 2445 | 247 | 267 |
| 256 | 1804 | 11 | 31 |
| 257 | 1774 | 149 | 168 |
| 258 | 2394 | 11 | 31 |
| 259 | 1697 | 87 | 107 |
| 260 | 2268 | 37 | 55 |
| 261 | 2063 | 281 | 304 |
| 262 | 1686 | 11 | 31 |
| 263 | 2184 | 11 | 31 |
| 264 | 2158 | 48 | 67 |
| 264 | 2399 | 217 | 236 |
| 265 | 2353 | 11 | 34 |
| 266 | 2524 | 11 | 31 |
| 267 | 2183 | 11 | 30 |
| 268 | 2140 | 146 | 169 |
| 269 | 2038 | 11 | 31 |
| 270 | 2257 | 54 | 74 |
| 271 | 2389 | 112 | 131 |
| 272 | 2522 | 256 | 275 |
| 273 | 2422 | 37 | 56 |
| 274 | 1969 | 11 | 29 |
| 275 | 2481 | 228 | 248 |
| 276 | 2080 | 92 | 112 |
| 277 | 2261 | 59 | 78 |
| 278 | 2368 | 166 | 188 |
| 279 | 1627 | 11 | 30 |
| 280 | 2006 | 11 | 31 |
| 281 | 2431 | 11 | 30 |
| 282 | 2200 | 228 | 248 |
| 283 | 2081 | 38 | 58 |
| 284 | 1902 | 11 | 31 |
| 285 | 2343 | 11 | 31 |
| 286 | 1887 | 233 | 253 |
| 287 | 2393 | 139 | 159 |
| 288 | 2262 | 47 | 67 |
| 289 | 2137 | 71 | 91 |
| 290 | 2684 | 11 | 31 |
| 291 | 1771 | 30 | 49 |
| 292 | 1807 | 238 | 256 |
| 292 | 1954 | 11 | 29 |
| 293 | 2103 | 11 | 30 |
| 294 | 2656 | 11 | 31 |
| 295 | 2488 | 11 | 30 |
| 296 | 1848 | 63 | 83 |
| 297 | 2514 | 37 | 57 |
| 298 | 1845 | 11 | 31 |
| 299 | 2157 | 11 | 30 |
| 300 | 2415 | 69 | 89 |
| 301 | 2520 | 278 | 298 |
| 302 | 2584 | 11 | 31 |
| 303 | 2474 | 11 | 30 |
| 304 | 2536 | 32 | 51 |
| 305 | 1728 | 281 | 301 |
| 306 | 2228 | 11 | 31 |
| 306 | 2240 | 11 | 31 |
| 307 | 2483 | 11 | 30 |
| 308 | 1784 | 11 | 29 |
| 309 | 1847 | 125 | 145 |
| 310 | 1872 | 42 | 61 |
| 311 | 1759 | 11 | 34 |
| 311 | 1999 | 11 | 34 |
| 311 | 2223 | 11 | 34 |
| 311 | 2543 | 11 | 34 |
| 312 | 2232 | 141 | 160 |
| 313 | 1658 | 103 | 122 |
| 313 | 2107 | 146 | 165 |
| 314 | 2581 | 11 | 31 |
| 315 | 2471 | 11 | 31 |
| 316 | 2106 | 72 | 92 |
| 317 | 2043 | 66 | 86 |
| 318 | 1963 | 200 | 219 |
| 319 | 2121 | 11 | 30 |
| 319 | 2373 | 11 | 30 |
| 319 | 2475 | 11 | 30 |
| 319 | 2566 | 96 | 115 |
| 320 | 1685 | 11 | 31 |
| 321 | 2464 | 11 | 31 |
| 322 | 1822 | 39 | 57 |
| 323 | 1858 | 11 | 31 |
| 324 | 2003 | 40 | 60 |
| 325 | 2531 | 35 | 54 |
| 326 | 1827 | 11 | 30 |
| 327 | 2465 | 11 | 30 |
| 328 | 1973 | 11 | 30 |
| 329 | 2279 | 262 | 281 |
| 330 | 1857 | 62 | 81 |
| 331 | 2527 | 11 | 31 |
| 332 | 1755 | 46 | 66 |
| 333 | 1850 | 11 | 31 |
| 333 | 2145 | 11 | 31 |
| 333 | 2296 | 11 | 31 |
| 333 | 2400 | 11 | 31 |
| 333 | 2636 | 11 | 31 |
| 334 | 1951 | 11 | 31 |
| 335 | 2510 | 36 | 55 |
| 336 | 1700 | 11 | 31 |
| 336 | 2622 | 11 | 31 |
| 337 | 2446 | 242 | 262 |
| 338 | 2082 | 11 | 32 |
| 339 | 2301 | 11 | 31 |
| 340 | 1721 | 11 | 30 |
| 341 | 1876 | 11 | 31 |
| 342 | 2659 | 11 | 30 |
| 343 | 1937 | 11 | 31 |
| 344 | 1864 | 11 | 30 |
| 345 | 1869 | 128 | 148 |
| 346 | 1692 | 11 | 30 |
| 347 | 2276 | 277 | 297 |
| 348 | 2141 | 11 | 29 |
| 349 | 2023 | 11 | 31 |
| 350 | 2219 | 11 | 31 |
| 351 | 2472 | 176 | 196 |
| 352 | 1724 | 11 | 31 |
| 353 | 1955 | 11 | 30 |
| 354 | 2426 | 11 | 31 |
| 355 | 1978 | 57 | 76 |
| 356 | 1881 | 60 | 80 |
| 357 | 1974 | 163 | 182 |
| 358 | 2466 | 11 | 30 |
| 359 | 1633 | 44 | 63 |
| 359 | 1797 | 102 | 121 |
| 359 | 1889 | 11 | 30 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 359 | 2128 | 281 | 300 |
| 359 | 2129 | 11 | 30 |
| 359 | 2254 | 11 | 30 |
| 360 | 2241 | 115 | 135 |
| 360 | 2363 | 114 | 134 |
| 361 | 2117 | 39 | 58 |
| 361 | 2513 | 11 | 30 |
| 361 | 2530 | 39 | 58 |
| 362 | 2533 | 51 | 69 |
| 363 | 1707 | 89 | 109 |
| 364 | 1801 | 41 | 61 |
| 365 | 2428 | 41 | 61 |
| 366 | 2221 | 31 | 50 |
| 366 | 2439 | 280 | 299 |
| 367 | 1852 | 29 | 48 |
| 367 | 2252 | 30 | 49 |
| 368 | 2069 | 11 | 30 |
| 369 | 2462 | 11 | 30 |
| 370 | 2031 | 11 | 30 |
| 371 | 2197 | 36 | 56 |
| 372 | 2603 | 11 | 30 |
| 373 | 2111 | 74 | 93 |
| 374 | 1790 | 11 | 31 |
| 375 | 1840 | 89 | 112 |
| 375 | 2463 | 89 | 112 |
| 375 | 2634 | 89 | 112 |
| 375 | 2655 | 89 | 112 |
| 376 | 1866 | 50 | 70 |
| 376 | 2004 | 280 | 300 |
| 377 | 1714 | 271 | 290 |
| 377 | 2482 | 271 | 290 |
| 378 | 2587 | 11 | 31 |
| 379 | 1675 | 11 | 31 |
| 379 | 2234 | 11 | 31 |
| 380 | 2249 | 11 | 31 |
| 381 | 1701 | 11 | 29 |
| 382 | 2555 | 64 | 83 |
| 383 | 2271 | 11 | 30 |
| 384 | 1796 | 45 | 64 |
| 385 | 2113 | 11 | 31 |
| 385 | 2230 | 60 | 80 |
| 385 | 2277 | 11 | 31 |
| 385 | 2302 | 11 | 31 |
| 385 | 2392 | 11 | 31 |
| 385 | 2590 | 60 | 80 |
| 386 | 1883 | 210 | 229 |
| 387 | 2494 | 40 | 59 |
| 388 | 1928 | 11 | 31 |
| 388 | 2193 | 11 | 31 |
| 388 | 2617 | 11 | 31 |
| 389 | 2013 | 11 | 30 |
| 390 | 1862 | 11 | 30 |
| 391 | 1824 | 276 | 294 |
| 391 | 1984 | 152 | 170 |
| 391 | 1985 | 11 | 29 |
| 392 | 1968 | 11 | 30 |
| 392 | 2505 | 11 | 30 |
| 393 | 1763 | 108 | 128 |
| 394 | 1667 | 137 | 157 |
| 395 | 1952 | 11 | 30 |
| 395 | 1983 | 11 | 30 |
| 396 | 1789 | 11 | 31 |
| 397 | 1907 | 42 | 60 |
| 398 | 2668 | 11 | 31 |
| 399 | 2138 | 11 | 31 |
| 400 | 2175 | 11 | 31 |
| 401 | 2323 | 11 | 31 |
| 402 | 2669 | 11 | 31 |
| 403 | 1795 | 95 | 114 |
| 403 | 2326 | 11 | 30 |
| 404 | 1948 | 47 | 67 |
| 404 | 2380 | 47 | 67 |
| 405 | 2470 | 11 | 30 |
| 406 | 1680 | 11 | 31 |
| 406 | 2355 | 11 | 31 |
| 407 | 2251 | 64 | 83 |
| 408 | 2499 | 71 | 90 |
| 409 | 1911 | 11 | 34 |
| 410 | 2162 | 11 | 30 |
| 411 | 2360 | 11 | 31 |
| 412 | 2073 | 11 | 30 |
| 413 | 2231 | 35 | 55 |
| 414 | 1637 | 11 | 30 |
| 415 | 1673 | 11 | 30 |
| 416 | 1819 | 11 | 29 |
| 417 | 2529 | 49 | 68 |
| 418 | 1785 | 277 | 296 |
| 419 | 2379 | 45 | 65 |
| 420 | 1958 | 248 | 268 |
| 420 | 2123 | 248 | 268 |
| 420 | 2218 | 247 | 267 |
| 421 | 1874 | 71 | 91 |
| 422 | 2352 | 11 | 30 |
| 422 | 2635 | 11 | 30 |
| 423 | 2297 | 245 | 265 |
| 424 | 2680 | 280 | 298 |
| 425 | 2552 | 252 | 272 |
| 426 | 1893 | 11 | 34 |
| 427 | 2068 | 183 | 203 |
| 428 | 2225 | 165 | 184 |
| 429 | 1738 | 11 | 31 |
| 430 | 2640 | 11 | 31 |
| 431 | 2083 | 11 | 30 |
| 432 | 2233 | 221 | 241 |
| 433 | 2097 | 102 | 121 |
| 434 | 2623 | 11 | 29 |
| 435 | 2272 | 11 | 34 |
| 436 | 2246 | 11 | 30 |
| 436 | 2449 | 11 | 30 |
| 437 | 2217 | 11 | 31 |
| 438 | 1638 | 11 | 29 |
| 438 | 1639 | 273 | 291 |
| 438 | 1695 | 11 | 29 |
| 439 | 2227 | 124 | 144 |
| 439 | 2660 | 118 | 138 |
| 440 | 1688 | 90 | 110 |
| 441 | 1622 | 120 | 140 |
| 442 | 2388 | 34 | 54 |
| 443 | 1708 | 240 | 258 |
| 443 | 1709 | 11 | 29 |
| 443 | 2179 | 11 | 29 |
| 443 | 2547 | 11 | 29 |
| 444 | 1699 | 11 | 31 |
| 444 | 2099 | 11 | 31 |
| 445 | 2550 | 11 | 31 |
| 445 | 2601 | 11 | 31 |
| 446 | 2020 | 11 | 31 |
| 447 | 1915 | 281 | 300 |
| 447 | 1916 | 11 | 30 |
| 448 | 1705 | 174 | 193 |
| 448 | 2027 | 173 | 192 |
| 449 | 1677 | 11 | 31 |
| 450 | 1870 | 77 | 97 |
| 451 | 1781 | 11 | 31 |
| 452 | 2480 | 85 | 105 |
| 452 | 2512 | 84 | 104 |
| 453 | 2454 | 129 | 149 |
| 454 | 1719 | 48 | 68 |
| 454 | 2347 | 48 | 68 |
| 455 | 2435 | 11 | 31 |
| 456 | 1811 | 11 | 31 |
| 456 | 2154 | 11 | 31 |
| 457 | 1901 | 207 | 227 |
| 458 | 1917 | 174 | 194 |
| 459 | 2053 | 55 | 74 |
| 460 | 2476 | 11 | 32 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 461 | 2091 | 11 | 30 |
| 462 | 1668 | 46 | 65 |
| 462 | 2503 | 46 | 65 |
| 463 | 2420 | 254 | 274 |
| 464 | 2626 | 281 | 302 |
| 465 | 2468 | 281 | 301 |
| 466 | 1908 | 281 | 301 |
| 467 | 2247 | 203 | 222 |
| 467 | 2553 | 182 | 201 |
| 468 | 2455 | 11 | 30 |
| 469 | 1859 | 34 | 54 |
| 469 | 2334 | 34 | 54 |
| 470 | 1828 | 11 | 30 |
| 471 | 2586 | 11 | 30 |
| 472 | 2014 | 11 | 30 |
| 473 | 1788 | 11 | 31 |
| 474 | 2632 | 11 | 31 |
| 475 | 2509 | 11 | 31 |
| 476 | 2535 | 11 | 30 |
| 477 | 2147 | 11 | 31 |
| 478 | 1960 | 11 | 31 |
| 479 | 1783 | 11 | 31 |
| 480 | 2541 | 11 | 31 |
| 481 | 2169 | 202 | 221 |
| 482 | 1703 | 147 | 167 |
| 483 | 1775 | 148 | 168 |
| 484 | 1839 | 11 | 30 |
| 485 | 2119 | 56 | 76 |
| 486 | 1906 | 152 | 170 |
| 486 | 2143 | 11 | 29 |
| 487 | 2633 | 76 | 96 |
| 488 | 1734 | 132 | 150 |
| 488 | 2045 | 133 | 151 |
| 488 | 2506 | 129 | 147 |
| 488 | 2672 | 134 | 152 |
| 489 | 1772 | 58 | 78 |
| 490 | 1687 | 11 | 34 |
| 491 | 2649 | 76 | 96 |
| 492 | 2436 | 73 | 93 |
| 493 | 1798 | 11 | 31 |
| 494 | 2335 | 11 | 30 |
| 495 | 2568 | 11 | 31 |
| 496 | 2627 | 80 | 100 |
| 497 | 2461 | 11 | 31 |
| 498 | 1745 | 141 | 161 |
| 498 | 1949 | 11 | 31 |
| 499 | 2130 | 30 | 50 |
| 500 | 1660 | 11 | 30 |
| 501 | 2002 | 11 | 30 |
| 502 | 1882 | 11 | 31 |
| 503 | 1956 | 11 | 34 |
| 504 | 1694 | 11 | 30 |
| 504 | 1903 | 11 | 30 |
| 504 | 2395 | 11 | 30 |
| 504 | 2515 | 11 | 30 |
| 505 | 2151 | 279 | 300 |
| 506 | 1787 | 11 | 31 |
| 506 | 2126 | 89 | 109 |
| 506 | 2127 | 11 | 31 |
| 507 | 2317 | 135 | 154 |
| 508 | 2180 | 11 | 31 |
| 509 | 2346 | 11 | 31 |
| 509 | 2645 | 11 | 31 |
| 510 | 1936 | 11 | 30 |
| 510 | 2516 | 11 | 30 |
| 511 | 2245 | 11 | 30 |
| 512 | 2354 | 137 | 157 |
| 512 | 2478 | 141 | 161 |
| 513 | 2411 | 47 | 67 |
| 514 | 1716 | 35 | 55 |
| 515 | 2283 | 11 | 31 |
| 516 | 2095 | 11 | 31 |
| 517 | 2432 | 11 | 31 |
| 518 | 2608 | 165 | 185 |
| 519 | 2041 | 11 | 30 |
| 520 | 2487 | 11 | 31 |
| 521 | 1757 | 35 | 54 |
| 522 | 1702 | 221 | 241 |
| 523 | 1792 | 72 | 94 |
| 523 | 2266 | 62 | 84 |
| 524 | 2258 | 11 | 31 |
| 525 | 2458 | 65 | 85 |
| 526 | 1682 | 80 | 100 |
| 526 | 1760 | 66 | 86 |
| 526 | 2035 | 80 | 100 |
| 526 | 2253 | 62 | 82 |
| 527 | 1765 | 42 | 62 |
| 528 | 2098 | 11 | 30 |
| 529 | 1710 | 196 | 215 |
| 530 | 2371 | 124 | 143 |
| 531 | 1920 | 11 | 30 |
| 532 | 2396 | 11 | 31 |
| 533 | 2518 | 126 | 145 |
| 534 | 1962 | 255 | 276 |
| 535 | 2366 | 54 | 74 |
| 536 | 2671 | 234 | 254 |
| 537 | 2308 | 178 | 197 |
| 538 | 1953 | 11 | 31 |
| 539 | 1704 | 41 | 60 |
| 540 | 1768 | 133 | 153 |
| 540 | 1803 | 129 | 149 |
| 540 | 2114 | 216 | 236 |
| 541 | 2374 | 11 | 31 |
| 542 | 2613 | 11 | 30 |
| 543 | 1820 | 176 | 195 |
| 544 | 1776 | 11 | 31 |
| 545 | 1897 | 158 | 177 |
| 546 | 2434 | 112 | 132 |
| 546 | 2517 | 112 | 132 |
| 547 | 2168 | 11 | 31 |
| 547 | 2690 | 11 | 31 |
| 548 | 1794 | 11 | 30 |
| 549 | 2311 | 55 | 75 |
| 550 | 1676 | 11 | 31 |
| 551 | 2131 | 11 | 31 |
| 552 | 1753 | 11 | 31 |
| 553 | 1867 | 11 | 31 |
| 554 | 2544 | 11 | 31 |
| 555 | 2407 | 11 | 31 |
| 556 | 2595 | 270 | 290 |
| 557 | 1681 | 251 | 271 |
| 557 | 2339 | 251 | 271 |
| 557 | 2375 | 222 | 242 |
| 557 | 2473 | 251 | 271 |
| 557 | 2589 | 251 | 271 |
| 558 | 2236 | 82 | 102 |
| 559 | 2629 | 11 | 30 |
| 560 | 1832 | 177 | 197 |
| 561 | 1737 | 11 | 31 |
| 562 | 2523 | 11 | 31 |
| 563 | 1625 | 11 | 31 |
| 563 | 2327 | 281 | 301 |
| 564 | 1930 | 55 | 74 |
| 564 | 2560 | 55 | 74 |
| 565 | 2325 | 40 | 60 |
| 566 | 1725 | 115 | 135 |
| 567 | 1684 | 11 | 31 |
| 568 | 1729 | 272 | 290 |
| 568 | 1766 | 205 | 223 |
| 568 | 2108 | 119 | 137 |
| 568 | 2307 | 262 | 280 |
| 568 | 2367 | 11 | 29 |
| 569 | 2644 | 54 | 73 |
| 570 | 1947 | 11 | 31 |
| 570 | 2185 | 11 | 31 |
| 570 | 2384 | 11 | 31 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 571 | 2594 | 78 | 97 |
| 572 | 2062 | 11 | 31 |
| 573 | 2290 | 232 | 250 |
| 574 | 2314 | 11 | 31 |
| 575 | 1793 | 11 | 31 |
| 576 | 1645 | 59 | 79 |
| 576 | 2239 | 280 | 300 |
| 577 | 2293 | 111 | 130 |
| 578 | 1629 | 11 | 30 |
| 579 | 2643 | 11 | 31 |
| 580 | 1970 | 11 | 30 |
| 581 | 1929 | 11 | 33 |
| 582 | 2538 | 11 | 30 |
| 583 | 1786 | 102 | 122 |
| 583 | 2639 | 50 | 70 |
| 584 | 1986 | 11 | 34 |
| 585 | 1698 | 53 | 72 |
| 585 | 2391 | 54 | 73 |
| 586 | 1894 | 11 | 30 |
| 587 | 2559 | 213 | 231 |
| 587 | 2576 | 11 | 29 |
| 588 | 1619 | 36 | 56 |
| 589 | 1868 | 11 | 30 |
| 590 | 1621 | 281 | 299 |
| 591 | 2067 | 245 | 265 |
| 592 | 2457 | 11 | 31 |
| 593 | 2163 | 11 | 31 |
| 594 | 2207 | 11 | 30 |
| 595 | 2190 | 34 | 53 |
| 596 | 2206 | 30 | 49 |
| 597 | 2364 | 11 | 31 |
| 598 | 2673 | 11 | 31 |
| 599 | 1886 | 244 | 264 |
| 600 | 1844 | 68 | 87 |
| 601 | 2016 | 11 | 31 |
| 601 | 2089 | 11 | 31 |
| 601 | 2161 | 11 | 31 |
| 601 | 2306 | 11 | 31 |
| 601 | 2429 | 11 | 31 |
| 602 | 2332 | 37 | 57 |
| 603 | 2338 | 68 | 88 |
| 604 | 2638 | 74 | 93 |
| 605 | 2036 | 11 | 29 |
| 606 | 2619 | 11 | 32 |
| 607 | 2001 | 90 | 109 |
| 608 | 1640 | 11 | 29 |
| 608 | 2502 | 11 | 29 |
| 609 | 1964 | 69 | 87 |
| 610 | 2152 | 11 | 31 |
| 611 | 1764 | 11 | 31 |
| 612 | 2146 | 179 | 198 |
| 613 | 1837 | 190 | 210 |
| 614 | 2427 | 105 | 125 |
| 615 | 2178 | 11 | 30 |
| 616 | 1750 | 11 | 31 |
| 616 | 1923 | 11 | 31 |
| 616 | 2172 | 11 | 31 |
| 616 | 2259 | 11 | 31 |
| 616 | 2275 | 11 | 31 |
| 616 | 2610 | 11 | 31 |
| 617 | 2548 | 112 | 132 |
| 618 | 2135 | 84 | 104 |
| 619 | 2479 | 100 | 119 |
| 620 | 2007 | 55 | 75 |
| 620 | 2008 | 11 | 31 |
| 621 | 1642 | 91 | 111 |
| 621 | 1865 | 98 | 118 |
| 621 | 2048 | 106 | 126 |
| 622 | 1654 | 11 | 30 |
| 623 | 2526 | 11 | 31 |
| 624 | 2410 | 11 | 31 |
| 625 | 2450 | 11 | 31 |
| 626 | 2571 | 274 | 292 |
| 627 | 1649 | 11 | 31 |
| 627 | 1717 | 11 | 31 |
| 627 | 1943 | 11 | 31 |
| 627 | 2094 | 11 | 31 |
| 627 | 2260 | 11 | 31 |
| 627 | 2303 | 11 | 31 |
| 627 | 2593 | 11 | 31 |
| 628 | 2646 | 125 | 145 |
| 629 | 2378 | 40 | 60 |
| 630 | 2451 | 53 | 72 |
| 631 | 1885 | 133 | 151 |
| 632 | 2153 | 245 | 264 |
| 633 | 2689 | 11 | 31 |
| 634 | 2133 | 11 | 31 |
| 635 | 1657 | 11 | 30 |
| 635 | 2040 | 80 | 99 |
| 636 | 2419 | 126 | 145 |
| 637 | 2024 | 247 | 265 |
| 638 | 1770 | 11 | 31 |
| 639 | 1626 | 73 | 93 |
| 640 | 2220 | 95 | 115 |
| 641 | 2430 | 11 | 31 |
| 642 | 2181 | 11 | 31 |
| 643 | 2447 | 11 | 31 |
| 644 | 1647 | 127 | 150 |
| 644 | 1995 | 183 | 206 |
| 644 | 2546 | 184 | 207 |
| 645 | 2324 | 11 | 31 |
| 646 | 2101 | 222 | 241 |
| 647 | 1931 | 11 | 31 |
| 648 | 1863 | 35 | 54 |
| 648 | 2115 | 279 | 298 |
| 649 | 2630 | 11 | 31 |
| 650 | 2609 | 84 | 103 |
| 651 | 2165 | 39 | 58 |
| 652 | 1980 | 38 | 58 |
| 653 | 2390 | 274 | 294 |
| 654 | 1918 | 105 | 125 |
| 655 | 1779 | 11 | 31 |
| 656 | 2424 | 110 | 129 |
| 657 | 1944 | 33 | 52 |
| 658 | 2049 | 165 | 184 |
| 659 | 2282 | 67 | 87 |
| 660 | 2194 | 11 | 30 |
| 661 | 2000 | 281 | 300 |
| 662 | 2061 | 275 | 295 |
| 663 | 2562 | 11 | 31 |
| 664 | 1988 | 11 | 30 |
| 665 | 1722 | 281 | 300 |
| 666 | 2285 | 11 | 31 |
| 667 | 2318 | 11 | 34 |
| 668 | 2421 | 11 | 31 |
| 669 | 2021 | 236 | 256 |
| 670 | 2212 | 146 | 166 |
| 671 | 1623 | 47 | 65 |
| 672 | 2029 | 11 | 30 |
| 673 | 1810 | 11 | 31 |
| 674 | 1875 | 11 | 31 |
| 675 | 2284 | 107 | 127 |
| 675 | 2397 | 107 | 127 |
| 676 | 2109 | 11 | 31 |
| 677 | 2337 | 11 | 30 |
| 678 | 1942 | 11 | 30 |
| 679 | 2572 | 11 | 31 |
| 680 | 2173 | 11 | 30 |
| 681 | 1992 | 11 | 31 |
| 682 | 1849 | 11 | 30 |
| 683 | 2565 | 63 | 82 |
| 684 | 2086 | 11 | 30 |
| 685 | 2561 | 53 | 72 |
| 685 | 2625 | 53 | 72 |
| 686 | 1834 | 60 | 80 |
| 687 | 2077 | 11 | 30 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 688 | 2051 | 92 | 112 |
| 688 | 2508 | 81 | 101 |
| 689 | 2484 | 11 | 31 |
| 690 | 1666 | 68 | 89 |
| 691 | 2105 | 11 | 30 |
| 691 | 2599 | 11 | 30 |
| 692 | 1630 | 33 | 53 |
| 693 | 1971 | 68 | 88 |
| 694 | 2047 | 11 | 30 |
| 695 | 1674 | 207 | 226 |
| 695 | 1909 | 72 | 91 |
| 695 | 2198 | 246 | 265 |
| 695 | 2199 | 11 | 30 |
| 695 | 2537 | 80 | 99 |
| 696 | 2319 | 11 | 35 |
| 697 | 2011 | 195 | 215 |
| 698 | 1818 | 11 | 29 |
| 698 | 1846 | 11 | 29 |
| 698 | 2030 | 11 | 29 |
| 698 | 2166 | 11 | 29 |
| 698 | 2242 | 37 | 55 |
| 698 | 2674 | 62 | 80 |
| 698 | 2675 | 11 | 29 |
| 699 | 2647 | 11 | 31 |
| 700 | 2686 | 214 | 234 |
| 701 | 2018 | 151 | 170 |
| 701 | 2351 | 125 | 144 |
| 702 | 2614 | 234 | 253 |
| 703 | 1957 | 11 | 31 |
| 704 | 1731 | 11 | 30 |
| 705 | 2079 | 218 | 238 |
| 706 | 2370 | 281 | 301 |
| 707 | 2340 | 11 | 31 |
| 708 | 1830 | 11 | 31 |
| 709 | 1921 | 11 | 31 |
| 710 | 2093 | 33 | 52 |
| 711 | 1665 | 191 | 210 |
| 712 | 2651 | 11 | 31 |
| 713 | 2534 | 79 | 100 |
| 713 | 2662 | 79 | 100 |
| 714 | 2144 | 11 | 35 |
| 715 | 2064 | 11 | 31 |
| 716 | 2545 | 86 | 105 |
| 717 | 1636 | 11 | 31 |
| 718 | 2248 | 11 | 30 |
| 719 | 2320 | 11 | 30 |
| 720 | 1739 | 99 | 119 |
| 721 | 2286 | 11 | 31 |
| 722 | 2321 | 11 | 31 |
| 723 | 2216 | 36 | 55 |
| 724 | 1814 | 82 | 105 |
| 725 | 2288 | 11 | 30 |
| 726 | 2256 | 245 | 263 |
| 727 | 1905 | 11 | 31 |
| 727 | 2440 | 11 | 31 |
| 728 | 1998 | 71 | 91 |
| 729 | 1624 | 54 | 74 |
| 730 | 1940 | 11 | 31 |
| 730 | 2328 | 111 | 131 |
| 731 | 1662 | 11 | 29 |
| 732 | 2118 | 11 | 30 |
| 733 | 1809 | 60 | 79 |
| 733 | 2037 | 183 | 202 |
| 733 | 2150 | 73 | 92 |
| 734 | 2596 | 11 | 31 |
| 735 | 2414 | 11 | 31 |
| 736 | 2192 | 11 | 31 |
| 737 | 2196 | 11 | 30 |
| 738 | 2521 | 39 | 59 |
| 739 | 1678 | 11 | 31 |
| 740 | 1791 | 152 | 172 |
| 740 | 1853 | 158 | 178 |
| 740 | 2134 | 155 | 175 |
| 741 | 2058 | 129 | 149 |
| 742 | 1635 | 194 | 214 |
| 742 | 1914 | 11 | 31 |
| 742 | 2362 | 11 | 31 |
| 743 | 1653 | 220 | 238 |
| 743 | 2104 | 281 | 299 |
| 744 | 2300 | 11 | 31 |
| 745 | 1648 | 82 | 102 |
| 746 | 2423 | 11 | 30 |
| 746 | 2648 | 11 | 30 |
| 747 | 2305 | 11 | 30 |
| 748 | 1855 | 11 | 30 |
| 748 | 1961 | 11 | 30 |
| 749 | 1982 | 11 | 34 |
| 749 | 2022 | 11 | 34 |
| 749 | 2075 | 11 | 34 |
| 749 | 2292 | 11 | 34 |
| 750 | 2344 | 11 | 29 |
| 751 | 2019 | 53 | 73 |
| 752 | 1758 | 74 | 94 |
| 753 | 1780 | 32 | 52 |
| 754 | 2631 | 99 | 119 |
| 755 | 2564 | 11 | 31 |
| 756 | 2570 | 11 | 31 |
| 757 | 2574 | 44 | 63 |
| 758 | 1880 | 11 | 29 |
| 759 | 1799 | 11 | 31 |
| 760 | 2469 | 85 | 104 |
| 761 | 2066 | 11 | 30 |
| 762 | 1826 | 11 | 31 |
| 763 | 2382 | 11 | 31 |
| 764 | 2132 | 233 | 253 |
| 764 | 2177 | 233 | 253 |
| 765 | 2688 | 11 | 31 |
| 766 | 1773 | 87 | 105 |
| 767 | 2160 | 11 | 31 |
| 768 | 1945 | 225 | 244 |
| 769 | 2342 | 266 | 284 |
| 770 | 1712 | 102 | 121 |
| 771 | 2087 | 11 | 30 |
| 771 | 2235 | 11 | 30 |
| 771 | 2567 | 11 | 30 |
| 772 | 2270 | 11 | 31 |
| 772 | 2312 | 11 | 31 |
| 772 | 2383 | 11 | 31 |
| 772 | 2657 | 11 | 31 |
| 773 | 2176 | 178 | 197 |
| 774 | 1748 | 11 | 30 |
| 774 | 1842 | 11 | 30 |
| 775 | 1723 | 45 | 64 |
| 775 | 2615 | 45 | 64 |
| 776 | 2072 | 11 | 31 |
| 777 | 1655 | 11 | 30 |
| 778 | 1989 | 123 | 146 |
| 779 | 2032 | 11 | 30 |
| 779 | 2263 | 11 | 30 |
| 779 | 2425 | 11 | 30 |
| 779 | 2620 | 11 | 30 |
| 780 | 1805 | 11 | 30 |
| 780 | 2149 | 11 | 30 |
| 780 | 2331 | 11 | 30 |
| 780 | 2477 | 11 | 30 |
| 780 | 2511 | 11 | 30 |
| 781 | 2563 | 164 | 184 |
| 782 | 2208 | 149 | 168 |
| 783 | 2186 | 275 | 294 |
| 784 | 1823 | 11 | 32 |
| 785 | 1879 | 11 | 31 |
| 786 | 2666 | 11 | 31 |
| 787 | 2490 | 279 | 298 |
| 788 | 1752 | 11 | 31 |
| 789 | 2052 | 89 | 109 |
| 789 | 2628 | 89 | 109 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 790 | 1733 | 62 | 82 |
| 791 | 1777 | 11 | 31 |
| 791 | 2412 | 11 | 31 |
| 791 | 2658 | 11 | 31 |
| 792 | 1898 | 281 | 301 |
| 793 | 1815 | 138 | 157 |
| 794 | 2456 | 181 | 201 |
| 795 | 2112 | 159 | 178 |
| 796 | 1740 | 116 | 136 |
| 797 | 2359 | 11 | 32 |
| 798 | 2441 | 11 | 31 |
| 799 | 2585 | 11 | 31 |
| 800 | 2665 | 11 | 31 |
| 801 | 2313 | 237 | 256 |
| 802 | 1941 | 11 | 30 |
| 803 | 1646 | 130 | 150 |
| 804 | 2349 | 11 | 31 |
| 805 | 1720 | 147 | 167 |
| 805 | 2191 | 147 | 167 |
| 806 | 2100 | 11 | 30 |
| 807 | 1659 | 269 | 289 |
| 808 | 2229 | 269 | 289 |
| 809 | 2443 | 281 | 300 |
| 810 | 2600 | 114 | 134 |
| 811 | 2215 | 216 | 236 |
| 812 | 1693 | 11 | 30 |
| 813 | 1749 | 72 | 92 |
| 813 | 2156 | 72 | 92 |
| 813 | 2278 | 72 | 92 |
| 813 | 2416 | 72 | 92 |
| 813 | 2551 | 116 | 136 |
| 814 | 2195 | 11 | 31 |
| 815 | 2281 | 271 | 291 |
| 816 | 2264 | 11 | 30 |
| 817 | 1711 | 11 | 30 |
| 818 | 1981 | 11 | 31 |
| 819 | 1854 | 11 | 30 |
| 820 | 2413 | 148 | 168 |
| 821 | 2404 | 262 | 282 |
| 822 | 2090 | 44 | 64 |
| 822 | 2654 | 112 | 132 |
| 823 | 2525 | 44 | 64 |
| 824 | 2402 | 128 | 147 |
| 824 | 2606 | 135 | 154 |
| 825 | 2387 | 11 | 31 |
| 826 | 1762 | 11 | 31 |
| 827 | 1895 | 36 | 55 |
| 828 | 2467 | 11 | 31 |
| 829 | 2102 | 11 | 31 |
| 830 | 2588 | 11 | 30 |
| 831 | 1671 | 11 | 31 |
| 832 | 1650 | 11 | 30 |
| 833 | 1843 | 281 | 300 |
| 834 | 1976 | 30 | 49 |
| 834 | 2448 | 30 | 49 |
| 835 | 2125 | 11 | 30 |
| 836 | 2255 | 11 | 31 |
| 837 | 2683 | 37 | 56 |
| 838 | 2274 | 11 | 30 |
| 839 | 1634 | 11 | 31 |
| 840 | 2605 | 281 | 300 |
| 841 | 2497 | 124 | 143 |
| 842 | 2685 | 11 | 31 |
| 843 | 2376 | 281 | 301 |
| 844 | 1925 | 82 | 102 |
| 845 | 2438 | 11 | 31 |
| 846 | 2607 | 11 | 31 |
| 847 | 2398 | 71 | 90 |
| 848 | 2459 | 165 | 185 |
| 849 | 2460 | 234 | 254 |
| 850 | 1975 | 11 | 30 |
| 851 | 2579 | 11 | 30 |
| 852 | 2042 | 11 | 30 |
| 852 | 2385 | 85 | 104 |
| 853 | 1933 | 11 | 31 |
| 854 | 2159 | 214 | 234 |
| 854 | 2369 | 214 | 234 |
| 855 | 2187 | 41 | 60 |
| 855 | 2237 | 44 | 63 |
| 856 | 2269 | 207 | 227 |
| 857 | 2050 | 11 | 31 |
| 858 | 1987 | 82 | 101 |
| 859 | 1656 | 11 | 31 |
| 860 | 2210 | 11 | 31 |
| 861 | 1900 | 11 | 30 |
| 861 | 1979 | 11 | 30 |
| 862 | 1727 | 44 | 64 |
| 863 | 2205 | 200 | 220 |
| 864 | 2164 | 53 | 71 |
| 865 | 2498 | 11 | 30 |
| 866 | 1769 | 42 | 62 |
| 867 | 1726 | 31 | 50 |
| 868 | 1652 | 11 | 29 |
| 868 | 1730 | 156 | 174 |
| 868 | 1884 | 11 | 29 |
| 868 | 1967 | 11 | 29 |
| 869 | 1821 | 279 | 299 |
| 870 | 1620 | 11 | 31 |
| 871 | 1767 | 281 | 300 |
| 872 | 2155 | 11 | 31 |
| 873 | 1800 | 39 | 57 |
| 874 | 2501 | 11 | 31 |
| 875 | 2211 | 226 | 246 |
| 876 | 2009 | 11 | 31 |
| 877 | 2110 | 11 | 31 |
| 878 | 1991 | 11 | 30 |
| 879 | 2044 | 11 | 29 |
| 880 | 1833 | 11 | 31 |
| 881 | 2124 | 173 | 193 |
| 882 | 2408 | 11 | 31 |
| 883 | 1751 | 122 | 142 |
| 884 | 1744 | 11 | 31 |
| 885 | 2289 | 190 | 209 |
| 886 | 1825 | 11 | 31 |
| 887 | 2171 | 11 | 30 |
| 888 | 2345 | 11 | 31 |
| 889 | 2034 | 50 | 69 |
| 890 | 2059 | 11 | 31 |
| 891 | 2026 | 194 | 212 |
| 892 | 2573 | 11 | 32 |
| 893 | 1689 | 11 | 30 |
| 893 | 2201 | 11 | 30 |
| 894 | 1904 | 56 | 76 |
| 895 | 2209 | 11 | 30 |
| 896 | 1736 | 11 | 30 |
| 897 | 2295 | 100 | 120 |
| 898 | 2330 | 11 | 31 |
| 899 | 1664 | 281 | 300 |
| 900 | 2641 | 54 | 74 |
| 901 | 2678 | 11 | 31 |
| 902 | 1932 | 11 | 31 |
| 903 | 1841 | 11 | 31 |
| 903 | 2583 | 11 | 31 |
| 903 | 2661 | 11 | 31 |
| 904 | 2348 | 70 | 90 |
| 905 | 2650 | 11 | 31 |
| 906 | 2507 | 46 | 65 |
| 907 | 1910 | 47 | 66 |
| 907 | 2618 | 35 | 54 |
| 908 | 2057 | 134 | 154 |
| 909 | 2070 | 11 | 31 |
| 909 | 2667 | 11 | 31 |
| 910 | 2167 | 73 | 92 |
| 911 | 2310 | 68 | 88 |
| 912 | 2578 | 11 | 30 |
| 913 | 1706 | 33 | 53 |

TABLE 1-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 914 | 1670 | 34 | 54 |
| 915 | 1683 | 71 | 91 |
| 916 | 1754 | 11 | 31 |
| 916 | 2226 | 11 | 31 |
| 917 | 2028 | 272 | 292 |
| 918 | 2214 | 11 | 30 |
| 919 | 1806 | 84 | 104 |
| 920 | 2333 | 281 | 301 |
| 921 | 2316 | 11 | 30 |
| 922 | 2025 | 11 | 31 |
| 922 | 2315 | 11 | 31 |
| 922 | 2405 | 11 | 31 |
| 922 | 2437 | 11 | 31 |
| 923 | 2357 | 261 | 281 |
| 924 | 2381 | 11 | 31 |
| 925 | 1871 | 82 | 101 |
| 926 | 2433 | 186 | 205 |
| 927 | 2377 | 273 | 292 |
| 928 | 1632 | 270 | 290 |
| 929 | 2485 | 118 | 138 |
| 930 | 2540 | 11 | 30 |
| 930 | 2602 | 11 | 30 |
| 930 | 2670 | 11 | 30 |
| 931 | 1812 | 11 | 31 |
| 932 | 2294 | 240 | 260 |
| 933 | 2687 | 37 | 56 |
| 934 | 2401 | 86 | 106 |
| 935 | 2084 | 11 | 31 |
| 936 | 1661 | 113 | 133 |
| 936 | 1939 | 112 | 132 |
| 936 | 2088 | 112 | 132 |
| 936 | 2677 | 90 | 110 |
| 937 | 2078 | 11 | 30 |
| 938 | 1934 | 273 | 292 |
| 939 | 1851 | 280 | 298 |
| 940 | 1817 | 11 | 30 |
| 941 | 1835 | 11 | 30 |
| 942 | 2495 | 11 | 30 |
| 943 | 2267 | 130 | 150 |
| 944 | 2621 | 11 | 31 |
| 945 | 1782 | 11 | 30 |
| 946 | 1669 | 11 | 31 |
| 947 | 2403 | 36 | 55 |
| 948 | 1927 | 11 | 31 |
| 949 | 2287 | 11 | 31 |
| 950 | 2356 | 11 | 31 |
| 951 | 2015 | 131 | 151 |
| 952 | 2616 | 11 | 29 |
| 953 | 2486 | 64 | 83 |
| 954 | 1899 | 255 | 275 |
| 955 | 1742 | 132 | 151 |
| 956 | 2493 | 11 | 30 |
| 957 | 1715 | 11 | 31 |
| 958 | 2492 | 11 | 31 |
| 959 | 1997 | 11 | 31 |
| 959 | 2213 | 11 | 31 |
| 960 | 1966 | 75 | 95 |
| 961 | 2012 | 11 | 31 |
| 962 | 2224 | 11 | 31 |
| 963 | 2188 | 176 | 195 |
| 964 | 2598 | 58 | 78 |
| 965 | 2418 | 11 | 30 |
| 966 | 2444 | 11 | 30 |
| 967 | 2372 | 11 | 31 |
| 968 | 1888 | 11 | 31 |
| 969 | 1651 | 11 | 31 |
| 970 | 2652 | 11 | 30 |
| 971 | 1965 | 275 | 295 |
| 972 | 1743 | 11 | 31 |
| 973 | 1877 | 11 | 33 |
| 974 | 2386 | 274 | 293 |
| 975 | 2580 | 11 | 31 |
| 976 | 2637 | 281 | 300 |
| 977 | 2577 | 39 | 59 |
| 978 | 1836 | 128 | 148 |
| 979 | 2452 | 11 | 30 |
| 980 | 2076 | 76 | 96 |
| 981 | 1838 | 281 | 301 |
| 982 | 1690 | 11 | 31 |
| 983 | 2222 | 11 | 30 |
| 984 | 1935 | 11 | 31 |
| 985 | 1816 | 11 | 30 |
| 986 | 1628 | 11 | 30 |
| 987 | 2504 | 11 | 31 |
| 988 | 2350 | 234 | 253 |
| 989 | 1831 | 11 | 30 |
| 990 | 2065 | 11 | 30 |
| 991 | 2142 | 11 | 31 |
| 992 | 1896 | 11 | 31 |
| 993 | 1672 | 11 | 34 |
| 994 | 2624 | 11 | 31 |
| 995 | 1959 | 97 | 117 |
| 996 | 2238 | 235 | 255 |
| 996 | 2612 | 271 | 291 |
| 997 | 1972 | 238 | 258 |
| 998 | 2204 | 11 | 31 |
| 999 | 2496 | 94 | 114 |
| 1000 | 2055 | 79 | 99 |
| 1001 | 1691 | 11 | 34 |
| 1002 | 2336 | 11 | 30 |
| 1003 | 2096 | 11 | 31 |
| 1003 | 2539 | 131 | 151 |
| 1004 | 2085 | 11 | 31 |
| 1005 | 2298 | 11 | 31 |
| 1006 | 1641 | 245 | 264 |
| 1006 | 1996 | 11 | 30 |
| 1006 | 2203 | 11 | 30 |
| 1007 | 2679 | 153 | 173 |
| 1008 | 1741 | 11 | 31 |
| 1008 | 2322 | 11 | 31 |
| 1009 | 2642 | 11 | 29 |
| 1010 | 2442 | 11 | 31 |
| 1011 | 2575 | 11 | 31 |
| 1012 | 2250 | 11 | 31 |
| 1013 | 1732 | 54 | 77 |
| 1013 | 2060 | 53 | 76 |
| 1013 | 2453 | 53 | 76 |
| 1014 | 2170 | 60 | 80 |
| 1015 | 2611 | 35 | 55 |
| 1016 | 2033 | 91 | 111 |
| 1017 | 2569 | 135 | 155 |
| 1018 | 2361 | 11 | 31 |
| 1019 | 1718 | 11 | 31 |
| 1020 | 2558 | 80 | 100 |
| 1021 | 2243 | 105 | 124 |
| 1022 | 2136 | 11 | 30 |
| 1023 | 1878 | 11 | 31 |
| 1024 | 2182 | 11 | 31 |
| 1025 | 1891 | 77 | 96 |
| 1026 | 1924 | 140 | 160 |
| 1027 | 2341 | 255 | 275 |
| 1028 | 2244 | 147 | 167 |
| 1028 | 2556 | 142 | 162 |
| 1028 | 2663 | 114 | 134 |
| 1029 | 1756 | 225 | 244 |
| 1029 | 2329 | 195 | 214 |
| 1030 | 1856 | 11 | 31 |
| 1031 | 1808 | 139 | 159 |
| 1032 | 1873 | 57 | 76 |
| 1033 | 1993 | 72 | 92 |
| 1034 | 1696 | 55 | 78 |
| 1035 | 1912 | 33 | 53 |
| 1035 | 1990 | 33 | 53 |
| 1035 | 2500 | 33 | 53 |
| 1035 | 2664 | 33 | 53 |

TABLE 2

Maize miRNAs

| sRNA ID | SEQ ID NO. | Homolog* | Predicted in Corn Kernel | Predicted in Corn Leaf |
|---|---|---|---|---|
| 15996 | 3 | ptc-miR390c | y | y |
| 19644 | 4 | osa-miR396e | y | y |
| 25372 | 7 | ptc-miR172f | y | y |
| 35979 | 9 | ath-miR167d | y | y |
| 36116 | 10 | osa-miR528 | y | y |
| 56811 | 133 | ptc-miR396e | n | y |
| 59250 | 16 | ptc-miR398c | y | y |
| 432006 | 138 | sbi-miR164c | y | y |
| 1392730 | 32 | ath-miR171a | y | n |

*"ptc", *Populus trichocarpa*; "osa", *Oryza sativa*; "ath", *Arabidopsis thaliana*; "sbi", *Sorghum bicolor*

Example 2

Rice genes predicted to be targets of the novel rice miRNAs were predicted from The Institute for Genomic Research's rice genome annotation version 4.0 (publicly available at tigr.org), based on sequence complementarity rules as described by Zhang (2005) *Nucleic Acids Res.*, 33:W701-704 and by Rhoades et al. (2002) *Cell*, 110:513-520. These predicted targets were sequences that included at least one miRNA recognition site recognized by a mature miRNA selected from SEQ ID NOS. 1 -1035, SEQ ID NOS. 2730 -3921, SEQ ID NOS. 5498 -6683, SEQ ID NOS. 8409 -8560, SEQ ID NO 8742, SEQ ID NO. 8744, SEQ ID NOS. 8812 -8815, SEQ ID NO. 8845, and SEQ ID NO. 8850 or a mature miRNA derived from a plant miRNA precursor sequence selected from SEQ ID NOS. 1036 -2690, SEQ ID NOS. 3922 -5497, SEQ ID NOS. 6684 -8408, SEQ ID NOS. 8561 -8417, SEQ ID NO. 8743, SEQ ID NO. 8800, and SEQ ID NOS. 8816 -8819. Table 3 lists non-limiting examples of miRNA recognition sites (SEQ ID NOS. 2691 -2729) that are recognized by a rice mature miRNA (SEQ ID NO. 197).

TABLE 3

Os_miRNA_60735 miRNA sequence UCCGUCCCAAAAUAUAGCCAC (SEQ ID NO. 197)

| Predicted rice target Locus name and annotation | Nucleotide position in locus | miRNA recognition site mRNA sequence corresponding to cDNA | SEQ ID NO. | Score | No. of mismatches |
|---|---|---|---|---|---|
| LOC_Os01g65130.1\|11971.m126 26\|cDNA expressed protein | 1086-1106 | guugcuauauuuugggacgga | 2691 | 1 | 1 |
| LOC_Os11g37540.1\|11981.m075 99\|cDNA Serine/threonine-protein kinase Doa, putative, expressed | 1925-1945 | guugcuauauuuugggacgga | 2692 | 1 | 1 |
| LOC_Os08g36030.1\|11978.m075 92\|cDNA Plant viral-response family protein, expressed | 1126-1146 | auugcuauauuuugggacgga | 2693 | 1 | 2 |
| LOC_Os12g12470.2\|11982.m268 68\|cDNA NADP-dependent oxidoreductase P1, putative, expressed | 1095-1115 | guuguuauauuuugggacgga | 2694 | 1.5 | 2 |
| LOC_Os09g20410.1\|11979.m052 48\|cDNA hypothetical protein | 587-607 | guugcuauauuuugggaugga | 2695 | 1.5 | 2 |
| LOC_Os06g12790.3\|11976.m320 28\|cDNA RAC-like GTP binding protein ARAC10, putative, expressed | 3792-3812 | auuguuauauuuugggacgga | 2696 | 1.5 | 3 |
| LOC_Os11g24540.1\|11981.m063 80\|cDNA signal peptide peptidase family protein, expressed | 2004-2024 | auuguuauauuuugggacgga | 2697 | 1.5 | 3 |
| LOC_Os02g38750.1\|11972.m089 63\|cDNA hypothetical protein | 55-75 | augcuuauauuuugggacgga | 2698 | 1.5 | 3 |
| LOC_Os07g49480.2\|11977.m290 28\|cDNA expressed protein | 2531-2551 | auuguuauauuuugggacgga | 2699 | 1.5 | 3 |
| LOC_Os01g56640.1\|11971.m975 46\|cDNA transcription factor jumonji, putative, expressed | 660-680 | augauuauauuuugggacgga | 2700 | 1.5 | 3 |
| LOC_Os06g12790.2111976.m322 47\|cDNA RAC-like GTP binding protein ARAC10, putative, expressed | 1947-1967 | uuugcuauauuuugggaugga | 2701 | 1.5 | 3 |

TABLE 3-continued

Os_miRNA_60735 miRNA sequence UCCGUCCCAAAAUAUAGCCAC (SEQ ID NO. 197)

| Predicted rice target Locus name and annotation | miRNA recognition site | | | | |
|---|---|---|---|---|---|
| | Nucleotide position in locus | mRNA sequence corresponding to cDNA | SEQ ID NO. | Score | No. of mismatches |
| LOC_Os10g22560.1\|11980.m05263\|cDNA POT family protein, expressed | 1954-1974 | uuugcuauauuuugggaugga | 2702 | 1.5 | 3 |
| LOC_Os06g30280.1\|11976.m07572\|cDNA expressed protein | 1895-1915 | guugcuauauuaugggacgga | 2703 | 2 | 2 |
| LOC_Os03g14800.3\|11973.m06917\|cDNA aminotransferase, classes I and II family protein, expressed | 1826-1846 | aaagcuauauuuugggacgga | 2704 | 2 | 3 |
| LOC_Os05g25430.1\|11975.m06836\|cDNA protein kinase family protein, putative, expressed | 684-704 | guuguuauauuuugggaugga | 2705 | 2 | 3 |
| LOC_Os04g41229.2\|11974.m78964\|cDNA Helix-loop-helix DNA-binding domain containing protein, expressed | 175-195 | guugcuauauuuuggcacgga | 2706 | 2.5 | 2 |
| LOC_Os01g06740.1\|11971.m07304\|cDNA Ribosome inactivating protein, expressed | 1362-1382 | gcaguuauauuuugggacgga | 2707 | 2.5 | 3 |
| LOC_Os03g14800.2\|11973.m35126\|cDNA aminotransferase, classes I and II family protein, expressed | 861-881 | augcuuacauuuugggacgga | 2708 | 2.5 | 4 |
| LOC_Os09g36100.1\|11979.m06560\|cDNA expressed protein | 1469-1489 | acaguuauauuuugggacgga | 2709 | 2.5 | 4 |
| LOC_Os10g40740.1\|11980.m06842\|cDNA Helix-loop-helix DNA-binding domain containing protein, expressed | 1049-1069 | auacuuauauuuugggacgga | 2710 | 2.5 | 4 |
| LOC_Os06g04970.1\|11976.m05226\|cDNA expressed protein | 989-1009 | auacuuauauuuugggacgga | 2711 | 2.5 | 4 |
| LOC_Os11g43760.1\|11981.m08211\|cDNA Lipase family protein | 2628-2648 | auacuuauauuuugggacgga | 2712 | 2.5 | 4 |
| LOC_Os12g11660.1\|11982.m05145\|cDNA expressed protein | 1479-1499 | guugauuuauuuugggacgga | 2713 | 3 | 3 |
| LOC_Os01g64330.1\|11971.m42582\|cDNA expressed protein | 630-650 | guugguuuauuuugggacgga | 2714 | 3 | 3 |
| LOC_Os07g04840.2\|11977.m29060\|cDNA Oxygen-evolving enhancer protein 2, chloroplast precursor, putative, expressed | 574-594 | guugcuauauucuaggacgga | 2715 | 3 | 3 |
| LOC_Os09g13440.2\|11979.m22062\|cDNA expressed protein | 2068-2088 | auugcuauauuuuggaaugga | 2716 | 3 | 4 |
| LOC_Os06g12790.1\|11976.m05995\|cDNA RAC-like GTP binding protein ARAC10, putative, expressed | 2271-2291 | auugcuauauuuuggaaugga | 2717 | 3 | 4 |
| LOC_Os09g17730.1\|11979.m05031\|cDNA proton pump interactor, putative, expressed | 958-978 | uucccuauauuuagggacgga | 2718 | 3 | 4 |
| LOC_Os11g40390.1\|11981.m07885\|cDNA expressed protein | 1302-1322 | augcuuauauuuuggaacgga | 2719 | 3 | 4 |

TABLE 3-continued

Os_miRNA_60735 miRNA sequence UCCGUCCCAAAAUAUAGCCAC (SEQ ID NO. 197)

| Predicted rice target Locus name and annotation | Nucleotide position in locus | miRNA recognition site mRNA sequence corresponding to cDNA | SEQ ID NO. | Score | No. of mismatches |
|---|---|---|---|---|---|
| LOC_Os11g39670.1\|11981.m07814\|cDNA seryl-tRNA synthetase family protein, expressed | 924-944 | auugcuauauuauaggacgga | 2720 | 3 | 4 |
| LOC_Os07g04840.1\|11977.m04951\|cDNA Oxygen-evolving enhancer protein 2, chloroplast precursor, putative, expressed | 4246-4266 | uugucuuuuuuugggacgga | 2721 | 3 | 4 |
| LOC_Os03g47960.1\|11973.m09809\|cDNA HECT-domain-containing protein, putative, expressed | 1125-1145 | uuugcuauauuugagaugga | 2722 | 3 | 4 |
| LOC_Os01g60780.1\|11971.m12206\|cDNA integral membrane protein, putative, expressed | 3110-3130 | ugcgauauauuugggacgga | 2723 | 3 | 4 |
| LOC_Os10g01820.1\|11980.m21747\|cDNA expressed protein | 711-731 | augcuauauuugagacgga | 2724 | 3 | 4 |
| LOC_Os06g48030.3\|11976.m32166\|cDNA Peroxidase 16 precursor, putative, expressed | 1475-1495 | cuguauuuauuugggacgga | 2725 | 3 | 4 |
| LOC_Os02g02980.1\|11972.m05648\|cDNA Enhanced disease susceptibility 5, putative, expressed | 1357-1377 | uuggcugaauuuggggcgga | 2726 | 3 | 5 |
| LOC_Os08g32170.1\|11978.m07211\|cDNA oxidoreductase, 2OG-Fe oxygenase family protein, expressed | 1297-1317 | uuggcugaauuuggggcgga | 2727 | 3 | 5 |
| LOC_Os11g39670.2\|11981.m28846\|cDNA seryl-tRNA synthetase family protein, expressed | 114-134 | guggcuuuauugugggguggu | 2728 | 3 | 5 |
| LOC_Os08g25010.1\|11978.m06520\|cDNA TBC domain containing protein, expressed | 367-387 | cugguuaaauugugggaugga | 2729 | 3 | 5 |

Example 3

This example describes non-limiting embodiments of recombinant DNA construct wherein the at least one transcribable DNA element for modulating the expression of at least one target gene includes a DNA element for suppressing expression of an endogenous miRNA derived from a plant miRNA precursor sequence selected from SEQ ID NOS. 1036-2690, SEQ ID NOS. 3922-5497, SEQ ID NOS. 6684-8408, SEQ ID NOS. 8561-8417, SEQ ID NO. 8743, SEQ ID NO. 8800, and SEQ ID NOS. 8816-8819. More specifically, this example illustrates non-limiting examples of DNA elements for suppressing expression of a target gene, e.g., an endogenous miRNA or an endogenous miRNA decoy sequence.

FIG. 2A schematically depicts non-limiting examples of DNA elements for suppressing expression of a target gene, e.g., an endogenous miRNA. These DNA elements include at least one first gene suppression element ("GSE" or "GSE1") for suppressing at least one first target gene, wherein the first gene suppression element is embedded in an intron flanked on one or on both sides by non-protein-coding DNA. These DNA elements utilize an intron (in many embodiments, an intron derived from a 5' untranslated region or an expression-enhancing intron is preferred) to deliver a gene suppression element without requiring the presence of any protein-coding exons (coding sequence). The DNA elements can optionally include at least one second gene suppression element ("GSE2") for suppressing at least one second target gene, at least one gene expression element ("GEE") for expressing at least one gene of interest (which can be coding or non-coding sequence or both), or both. In embodiments containing an optional gene expression element, the gene expression element can be located outside of (e.g., adjacent to) the intron. In some embodiments, the intron containing the first gene suppression element is 3' to a terminator.

To more clearly differentiate DNA elements of the invention (containing at least one gene suppression element embedded within a single intron flanked on one or on both sides by non-protein-coding DNA) from the prior art, FIG. 2B schematically depicts examples of prior art recombinant DNA constructs. These constructs can contain a gene suppression element that is located adjacent to an intron flanked by protein-coding sequence, or between two discrete introns (wherein the gene suppression element is not embedded in either of the two discrete introns), or can include a gene expression element including a gene suppression element embedded within an intron which is flanked by multiple exons (e.g., exons including the coding sequence of a protein).

FIG. 3 depicts various non-limiting examples of DNA elements for suppressing expression of a target gene, e.g., an endogenous miRNA, useful in the recombinant DNA constructs of the invention. Where drawn as a single strand (FIGS. 3A through 3E), these are conventionally depicted in 5' to 3' (left to right) transcriptional direction; the arrows indicate anti-sense sequence (arrowhead pointing to the left), or sense sequence (arrowhead pointing to the right). These DNA elements can include: DNA that includes at least one anti-sense DNA segment that is anti-sense to at least one segment of the at least one first target gene, or DNA that includes multiple copies of at least one anti-sense DNA segment that is anti-sense to at least one segment of the at least one first target gene (FIG. 3A); DNA that includes at least one sense DNA segment that is at least one segment of the at least one first target gene, or DNA that includes multiple copies of at least one sense DNA segment that is at least one segment of the at least one first target gene (FIG. 3B); DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene (FIG. 3C); DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene (FIG. 3D); DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein said multiple anti-sense DNA segments and the multiple sense DNA segments are arranged in a series of inverted repeats (FIG. 3E); and DNA that includes nucleotides derived from a miRNA, or DNA that includes nucleotides of a siRNA (FIG. 3F).

FIG. 3F depicts various non-limiting arrangements of double-stranded RNA that can be transcribed from embodiments of DNA elements for suppressing expression of a target gene, e.g., an endogenous miRNA, useful in the recombinant DNA constructs of the invention. When such double-stranded RNA is formed, it can suppress one or more target genes, and can form a single double-stranded RNA or multiple double strands of RNA, or a single double-stranded RNA "stem" or multiple "stems". Where multiple double-stranded RNA "stems" are formed, they can be arranged in "hammerheads" or "cloverleaf" arrangements. In some embodiments, the double-stranded stems can form a "pseudoknot" arrangement (e.g., where spacer or loop RNA of one double-stranded stem forms part of a second double-stranded stem); see, for example, depictions of pseudoknot architectures in Staple and Butcher (2005) *PLoS Biol.*, 3(6):e213. Spacer DNA (located between or adjacent to dsRNA regions) is optional but commonly included and generally includes DNA that does not correspond to the target gene (although in some embodiments can include sense or anti-sense DNA of the target gene). Spacer DNA can include sequence that transcribes to single-stranded RNA or to at least partially double-stranded RNA (such as in a "kissing stem-loop" arrangement), or to an RNA that assumes a secondary structure or three-dimensional configuration (e.g., a large loop of antisense sequence of the target gene or an aptamer) that confers on the transcript an additional desired characteristic, such as increased stability, increased half-life in vivo, or cell or tissue specificity.

Additional description of DNA elements and methods for suppressing expression of a target gene can be found, for example, in U.S. Patent Application Publication 2006/0200878, which is incorporated by reference herein.

Example 4

This example describes non-limiting embodiments of methods for using microRNAs, microRNA precursors, microRNA recognition sites, and microRNA promoters for modulating the expression of at least one target gene.

Various potential utilities of a miRNA or its recognition site are revealed by the miRNA's expression pattern. Knowledge of the spatial or temporal distribution or inducibility of a given mature miRNA's expression is useful, e.g., in designing recombinant constructs to be expressed in a spatially or temporally or inducibly specific manner. One non-limiting method of determining a mature miRNA's expression pattern is by isolation of the mature miRNA (or its precursor) and analyzing the expression pattern by Northern blots with the appropriate probe (i.e., probes specific for the mature miRNA or for the miRNA precursor).

Figure 4:
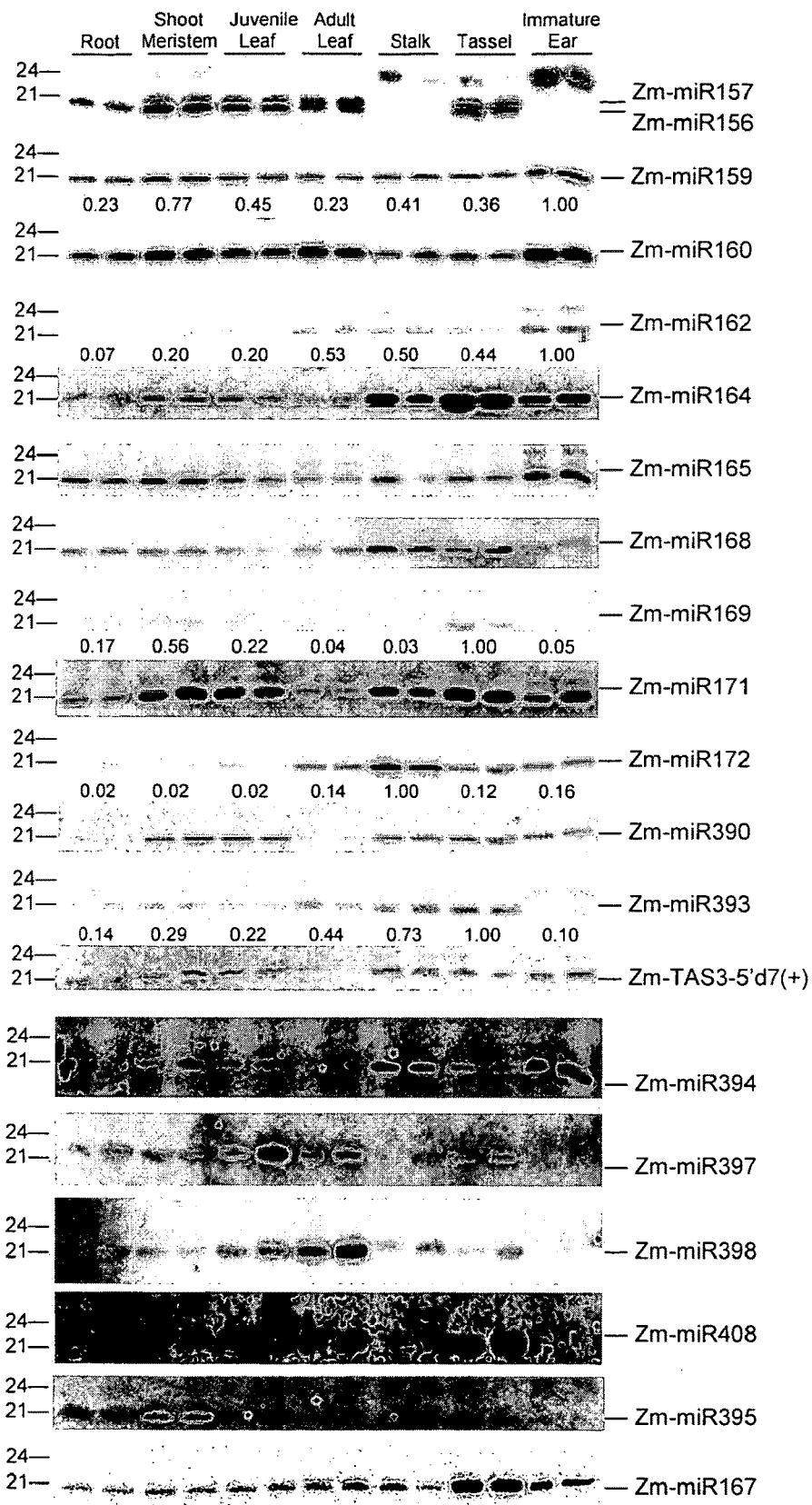
FIG. 4 depicts Northern blot results for mature miRNAs isolated from different maize tissues, as described in Example 4.

FIG. 4 depicts a non-limiting example of Northern blot results for mature miRNAs isolated from different maize tissues. One probe hybridized to mature miRNAs from two families (miR156 and miR157). Individual mature miRNAs were expressed at differing levels in specific cells or tissues, e.g., Zm-miR390 was not expressed, or expressed only at low levels, in root and adult leaf, and miR156 is expressed in roots, leaves, and tassel. Thus, for example, recombinant DNA construct of this invention including a transgene transcription unit driven by a constitutive promoter and a miRNA recognition site recognized by a maize miR390 mature miRNA is useful for expression of the transgene in root and adult leaf tissues but not in tissues where the mature miR390 is expressed at high levels. To further illustrate use of the constructs and methods of the invention to control expression of a transgene, a reporter gene is used as the transgene itself, or as a surrogate for the transgene. For example, where expression of a reporter gene (e.g., green fluorescent protein, GFP) is desired in maize stalk and immature ear tissue, a miR156 target site is included in a GFP expression cassette and expressed in a stably transgenic maize plant under the control of the CaMV 35S promoter. In tissues (e.g., roots, leaves, and tassel) where miR156 is strongly expressed, GFP expression is suppressed. The suppression phenotype may be limited to very specific cell types within the suppressed tissues, with neighboring cells showing expression or a gradient of expression of GFP adjacent to those cells expressing the mature miR156.

Another non-limiting method of determining a mature miRNA's expression pattern is by analyzing transcription profiles of nucleic acid sequences that include the mature miRNA sequence, for example, by following a general procedure including the steps of:

(a) providing an initial miR sequence including the stem-loop region, e.g., from the publicly available miR sequences at the 'miRBase" database (available on line at microrna.sanger.ac.uk/sequences);

(b) applying sequence analysis algorithms, such as BLAST as is well known in the art (see Altschul et al. (1990) *J. Mol. Biol.*, 215:403-410) to identify homologous or identical sequences (e.g., from proprietary sequences on microarray probesets made with corn whole genome DNA); and (c) analyzing the transcription profiles of the homologous probeset sequences identified in step (b) and identifying miRNAs having an expression pattern in the desired tissues (i.e., male or female reproductive tissues).

Preferably, a fourth step is added:

(d) for homologous probeset sequences found to have the desired transcription profiles, confirming identification of the miRNA gene by either aligning the stem-loop sequence of the initial miR sequence to the probeset sequence, or for potentially novel miRNAs, determining the sequence is predicted to fold into a stem-loop structure characteristic of a miRNA. Also preferably, an optional step is used, wherein one or more BLAST comparisons against additional sequence datasets other than the probeset sequence dataset is included (prior to step (b) above), allowing the further identification of probes that fall outside of the predicted fold-back region of the miR gene; false positives, e.g., due to matches in the additional sequence dataset(s) that include incorrectly spliced contigs, are identified by their lack of miRNA characteristics such as proper fold-back structure, and removed.

Figure 5:
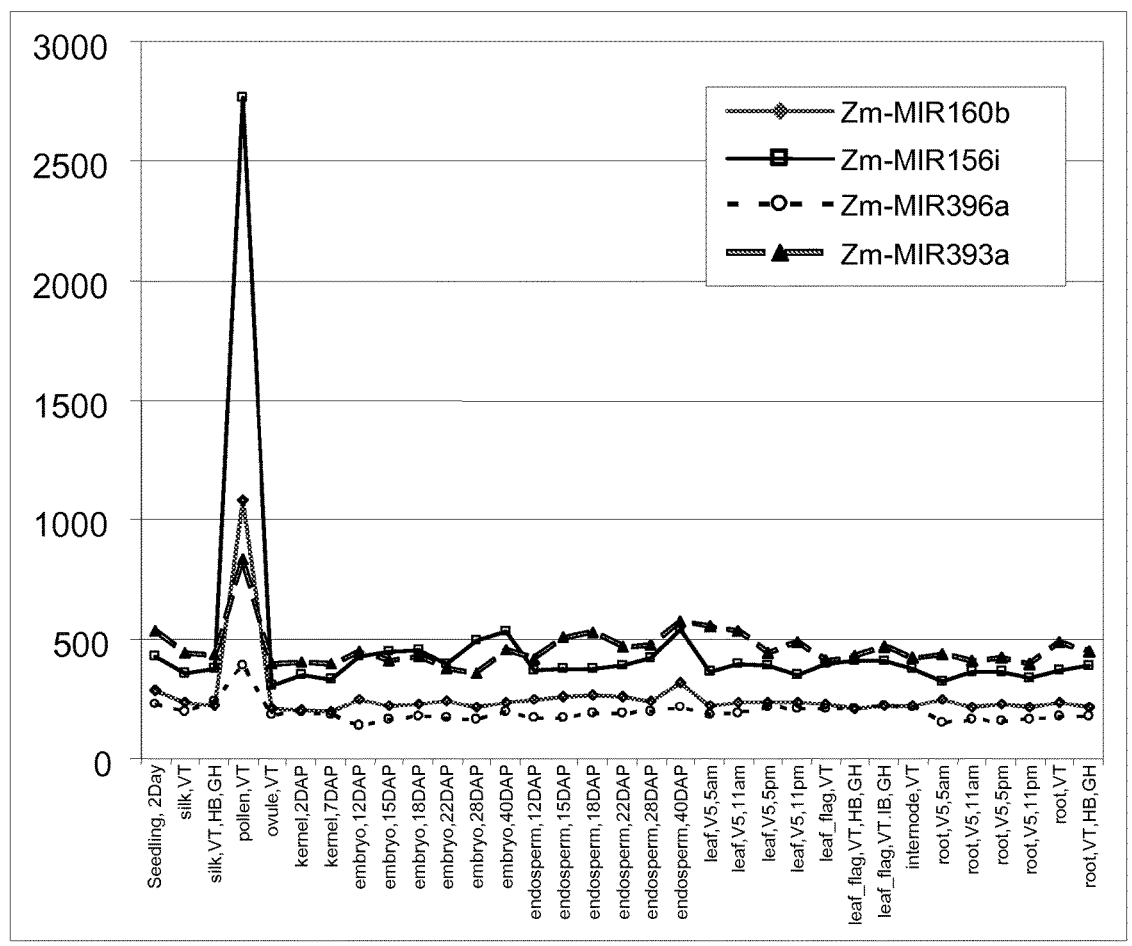
FIG. 5 depicts transcription profiles of probeset sequences including miRNA precursor sequences having expression patterns specific to maize male reproductive tissue (pollen), as described in Example 4.

FIG. 5 depicts transcription profiles of probeset sequences that were identified, using the procedure described in the preceding paragraphs, as including miRNA precursor sequences having expression patterns specific to maize male reproductive tissue (pollen). Such miRNA precursors are suitable for use in recombinant DNA constructs of this invention designed for expression of a native miRNA (in this example, a pollen-specific miRNA) under non-native conditions (e.g., under the control of a promoter other than the promoter native to the miRNA precursor). These miRNA precursors are also useful for providing a "scaffold" sequence that can be modified or engineered to suppress a target gene other than the native or endogenous target gene. One non-limiting example of a recombinant DNA construct of this invention includes a strong constitutive promoter that is used to drive expression of transgene transcription unit encoding a *Bacillus thuringiensis* insecticidal protein or protein fragment ("Bt"), and a recognition site for a pollen-specific miRNA, resulting in strong Bt expression in tissues of the plant except for the pollen. Additionally, the native promoters of these miRNA precursors are useful for pollen-specific expression of any gene of interest.

In an alternative approach, an existing (native or endogenous) miRNA recognition site is identified, for example, using sequence complementarity rules as described by Zhang (2005) *Nucleic Acids Res.*, 33:W701-704 and by Rhoades et al. (2002) *Cell*, 110:513-520. The native miRNA recognition site is mutated (e.g., by chemical mutagenesis) sufficiently to reduce or prevent cleavage (see Mallory et al. (2004) *Curr. Biol.*, 14:1035-1046). In this way a gene containing a native miRNA recognition site and having desirable effects, e.g., increased leaf or seed size, can be mutated and thus expressed at levels higher than when the unmutated native or endogenous miRNA recognition site was present. One embodiment is to replace a native gene with an engineered homologue, wherein a native miRNA has been mutated or even deleted, that is less susceptible to cleavage by a given miRNA.

Another specific example of this approach is the inclusion of one or more recognition site for a mature miRNA not substantially expressed in maize roots but expressed in most other tissues (such as, but not limited to, miRNA162, miRNA164, or miRNA390 as depicted in FIG. 4) in a recombinant DNA construct for the expression of a *Bacillus thuringiensis* insecticidal protein or protein fragment ("Bt", see, for example, the *B. thuringiensis* insecticidal sequences and methods of use thereof disclosed in U.S. Pat. No. 6,953,835 and in U.S. Provisional Patent Application No. 60/713,111, filed on 31 Aug. 2005, which are incorporated by reference herein) as the transgene, e.g., in a construct including the expression cassette e35S/Bt/hsp17. Including one or more of these recognition sites within the expression cassette reduces the expression of transcripts in most tissues other than root, but maintains high Bt target RNA expression levels in roots, such as is desirable for control of pests such as corn rootworm. In similar embodiments, combinations of different miRNA recognition sites are included in the construct to achieve the desired expression pattern in one or more specific tissues.

Example 5

This example describes additional non-limiting embodiments of crop plant microRNAs and their precursor (foldback) structures, useful in making recombinant DNA constructs of this invention. A total of 1327933 unique small RNAs (20 to 24 nucleotides long) were obtained by high-throughput sequencing of 30 corn (maize) libraries (Margulies et al. (2005) *Nature*, 437:376-380). The sequences obtained were used for predicting corn microRNAs and their precursor structures from maize genomic sequences using the procedures described above in Example 1. In total, 1192 small RNAs in 1576 proprietary maize genomic sequences were predicted to be new miRNAs. The corn miRNAs and their corresponding miRNA precursors, as well as the nucleotide position of the mature miRNA in each miRNA precursor sequence, are referred to by their respective sequence identification numbers in Table 4 as follows: corn miRNAs (SEQ ID NOS. 2730-3921) and corn miRNA precursor sequences (SEQ ID NOS. 3922-5497).

TABLE 4

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 2730 | 3928 | 84 | 104 |
| 2731 | 4099 | 92 | 113 |
| 2732 | 3935 | 11 | 31 |
| 2733 | 4093 | 11 | 31 |
| 2734 | 5134 | 11 | 32 |
| 2735 | 4864 | 188 | 211 |
| 2736 | 4123 | 11 | 30 |
| 2737 | 4108 | 4 | 27 |
| 2738 | 5217 | 11 | 33 |
| 2738 | 5277 | 11 | 33 |
| 2739 | 4328 | 71 | 90 |
| 2740 | 4635 | 42 | 62 |
| 2741 | 4591 | 11 | 34 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 2742 | 3925 | 11 | 34 |
| 2743 | 4036 | 11 | 34 |
| 2744 | 4586 | 11 | 32 |
| 2745 | 5245 | 37 | 57 |
| 2746 | 5417 | 30 | 53 |
| 2747 | 4527 | 171 | 190 |
| 2748 | 5486 | 11 | 32 |
| 2749 | 4440 | 11 | 32 |
| 2749 | 4428 | 11 | 32 |
| 2750 | 5469 | 241 | 261 |
| 2751 | 5066 | 11 | 30 |
| 2752 | 5095 | 61 | 82 |
| 2753 | 4468 | 113 | 133 |
| 2754 | 4924 | 37 | 59 |
| 2755 | 5242 | 11 | 30 |
| 2756 | 5292 | 83 | 103 |
| 2757 | 3959 | 11 | 33 |
| 2758 | 5489 | 150 | 171 |
| 2759 | 3929 | 11 | 34 |
| 2760 | 5153 | 11 | 30 |
| 2761 | 4251 | 11 | 34 |
| 2762 | 5361 | 35 | 55 |
| 2763 | 3995 | 11 | 34 |
| 2764 | 4448 | 11 | 30 |
| 2764 | 4473 | 11 | 30 |
| 2765 | 4784 | 11 | 30 |
| 2766 | 4478 | 63 | 83 |
| 2767 | 4477 | 11 | 34 |
| 2768 | 4275 | 11 | 33 |
| 2768 | 4223 | 11 | 33 |
| 2769 | 5084 | 11 | 31 |
| 2769 | 5063 | 61 | 81 |
| 2770 | 3985 | 11 | 34 |
| 2771 | 5384 | 11 | 32 |
| 2772 | 4053 | 11 | 34 |
| 2772 | 4058 | 113 | 136 |
| 2772 | 4057 | 113 | 136 |
| 2772 | 4059 | 11 | 34 |
| 2772 | 4051 | 104 | 127 |
| 2772 | 4056 | 11 | 34 |
| 2773 | 4215 | 11 | 34 |
| 2774 | 4718 | 215 | 237 |
| 2775 | 5098 | 37 | 56 |
| 2776 | 5011 | 11 | 30 |
| 2777 | 5262 | 62 | 82 |
| 2778 | 5022 | 11 | 30 |
| 2779 | 5369 | 47 | 66 |
| 2780 | 5038 | 11 | 34 |
| 2781 | 3974 | 1 | 24 |
| 2782 | 4933 | 103 | 124 |
| 2783 | 4380 | 89 | 109 |
| 2784 | 4752 | 11 | 33 |
| 2785 | 4341 | 209 | 232 |
| 2786 | 5408 | 11 | 31 |
| 2786 | 5356 | 11 | 31 |
| 2787 | 5048 | 37 | 57 |
| 2788 | 4920 | 153 | 174 |
| 2789 | 5366 | 35 | 55 |
| 2790 | 4159 | 203 | 222 |
| 2791 | 4798 | 44 | 67 |
| 2792 | 4530 | 11 | 31 |
| 2793 | 5269 | 11 | 31 |
| 2794 | 4334 | 6 | 29 |
| 2795 | 5287 | 11 | 30 |
| 2796 | 5362 | 11 | 30 |
| 2796 | 5396 | 11 | 30 |
| 2796 | 5344 | 11 | 30 |
| 2796 | 5310 | 11 | 30 |
| 2796 | 5360 | 11 | 30 |
| 2797 | 5440 | 118 | 138 |
| 2797 | 5456 | 118 | 138 |
| 2798 | 4962 | 70 | 93 |
| 2799 | 4522 | 11 | 34 |
| 2800 | 4286 | 11 | 34 |
| 2801 | 4299 | 11 | 30 |
| 2801 | 4235 | 11 | 30 |
| 2802 | 4103 | 11 | 32 |
| 2803 | 5136 | 37 | 58 |
| 2803 | 5208 | 37 | 58 |
| 2804 | 4894 | 11 | 31 |
| 2805 | 4413 | 11 | 30 |
| 2806 | 4807 | 11 | 34 |
| 2807 | 4844 | 426 | 449 |
| 2808 | 4022 | 118 | 141 |
| 2809 | 5312 | 11 | 30 |
| 2810 | 4270 | 52 | 71 |
| 2811 | 4233 | 8 | 30 |
| 2811 | 4244 | 253 | 275 |
| 2811 | 4293 | 75 | 97 |
| 2812 | 4517 | 55 | 77 |
| 2813 | 4456 | 40 | 59 |
| 2814 | 4258 | 87 | 107 |
| 2815 | 5276 | 242 | 261 |
| 2816 | 4638 | 54 | 77 |
| 2816 | 4815 | 54 | 77 |
| 2817 | 4378 | 11 | 34 |
| 2818 | 5298 | 33 | 54 |
| 2819 | 4208 | 11 | 30 |
| 2820 | 4187 | 11 | 30 |
| 2820 | 4176 | 11 | 30 |
| 2821 | 5333 | 103 | 123 |
| 2822 | 4958 | 11 | 31 |
| 2823 | 4500 | 11 | 34 |
| 2824 | 4373 | 11 | 34 |
| 2825 | 4024 | 11 | 34 |
| 2826 | 5407 | 47 | 67 |
| 2826 | 5448 | 11 | 31 |
| 2827 | 5479 | 230 | 253 |
| 2828 | 4201 | 53 | 72 |
| 2829 | 4709 | 204 | 224 |
| 2830 | 4525 | 141 | 160 |
| 2831 | 4876 | 125 | 147 |
| 2832 | 4122 | 11 | 31 |
| 2833 | 4060 | 109 | 132 |
| 2833 | 4055 | 11 | 34 |
| 2834 | 5302 | 74 | 94 |
| 2835 | 5308 | 60 | 79 |
| 2836 | 4238 | 75 | 95 |
| 2837 | 5119 | 11 | 32 |
| 2838 | 4873 | 83 | 103 |
| 2839 | 4947 | 11 | 30 |
| 2840 | 4791 | 231 | 253 |
| 2841 | 4567 | 11 | 33 |
| 2842 | 5463 | 11 | 33 |
| 2843 | 4957 | 42 | 62 |
| 2844 | 5205 | 38 | 61 |
| 2845 | 4239 | 65 | 85 |
| 2846 | 5059 | 149 | 169 |
| 2847 | 3964 | 79 | 102 |
| 2848 | 4516 | 48 | 71 |
| 2849 | 4121 | 11 | 32 |
| 2850 | 4526 | 72 | 95 |
| 2851 | 4659 | 11 | 30 |
| 2851 | 4670 | 11 | 30 |
| 2851 | 4668 | 11 | 30 |
| 2852 | 4206 | 616 | 636 |
| 2853 | 5331 | 443 | 465 |
| 2854 | 4726 | 11 | 34 |
| 2855 | 4606 | 11 | 34 |
| 2855 | 4729 | 11 | 34 |
| 2855 | 4565 | 11 | 34 |
| 2856 | 4684 | 11 | 33 |

TABLE 4-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 2857 | 4660 | 11 | 34 |
| 2858 | 5284 | 92 | 115 |
| 2859 | 5354 | 60 | 83 |
| 2859 | 5395 | 61 | 84 |
| 2859 | 5336 | 11 | 34 |
| 2859 | 5394 | 11 | 34 |
| 2859 | 5430 | 11 | 34 |
| 2859 | 5449 | 11 | 34 |
| 2859 | 5355 | 11 | 34 |
| 2859 | 5444 | 226 | 249 |
| 2860 | 5070 | 56 | 77 |
| 2860 | 5077 | 11 | 32 |
| 2861 | 4086 | 111 | 134 |
| 2861 | 4089 | 11 | 34 |
| 2862 | 4461 | 298 | 321 |
| 2863 | 4663 | 54 | 75 |
| 2864 | 4878 | 37 | 57 |
| 2865 | 4965 | 11 | 34 |
| 2866 | 4232 | 11 | 34 |
| 2867 | 4007 | 40 | 62 |
| 2868 | 4991 | 64 | 83 |
| 2869 | 5180 | 35 | 56 |
| 2870 | 4247 | 71 | 92 |
| 2871 | 4179 | 11 | 34 |
| 2872 | 5470 | 35 | 56 |
| 2873 | 3983 | 65 | 88 |
| 2874 | 4263 | 11 | 31 |
| 2875 | 5204 | 64 | 83 |
| 2876 | 4364 | 11 | 30 |
| 2877 | 5359 | 218 | 238 |
| 2878 | 4291 | 11 | 34 |
| 2879 | 4217 | 11 | 34 |
| 2880 | 4921 | 11 | 30 |
| 2881 | 4075 | 11 | 34 |
| 2881 | 4067 | 11 | 34 |
| 2882 | 4508 | 11 | 34 |
| 2883 | 5120 | 11 | 33 |
| 2884 | 4276 | 34 | 53 |
| 2884 | 4318 | 34 | 53 |
| 2885 | 4598 | 11 | 32 |
| 2886 | 5445 | 72 | 91 |
| 2887 | 4045 | 38 | 60 |
| 2888 | 5473 | 11 | 34 |
| 2888 | 5324 | 11 | 34 |
| 2889 | 4030 | 11 | 33 |
| 2889 | 5363 | 116 | 138 |
| 2889 | 4039 | 11 | 33 |
| 2889 | 4035 | 11 | 33 |
| 2889 | 4029 | 106 | 128 |
| 2889 | 4031 | 11 | 33 |
| 2889 | 4032 | 11 | 33 |
| 2890 | 4174 | 11 | 34 |
| 2891 | 5271 | 35 | 58 |
| 2891 | 5109 | 36 | 59 |
| 2891 | 5163 | 35 | 58 |
| 2891 | 5159 | 35 | 58 |
| 2892 | 4578 | 11 | 34 |
| 2892 | 4774 | 11 | 34 |
| 2893 | 3934 | 155 | 178 |
| 2893 | 3923 | 11 | 34 |
| 2894 | 4504 | 11 | 31 |
| 2895 | 5196 | 60 | 80 |
| 2896 | 4863 | 11 | 33 |
| 2897 | 3953 | 11 | 34 |
| 2897 | 3967 | 46 | 69 |
| 2897 | 3955 | 11 | 34 |
| 2897 | 3949 | 49 | 72 |
| 2898 | 5397 | 11 | 32 |
| 2898 | 5392 | 11 | 32 |
| 2899 | 4383 | 36 | 59 |
| 2900 | 5240 | 36 | 59 |
| 2901 | 5005 | 58 | 80 |
| 2901 | 4880 | 58 | 80 |
| 2902 | 4750 | 11 | 32 |
| 2903 | 4279 | 11 | 34 |
| 2904 | 4230 | 229 | 248 |
| 2905 | 4955 | 39 | 59 |
| 2906 | 4736 | 51 | 70 |
| 2906 | 4605 | 51 | 70 |
| 2907 | 5379 | 138 | 158 |
| 2908 | 5435 | 11 | 32 |
| 2909 | 5127 | 11 | 31 |
| 2910 | 5368 | 11 | 31 |
| 2911 | 4877 | 11 | 34 |
| 2912 | 5023 | 50 | 73 |
| 2913 | 4087 | 11 | 32 |
| 2914 | 5303 | 174 | 193 |
| 2915 | 5461 | 54 | 77 |
| 2916 | 4789 | 44 | 63 |
| 2917 | 3937 | 11 | 34 |
| 2918 | 4218 | 135 | 158 |
| 2919 | 5040 | 119 | 139 |
| 2920 | 5147 | 11 | 34 |
| 2921 | 5329 | 54 | 77 |
| 2922 | 4135 | 67 | 86 |
| 2923 | 4981 | 122 | 141 |
| 2924 | 5071 | 11 | 32 |
| 2925 | 4620 | 45 | 65 |
| 2926 | 4008 | 11 | 34 |
| 2927 | 3994 | 252 | 275 |
| 2928 | 4280 | 11 | 34 |
| 2929 | 4142 | 77 | 97 |
| 2930 | 4982 | 11 | 30 |
| 2931 | 4917 | 4 | 27 |
| 2932 | 4126 | 106 | 128 |
| 2933 | 3945 | 202 | 222 |
| 2934 | 4269 | 11 | 32 |
| 2935 | 4483 | 154 | 177 |
| 2936 | 5393 | 46 | 69 |
| 2937 | 4319 | 186 | 208 |
| 2938 | 4080 | 69 | 92 |
| 2939 | 4918 | 11 | 33 |
| 2940 | 4499 | 11 | 30 |
| 2941 | 4327 | 304 | 323 |
| 2942 | 5146 | 121 | 144 |
| 2943 | 5106 | 208 | 228 |
| 2944 | 4680 | 11 | 30 |
| 2945 | 4209 | 11 | 34 |
| 2946 | 5453 | 132 | 151 |
| 2947 | 4166 | 137 | 157 |
| 2948 | 5386 | 11 | 32 |
| 2949 | 5199 | 11 | 32 |
| 2950 | 4969 | 44 | 63 |
| 2951 | 5033 | 179 | 199 |
| 2951 | 5091 | 180 | 200 |
| 2952 | 4063 | 11 | 34 |
| 2953 | 5232 | 138 | 158 |
| 2954 | 5494 | 11 | 31 |
| 2955 | 4972 | 11 | 30 |
| 2956 | 5008 | 245 | 268 |
| 2957 | 4111 | 6 | 26 |
| 2958 | 4501 | 37 | 56 |
| 2959 | 5349 | 11 | 34 |
| 2960 | 3971 | 11 | 31 |
| 2960 | 3956 | 217 | 237 |
| 2960 | 3963 | 92 | 112 |
| 2961 | 4044 | 54 | 76 |
| 2962 | 5050 | 11 | 33 |
| 2963 | 4421 | 116 | 138 |
| 2964 | 4083 | 200 | 219 |
| 2965 | 4566 | 11 | 32 |
| 2966 | 4193 | 11 | 34 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 2967 | 5376 | 62 | 85 |
| 2968 | 4787 | 31 | 50 |
| 2968 | 4759 | 31 | 50 |
| 2969 | 4333 | 53 | 72 |
| 2969 | 4385 | 53 | 72 |
| 2970 | 4391 | 11 | 32 |
| 2971 | 4537 | 11 | 30 |
| 2972 | 5317 | 133 | 153 |
| 2972 | 5318 | 136 | 156 |
| 2972 | 5446 | 62 | 82 |
| 2972 | 5380 | 136 | 156 |
| 2972 | 5471 | 162 | 182 |
| 2972 | 5452 | 136 | 156 |
| 2972 | 5341 | 140 | 160 |
| 2972 | 5460 | 11 | 31 |
| 2972 | 5374 | 11 | 31 |
| 2972 | 5451 | 137 | 157 |
| 2973 | 4084 | 11 | 34 |
| 2974 | 4116 | 41 | 60 |
| 2975 | 5468 | 11 | 31 |
| 2976 | 4474 | 11 | 34 |
| 2977 | 4744 | 11 | 34 |
| 2978 | 4447 | 11 | 34 |
| 2979 | 4738 | 11 | 30 |
| 2980 | 4132 | 11 | 34 |
| 2981 | 4505 | 11 | 30 |
| 2982 | 5124 | 11 | 33 |
| 2983 | 4888 | 35 | 58 |
| 2984 | 4558 | 11 | 34 |
| 2985 | 4449 | 41 | 60 |
| 2986 | 5410 | 116 | 136 |
| 2987 | 5030 | 11 | 34 |
| 2988 | 4767 | 11 | 30 |
| 2988 | 4633 | 11 | 30 |
| 2989 | 5288 | 35 | 56 |
| 2990 | 4101 | 245 | 266 |
| 2991 | 5178 | 11 | 32 |
| 2991 | 5198 | 8 | 29 |
| 2991 | 5275 | 11 | 32 |
| 2991 | 5185 | 11 | 32 |
| 2991 | 5160 | 11 | 32 |
| 2992 | 4097 | 11 | 34 |
| 2993 | 4656 | 11 | 31 |
| 2994 | 4514 | 219 | 241 |
| 2994 | 4398 | 219 | 241 |
| 2995 | 5437 | 11 | 34 |
| 2996 | 4117 | 39 | 58 |
| 2997 | 4446 | 11 | 31 |
| 2998 | 5421 | 6 | 27 |
| 2999 | 4259 | 11 | 30 |
| 3000 | 5423 | 11 | 31 |
| 3001 | 4948 | 101 | 121 |
| 3002 | 5268 | 11 | 31 |
| 3003 | 4285 | 11 | 34 |
| 3004 | 5351 | 11 | 32 |
| 3005 | 5477 | 49 | 69 |
| 3006 | 5237 | 11 | 34 |
| 3006 | 5219 | 11 | 34 |
| 3006 | 5238 | 11 | 34 |
| 3007 | 4246 | 11 | 31 |
| 3008 | 4466 | 41 | 62 |
| 3009 | 3977 | 11 | 34 |
| 3009 | 3979 | 37 | 60 |
| 3009 | 3975 | 37 | 60 |
| 3009 | 3972 | 38 | 61 |
| 3010 | 5112 | 11 | 32 |
| 3011 | 4085 | 254 | 277 |
| 3012 | 5003 | 313 | 336 |
| 3013 | 4625 | 11 | 30 |
| 3014 | 5459 | 108 | 131 |
| 3015 | 5143 | 85 | 104 |
| 3016 | 5334 | 34 | 57 |
| 3017 | 5482 | 11 | 30 |
| 3018 | 5326 | 139 | 161 |
| 3019 | 3941 | 69 | 92 |
| 3019 | 3938 | 69 | 92 |
| 3019 | 3943 | 69 | 92 |
| 3020 | 4682 | 11 | 30 |
| 3021 | 4214 | 115 | 138 |
| 3022 | 4691 | 11 | 32 |
| 3022 | 4753 | 11 | 32 |
| 3023 | 4717 | 11 | 30 |
| 3024 | 5018 | 78 | 97 |
| 3025 | 4776 | 11 | 31 |
| 3026 | 4105 | 11 | 34 |
| 3027 | 4115 | 11 | 30 |
| 3027 | 4167 | 173 | 192 |
| 3028 | 4892 | 640 | 659 |
| 3029 | 4154 | 11 | 32 |
| 3030 | 4749 | 11 | 32 |
| 3030 | 4783 | 11 | 32 |
| 3031 | 4611 | 179 | 200 |
| 3032 | 4721 | 11 | 34 |
| 3033 | 5365 | 118 | 138 |
| 3034 | 4705 | 112 | 131 |
| 3034 | 4570 | 113 | 132 |
| 3034 | 4827 | 104 | 123 |
| 3035 | 4714 | 42 | 63 |
| 3035 | 4829 | 11 | 32 |
| 3035 | 4733 | 43 | 64 |
| 3036 | 4617 | 11 | 33 |
| 3037 | 4847 | 126 | 146 |
| 3038 | 5130 | 11 | 31 |
| 3038 | 5223 | 11 | 31 |
| 3038 | 5156 | 11 | 31 |
| 3038 | 5248 | 11 | 31 |
| 3038 | 5183 | 11 | 31 |
| 3038 | 5278 | 11 | 31 |
| 3039 | 4314 | 60 | 80 |
| 3040 | 4502 | 113 | 136 |
| 3041 | 5327 | 117 | 140 |
| 3042 | 4363 | 11 | 31 |
| 3042 | 4503 | 11 | 31 |
| 3042 | 4388 | 107 | 127 |
| 3043 | 4370 | 39 | 59 |
| 3044 | 4151 | 138 | 161 |
| 3045 | 5170 | 11 | 30 |
| 3046 | 4061 | 11 | 34 |
| 3046 | 4073 | 11 | 34 |
| 3046 | 4070 | 11 | 34 |
| 3046 | 4065 | 11 | 34 |
| 3046 | 4062 | 102 | 125 |
| 3046 | 4064 | 11 | 34 |
| 3046 | 4076 | 11 | 34 |
| 3047 | 4546 | 11 | 33 |
| 3048 | 5311 | 118 | 137 |
| 3049 | 4204 | 11 | 31 |
| 3050 | 5370 | 11 | 34 |
| 3050 | 5357 | 49 | 72 |
| 3051 | 4671 | 11 | 32 |
| 3051 | 4716 | 11 | 32 |
| 3052 | 5346 | 102 | 123 |
| 3052 | 5465 | 102 | 123 |
| 3053 | 4409 | 59 | 80 |
| 3053 | 4467 | 59 | 80 |
| 3054 | 5001 | 59 | 82 |
| 3054 | 4853 | 60 | 83 |
| 3055 | 5429 | 39 | 61 |
| 3056 | 4518 | 6 | 26 |
| 3057 | 5062 | 11 | 34 |
| 3058 | 4207 | 155 | 174 |
| 3059 | 4492 | 11 | 34 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 3060 | 5224 | 50 | 73 |
| 3061 | 4047 | 97 | 120 |
| 3062 | 3984 | 1 | 24 |
| 3063 | 5385 | 50 | 73 |
| 3064 | 5090 | 58 | 77 |
| 3065 | 3940 | 11 | 30 |
| 3066 | 5353 | 36 | 56 |
| 3067 | 5358 | 11 | 34 |
| 3068 | 4697 | 206 | 226 |
| 3068 | 4674 | 207 | 227 |
| 3068 | 4560 | 206 | 226 |
| 3069 | 5258 | 11 | 34 |
| 3070 | 5188 | 44 | 67 |
| 3071 | 4054 | 43 | 66 |
| 3072 | 4542 | 38 | 60 |
| 3072 | 4742 | 38 | 60 |
| 3073 | 5260 | 11 | 30 |
| 3074 | 5434 | 213 | 234 |
| 3075 | 5381 | 11 | 30 |
| 3076 | 4312 | 94 | 117 |
| 3077 | 4874 | 11 | 34 |
| 3078 | 4930 | 89 | 108 |
| 3079 | 4139 | 11 | 34 |
| 3080 | 5174 | 94 | 116 |
| 3081 | 5121 | 120 | 139 |
| 3081 | 5184 | 121 | 140 |
| 3082 | 4722 | 11 | 34 |
| 3083 | 4836 | 11 | 30 |
| 3084 | 5193 | 11 | 34 |
| 3085 | 5315 | 115 | 138 |
| 3086 | 4664 | 172 | 195 |
| 3087 | 5162 | 11 | 31 |
| 3088 | 4914 | 70 | 89 |
| 3089 | 4110 | 220 | 243 |
| 3090 | 4102 | 11 | 34 |
| 3091 | 5279 | 11 | 34 |
| 3092 | 4141 | 193 | 216 |
| 3093 | 4869 | 11 | 34 |
| 3094 | 5135 | 11 | 30 |
| 3095 | 5041 | 56 | 79 |
| 3096 | 4553 | 42 | 63 |
| 3097 | 5020 | 37 | 58 |
| 3097 | 5017 | 37 | 58 |
| 3098 | 5442 | 174 | 194 |
| 3099 | 5382 | 74 | 94 |
| 3099 | 5330 | 11 | 31 |
| 3100 | 4495 | 11 | 34 |
| 3101 | 4253 | 75 | 96 |
| 3102 | 3944 | 41 | 64 |
| 3102 | 3942 | 11 | 34 |
| 3103 | 5073 | 58 | 77 |
| 3104 | 4137 | 142 | 163 |
| 3105 | 4066 | 11 | 31 |
| 3106 | 5028 | 70 | 90 |
| 3107 | 5267 | 105 | 128 |
| 3108 | 5169 | 11 | 33 |
| 3109 | 4543 | 165 | 184 |
| 3110 | 4702 | 11 | 31 |
| 3111 | 4313 | 11 | 34 |
| 3112 | 5132 | 140 | 159 |
| 3113 | 5404 | 4 | 24 |
| 3113 | 5398 | 4 | 24 |
| 3114 | 5116 | 11 | 34 |
| 3115 | 4818 | 11 | 31 |
| 3116 | 4026 | 48 | 71 |
| 3117 | 5141 | 136 | 159 |
| 3118 | 4420 | 11 | 30 |
| 3119 | 5013 | 11 | 30 |
| 3120 | 4336 | 11 | 30 |
| 3121 | 3999 | 34 | 53 |
| 3121 | 3998 | 34 | 53 |
| 3122 | 4631 | 37 | 58 |
| 3123 | 4127 | 11 | 30 |
| 3124 | 4180 | 11 | 31 |
| 3125 | 4104 | 11 | 34 |
| 3125 | 4106 | 11 | 34 |
| 3126 | 5047 | 11 | 31 |
| 3126 | 4908 | 11 | 31 |
| 3127 | 5350 | 38 | 59 |
| 3127 | 5457 | 38 | 59 |
| 3128 | 5467 | 41 | 61 |
| 3129 | 4602 | 11 | 31 |
| 3130 | 5348 | 70 | 90 |
| 3131 | 5034 | 11 | 31 |
| 3132 | 4773 | 43 | 62 |
| 3132 | 4614 | 51 | 70 |
| 3132 | 4687 | 51 | 70 |
| 3133 | 5026 | 8 | 28 |
| 3134 | 4376 | 11 | 33 |
| 3135 | 4748 | 66 | 87 |
| 3136 | 4402 | 160 | 180 |
| 3137 | 4379 | 188 | 208 |
| 3138 | 4779 | 115 | 135 |
| 3139 | 5426 | 52 | 71 |
| 3140 | 5295 | 38 | 57 |
| 3141 | 5094 | 11 | 31 |
| 3142 | 5415 | 50 | 73 |
| 3143 | 4794 | 104 | 125 |
| 3144 | 5250 | 11 | 34 |
| 3145 | 4735 | 11 | 34 |
| 3146 | 4799 | 11 | 34 |
| 3146 | 4703 | 6 | 29 |
| 3146 | 4615 | 45 | 68 |
| 3147 | 4686 | 205 | 224 |
| 3148 | 3980 | 70 | 90 |
| 3149 | 4109 | 221 | 244 |
| 3150 | 4610 | 57 | 76 |
| 3151 | 5167 | 176 | 196 |
| 3152 | 4149 | 11 | 34 |
| 3153 | 4384 | 1 | 20 |
| 3154 | 4899 | 143 | 164 |
| 3155 | 4405 | 11 | 31 |
| 3155 | 4462 | 11 | 31 |
| 3156 | 4990 | 200 | 220 |
| 3157 | 4497 | 74 | 96 |
| 3158 | 4041 | 11 | 34 |
| 3159 | 4646 | 46 | 67 |
| 3160 | 4623 | 385 | 404 |
| 3161 | 5202 | 11 | 30 |
| 3162 | 4970 | 11 | 33 |
| 3163 | 4788 | 204 | 227 |
| 3164 | 4937 | 11 | 30 |
| 3164 | 4837 | 11 | 30 |
| 3164 | 4893 | 11 | 30 |
| 3165 | 4694 | 11 | 32 |
| 3165 | 4792 | 11 | 32 |
| 3166 | 5388 | 71 | 90 |
| 3166 | 5387 | 71 | 90 |
| 3167 | 4443 | 35 | 58 |
| 3168 | 4867 | 59 | 78 |
| 3169 | 4692 | 29 | 48 |
| 3170 | 4224 | 11 | 31 |
| 3171 | 4498 | 11 | 34 |
| 3172 | 5273 | 11 | 32 |
| 3173 | 4927 | 54 | 77 |
| 3174 | 5024 | 11 | 31 |
| 3175 | 5431 | 265 | 285 |
| 3176 | 4315 | 40 | 63 |
| 3177 | 4575 | 11 | 33 |
| 3178 | 4459 | 193 | 216 |
| 3178 | 4340 | 194 | 217 |
| 3179 | 4194 | 11 | 34 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 3179 | 4152 | 99 | 122 |
| 3180 | 5436 | 92 | 111 |
| 3181 | 5427 | 35 | 54 |
| 3182 | 4033 | 39 | 61 |
| 3183 | 4643 | 223 | 243 |
| 3183 | 4609 | 223 | 243 |
| 3183 | 4808 | 223 | 243 |
| 3183 | 4802 | 181 | 201 |
| 3184 | 5145 | 227 | 250 |
| 3185 | 5029 | 67 | 90 |
| 3186 | 4261 | 185 | 207 |
| 3187 | 5036 | 169 | 188 |
| 3188 | 4146 | 11 | 33 |
| 3189 | 4549 | 11 | 31 |
| 3189 | 4576 | 11 | 31 |
| 3189 | 4548 | 11 | 31 |
| 3189 | 4594 | 11 | 31 |
| 3189 | 4732 | 4 | 24 |
| 3190 | 5015 | 11 | 34 |
| 3191 | 5046 | 64 | 84 |
| 3192 | 5280 | 11 | 34 |
| 3193 | 5343 | 152 | 173 |
| 3193 | 5352 | 11 | 32 |
| 3193 | 5490 | 11 | 32 |
| 3194 | 4465 | 11 | 34 |
| 3195 | 5142 | 11 | 32 |
| 3196 | 5039 | 11 | 31 |
| 3196 | 5053 | 11 | 31 |
| 3197 | 4521 | 68 | 88 |
| 3198 | 4975 | 11 | 30 |
| 3199 | 4415 | 11 | 33 |
| 3200 | 5261 | 37 | 59 |
| 3200 | 5113 | 11 | 33 |
| 3201 | 5087 | 11 | 34 |
| 3201 | 4866 | 122 | 145 |
| 3202 | 4834 | 11 | 31 |
| 3202 | 4651 | 11 | 31 |
| 3203 | 4513 | 217 | 239 |
| 3204 | 4175 | 57 | 80 |
| 3205 | 4839 | 11 | 34 |
| 3206 | 5253 | 41 | 60 |
| 3207 | 4881 | 11 | 33 |
| 3208 | 4715 | 11 | 31 |
| 3209 | 4618 | 400 | 423 |
| 3210 | 4648 | 11 | 30 |
| 3211 | 4362 | 45 | 65 |
| 3212 | 5149 | 226 | 248 |
| 3213 | 5286 | 81 | 102 |
| 3213 | 5300 | 81 | 102 |
| 3214 | 5074 | 11 | 34 |
| 3214 | 4849 | 11 | 34 |
| 3215 | 4762 | 52 | 72 |
| 3216 | 5377 | 11 | 34 |
| 3217 | 4751 | 34 | 53 |
| 3218 | 4841 | 11 | 30 |
| 3219 | 5186 | 11 | 31 |
| 3220 | 4520 | 30 | 49 |
| 3221 | 3986 | 116 | 139 |
| 3222 | 5420 | 149 | 168 |
| 3222 | 5450 | 149 | 168 |
| 3223 | 5282 | 35 | 57 |
| 3224 | 5319 | 104 | 124 |
| 3225 | 5100 | 35 | 56 |
| 3226 | 4250 | 11 | 31 |
| 3226 | 4268 | 11 | 31 |
| 3227 | 3936 | 111 | 131 |
| 3228 | 4191 | 37 | 60 |
| 3229 | 4740 | 11 | 34 |
| 3230 | 4300 | 118 | 141 |
| 3231 | 4819 | 11 | 32 |
| 3231 | 4689 | 11 | 32 |
| 3231 | 4662 | 11 | 32 |
| 3232 | 4658 | 10 | 33 |
| 3233 | 5340 | 154 | 176 |
| 3234 | 4375 | 11 | 33 |
| 3235 | 5131 | 9 | 31 |
| 3236 | 4724 | 139 | 159 |
| 3237 | 4256 | 52 | 74 |
| 3238 | 5051 | 34 | 55 |
| 3239 | 4453 | 32 | 55 |
| 3240 | 5372 | 11 | 30 |
| 3241 | 4444 | 135 | 154 |
| 3241 | 4365 | 11 | 30 |
| 3242 | 4731 | 150 | 169 |
| 3243 | 5213 | 11 | 31 |
| 3244 | 5314 | 11 | 31 |
| 3245 | 4854 | 11 | 30 |
| 3246 | 5320 | 187 | 207 |
| 3247 | 4938 | 99 | 122 |
| 3248 | 4489 | 11 | 32 |
| 3249 | 5474 | 11 | 30 |
| 3249 | 5371 | 11 | 30 |
| 3250 | 5002 | 11 | 30 |
| 3251 | 4699 | 34 | 57 |
| 3252 | 4153 | 11 | 31 |
| 3253 | 4130 | 11 | 34 |
| 3254 | 5138 | 11 | 33 |
| 3255 | 5222 | 50 | 72 |
| 3255 | 5200 | 50 | 72 |
| 3256 | 4107 | 11 | 31 |
| 3257 | 4858 | 75 | 94 |
| 3258 | 4826 | 11 | 33 |
| 3259 | 5042 | 44 | 67 |
| 3260 | 4696 | 11 | 32 |
| 3261 | 4953 | 221 | 241 |
| 3262 | 4931 | 11 | 32 |
| 3263 | 3987 | 212 | 235 |
| 3264 | 3968 | 96 | 119 |
| 3265 | 4629 | 71 | 90 |
| 3266 | 4600 | 11 | 31 |
| 3266 | 4564 | 207 | 227 |
| 3267 | 4419 | 45 | 67 |
| 3268 | 4964 | 41 | 60 |
| 3269 | 4950 | 153 | 172 |
| 3270 | 4801 | 33 | 52 |
| 3271 | 4048 | 238 | 261 |
| 3272 | 5118 | 11 | 34 |
| 3272 | 5151 | 11 | 34 |
| 3272 | 5264 | 11 | 34 |
| 3273 | 4357 | 11 | 32 |
| 3274 | 4009 | 11 | 32 |
| 3275 | 5265 | 11 | 30 |
| 3275 | 5225 | 29 | 48 |
| 3275 | 5126 | 11 | 30 |
| 3275 | 5270 | 11 | 30 |
| 3275 | 5251 | 105 | 124 |
| 3275 | 5137 | 1 | 20 |
| 3276 | 4213 | 218 | 238 |
| 3277 | 4071 | 36 | 59 |
| 3278 | 4678 | 11 | 31 |
| 3279 | 4377 | 11 | 30 |
| 3280 | 4895 | 40 | 59 |
| 3280 | 5108 | 40 | 59 |
| 3280 | 4997 | 40 | 59 |
| 3280 | 4840 | 40 | 59 |
| 3280 | 5014 | 40 | 59 |
| 3280 | 4890 | 40 | 59 |
| 3280 | 4851 | 40 | 59 |
| 3281 | 4506 | 11 | 30 |
| 3282 | 4353 | 38 | 59 |
| 3282 | 4346 | 38 | 59 |
| 3283 | 4234 | 257 | 277 |

TABLE 4-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 3283 | 4168 | 323 | 343 |
| 3283 | 4220 | 245 | 265 |
| 3284 | 4273 | 11 | 33 |
| 3285 | 5243 | 166 | 187 |
| 3286 | 4393 | 142 | 165 |
| 3287 | 4359 | 11 | 30 |
| 3288 | 5211 | 11 | 34 |
| 3288 | 5175 | 11 | 34 |
| 3288 | 5283 | 11 | 34 |
| 3289 | 4308 | 157 | 178 |
| 3290 | 3982 | 11 | 34 |
| 3291 | 4052 | 11 | 32 |
| 3292 | 4589 | 11 | 34 |
| 3293 | 4852 | 52 | 72 |
| 3294 | 4389 | 118 | 141 |
| 3295 | 4768 | 36 | 57 |
| 3296 | 4812 | 11 | 32 |
| 3297 | 3978 | 37 | 56 |
| 3298 | 4761 | 11 | 30 |
| 3298 | 4685 | 11 | 30 |
| 3299 | 4825 | 11 | 33 |
| 3299 | 4745 | 11 | 33 |
| 3299 | 4770 | 11 | 33 |
| 3300 | 5086 | 56 | 78 |
| 3301 | 4486 | 11 | 31 |
| 3302 | 4870 | 41 | 61 |
| 3302 | 5060 | 41 | 61 |
| 3303 | 4321 | 11 | 34 |
| 3304 | 4185 | 49 | 69 |
| 3304 | 4136 | 49 | 69 |
| 3304 | 4287 | 49 | 69 |
| 3304 | 4322 | 49 | 69 |
| 3305 | 4588 | 11 | 34 |
| 3306 | 5236 | 11 | 34 |
| 3307 | 4143 | 11 | 30 |
| 3308 | 4302 | 11 | 30 |
| 3308 | 4240 | 11 | 30 |
| 3309 | 4366 | 11 | 32 |
| 3310 | 5472 | 52 | 73 |
| 3311 | 4649 | 11 | 30 |
| 3312 | 4490 | 11 | 34 |
| 3313 | 4642 | 113 | 133 |
| 3314 | 4559 | 232 | 252 |
| 3314 | 4701 | 232 | 252 |
| 3315 | 4216 | 11 | 31 |
| 3316 | 4339 | 37 | 59 |
| 3317 | 4423 | 138 | 157 |
| 3318 | 5241 | 55 | 78 |
| 3319 | 5255 | 34 | 54 |
| 3320 | 3927 | 40 | 60 |
| 3320 | 3930 | 40 | 60 |
| 3320 | 3926 | 40 | 60 |
| 3320 | 3932 | 45 | 65 |
| 3320 | 3922 | 39 | 59 |
| 3320 | 3924 | 132 | 152 |
| 3320 | 3933 | 40 | 60 |
| 3321 | 4254 | 60 | 79 |
| 3322 | 5166 | 213 | 236 |
| 3323 | 4647 | 61 | 81 |
| 3323 | 4657 | 61 | 81 |
| 3323 | 4603 | 61 | 81 |
| 3324 | 5235 | 73 | 96 |
| 3325 | 4406 | 34 | 55 |
| 3326 | 5207 | 8 | 30 |
| 3327 | 4800 | 11 | 32 |
| 3328 | 4942 | 11 | 32 |
| 3329 | 4796 | 11 | 34 |
| 3330 | 4998 | 35 | 56 |
| 3331 | 4741 | 240 | 261 |
| 3332 | 5306 | 60 | 83 |
| 3333 | 4555 | 181 | 203 |
| 3334 | 4909 | 41 | 60 |
| 3335 | 5304 | 11 | 34 |
| 3335 | 5383 | 11 | 34 |
| 3336 | 5462 | 31 | 50 |
| 3337 | 4636 | 11 | 33 |
| 3337 | 4683 | 11 | 33 |
| 3338 | 5105 | 40 | 63 |
| 3339 | 4552 | 100 | 122 |
| 3340 | 4078 | 39 | 62 |
| 3341 | 4835 | 11 | 31 |
| 3342 | 5187 | 75 | 96 |
| 3343 | 4679 | 158 | 181 |
| 3344 | 4865 | 11 | 32 |
| 3344 | 4862 | 11 | 32 |
| 3345 | 5274 | 11 | 34 |
| 3346 | 4936 | 11 | 33 |
| 3347 | 4352 | 11 | 31 |
| 3348 | 4221 | 11 | 31 |
| 3349 | 5072 | 11 | 31 |
| 3349 | 5083 | 11 | 31 |
| 3350 | 4695 | 117 | 139 |
| 3351 | 5230 | 71 | 94 |
| 3352 | 4961 | 167 | 187 |
| 3353 | 5227 | 11 | 30 |
| 3354 | 4147 | 92 | 115 |
| 3355 | 4536 | 11 | 33 |
| 3356 | 5443 | 110 | 130 |
| 3357 | 5321 | 247 | 266 |
| 3358 | 4196 | 28 | 47 |
| 3359 | 5487 | 35 | 56 |
| 3360 | 4227 | 11 | 30 |
| 3361 | 4488 | 119 | 139 |
| 3362 | 4001 | 107 | 130 |
| 3362 | 4003 | 8 | 31 |
| 3362 | 4012 | 105 | 128 |
| 3362 | 4011 | 112 | 135 |
| 3363 | 4926 | 136 | 155 |
| 3364 | 5433 | 11 | 34 |
| 3364 | 3961 | 11 | 34 |
| 3364 | 4005 | 11 | 34 |
| 3364 | 3960 | 11 | 34 |
| 3364 | 3947 | 151 | 174 |
| 3364 | 3976 | 11 | 34 |
| 3364 | 3966 | 106 | 129 |
| 3364 | 3973 | 11 | 34 |
| 3364 | 3950 | 11 | 34 |
| 3364 | 3958 | 11 | 34 |
| 3364 | 3962 | 11 | 34 |
| 3364 | 3969 | 11 | 34 |
| 3364 | 3957 | 11 | 34 |
| 3364 | 4002 | 104 | 127 |
| 3364 | 3954 | 11 | 34 |
| 3364 | 3952 | 7 | 30 |
| 3364 | 3946 | 11 | 34 |
| 3364 | 3948 | 11 | 34 |
| 3364 | 4006 | 11 | 34 |
| 3364 | 3970 | 11 | 34 |
| 3364 | 3965 | 11 | 34 |
| 3365 | 5161 | 50 | 71 |
| 3365 | 5165 | 50 | 71 |
| 3365 | 5173 | 50 | 71 |
| 3366 | 4460 | 11 | 30 |
| 3367 | 4690 | 11 | 31 |
| 3368 | 4337 | 87 | 110 |
| 3369 | 4534 | 201 | 222 |
| 3370 | 4040 | 7 | 30 |
| 3371 | 5004 | 11 | 34 |
| 3372 | 4720 | 41 | 63 |
| 3372 | 4554 | 40 | 62 |
| 3372 | 4688 | 40 | 62 |
| 3373 | 4401 | 11 | 31 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 3373 | 4355 | 139 | 159 |
| 3374 | 4418 | 11 | 33 |
| 3374 | 4412 | 11 | 33 |
| 3375 | 4098 | 38 | 58 |
| 3376 | 5378 | 11 | 31 |
| 3377 | 4562 | 11 | 30 |
| 3378 | 4813 | 38 | 57 |
| 3379 | 4804 | 153 | 173 |
| 3379 | 4613 | 153 | 173 |
| 3380 | 4088 | 11 | 34 |
| 3381 | 4644 | 229 | 252 |
| 3382 | 4708 | 11 | 31 |
| 3383 | 5206 | 11 | 30 |
| 3384 | 4301 | 36 | 59 |
| 3385 | 4471 | 11 | 31 |
| 3386 | 4951 | 11 | 30 |
| 3386 | 5097 | 11 | 30 |
| 3386 | 4904 | 11 | 30 |
| 3386 | 5107 | 11 | 30 |
| 3386 | 5007 | 11 | 30 |
| 3387 | 4298 | 204 | 223 |
| 3388 | 4984 | 41 | 64 |
| 3389 | 5027 | 11 | 31 |
| 3390 | 4082 | 51 | 73 |
| 3391 | 4640 | 165 | 184 |
| 3392 | 4427 | 11 | 31 |
| 3393 | 4411 | 11 | 30 |
| 3394 | 4855 | 45 | 68 |
| 3395 | 5220 | 11 | 32 |
| 3395 | 5272 | 11 | 32 |
| 3396 | 4335 | 11 | 32 |
| 3397 | 5476 | 215 | 236 |
| 3397 | 5390 | 215 | 236 |
| 3398 | 4442 | 87 | 107 |
| 3399 | 4838 | 11 | 30 |
| 3400 | 4222 | 37 | 58 |
| 3401 | 4435 | 11 | 34 |
| 3402 | 3990 | 11 | 34 |
| 3403 | 5176 | 200 | 219 |
| 3404 | 5297 | 49 | 72 |
| 3405 | 4095 | 61 | 84 |
| 3406 | 4906 | 11 | 32 |
| 3407 | 4172 | 11 | 31 |
| 3408 | 4226 | 74 | 96 |
| 3409 | 5195 | 79 | 98 |
| 3410 | 4941 | 33 | 54 |
| 3411 | 4330 | 11 | 31 |
| 3412 | 4666 | 11 | 30 |
| 3413 | 4316 | 72 | 95 |
| 3414 | 5168 | 33 | 53 |
| 3414 | 5210 | 33 | 53 |
| 3415 | 5484 | 37 | 60 |
| 3415 | 5491 | 47 | 70 |
| 3415 | 5401 | 37 | 60 |
| 3415 | 5455 | 37 | 60 |
| 3415 | 5458 | 37 | 60 |
| 3415 | 5402 | 38 | 61 |
| 3416 | 4960 | 11 | 34 |
| 3416 | 4919 | 11 | 34 |
| 3416 | 5035 | 11 | 34 |
| 3416 | 5093 | 11 | 34 |
| 3417 | 5406 | 64 | 84 |
| 3418 | 4512 | 56 | 78 |
| 3419 | 4793 | 197 | 217 |
| 3420 | 4712 | 42 | 61 |
| 3420 | 4675 | 42 | 61 |
| 3421 | 5103 | 11 | 30 |
| 3421 | 4923 | 11 | 30 |
| 3421 | 5043 | 11 | 30 |
| 3422 | 4203 | 11 | 30 |
| 3423 | 4369 | 255 | 274 |
| 3424 | 5488 | 11 | 31 |
| 3425 | 4857 | 11 | 33 |
| 3425 | 4910 | 11 | 33 |
| 3426 | 4403 | 11 | 34 |
| 3427 | 4356 | 75 | 98 |
| 3428 | 4354 | 11 | 32 |
| 3429 | 4766 | 11 | 31 |
| 3429 | 4730 | 11 | 31 |
| 3429 | 4760 | 11 | 31 |
| 3429 | 4561 | 11 | 31 |
| 3430 | 5244 | 11 | 30 |
| 3431 | 5294 | 11 | 34 |
| 3432 | 4985 | 74 | 93 |
| 3433 | 4000 | 11 | 34 |
| 3434 | 4574 | 11 | 34 |
| 3435 | 4231 | 11 | 34 |
| 3436 | 4439 | 215 | 238 |
| 3437 | 5454 | 84 | 104 |
| 3437 | 5328 | 78 | 98 |
| 3438 | 5228 | 11 | 30 |
| 3439 | 5432 | 34 | 53 |
| 3440 | 5144 | 11 | 30 |
| 3441 | 4424 | 136 | 159 |
| 3442 | 5290 | 11 | 30 |
| 3443 | 5332 | 11 | 31 |
| 3444 | 4090 | 11 | 34 |
| 3445 | 4743 | 190 | 210 |
| 3446 | 4438 | 11 | 34 |
| 3447 | 4069 | 11 | 31 |
| 3447 | 4072 | 11 | 31 |
| 3448 | 4392 | 11 | 34 |
| 3449 | 4828 | 11 | 31 |
| 3450 | 3992 | 81 | 104 |
| 3451 | 4868 | 45 | 64 |
| 3452 | 4128 | 11 | 31 |
| 3453 | 4338 | 111 | 134 |
| 3454 | 4288 | 11 | 31 |
| 3455 | 4202 | 11 | 30 |
| 3456 | 5010 | 11 | 34 |
| 3457 | 4928 | 48 | 71 |
| 3458 | 4601 | 43 | 64 |
| 3458 | 4723 | 43 | 64 |
| 3458 | 4582 | 11 | 32 |
| 3458 | 4786 | 11 | 32 |
| 3459 | 4929 | 117 | 136 |
| 3460 | 4074 | 11 | 34 |
| 3461 | 4183 | 11 | 30 |
| 3462 | 4450 | 126 | 149 |
| 3463 | 4805 | 39 | 62 |
| 3464 | 4898 | 11 | 30 |
| 3465 | 4949 | 76 | 97 |
| 3466 | 4769 | 32 | 51 |
| 3467 | 4833 | 43 | 66 |
| 3467 | 4550 | 43 | 66 |
| 3468 | 4988 | 50 | 73 |
| 3469 | 4414 | 47 | 66 |
| 3470 | 5064 | 34 | 55 |
| 3471 | 4381 | 117 | 138 |
| 3472 | 4939 | 11 | 34 |
| 3473 | 5115 | 11 | 32 |
| 3474 | 5139 | 11 | 33 |
| 3475 | 4907 | 83 | 102 |
| 3476 | 4343 | 11 | 34 |
| 3476 | 4348 | 42 | 65 |
| 3477 | 4091 | 54 | 75 |
| 3478 | 4932 | 60 | 80 |
| 3479 | 4775 | 11 | 32 |
| 3480 | 4345 | 11 | 32 |
| 3481 | 4900 | 11 | 31 |
| 3482 | 4155 | 11 | 34 |
| 3483 | 5226 | 287 | 309 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 3484 | 4283 | 45 | 64 |
| 3485 | 4935 | 245 | 265 |
| 3486 | 5214 | 72 | 91 |
| 3487 | 5189 | 46 | 69 |
| 3488 | 4529 | 156 | 179 |
| 3489 | 4367 | 11 | 34 |
| 3490 | 4563 | 11 | 32 |
| 3491 | 4585 | 11 | 30 |
| 3492 | 4049 | 114 | 137 |
| 3493 | 4795 | 39 | 60 |
| 3494 | 3988 | 11 | 30 |
| 3495 | 4050 | 74 | 97 |
| 3496 | 5335 | 11 | 32 |
| 3497 | 4634 | 11 | 30 |
| 3498 | 4934 | 11 | 30 |
| 3499 | 4624 | 65 | 84 |
| 3500 | 4911 | 76 | 96 |
| 3501 | 5466 | 11 | 33 |
| 3502 | 5316 | 146 | 165 |
| 3503 | 4832 | 34 | 54 |
| 3503 | 4756 | 34 | 54 |
| 3504 | 4342 | 11 | 33 |
| 3505 | 4622 | 37 | 56 |
| 3506 | 5289 | 11 | 30 |
| 3507 | 5464 | 130 | 153 |
| 3508 | 5054 | 11 | 30 |
| 3509 | 4480 | 11 | 34 |
| 3509 | 4351 | 11 | 34 |
| 3510 | 5325 | 11 | 33 |
| 3511 | 5475 | 11 | 31 |
| 3512 | 5305 | 11 | 33 |
| 3513 | 4307 | 63 | 86 |
| 3514 | 4290 | 37 | 59 |
| 3515 | 5281 | 11 | 33 |
| 3516 | 4544 | 114 | 137 |
| 3516 | 4739 | 214 | 237 |
| 3516 | 4681 | 32 | 55 |
| 3517 | 4332 | 79 | 102 |
| 3518 | 4747 | 52 | 74 |
| 3519 | 5391 | 11 | 32 |
| 3520 | 5192 | 11 | 30 |
| 3521 | 4249 | 40 | 62 |
| 3522 | 4816 | 303 | 326 |
| 3523 | 4150 | 11 | 31 |
| 3523 | 4296 | 11 | 31 |
| 3523 | 4118 | 11 | 31 |
| 3523 | 4320 | 11 | 31 |
| 3523 | 4294 | 11 | 31 |
| 3523 | 4225 | 11 | 31 |
| 3524 | 5447 | 1 | 22 |
| 3525 | 4612 | 11 | 31 |
| 3526 | 5057 | 87 | 106 |
| 3527 | 5122 | 11 | 30 |
| 3528 | 5291 | 133 | 153 |
| 3529 | 3931 | 123 | 143 |
| 3530 | 5068 | 119 | 138 |
| 3531 | 4971 | 32 | 52 |
| 3531 | 4885 | 32 | 52 |
| 3531 | 4915 | 33 | 53 |
| 3532 | 5079 | 11 | 30 |
| 3533 | 5293 | 53 | 76 |
| 3534 | 4331 | 11 | 32 |
| 3535 | 4094 | 231 | 254 |
| 3536 | 4368 | 11 | 33 |
| 3536 | 4484 | 11 | 33 |
| 3537 | 5342 | 142 | 161 |
| 3538 | 4482 | 45 | 68 |
| 3539 | 4886 | 127 | 146 |
| 3540 | 4015 | 86 | 109 |
| 3540 | 4018 | 11 | 34 |
| 3540 | 4017 | 85 | 108 |
| 3540 | 4025 | 85 | 108 |
| 3540 | 4016 | 85 | 108 |
| 3540 | 4014 | 11 | 34 |
| 3540 | 4023 | 85 | 108 |
| 3540 | 4021 | 85 | 108 |
| 3540 | 4020 | 85 | 108 |
| 3540 | 4027 | 11 | 34 |
| 3540 | 4028 | 11 | 34 |
| 3540 | 4013 | 85 | 108 |
| 3540 | 4019 | 85 | 108 |
| 3541 | 5140 | 11 | 30 |
| 3542 | 4823 | 185 | 205 |
| 3543 | 4806 | 11 | 32 |
| 3544 | 4954 | 11 | 30 |
| 3545 | 4292 | 11 | 30 |
| 3546 | 4184 | 11 | 32 |
| 3547 | 4989 | 11 | 31 |
| 3548 | 4496 | 11 | 34 |
| 3549 | 4311 | 50 | 69 |
| 3549 | 4112 | 11 | 30 |
| 3550 | 4568 | 11 | 30 |
| 3550 | 4540 | 11 | 30 |
| 3551 | 4822 | 78 | 99 |
| 3552 | 5389 | 11 | 31 |
| 3553 | 5285 | 227 | 246 |
| 3554 | 5493 | 11 | 32 |
| 3555 | 4140 | 153 | 172 |
| 3556 | 5065 | 41 | 60 |
| 3557 | 5323 | 11 | 34 |
| 3558 | 4974 | 11 | 33 |
| 3559 | 4297 | 303 | 324 |
| 3560 | 4510 | 11 | 34 |
| 3561 | 4781 | 139 | 162 |
| 3562 | 4242 | 223 | 245 |
| 3562 | 4178 | 223 | 245 |
| 3562 | 4177 | 223 | 245 |
| 3562 | 4190 | 223 | 245 |
| 3562 | 4257 | 223 | 245 |
| 3563 | 3996 | 11 | 31 |
| 3564 | 4081 | 69 | 92 |
| 3565 | 4579 | 60 | 79 |
| 3566 | 5099 | 136 | 155 |
| 3567 | 4665 | 238 | 259 |
| 3568 | 5069 | 101 | 120 |
| 3569 | 5367 | 11 | 32 |
| 3570 | 4010 | 50 | 73 |
| 3571 | 5413 | 11 | 31 |
| 3572 | 4532 | 11 | 32 |
| 3573 | 4654 | 11 | 31 |
| 3574 | 4422 | 49 | 71 |
| 3575 | 5080 | 11 | 34 |
| 3576 | 4979 | 11 | 31 |
| 3576 | 5067 | 11 | 31 |
| 3577 | 4856 | 11 | 32 |
| 3578 | 4966 | 38 | 61 |
| 3579 | 4400 | 48 | 67 |
| 3580 | 4437 | 11 | 31 |
| 3581 | 5123 | 39 | 62 |
| 3582 | 5215 | 11 | 34 |
| 3582 | 5155 | 40 | 63 |
| 3582 | 5182 | 40 | 63 |
| 3582 | 5266 | 40 | 63 |
| 3583 | 4672 | 11 | 32 |
| 3584 | 5082 | 51 | 71 |
| 3584 | 4913 | 37 | 57 |
| 3585 | 4956 | 88 | 111 |
| 3586 | 5203 | 11 | 31 |
| 3587 | 4455 | 133 | 152 |
| 3588 | 4145 | 11 | 34 |
| 3588 | 4323 | 11 | 34 |
| 3589 | 5412 | 11 | 31 |

TABLE 4-continued

Maize and rice miRNAs and miRNA precursors

| miRNA SEQ ID NO. | pre-miRNA SEQ ID NO. | Nucleotide position of miRNA in pre-miRNA from | Nucleotide position of miRNA in pre-miRNA to |
|---|---|---|---|
| 3590 | 4161 | 11 | 32 |
| 3590 | 4252 | 11 | 32 |
| 3591 | 5212 | 133 | 153 |
| 3591 | 5179 | 133 | 153 |
| 3592 | 4946 | 113 | 135 |
| 3593 | 4632 | 226 | 249 |
| 3594 | 5441 | 94 | 117 |
| 3595 | 4551 | 11 | 32 |
| 3596 | 5078 | 11 | 33 |
| 3597 | 4430 | 11 | 32 |
| 3598 | 4170 | 43 | 65 |
| 3599 | 4266 | 11 | 33 |
| 3599 | 4267 | 11 | 33 |
| 3599 | 4165 | 11 | 33 |
| 3599 | 4305 | 11 | 33 |
| 3600 | 4282 | 33 | 53 |
| 3601 | 5150 | 68 | 87 |
| 3602 | 5403 | 81 | 103 |
| 3602 | 5492 | 81 | 103 |
| 3603 | 4493 | 373 | 392 |
| 3604 | 4211 | 11 | 34 |
| 3605 | 5075 | 11 | 31 |
| 3606 | 4973 | 11 | 30 |
| 3607 | 4884 | 107 | 126 |
| 3608 | 5438 | 11 | 31 |
| 3608 | 5416 | 11 | 31 |
| 3609 | 4780 | 214 | 234 |
| 3610 | 4426 | 11 | 33 |
| 3611 | 4344 | 11 | 32 |
| 3612 | 4887 | 163 | 186 |
| 3613 | 4144 | 11 | 31 |
| 3614 | 4667 | 102 | 125 |
| 3615 | 5249 | 37 | 60 |
| 3615 | 5218 | 36 | 59 |
| 3615 | 5129 | 36 | 59 |
| 3616 | 4725 | 11 | 32 |
| 3616 | 4719 | 11 | 32 |
| 3616 | 4538 | 11 | 32 |
| 3616 | 4765 | 11 | 32 |
| 3616 | 4547 | 11 | 32 |
| 3616 | 4661 | 11 | 32 |
| 3616 | 4809 | 11 | 32 |
| 3616 | 4604 | 11 | 32 |
| 3616 | 4541 | 11 | 32 |
| 3616 | 4650 | 11 | 32 |
| 3617 | 4349 | 11 | 30 |
| 3618 | 5400 | 57 | 79 |
| 3619 | 4515 | 11 | 31 |
| 3620 | 5114 | 11 | 32 |
| 3621 | 4569 | 92 | 112 |
| 3622 | 4830 | 143 | 162 |
| 3623 | 4810 | 35 | 56 |
| 3623 | 4764 | 198 | 219 |
| 3624 | 4616 | 99 | 118 |
| 3625 | 4487 | 111 | 131 |
| 3626 | 4472 | 43 | 62 |
| 3627 | 5337 | 11 | 34 |
| 3628 | 5158 | 11 | 31 |
| 3629 | 5309 | 11 | 34 |
| 3630 | 5418 | 94 | 117 |
| 3630 | 5439 | 94 | 117 |
| 3631 | 5424 | 36 | 56 |
| 3632 | 5307 | 42 | 65 |
| 3633 | 4245 | 11 | 33 |
| 3634 | 4523 | 134 | 157 |
| 3634 | 4507 | 41 | 64 |
| 3635 | 4653 | 119 | 142 |
| 3636 | 5171 | 38 | 58 |
| 3637 | 5322 | 88 | 107 |
| 3637 | 5347 | 85 | 104 |
| 3638 | 4469 | 11 | 31 |
| 3638 | 4371 | 11 | 31 |
| 3638 | 4404 | 108 | 128 |
| 3639 | 4875 | 11 | 32 |
| 3640 | 5133 | 67 | 90 |
| 3641 | 5092 | 11 | 34 |
| 3642 | 4587 | 11 | 30 |
| 3643 | 4329 | 78 | 100 |
| 3644 | 4896 | 50 | 71 |
| 3645 | 3991 | 7 | 29 |
| 3646 | 4347 | 51 | 74 |
| 3647 | 4037 | 94 | 114 |
| 3647 | 4038 | 11 | 31 |
| 3647 | 4034 | 104 | 124 |
| 3648 | 5104 | 81 | 101 |
| 3649 | 4188 | 58 | 81 |
| 3650 | 4711 | 162 | 183 |
| 3650 | 4831 | 162 | 183 |
| 3650 | 4652 | 162 | 183 |
| 3651 | 4079 | 11 | 33 |
| 3652 | 4219 | 11 | 34 |
| 3653 | 4959 | 131 | 150 |
| 3654 | 4173 | 240 | 263 |
| 3655 | 4134 | 11 | 30 |
| 3656 | 4361 | 11 | 30 |
| 3657 | 4451 | 11 | 31 |
| 3658 | 4871 | 11 | 33 |
| 3659 | 4043 | 11 | 34 |
| 3660 | 4387 | 11 | 32 |
| 3661 | 4425 | 41 | 61 |
| 3661 | 4457 | 42 | 62 |
| 3662 | 5409 | 56 | 75 |
| 3662 | 5497 | 62 | 81 |
| 3663 | 4129 | 11 | 31 |
| 3664 | 4746 | 11 | 33 |
| 3665 | 5425 | 11 | 33 |
| 3666 | 4860 | 11 | 31 |
| 3667 | 4655 | 11 | 32 |
| 3668 | 4967 | 11 | 30 |
| 3668 | 4843 | 71 | 90 |
| 3669 | 5485 | 11 | 30 |
| 3669 | 5338 | 11 | 30 |
| 3669 | 5478 | 11 | 30 |
| 3670 | 3989 | 11 | 33 |
| 3671 | 4978 | 11 | 30 |
| 3672 | 4325 | 11 | 34 |
| 3672 | 4197 | 201 | 224 |
| 3672 | 4181 | 11 | 34 |
| 3673 | 4046 | 128 | 151 |
| 3674 | 5246 | 209 | 232 |
| 3675 | 4952 | 34 | 53 |
| 3676 | 4976 | 62 | 83 |
| 3677 | 4163 | 11 | 30 |
| 3678 | 4445 | 11 | 30 |
| 3679 | 4777 | 84 | 103 |
| 3680 | 5422 | 47 | 70 |
| 3681 | 4524 | 42 | 61 |
| 3682 | 4068 | 11 | 31 |
| 3683 | 4511 | 183 | 206 |
| 3684 | 5496 | 11 | 31 |
| 3685 | 4557 | 155 | 178 |
| 3686 | 4310 | 11 | 31 |
| 3687 | 5254 | 46 | 68 |
| 3688 | 5000 | 44 | 64 |
| 3688 | 4905 | 11 | 31 |
| 3689 | 4848 | 150 | 170 |
| 3689 | 4903 | 150 | 170 |
| 3689 | 4889 | 177 | 197 |
| 3689 | 4994 | 150 | 170 |
| 3690 | 4995 | 43 | 63 |
| 3690 | 4943 | 43 | 63 |
| 3691 | 5399 | 38 | 57 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 3692 | 5480 | 128 | 151 |
| 3693 | 4817 | 11 | 34 |
| 3694 | 5301 | 11 | 34 |
| 3695 | 5009 | 79 | 100 |
| 3696 | 4125 | 43 | 63 |
| 3697 | 4360 | 11 | 32 |
| 3698 | 4113 | 71 | 90 |
| 3699 | 4901 | 11 | 31 |
| 3699 | 4922 | 11 | 31 |
| 3700 | 5012 | 231 | 250 |
| 3700 | 4980 | 231 | 250 |
| 3701 | 4284 | 73 | 95 |
| 3702 | 4639 | 11 | 34 |
| 3703 | 4189 | 36 | 59 |
| 3704 | 5483 | 68 | 87 |
| 3705 | 5058 | 11 | 34 |
| 3706 | 5037 | 57 | 77 |
| 3707 | 4382 | 31 | 51 |
| 3708 | 5364 | 11 | 31 |
| 3708 | 5419 | 11 | 31 |
| 3709 | 4669 | 11 | 32 |
| 3710 | 4519 | 151 | 174 |
| 3711 | 4693 | 11 | 30 |
| 3712 | 4433 | 11 | 34 |
| 3713 | 4790 | 11 | 33 |
| 3714 | 4595 | 67 | 89 |
| 3715 | 4248 | 41 | 60 |
| 3716 | 4164 | 156 | 176 |
| 3717 | 4993 | 110 | 133 |
| 3718 | 4186 | 11 | 32 |
| 3718 | 4133 | 63 | 84 |
| 3719 | 4463 | 11 | 34 |
| 3720 | 4963 | 11 | 34 |
| 3721 | 4324 | 11 | 30 |
| 3721 | 4281 | 11 | 30 |
| 3722 | 4198 | 11 | 32 |
| 3723 | 4811 | 149 | 172 |
| 3724 | 4676 | 220 | 239 |
| 3725 | 4706 | 43 | 64 |
| 3726 | 4004 | 11 | 31 |
| 3727 | 5252 | 11 | 32 |
| 3728 | 5259 | 11 | 34 |
| 3729 | 5256 | 35 | 54 |
| 3730 | 4539 | 138 | 159 |
| 3730 | 4599 | 11 | 32 |
| 3731 | 4700 | 40 | 63 |
| 3732 | 4533 | 11 | 34 |
| 3733 | 4264 | 11 | 31 |
| 3734 | 4996 | 11 | 31 |
| 3735 | 4148 | 11 | 33 |
| 3736 | 4481 | 11 | 30 |
| 3737 | 4607 | 11 | 30 |
| 3738 | 4627 | 242 | 261 |
| 3739 | 5239 | 37 | 58 |
| 3740 | 5154 | 11 | 34 |
| 3741 | 4925 | 11 | 32 |
| 3742 | 4754 | 101 | 120 |
| 3743 | 4785 | 70 | 89 |
| 3743 | 4619 | 70 | 89 |
| 3743 | 4597 | 70 | 89 |
| 3743 | 4797 | 105 | 124 |
| 3744 | 5191 | 11 | 34 |
| 3744 | 5172 | 11 | 34 |
| 3745 | 5177 | 176 | 199 |
| 3746 | 4192 | 11 | 32 |
| 3747 | 4326 | 11 | 31 |
| 3748 | 3939 | 11 | 34 |
| 3749 | 4983 | 11 | 34 |
| 3749 | 4944 | 11 | 34 |
| 3750 | 5101 | 94 | 113 |
| 3751 | 4374 | 69 | 92 |
| 3752 | 4987 | 11 | 30 |
| 3753 | 4572 | 11 | 30 |
| 3754 | 4755 | 43 | 66 |
| 3755 | 5234 | 11 | 34 |
| 3756 | 4396 | 11 | 30 |
| 3757 | 4120 | 212 | 231 |
| 3758 | 4210 | 136 | 157 |
| 3759 | 5157 | 11 | 34 |
| 3760 | 3993 | 33 | 54 |
| 3761 | 5373 | 118 | 138 |
| 3762 | 4621 | 37 | 56 |
| 3762 | 4581 | 37 | 56 |
| 3762 | 4803 | 37 | 56 |
| 3763 | 5052 | 5 | 24 |
| 3764 | 4372 | 11 | 31 |
| 3765 | 4429 | 11 | 31 |
| 3766 | 5375 | 227 | 250 |
| 3767 | 4883 | 44 | 64 |
| 3767 | 4916 | 44 | 64 |
| 3768 | 4728 | 11 | 34 |
| 3769 | 4757 | 45 | 67 |
| 3770 | 3951 | 11 | 31 |
| 3771 | 5164 | 41 | 64 |
| 3772 | 4556 | 11 | 32 |
| 3772 | 4821 | 162 | 183 |
| 3773 | 5428 | 44 | 67 |
| 3774 | 4491 | 11 | 31 |
| 3775 | 5263 | 116 | 136 |
| 3776 | 4205 | 11 | 30 |
| 3776 | 4236 | 32 | 51 |
| 3776 | 4243 | 230 | 249 |
| 3776 | 4195 | 33 | 52 |
| 3777 | 4260 | 52 | 75 |
| 3778 | 4727 | 51 | 74 |
| 3779 | 4160 | 11 | 31 |
| 3779 | 4157 | 11 | 31 |
| 3780 | 5117 | 79 | 99 |
| 3781 | 4434 | 162 | 181 |
| 3782 | 5021 | 11 | 34 |
| 3783 | 4479 | 11 | 30 |
| 3783 | 4395 | 11 | 30 |
| 3784 | 5411 | 181 | 203 |
| 3784 | 5414 | 214 | 236 |
| 3784 | 5339 | 214 | 236 |
| 3785 | 5209 | 134 | 154 |
| 3786 | 4265 | 11 | 30 |
| 3787 | 5128 | 11 | 30 |
| 3788 | 5181 | 86 | 105 |
| 3789 | 5194 | 11 | 30 |
| 3790 | 4778 | 194 | 215 |
| 3791 | 4902 | 32 | 53 |
| 3791 | 4861 | 32 | 53 |
| 3792 | 4272 | 11 | 34 |
| 3793 | 5233 | 11 | 32 |
| 3794 | 4608 | 199 | 222 |
| 3795 | 4228 | 42 | 65 |
| 3796 | 4350 | 11 | 34 |
| 3797 | 5111 | 11 | 32 |
| 3798 | 4306 | 66 | 85 |
| 3799 | 5313 | 31 | 51 |
| 3799 | 5345 | 32 | 52 |
| 3800 | 5049 | 110 | 130 |
| 3801 | 5231 | 99 | 121 |
| 3802 | 5257 | 11 | 34 |
| 3803 | 4992 | 119 | 139 |
| 3804 | 4590 | 11 | 30 |
| 3805 | 4470 | 49 | 70 |
| 3806 | 5495 | 78 | 100 |
| 3807 | 5405 | 203 | 226 |
| 3808 | 4454 | 37 | 57 |
| 3808 | 4535 | 37 | 57 |

TABLE 4-continued

Maize and rice miRNAs and miRNA precursors

| miRNA SEQ ID NO. | pre-miRNA SEQ ID NO. | Nucleotide position of miRNA in pre-miRNA | |
|---|---|---|---|
| | | from | to |
| 3809 | 5481 | 42 | 64 |
| 3810 | 4100 | 135 | 154 |
| 3811 | 4077 | 49 | 72 |
| 3812 | 4859 | 11 | 31 |
| 3812 | 5088 | 11 | 31 |
| 3813 | 5089 | 11 | 34 |
| 3814 | 4452 | 66 | 87 |
| 3815 | 4698 | 45 | 65 |
| 3816 | 4394 | 11 | 30 |
| 3817 | 4410 | 49 | 72 |
| 3818 | 4158 | 71 | 90 |
| 3819 | 4891 | 45 | 65 |
| 3820 | 4758 | 68 | 91 |
| 3821 | 4509 | 11 | 31 |
| 3822 | 4295 | 33 | 52 |
| 3822 | 4317 | 33 | 52 |
| 3823 | 5201 | 11 | 34 |
| 3824 | 5045 | 112 | 131 |
| 3825 | 4237 | 79 | 102 |
| 3826 | 4897 | 11 | 30 |
| 3827 | 4485 | 233 | 254 |
| 3828 | 4408 | 28 | 51 |
| 3829 | 4417 | 11 | 32 |
| 3829 | 4528 | 36 | 57 |
| 3830 | 4303 | 179 | 202 |
| 3831 | 3981 | 11 | 34 |
| 3832 | 5076 | 11 | 31 |
| 3833 | 4580 | 11 | 32 |
| 3834 | 4494 | 11 | 31 |
| 3835 | 4119 | 11 | 34 |
| 3836 | 4637 | 92 | 115 |
| 3837 | 4407 | 11 | 34 |
| 3838 | 4912 | 11 | 30 |
| 3839 | 4673 | 11 | 32 |
| 3840 | 4882 | 241 | 261 |
| 3841 | 4278 | 76 | 96 |
| 3842 | 4879 | 11 | 32 |
| 3843 | 5125 | 29 | 48 |
| 3844 | 4476 | 41 | 64 |
| 3845 | 4641 | 11 | 31 |
| 3846 | 5216 | 11 | 33 |
| 3847 | 4241 | 49 | 70 |
| 3848 | 4945 | 11 | 30 |
| 3849 | 4162 | 11 | 30 |
| 3850 | 5032 | 11 | 33 |
| 3851 | 4593 | 11 | 34 |
| 3852 | 3997 | 11 | 34 |
| 3853 | 4431 | 11 | 31 |
| 3854 | 4571 | 40 | 59 |
| 3854 | 4630 | 40 | 59 |
| 3855 | 4096 | 36 | 57 |
| 3855 | 4092 | 11 | 32 |
| 3856 | 5296 | 38 | 59 |
| 3857 | 4626 | 11 | 30 |
| 3858 | 4212 | 104 | 127 |
| 3859 | 4577 | 177 | 197 |
| 3860 | 4229 | 11 | 30 |
| 3860 | 4182 | 11 | 30 |
| 3861 | 4968 | 11 | 30 |
| 3862 | 5299 | 11 | 32 |
| 3863 | 4042 | 11 | 34 |
| 3864 | 4475 | 11 | 32 |
| 3865 | 4386 | 34 | 54 |
| 3865 | 4432 | 34 | 54 |
| 3866 | 4441 | 11 | 32 |
| 3866 | 4416 | 11 | 32 |
| 3867 | 4545 | 11 | 30 |
| 3868 | 4820 | 34 | 54 |
| 3869 | 5056 | 61 | 80 |
| 3870 | 5102 | 11 | 31 |
| 3871 | 5019 | 93 | 114 |
| 3872 | 4262 | 43 | 66 |
| 3872 | 4200 | 43 | 66 |
| 3873 | 5081 | 34 | 53 |
| 3873 | 5044 | 34 | 53 |
| 3874 | 4986 | 122 | 141 |
| 3875 | 4271 | 11 | 31 |
| 3876 | 4397 | 43 | 62 |
| 3877 | 4850 | 104 | 124 |
| 3878 | 4584 | 11 | 30 |
| 3879 | 5016 | 49 | 72 |
| 3880 | 4156 | 8 | 31 |
| 3881 | 4274 | 44 | 63 |
| 3881 | 4131 | 44 | 63 |
| 3881 | 4114 | 44 | 63 |
| 3881 | 4124 | 11 | 30 |
| 3881 | 4289 | 44 | 63 |
| 3882 | 5148 | 11 | 34 |
| 3882 | 5229 | 11 | 34 |
| 3883 | 4436 | 11 | 32 |
| 3884 | 4940 | 47 | 68 |
| 3884 | 4845 | 47 | 68 |
| 3884 | 5025 | 47 | 68 |
| 3885 | 5055 | 11 | 34 |
| 3886 | 4255 | 65 | 85 |
| 3887 | 5096 | 11 | 32 |
| 3888 | 4304 | 141 | 161 |
| 3888 | 4277 | 141 | 161 |
| 3889 | 4358 | 11 | 30 |
| 3890 | 4645 | 11 | 34 |
| 3891 | 4977 | 11 | 30 |
| 3892 | 4628 | 11 | 32 |
| 3893 | 4592 | 37 | 57 |
| 3893 | 4772 | 37 | 57 |
| 3894 | 4458 | 11 | 32 |
| 3894 | 4464 | 11 | 32 |
| 3895 | 5006 | 11 | 34 |
| 3896 | 4399 | 11 | 30 |
| 3897 | 4999 | 46 | 65 |
| 3898 | 5110 | 57 | 79 |
| 3899 | 5152 | 54 | 75 |
| 3900 | 4710 | 41 | 62 |
| 3901 | 4199 | 42 | 61 |
| 3902 | 4872 | 74 | 97 |
| 3903 | 4782 | 36 | 56 |
| 3904 | 4771 | 102 | 121 |
| 3905 | 4573 | 11 | 30 |
| 3905 | 4824 | 11 | 30 |
| 3905 | 4713 | 11 | 30 |
| 3905 | 4734 | 11 | 30 |
| 3905 | 4596 | 11 | 30 |
| 3905 | 4707 | 11 | 30 |
| 3905 | 4583 | 11 | 30 |
| 3906 | 4842 | 11 | 30 |
| 3906 | 5085 | 11 | 30 |
| 3907 | 5061 | 11 | 31 |
| 3908 | 5197 | 38 | 58 |
| 3909 | 4846 | 79 | 99 |
| 3910 | 4169 | 11 | 33 |
| 3911 | 5190 | 11 | 32 |
| 3912 | 4704 | 11 | 33 |
| 3912 | 4763 | 11 | 33 |
| 3913 | 4531 | 37 | 56 |
| 3914 | 4737 | 11 | 32 |
| 3915 | 4814 | 11 | 33 |
| 3916 | 5221 | 132 | 153 |
| 3916 | 5247 | 132 | 153 |
| 3917 | 4390 | 33 | 53 |
| 3918 | 4138 | 173 | 196 |
| 3919 | 4677 | 42 | 64 |
| 3920 | 4171 | 11 | 34 |
| 3920 | 4309 | 11 | 34 |

TABLE 4-continued

Maize and rice miRNAs and miRNA precursors

| miRNA SEQ ID NO. | pre-miRNA SEQ ID NO. | Nucleotide position of miRNA in pre-miRNA from | to |
|---|---|---|---|
| 3921 | 5031 | 64 | 87 |

Example 5

This example describes additional non-limiting embodiments of crop plant microRNAs and their precursor (foldback) structures, useful in making recombinant DNA constructs of this invention.

Figure 6:
FIG. 6 depicts drought stages for soybean plants a relative scoring system from 1.0 (no effect or control) to 4.0, as described in Example 5.

Small-RNA libraries were prepared from maize (corn, *Zea mays*) or from soybean (*Glycine max*) grown under water stress and control conditions (Table 5). Drought stages for soybean were assessed using a relative scoring system from 1.0 (no effect or control) to 4.0; examples of soybean plants at each stage are illustrated in FIG. 6. The small RNA sequences thus obtained were used for predicting additional novel microRNAs and their precursor (foldback) structures from maize or soybean genomic sequences, respectively, using the procedures described above in Example 1. From maize, 1186 maize miRNAs were predicted in 1725 maize genomic sequences, and from soybean, 134 soybean miRNAs are predicted in 181 soybean genomic sequences (Table 6). These miRNAs and their corresponding miRNA precursor sequences, as well as the nucleotide position of the mature miRNA in each miRNA precursor sequence, are referred to by their respective sequence identification numbers in Table 6 as follows: maize miRNAs (SEQ ID NOS. 5498-6683), corn miRNA precursor sequences (SEQ ID NOS. 6684-8408), soybean miRNAs (SEQ ID NOS. 8409-8560), and soybean miRNA precursor sequences (SEQ ID NOS. 8561-8417).

TABLE 5

| Library Number | Crop Plant | Tissue | Developmental stage | Treatment |
|---|---|---|---|---|
| 42 | maize (*Zea mays*) | young sink leaf | V8 | control |
| 43 | maize (*Zea mays*) | young sink leaf | V8 | mild drought |
| 44 | maize (*Zea mays*) | young sink leaf | V8 | control |
| 45 | maize (*Zea mays*) | young sink leaf | V8 | severe drought |
| 46 | maize (*Zea mays*) | root | V8 | control |
| 47 | maize (*Zea mays*) | root | V8 | mild drought |
| 48 | maize (*Zea mays*) | root | V8 | control |
| 38 | soybean (*Glycine max*) | seedling leaf | seedling | control |
| 39 | soybean (*Glycine max*) | pooled seedling leaf | seedling | drought, stage 3.0 and 3.5 pooled * |
| 40 | soybean (*Glycine max*) | root | mature | control |
| 41 | soybean (*Glycine max*) | pooled root mature | mature | drought, all stages 1.5 through 3.5 pooled * |

* For libraries 39 and 41 prepared from soybean, samples from the stages indicated were pooled; drought stages for soybean are assessed using a relative scoring system as follows:
1.0 = no effect
1.5 = meristem or one trifoliate wilted
2.0 = two trifoliates wilted
2.5 = all trifoliates wilted
3.0 = bottom trifoliate completely dried out and brittle
3.5 = all trifoliates but the top one completely dried out and brittle, top trifoliate still soft
4.0 = all completely dried out and brittle

TABLE 6

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 5498 | 8176 | 11 | 34 |
| 5499 | 7089 | 11 | 34 |
| 5500 | 6978 | 99 | 119 |
| 5500 | 8029 | 97 | 117 |
| 5500 | 8030 | 97 | 117 |
| 5500 | 8195 | 99 | 119 |
| 5500 | 8205 | 99 | 119 |
| 5500 | 8236 | 99 | 119 |
| 5501 | 7554 | 143 | 164 |
| 5502 | 7902 | 11 | 34 |
| 5503 | 6723 | 57 | 80 |
| 5503 | 7359 | 11 | 34 |
| 5504 | 7087 | 11 | 34 |
| 5504 | 8156 | 11 | 34 |
| 5505 | 7303 | 62 | 85 |
| 5506 | 8120 | 35 | 56 |
| 5507 | 8047 | 11 | 32 |
| 5508 | 6970 | 5 | 28 |
| 5509 | 7685 | 74 | 97 |
| 5510 | 6881 | 63 | 84 |
| 5511 | 7068 | 70 | 91 |
| 5511 | 8217 | 69 | 90 |
| 5512 | 7772 | 55 | 74 |
| 5513 | 7585 | 11 | 34 |
| 5514 | 7009 | 42 | 61 |
| 5514 | 7335 | 42 | 61 |
| 5514 | 7912 | 42 | 61 |
| 5514 | 8272 | 42 | 61 |
| 5514 | 8354 | 42 | 61 |
| 5515 | 8130 | 11 | 32 |
| 5516 | 7085 | 55 | 77 |
| 5517 | 7845 | 11 | 32 |
| 5518 | 8270 | 135 | 158 |
| 5519 | 7363 | 50 | 69 |
| 5520 | 7853 | 11 | 32 |
| 5520 | 8147 | 11 | 32 |
| 5521 | 7710 | 11 | 30 |
| 5522 | 7521 | 2 | 25 |
| 5522 | 7655 | 187 | 210 |
| 5523 | 7152 | 11 | 34 |
| 5524 | 6774 | 145 | 167 |
| 5525 | 6790 | 159 | 179 |
| 5526 | 7947 | 11 | 34 |
| 5527 | 7744 | 6 | 25 |
| 5528 | 7233 | 11 | 32 |
| 5529 | 7476 | 11 | 30 |
| 5530 | 7933 | 11 | 33 |
| 5531 | 7971 | 11 | 34 |
| 5532 | 6815 | 11 | 34 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 5533 | 8034 | 41 | 63 |
| 5534 | 6824 | 11 | 31 |
| 5535 | 6912 | 136 | 155 |
| 5535 | 7220 | 137 | 156 |
| 5535 | 7779 | 140 | 159 |
| 5536 | 7920 | 45 | 65 |
| 5537 | 7921 | 11 | 35 |
| 5538 | 8284 | 11 | 31 |
| 5539 | 6829 | 143 | 164 |
| 5539 | 6864 | 11 | 32 |
| 5539 | 6905 | 11 | 32 |
| 5539 | 6952 | 144 | 165 |
| 5539 | 7709 | 11 | 32 |
| 5540 | 7045 | 91 | 115 |
| 5540 | 7207 | 91 | 115 |
| 5540 | 7641 | 91 | 115 |
| 5540 | 7834 | 91 | 115 |
| 5540 | 7835 | 91 | 115 |
| 5541 | 8303 | 11 | 31 |
| 5542 | 8230 | 109 | 132 |
| 5543 | 7839 | 34 | 55 |
| 5543 | 7840 | 34 | 55 |
| 5544 | 6856 | 11 | 34 |
| 5545 | 6686 | 204 | 224 |
| 5545 | 7092 | 199 | 219 |
| 5546 | 7888 | 38 | 61 |
| 5547 | 7293 | 11 | 34 |
| 5548 | 7871 | 11 | 32 |
| 5549 | 7979 | 39 | 62 |
| 5550 | 7324 | 11 | 34 |
| 5550 | 7922 | 157 | 180 |
| 5551 | 7691 | 45 | 68 |
| 5552 | 8233 | 40 | 63 |
| 5553 | 7170 | 47 | 70 |
| 5554 | 8390 | 36 | 59 |
| 5555 | 7177 | 11 | 31 |
| 5556 | 7525 | 61 | 81 |
| 5557 | 6991 | 39 | 62 |
| 5558 | 7879 | 111 | 132 |
| 5559 | 7627 | 11 | 32 |
| 5560 | 7485 | 11 | 34 |
| 5560 | 7565 | 40 | 63 |
| 5560 | 8056 | 11 | 34 |
| 5561 | 6690 | 11 | 34 |
| 5562 | 6832 | 54 | 75 |
| 5563 | 7459 | 45 | 65 |
| 5563 | 7460 | 45 | 65 |
| 5563 | 7507 | 46 | 66 |
| 5563 | 7730 | 45 | 65 |
| 5563 | 7756 | 46 | 66 |
| 5563 | 8058 | 46 | 66 |
| 5563 | 8064 | 47 | 67 |
| 5563 | 8065 | 46 | 66 |
| 5564 | 7571 | 47 | 70 |
| 5565 | 7030 | 11 | 30 |
| 5566 | 7059 | 11 | 34 |
| 5566 | 7514 | 11 | 34 |
| 5566 | 8111 | 11 | 34 |
| 5566 | 8215 | 11 | 34 |
| 5566 | 8337 | 11 | 34 |
| 5567 | 6748 | 66 | 89 |
| 5568 | 6725 | 97 | 117 |
| 5568 | 6830 | 97 | 117 |
| 5568 | 8307 | 11 | 31 |
| 5569 | 7287 | 11 | 31 |
| 5570 | 6778 | 11 | 31 |
| 5570 | 8172 | 213 | 233 |
| 5571 | 7882 | 45 | 66 |
| 5572 | 7227 | 56 | 79 |
| 5573 | 7491 | 33 | 56 |
| 5574 | 7296 | 122 | 142 |
| 5575 | 7614 | 11 | 34 |
| 5576 | 6793 | 112 | 132 |
| 5577 | 6741 | 40 | 63 |
| 5577 | 6942 | 39 | 62 |
| 5577 | 7057 | 40 | 63 |
| 5577 | 7206 | 39 | 62 |
| 5577 | 7381 | 40 | 63 |
| 5577 | 7388 | 39 | 62 |
| 5577 | 7423 | 40 | 63 |
| 5577 | 7427 | 39 | 62 |
| 5577 | 7504 | 40 | 63 |
| 5577 | 7907 | 39 | 62 |
| 5577 | 7956 | 40 | 63 |
| 5577 | 7958 | 39 | 62 |
| 5577 | 7965 | 39 | 62 |
| 5577 | 7966 | 40 | 63 |
| 5577 | 7997 | 39 | 62 |
| 5577 | 8011 | 40 | 63 |
| 5577 | 8025 | 40 | 63 |
| 5577 | 8170 | 39 | 62 |
| 5577 | 8185 | 39 | 62 |
| 5577 | 8312 | 40 | 63 |
| 5578 | 7978 | 58 | 81 |
| 5578 | 8131 | 58 | 81 |
| 5579 | 7430 | 62 | 83 |
| 5579 | 7442 | 62 | 83 |
| 5579 | 7698 | 62 | 83 |
| 5580 | 7914 | 55 | 78 |
| 5581 | 6869 | 113 | 136 |
| 5582 | 7396 | 11 | 34 |
| 5583 | 7668 | 11 | 31 |
| 5584 | 6762 | 80 | 103 |
| 5585 | 7937 | 11 | 30 |
| 5586 | 8175 | 11 | 31 |
| 5587 | 7477 | 73 | 96 |
| 5588 | 8180 | 37 | 60 |
| 5589 | 7934 | 35 | 58 |
| 5590 | 7517 | 123 | 146 |
| 5591 | 7566 | 11 | 34 |
| 5592 | 7781 | 11 | 32 |
| 5593 | 7760 | 87 | 110 |
| 5594 | 7223 | 11 | 31 |
| 5594 | 7417 | 11 | 31 |
| 5594 | 7496 | 11 | 31 |
| 5594 | 7816 | 11 | 31 |
| 5594 | 7872 | 11 | 31 |
| 5594 | 7897 | 11 | 31 |
| 5594 | 8024 | 11 | 31 |
| 5594 | 8026 | 11 | 31 |
| 5595 | 6958 | 40 | 63 |
| 5595 | 8016 | 11 | 34 |
| 5596 | 8285 | 76 | 99 |
| 5597 | 8125 | 11 | 34 |
| 5598 | 8008 | 42 | 63 |
| 5599 | 7414 | 38 | 61 |
| 5600 | 6708 | 74 | 93 |
| 5600 | 8041 | 11 | 30 |
| 5600 | 8042 | 11 | 30 |
| 5601 | 7823 | 11 | 34 |
| 5602 | 7483 | 338 | 359 |
| 5603 | 6685 | 71 | 91 |
| 5603 | 7780 | 102 | 122 |
| 5604 | 7072 | 118 | 138 |
| 5605 | 7893 | 11 | 31 |
| 5606 | 7646 | 70 | 92 |
| 5607 | 8348 | 104 | 127 |
| 5608 | 7290 | 60 | 80 |
| 5609 | 7670 | 189 | 212 |
| 5610 | 6949 | 92 | 112 |
| 5611 | 6870 | 39 | 61 |
| 5611 | 6878 | 218 | 240 |

TABLE 6-continued

Maize and soybean miRNAs and miRNA precursors

| miRNA SEQ ID NO. | pre-miRNA SEQ ID NO. | Nucleotide position of miRNA in pre-miRNA | |
|---|---|---|---|
| | | from | to |
| 5611 | 7243 | 218 | 240 |
| 5611 | 8235 | 39 | 61 |
| 5612 | 7546 | 11 | 32 |
| 5613 | 8264 | 11 | 34 |
| 5614 | 7829 | 11 | 31 |
| 5614 | 8314 | 11 | 31 |
| 5615 | 6760 | 11 | 31 |
| 5616 | 7310 | 51 | 71 |
| 5617 | 7373 | 11 | 32 |
| 5618 | 7440 | 11 | 34 |
| 5619 | 7475 | 211 | 234 |
| 5620 | 8356 | 404 | 423 |
| 5621 | 7715 | 11 | 32 |
| 5622 | 6993 | 99 | 122 |
| 5623 | 7841 | 11 | 31 |
| 5624 | 7183 | 81 | 101 |
| 5625 | 6861 | 35 | 55 |
| 5626 | 8122 | 11 | 34 |
| 5627 | 6767 | 11 | 33 |
| 5627 | 7919 | 11 | 33 |
| 5628 | 6957 | 11 | 34 |
| 5629 | 7383 | 73 | 95 |
| 5629 | 7634 | 73 | 95 |
| 5630 | 7809 | 38 | 59 |
| 5630 | 7810 | 37 | 58 |
| 5630 | 7936 | 38 | 59 |
| 5631 | 7140 | 40 | 61 |
| 5631 | 7197 | 40 | 61 |
| 5632 | 6730 | 215 | 234 |
| 5632 | 7754 | 218 | 237 |
| 5633 | 7577 | 134 | 153 |
| 5633 | 7613 | 134 | 153 |
| 5634 | 7003 | 72 | 91 |
| 5635 | 7812 | 11 | 30 |
| 5636 | 8049 | 60 | 83 |
| 5637 | 8375 | 11 | 33 |
| 5638 | 8164 | 11 | 31 |
| 5639 | 7573 | 37 | 56 |
| 5640 | 8259 | 11 | 34 |
| 5641 | 7240 | 11 | 30 |
| 5642 | 8128 | 222 | 245 |
| 5643 | 7660 | 11 | 32 |
| 5644 | 6804 | 37 | 59 |
| 5644 | 6924 | 37 | 59 |
| 5644 | 7138 | 37 | 59 |
| 5644 | 7439 | 37 | 59 |
| 5644 | 7450 | 37 | 59 |
| 5644 | 7588 | 37 | 59 |
| 5644 | 7591 | 37 | 59 |
| 5644 | 7786 | 37 | 59 |
| 5644 | 7905 | 37 | 59 |
| 5644 | 7928 | 37 | 59 |
| 5645 | 8204 | 38 | 60 |
| 5646 | 6687 | 187 | 209 |
| 5647 | 7330 | 11 | 32 |
| 5648 | 7587 | 11 | 34 |
| 5649 | 7435 | 292 | 315 |
| 5650 | 7653 | 11 | 34 |
| 5650 | 8066 | 11 | 34 |
| 5651 | 7055 | 11 | 33 |
| 5651 | 7763 | 11 | 33 |
| 5652 | 7755 | 11 | 34 |
| 5652 | 7828 | 11 | 34 |
| 5653 | 8115 | 32 | 51 |
| 5654 | 7821 | 48 | 71 |
| 5655 | 6694 | 11 | 33 |
| 5656 | 6990 | 11 | 31 |
| 5656 | 7793 | 11 | 31 |
| 5657 | 8250 | 11 | 30 |
| 5658 | 8080 | 11 | 34 |
| 5659 | 7394 | 11 | 34 |
| 5660 | 8305 | 11 | 31 |
| 5661 | 6873 | 11 | 31 |
| 5662 | 7264 | 51 | 74 |
| 5662 | 8287 | 11 | 34 |
| 5663 | 7001 | 11 | 32 |
| 5664 | 8394 | 11 | 34 |
| 5665 | 7406 | 78 | 97 |
| 5665 | 7470 | 11 | 30 |
| 5666 | 7144 | 41 | 62 |
| 5666 | 7635 | 41 | 62 |
| 5667 | 6698 | 11 | 34 |
| 5668 | 7117 | 11 | 32 |
| 5668 | 7154 | 11 | 32 |
| 5668 | 7457 | 11 | 32 |
| 5669 | 8135 | 117 | 137 |
| 5670 | 6906 | 58 | 78 |
| 5671 | 7167 | 11 | 34 |
| 5672 | 7217 | 165 | 184 |
| 5672 | 7326 | 165 | 184 |
| 5673 | 6977 | 66 | 85 |
| 5674 | 7526 | 130 | 149 |
| 5675 | 7820 | 11 | 32 |
| 5676 | 7765 | 11 | 34 |
| 5677 | 7110 | 48 | 69 |
| 5678 | 7319 | 11 | 35 |
| 5679 | 8171 | 46 | 65 |
| 5679 | 8241 | 46 | 65 |
| 5680 | 7555 | 31 | 54 |
| 5680 | 8143 | 31 | 54 |
| 5681 | 6707 | 11 | 31 |
| 5682 | 8129 | 1 | 22 |
| 5683 | 7060 | 11 | 31 |
| 5683 | 7078 | 52 | 72 |
| 5684 | 7802 | 11 | 34 |
| 5685 | 7356 | 11 | 34 |
| 5686 | 6847 | 11 | 34 |
| 5687 | 8326 | 11 | 31 |
| 5688 | 7314 | 144 | 164 |
| 5689 | 7512 | 11 | 34 |
| 5690 | 8193 | 157 | 177 |
| 5691 | 8210 | 11 | 34 |
| 5692 | 7323 | 47 | 69 |
| 5693 | 8278 | 11 | 34 |
| 5694 | 8393 | 69 | 89 |
| 5695 | 8004 | 70 | 91 |
| 5696 | 6765 | 36 | 55 |
| 5696 | 7556 | 36 | 55 |
| 5696 | 7771 | 36 | 55 |
| 5697 | 7601 | 83 | 104 |
| 5698 | 7266 | 11 | 35 |
| 5699 | 7873 | 137 | 157 |
| 5700 | 7093 | 11 | 34 |
| 5701 | 7034 | 11 | 30 |
| 5701 | 7246 | 11 | 30 |
| 5702 | 6968 | 56 | 79 |
| 5703 | 7469 | 42 | 63 |
| 5704 | 7891 | 11 | 34 |
| 5705 | 8166 | 11 | 31 |
| 5706 | 7295 | 58 | 78 |
| 5707 | 7752 | 11 | 32 |
| 5708 | 6909 | 11 | 34 |
| 5708 | 7581 | 97 | 120 |
| 5709 | 8155 | 55 | 75 |
| 5710 | 7704 | 11 | 33 |
| 5711 | 8032 | 11 | 31 |
| 5712 | 7868 | 11 | 34 |
| 5712 | 7869 | 11 | 34 |
| 5713 | 6766 | 42 | 62 |
| 5714 | 7644 | 11 | 34 |
| 5715 | 7132 | 75 | 98 |
| 5715 | 7245 | 11 | 34 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 5715 | 8276 | 11 | 34 |
| 5715 | 8344 | 11 | 34 |
| 5716 | 6781 | 11 | 33 |
| 5717 | 6754 | 11 | 35 |
| 5718 | 7358 | 11 | 31 |
| 5718 | 8178 | 11 | 31 |
| 5719 | 7895 | 29 | 49 |
| 5720 | 7813 | 11 | 31 |
| 5721 | 7631 | 11 | 31 |
| 5722 | 7105 | 11 | 31 |
| 5723 | 7063 | 42 | 61 |
| 5723 | 7163 | 42 | 61 |
| 5723 | 8308 | 42 | 61 |
| 5724 | 6734 | 11 | 32 |
| 5724 | 7121 | 11 | 32 |
| 5724 | 7632 | 11 | 32 |
| 5725 | 8046 | 11 | 32 |
| 5725 | 8396 | 11 | 32 |
| 5726 | 7836 | 211 | 232 |
| 5727 | 8148 | 11 | 34 |
| 5727 | 8149 | 49 | 72 |
| 5728 | 7175 | 11 | 33 |
| 5729 | 7134 | 11 | 34 |
| 5730 | 6858 | 86 | 108 |
| 5731 | 6836 | 11 | 33 |
| 5732 | 7910 | 107 | 126 |
| 5733 | 6884 | 233 | 256 |
| 5734 | 7010 | 11 | 30 |
| 5735 | 8158 | 11 | 30 |
| 5736 | 6989 | 11 | 33 |
| 5737 | 7964 | 11 | 34 |
| 5738 | 7041 | 76 | 97 |
| 5738 | 8268 | 75 | 96 |
| 5739 | 6850 | 11 | 32 |
| 5740 | 6724 | 182 | 204 |
| 5740 | 8209 | 84 | 106 |
| 5741 | 7193 | 181 | 204 |
| 5741 | 7194 | 191 | 214 |
| 5741 | 7798 | 181 | 204 |
| 5742 | 7354 | 83 | 104 |
| 5743 | 6716 | 50 | 73 |
| 5743 | 6736 | 11 | 34 |
| 5744 | 7253 | 240 | 262 |
| 5745 | 8084 | 97 | 120 |
| 5746 | 6853 | 113 | 133 |
| 5747 | 7564 | 11 | 31 |
| 5747 | 8330 | 11 | 31 |
| 5748 | 7166 | 11 | 34 |
| 5749 | 7182 | 96 | 116 |
| 5750 | 8222 | 211 | 231 |
| 5751 | 6860 | 178 | 199 |
| 5752 | 7018 | 11 | 34 |
| 5753 | 7026 | 11 | 31 |
| 5754 | 7484 | 124 | 145 |
| 5755 | 8255 | 11 | 31 |
| 5756 | 7944 | 11 | 34 |
| 5757 | 7297 | 11 | 34 |
| 5758 | 7650 | 11 | 30 |
| 5759 | 8174 | 46 | 67 |
| 5760 | 7474 | 11 | 34 |
| 5760 | 7510 | 11 | 34 |
| 5760 | 7511 | 11 | 34 |
| 5761 | 7360 | 11 | 30 |
| 5761 | 8246 | 11 | 30 |
| 5762 | 8403 | 29 | 52 |
| 5763 | 7005 | 64 | 86 |
| 5764 | 8310 | 11 | 33 |
| 5765 | 6894 | 3 | 24 |
| 5766 | 7558 | 46 | 67 |
| 5767 | 7520 | 232 | 252 |
| 5767 | 8017 | 148 | 168 |
| 5767 | 8100 | 70 | 90 |
| 5768 | 7611 | 236 | 255 |
| 5769 | 8345 | 107 | 127 |
| 5770 | 7025 | 11 | 31 |
| 5771 | 7143 | 11 | 34 |
| 5772 | 7447 | 11 | 32 |
| 5773 | 7590 | 11 | 34 |
| 5774 | 6739 | 152 | 175 |
| 5774 | 7669 | 151 | 174 |
| 5774 | 8013 | 152 | 175 |
| 5775 | 6720 | 11 | 32 |
| 5775 | 7165 | 11 | 32 |
| 5775 | 7638 | 11 | 32 |
| 5775 | 8377 | 11 | 32 |
| 5776 | 7686 | 74 | 97 |
| 5777 | 7340 | 11 | 32 |
| 5777 | 7397 | 11 | 32 |
| 5777 | 8239 | 77 | 98 |
| 5778 | 8192 | 11 | 30 |
| 5779 | 8048 | 11 | 34 |
| 5780 | 7239 | 78 | 101 |
| 5781 | 7945 | 11 | 31 |
| 5782 | 8408 | 11 | 31 |
| 5783 | 8057 | 11 | 30 |
| 5784 | 7204 | 237 | 256 |
| 5785 | 7599 | 135 | 158 |
| 5786 | 6921 | 11 | 31 |
| 5787 | 7677 | 11 | 31 |
| 5788 | 8124 | 55 | 76 |
| 5789 | 7817 | 11 | 32 |
| 5790 | 6934 | 11 | 32 |
| 5790 | 7015 | 11 | 32 |
| 5790 | 7124 | 11 | 32 |
| 5790 | 7317 | 11 | 32 |
| 5790 | 7428 | 11 | 32 |
| 5790 | 7488 | 11 | 32 |
| 5790 | 7532 | 11 | 32 |
| 5790 | 7575 | 11 | 32 |
| 5790 | 7576 | 11 | 32 |
| 5790 | 7665 | 11 | 32 |
| 5791 | 7738 | 11 | 34 |
| 5792 | 7040 | 44 | 68 |
| 5793 | 7530 | 11 | 33 |
| 5794 | 7076 | 47 | 70 |
| 5795 | 7988 | 3 | 23 |
| 5796 | 6718 | 52 | 75 |
| 5797 | 7336 | 184 | 204 |
| 5798 | 7073 | 43 | 64 |
| 5798 | 8001 | 33 | 54 |
| 5799 | 7499 | 11 | 32 |
| 5800 | 8385 | 218 | 238 |
| 5801 | 6865 | 117 | 137 |
| 5801 | 7524 | 117 | 137 |
| 5802 | 7037 | 96 | 117 |
| 5803 | 7822 | 36 | 56 |
| 5804 | 8145 | 114 | 137 |
| 5805 | 7398 | 36 | 59 |
| 5806 | 7992 | 11 | 34 |
| 5807 | 6820 | 40 | 63 |
| 5808 | 7205 | 82 | 103 |
| 5809 | 7899 | 11 | 34 |
| 5810 | 7490 | 58 | 81 |
| 5811 | 6833 | 11 | 32 |
| 5811 | 7727 | 11 | 32 |
| 5812 | 7408 | 11 | 31 |
| 5813 | 6848 | 11 | 31 |
| 5814 | 6941 | 192 | 211 |
| 5815 | 7069 | 37 | 58 |
| 5815 | 8368 | 37 | 58 |
| 5816 | 8357 | 11 | 31 |
| 5817 | 8108 | 11 | 30 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 5818 | 7814 | 11 | 30 |
| 5819 | 7529 | 28 | 48 |
| 5819 | 8248 | 28 | 48 |
| 5820 | 6763 | 47 | 66 |
| 5821 | 8012 | 11 | 30 |
| 5821 | 8091 | 11 | 30 |
| 5822 | 8054 | 54 | 73 |
| 5823 | 7268 | 239 | 259 |
| 5824 | 6732 | 11 | 34 |
| 5824 | 6827 | 11 | 34 |
| 5824 | 7184 | 11 | 34 |
| 5825 | 8340 | 11 | 30 |
| 5826 | 7300 | 11 | 34 |
| 5827 | 8050 | 11 | 30 |
| 5828 | 8245 | 68 | 90 |
| 5829 | 7981 | 11 | 33 |
| 5829 | 7983 | 11 | 33 |
| 5830 | 7331 | 185 | 205 |
| 5831 | 7862 | 35 | 54 |
| 5832 | 7642 | 57 | 80 |
| 5832 | 8266 | 57 | 80 |
| 5833 | 8247 | 40 | 61 |
| 5834 | 7931 | 11 | 30 |
| 5834 | 8359 | 11 | 30 |
| 5835 | 7697 | 35 | 56 |
| 5836 | 7759 | 11 | 33 |
| 5837 | 8187 | 41 | 64 |
| 5838 | 7279 | 44 | 63 |
| 5839 | 8038 | 189 | 210 |
| 5839 | 8200 | 189 | 210 |
| 5840 | 7860 | 2 | 22 |
| 5841 | 6959 | 11 | 34 |
| 5841 | 7462 | 11 | 34 |
| 5842 | 6784 | 52 | 71 |
| 5842 | 8378 | 11 | 30 |
| 5843 | 6772 | 73 | 96 |
| 5843 | 7181 | 73 | 96 |
| 5844 | 7932 | 155 | 178 |
| 5845 | 8074 | 11 | 32 |
| 5846 | 8306 | 11 | 30 |
| 5847 | 7202 | 38 | 61 |
| 5848 | 6780 | 41 | 61 |
| 5849 | 7833 | 11 | 34 |
| 5850 | 7619 | 11 | 31 |
| 5851 | 6819 | 11 | 34 |
| 5851 | 7274 | 38 | 61 |
| 5851 | 8144 | 38 | 61 |
| 5851 | 8386 | 38 | 61 |
| 5852 | 6787 | 34 | 55 |
| 5852 | 8189 | 34 | 55 |
| 5853 | 7247 | 11 | 31 |
| 5854 | 6938 | 143 | 164 |
| 5855 | 7191 | 168 | 188 |
| 5855 | 7316 | 168 | 188 |
| 5856 | 7737 | 76 | 97 |
| 5857 | 7918 | 44 | 67 |
| 5858 | 7551 | 11 | 34 |
| 5859 | 7774 | 11 | 34 |
| 5860 | 7375 | 11 | 33 |
| 5861 | 7745 | 132 | 152 |
| 5862 | 8211 | 181 | 203 |
| 5863 | 7652 | 132 | 155 |
| 5864 | 7355 | 11 | 33 |
| 5865 | 7927 | 42 | 61 |
| 5866 | 7434 | 196 | 218 |
| 5867 | 8039 | 67 | 86 |
| 5868 | 6731 | 11 | 34 |
| 5869 | 6929 | 63 | 84 |
| 5870 | 7864 | 7 | 27 |
| 5871 | 8133 | 30 | 50 |
| 5872 | 8292 | 211 | 230 |
| 5873 | 7226 | 11 | 34 |
| 5874 | 7237 | 66 | 89 |
| 5875 | 8079 | 11 | 33 |
| 5876 | 7508 | 172 | 191 |
| 5876 | 7913 | 159 | 178 |
| 5877 | 8263 | 137 | 161 |
| 5878 | 8083 | 11 | 32 |
| 5879 | 8087 | 11 | 30 |
| 5880 | 7705 | 49 | 72 |
| 5881 | 7262 | 11 | 31 |
| 5881 | 7277 | 11 | 31 |
| 5881 | 8194 | 11 | 31 |
| 5882 | 7664 | 53 | 72 |
| 5883 | 6849 | 36 | 55 |
| 5883 | 7410 | 11 | 30 |
| 5884 | 7874 | 11 | 32 |
| 5885 | 6948 | 11 | 32 |
| 5886 | 6756 | 11 | 31 |
| 5886 | 6837 | 11 | 31 |
| 5886 | 7016 | 11 | 31 |
| 5886 | 7654 | 11 | 31 |
| 5887 | 8159 | 48 | 68 |
| 5888 | 7948 | 79 | 98 |
| 5889 | 7353 | 32 | 52 |
| 5890 | 6972 | 57 | 77 |
| 5891 | 8275 | 11 | 31 |
| 5892 | 7020 | 11 | 34 |
| 5893 | 7625 | 11 | 31 |
| 5894 | 7606 | 41 | 60 |
| 5894 | 7608 | 9 | 28 |
| 5895 | 6809 | 11 | 34 |
| 5896 | 6823 | 98 | 120 |
| 5896 | 6893 | 98 | 120 |
| 5896 | 7848 | 100 | 122 |
| 5897 | 6795 | 11 | 30 |
| 5898 | 7843 | 11 | 32 |
| 5899 | 8298 | 11 | 32 |
| 5900 | 8363 | 11 | 34 |
| 5901 | 7248 | 10 | 33 |
| 5902 | 7885 | 11 | 31 |
| 5903 | 6875 | 11 | 35 |
| 5904 | 6975 | 112 | 133 |
| 5905 | 7461 | 11 | 34 |
| 5906 | 6951 | 46 | 69 |
| 5907 | 6877 | 11 | 35 |
| 5907 | 7390 | 11 | 35 |
| 5908 | 8199 | 75 | 97 |
| 5909 | 7883 | 39 | 62 |
| 5910 | 7088 | 85 | 108 |
| 5911 | 6709 | 11 | 34 |
| 5912 | 7265 | 30 | 50 |
| 5912 | 7663 | 30 | 50 |
| 5912 | 8339 | 30 | 50 |
| 5913 | 6885 | 221 | 244 |
| 5914 | 8406 | 11 | 30 |
| 5915 | 7550 | 11 | 34 |
| 5916 | 7804 | 75 | 98 |
| 5917 | 8327 | 60 | 83 |
| 5918 | 7487 | 11 | 34 |
| 5919 | 7681 | 44 | 65 |
| 5920 | 7012 | 115 | 136 |
| 5921 | 7256 | 11 | 34 |
| 5922 | 7000 | 42 | 66 |
| 5923 | 8367 | 11 | 31 |
| 5924 | 6919 | 11 | 34 |
| 5925 | 7749 | 36 | 55 |
| 5926 | 8352 | 11 | 30 |
| 5927 | 7838 | 11 | 32 |
| 5928 | 7074 | 38 | 57 |
| 5928 | 8063 | 38 | 57 |
| 5929 | 6826 | 40 | 60 |

TABLE 6-continued

Maize and soybean miRNAs and miRNA precursors

| miRNA SEQ ID NO. | pre-miRNA SEQ ID NO. | Nucleotide position of miRNA in pre-miRNA | |
|---|---|---|---|
| | | from | to |
| 5930 | 8109 | 125 | 144 |
| 5931 | 8387 | 76 | 96 |
| 5932 | 7042 | 11 | 31 |
| 5932 | 7049 | 11 | 31 |
| 5932 | 7210 | 11 | 31 |
| 5932 | 7875 | 11 | 31 |
| 5933 | 6764 | 11 | 31 |
| 5933 | 8365 | 11 | 31 |
| 5934 | 8202 | 115 | 136 |
| 5935 | 7991 | 11 | 30 |
| 5936 | 7118 | 11 | 31 |
| 5936 | 7850 | 11 | 31 |
| 5936 | 7851 | 11 | 31 |
| 5936 | 8141 | 11 | 31 |
| 5936 | 8213 | 11 | 31 |
| 5936 | 8228 | 11 | 31 |
| 5937 | 7115 | 11 | 32 |
| 5938 | 6713 | 11 | 30 |
| 5938 | 6947 | 11 | 30 |
| 5939 | 6976 | 134 | 155 |
| 5940 | 6984 | 11 | 34 |
| 5941 | 7857 | 11 | 32 |
| 5941 | 8075 | 11 | 32 |
| 5942 | 7713 | 38 | 57 |
| 5943 | 7622 | 50 | 69 |
| 5944 | 6852 | 11 | 31 |
| 5945 | 7528 | 11 | 33 |
| 5946 | 7954 | 54 | 74 |
| 5947 | 8198 | 11 | 34 |
| 5948 | 6910 | 236 | 257 |
| 5949 | 7975 | 11 | 31 |
| 5950 | 7844 | 230 | 251 |
| 5951 | 8094 | 73 | 93 |
| 5952 | 6892 | 11 | 31 |
| 5953 | 6703 | 130 | 151 |
| 5953 | 6789 | 130 | 151 |
| 5954 | 7127 | 11 | 33 |
| 5955 | 7728 | 73 | 96 |
| 5955 | 8208 | 73 | 96 |
| 5956 | 7801 | 52 | 74 |
| 5957 | 7612 | 11 | 31 |
| 5958 | 7213 | 33 | 52 |
| 5958 | 7768 | 33 | 52 |
| 5959 | 6786 | 40 | 60 |
| 5960 | 7633 | 11 | 32 |
| 5961 | 7790 | 11 | 31 |
| 5961 | 7950 | 11 | 31 |
| 5962 | 7351 | 11 | 34 |
| 5963 | 6995 | 54 | 77 |
| 5964 | 8027 | 42 | 65 |
| 5964 | 8347 | 42 | 65 |
| 5965 | 7466 | 108 | 127 |
| 5966 | 7500 | 11 | 34 |
| 5967 | 7495 | 49 | 69 |
| 5968 | 7463 | 80 | 104 |
| 5968 | 8296 | 80 | 104 |
| 5969 | 7156 | 11 | 31 |
| 5969 | 7377 | 39 | 59 |
| 5970 | 8099 | 52 | 75 |
| 5971 | 6821 | 11 | 34 |
| 5971 | 7549 | 198 | 221 |
| 5971 | 7807 | 198 | 221 |
| 5971 | 7880 | 198 | 221 |
| 5972 | 8253 | 11 | 35 |
| 5973 | 8154 | 107 | 130 |
| 5974 | 8214 | 11 | 31 |
| 5975 | 7986 | 11 | 32 |
| 5976 | 7150 | 89 | 109 |
| 5977 | 7723 | 42 | 65 |
| 5978 | 6845 | 139 | 159 |
| 5978 | 6902 | 139 | 159 |
| 5978 | 7275 | 11 | 31 |
| 5978 | 7707 | 140 | 160 |
| 5979 | 7887 | 11 | 30 |
| 5980 | 6710 | 86 | 107 |
| 5980 | 6998 | 86 | 107 |
| 5980 | 7302 | 86 | 107 |
| 5981 | 7855 | 11 | 33 |
| 5982 | 6722 | 46 | 67 |
| 5982 | 7436 | 46 | 67 |
| 5982 | 8023 | 46 | 67 |
| 5983 | 6930 | 202 | 224 |
| 5984 | 8364 | 42 | 63 |
| 5985 | 7392 | 48 | 67 |
| 5986 | 7100 | 42 | 61 |
| 5986 | 7208 | 42 | 61 |
| 5986 | 7209 | 42 | 61 |
| 5986 | 7569 | 42 | 61 |
| 5986 | 7865 | 42 | 61 |
| 5986 | 7866 | 42 | 61 |
| 5986 | 7867 | 42 | 61 |
| 5986 | 8053 | 42 | 61 |
| 5986 | 8244 | 42 | 61 |
| 5987 | 7014 | 11 | 31 |
| 5988 | 7116 | 11 | 32 |
| 5988 | 8404 | 11 | 32 |
| 5989 | 6866 | 92 | 115 |
| 5990 | 7849 | 137 | 160 |
| 5991 | 7630 | 168 | 187 |
| 5991 | 8260 | 168 | 187 |
| 5992 | 6791 | 11 | 32 |
| 5993 | 8116 | 10 | 29 |
| 5994 | 7407 | 175 | 195 |
| 5995 | 7158 | 11 | 31 |
| 5996 | 8107 | 88 | 111 |
| 5997 | 7252 | 188 | 209 |
| 5997 | 7675 | 182 | 203 |
| 5998 | 7106 | 38 | 58 |
| 5999 | 8045 | 46 | 69 |
| 6000 | 7224 | 56 | 76 |
| 6001 | 7225 | 36 | 56 |
| 6001 | 7735 | 36 | 56 |
| 6002 | 6749 | 11 | 34 |
| 6003 | 7273 | 64 | 83 |
| 6004 | 6983 | 56 | 79 |
| 6004 | 7832 | 56 | 79 |
| 6005 | 6859 | 119 | 141 |
| 6006 | 7692 | 11 | 32 |
| 6007 | 7773 | 36 | 55 |
| 6008 | 8096 | 11 | 32 |
| 6009 | 8146 | 80 | 99 |
| 6010 | 7133 | 236 | 256 |
| 6010 | 7568 | 204 | 224 |
| 6011 | 8078 | 11 | 34 |
| 6012 | 8092 | 241 | 261 |
| 6013 | 6816 | 211 | 232 |
| 6014 | 6817 | 11 | 35 |
| 6014 | 7909 | 11 | 35 |
| 6015 | 6705 | 35 | 55 |
| 6016 | 7379 | 45 | 68 |
| 6017 | 7762 | 68 | 92 |
| 6018 | 7027 | 11 | 35 |
| 6018 | 7173 | 11 | 35 |
| 6019 | 7819 | 11 | 32 |
| 6020 | 7192 | 11 | 35 |
| 6021 | 8119 | 11 | 32 |
| 6022 | 6911 | 30 | 49 |
| 6023 | 7031 | 11 | 31 |
| 6024 | 7232 | 11 | 32 |
| 6025 | 6840 | 173 | 194 |
| 6026 | 8062 | 160 | 180 |
| 6027 | 8035 | 54 | 78 |

TABLE 6-continued

Maize and soybean miRNAs and miRNA precursors

| miRNA SEQ ID NO. | pre-miRNA SEQ ID NO. | Nucleotide position of miRNA in pre-miRNA | |
|---|---|---|---|
| | | from | to |
| 6028 | 8186 | 11 | 33 |
| 6029 | 6880 | 39 | 59 |
| 6030 | 8076 | 33 | 53 |
| 6031 | 6992 | 11 | 30 |
| 6032 | 7230 | 119 | 141 |
| 6032 | 8229 | 11 | 33 |
| 6033 | 6798 | 57 | 76 |
| 6034 | 7064 | 201 | 222 |
| 6035 | 8383 | 65 | 86 |
| 6036 | 8289 | 11 | 34 |
| 6037 | 7082 | 11 | 31 |
| 6038 | 7648 | 48 | 70 |
| 6039 | 8407 | 200 | 220 |
| 6040 | 7095 | 54 | 77 |
| 6041 | 8163 | 11 | 34 |
| 6042 | 7501 | 45 | 69 |
| 6042 | 7580 | 45 | 69 |
| 6042 | 7962 | 45 | 69 |
| 6043 | 6955 | 11 | 31 |
| 6043 | 7446 | 11 | 31 |
| 6043 | 7515 | 11 | 31 |
| 6043 | 7543 | 11 | 31 |
| 6043 | 7617 | 11 | 31 |
| 6043 | 7618 | 11 | 31 |
| 6043 | 7726 | 11 | 31 |
| 6043 | 8098 | 11 | 31 |
| 6043 | 8290 | 11 | 31 |
| 6044 | 7086 | 11 | 34 |
| 6044 | 7306 | 11 | 34 |
| 6044 | 7736 | 11 | 34 |
| 6045 | 7620 | 231 | 252 |
| 6045 | 7906 | 231 | 252 |
| 6046 | 7321 | 11 | 33 |
| 6047 | 6967 | 11 | 31 |
| 6048 | 7101 | 11 | 30 |
| 6048 | 8333 | 11 | 30 |
| 6048 | 8362 | 11 | 30 |
| 6049 | 7216 | 11 | 30 |
| 6049 | 7706 | 11 | 30 |
| 6050 | 7481 | 11 | 33 |
| 6051 | 8040 | 11 | 33 |
| 6052 | 6807 | 11 | 31 |
| 6053 | 7431 | 11 | 32 |
| 6053 | 8203 | 11 | 32 |
| 6054 | 7218 | 11 | 34 |
| 6054 | 7968 | 11 | 34 |
| 6055 | 8043 | 38 | 57 |
| 6056 | 8336 | 11 | 30 |
| 6057 | 8225 | 11 | 33 |
| 6058 | 6818 | 52 | 71 |
| 6059 | 7996 | 11 | 34 |
| 6060 | 6918 | 11 | 32 |
| 6061 | 8090 | 11 | 32 |
| 6062 | 7021 | 11 | 30 |
| 6063 | 7441 | 51 | 71 |
| 6064 | 7667 | 385 | 408 |
| 6065 | 8273 | 50 | 72 |
| 6066 | 7046 | 11 | 34 |
| 6067 | 8021 | 31 | 50 |
| 6068 | 6769 | 100 | 121 |
| 6068 | 7033 | 100 | 121 |
| 6069 | 7438 | 49 | 71 |
| 6070 | 6931 | 42 | 63 |
| 6070 | 7930 | 42 | 63 |
| 6071 | 8384 | 11 | 30 |
| 6072 | 8349 | 11 | 30 |
| 6072 | 8350 | 11 | 30 |
| 6073 | 6944 | 11 | 30 |
| 6073 | 8315 | 11 | 30 |
| 6074 | 6862 | 11 | 30 |
| 6075 | 7748 | 11 | 32 |
| 6076 | 6974 | 73 | 93 |
| 6077 | 7393 | 11 | 31 |
| 6077 | 7680 | 11 | 31 |
| 6077 | 7732 | 11 | 31 |
| 6077 | 7859 | 11 | 31 |
| 6078 | 6750 | 211 | 230 |
| 6079 | 8376 | 11 | 30 |
| 6080 | 6792 | 11 | 33 |
| 6081 | 8281 | 11 | 32 |
| 6082 | 7552 | 11 | 30 |
| 6083 | 7168 | 47 | 70 |
| 6084 | 7443 | 45 | 68 |
| 6085 | 7061 | 11 | 31 |
| 6085 | 7583 | 35 | 55 |
| 6086 | 6738 | 40 | 60 |
| 6087 | 7367 | 11 | 34 |
| 6088 | 8399 | 11 | 32 |
| 6089 | 6752 | 36 | 59 |
| 6090 | 6863 | 11 | 31 |
| 6091 | 7806 | 11 | 30 |
| 6092 | 7308 | 51 | 73 |
| 6092 | 7688 | 51 | 73 |
| 6092 | 8301 | 51 | 73 |
| 6093 | 7539 | 11 | 33 |
| 6094 | 7380 | 58 | 79 |
| 6094 | 8293 | 58 | 79 |
| 6095 | 7135 | 11 | 31 |
| 6096 | 8257 | 11 | 34 |
| 6096 | 8291 | 11 | 34 |
| 6097 | 7129 | 34 | 53 |
| 6098 | 7747 | 11 | 31 |
| 6099 | 6943 | 86 | 106 |
| 6100 | 8182 | 11 | 34 |
| 6100 | 8221 | 11 | 34 |
| 6101 | 6904 | 11 | 32 |
| 6101 | 8254 | 11 | 32 |
| 6102 | 7972 | 118 | 142 |
| 6103 | 6693 | 11 | 32 |
| 6104 | 7190 | 82 | 101 |
| 6105 | 7673 | 11 | 34 |
| 6106 | 7142 | 11 | 34 |
| 6107 | 7892 | 11 | 31 |
| 6108 | 7672 | 34 | 53 |
| 6109 | 7628 | 11 | 31 |
| 6110 | 8282 | 11 | 33 |
| 6111 | 6935 | 11 | 30 |
| 6111 | 7259 | 11 | 30 |
| 6111 | 7678 | 234 | 253 |
| 6112 | 6770 | 41 | 60 |
| 6112 | 7352 | 41 | 60 |
| 6113 | 7775 | 11 | 35 |
| 6114 | 7700 | 11 | 30 |
| 6115 | 6854 | 11 | 31 |
| 6115 | 7294 | 11 | 31 |
| 6116 | 8328 | 11 | 31 |
| 6117 | 7357 | 304 | 326 |
| 6118 | 7051 | 210 | 232 |
| 6119 | 7572 | 204 | 227 |
| 6120 | 8085 | 66 | 85 |
| 6121 | 7125 | 11 | 30 |
| 6121 | 7305 | 11 | 30 |
| 6122 | 8358 | 11 | 34 |
| 6123 | 7285 | 53 | 73 |
| 6123 | 7312 | 53 | 73 |
| 6123 | 7458 | 52 | 72 |
| 6123 | 7502 | 53 | 73 |
| 6123 | 7544 | 53 | 73 |
| 6123 | 7545 | 53 | 73 |
| 6123 | 7643 | 53 | 73 |
| 6123 | 7717 | 53 | 73 |
| 6123 | 7718 | 53 | 73 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 6123 | 7719 | 53 | 73 |
| 6123 | 7720 | 53 | 73 |
| 6123 | 7721 | 53 | 73 |
| 6123 | 7890 | 53 | 73 |
| 6123 | 8123 | 53 | 73 |
| 6123 | 8150 | 53 | 73 |
| 6123 | 8151 | 53 | 73 |
| 6123 | 8152 | 53 | 73 |
| 6123 | 8153 | 53 | 73 |
| 6124 | 7119 | 53 | 76 |
| 6125 | 7141 | 11 | 33 |
| 6126 | 6895 | 11 | 31 |
| 6127 | 6923 | 11 | 30 |
| 6127 | 7188 | 11 | 30 |
| 6128 | 8112 | 51 | 74 |
| 6129 | 6867 | 36 | 58 |
| 6129 | 8343 | 36 | 58 |
| 6130 | 8127 | 69 | 89 |
| 6131 | 7915 | 11 | 34 |
| 6132 | 6986 | 11 | 30 |
| 6133 | 7984 | 11 | 32 |
| 6134 | 7753 | 11 | 32 |
| 6135 | 6879 | 11 | 34 |
| 6136 | 8341 | 45 | 68 |
| 6137 | 7503 | 126 | 145 |
| 6138 | 6886 | 85 | 104 |
| 6139 | 6768 | 34 | 53 |
| 6139 | 6916 | 34 | 53 |
| 6140 | 7318 | 11 | 30 |
| 6141 | 7778 | 11 | 33 |
| 6142 | 8179 | 11 | 30 |
| 6143 | 6721 | 11 | 30 |
| 6143 | 8019 | 11 | 30 |
| 6144 | 7322 | 147 | 169 |
| 6145 | 7395 | 42 | 62 |
| 6146 | 7815 | 72 | 92 |
| 6147 | 8237 | 96 | 117 |
| 6148 | 7412 | 35 | 56 |
| 6149 | 6932 | 11 | 34 |
| 6150 | 6719 | 37 | 61 |
| 6150 | 6940 | 37 | 61 |
| 6150 | 7361 | 37 | 61 |
| 6150 | 8267 | 38 | 62 |
| 6150 | 8286 | 37 | 61 |
| 6151 | 7605 | 11 | 35 |
| 6152 | 7378 | 37 | 60 |
| 6152 | 8366 | 11 | 34 |
| 6153 | 6771 | 11 | 31 |
| 6154 | 7112 | 11 | 32 |
| 6155 | 7035 | 89 | 109 |
| 6155 | 7109 | 89 | 109 |
| 6156 | 7028 | 11 | 35 |
| 6156 | 7400 | 11 | 35 |
| 6156 | 8103 | 11 | 35 |
| 6157 | 7288 | 11 | 32 |
| 6157 | 8355 | 11 | 32 |
| 6158 | 8360 | 58 | 81 |
| 6159 | 8095 | 37 | 56 |
| 6160 | 7666 | 38 | 58 |
| 6161 | 7036 | 11 | 33 |
| 6162 | 8067 | 11 | 35 |
| 6163 | 7637 | 11 | 34 |
| 6164 | 6907 | 173 | 195 |
| 6164 | 7401 | 173 | 195 |
| 6164 | 8031 | 173 | 195 |
| 6165 | 6900 | 11 | 31 |
| 6166 | 7989 | 11 | 34 |
| 6167 | 7249 | 11 | 31 |
| 6168 | 7038 | 157 | 176 |
| 6169 | 7270 | 49 | 68 |
| 6170 | 7547 | 6 | 27 |
| 6171 | 7985 | 11 | 31 |
| 6172 | 7782 | 11 | 34 |
| 6173 | 7769 | 11 | 34 |
| 6174 | 7595 | 11 | 34 |
| 6175 | 7953 | 11 | 35 |
| 6176 | 8392 | 11 | 32 |
| 6177 | 7731 | 248 | 269 |
| 6177 | 8279 | 242 | 263 |
| 6178 | 7826 | 11 | 32 |
| 6179 | 6882 | 39 | 62 |
| 6179 | 7344 | 11 | 34 |
| 6179 | 7584 | 39 | 62 |
| 6179 | 7695 | 39 | 62 |
| 6179 | 8117 | 38 | 61 |
| 6180 | 7767 | 11 | 32 |
| 6180 | 7789 | 11 | 32 |
| 6180 | 7926 | 11 | 32 |
| 6181 | 7472 | 11 | 30 |
| 6182 | 8389 | 70 | 89 |
| 6183 | 7370 | 11 | 31 |
| 6183 | 7878 | 11 | 31 |
| 6184 | 6794 | 71 | 93 |
| 6185 | 6697 | 11 | 31 |
| 6185 | 7337 | 11 | 31 |
| 6185 | 8294 | 11 | 31 |
| 6186 | 7881 | 43 | 62 |
| 6187 | 7777 | 11 | 33 |
| 6188 | 6890 | 11 | 34 |
| 6189 | 7179 | 174 | 197 |
| 6190 | 6898 | 11 | 34 |
| 6191 | 7451 | 11 | 34 |
| 6192 | 7594 | 11 | 34 |
| 6193 | 7136 | 59 | 79 |
| 6193 | 8373 | 59 | 79 |
| 6193 | 8382 | 59 | 79 |
| 6194 | 8142 | 42 | 65 |
| 6195 | 6962 | 11 | 33 |
| 6195 | 6981 | 11 | 33 |
| 6195 | 7350 | 11 | 33 |
| 6195 | 7418 | 11 | 33 |
| 6195 | 7536 | 11 | 33 |
| 6195 | 7537 | 11 | 33 |
| 6195 | 7538 | 11 | 33 |
| 6195 | 8391 | 11 | 33 |
| 6196 | 7114 | 100 | 121 |
| 6197 | 6776 | 104 | 123 |
| 6197 | 6810 | 104 | 123 |
| 6198 | 7198 | 11 | 32 |
| 6198 | 7222 | 11 | 32 |
| 6198 | 7924 | 51 | 72 |
| 6199 | 6689 | 72 | 93 |
| 6199 | 7342 | 72 | 93 |
| 6199 | 7498 | 72 | 93 |
| 6200 | 7236 | 11 | 31 |
| 6201 | 8052 | 11 | 34 |
| 6202 | 7235 | 11 | 35 |
| 6202 | 8162 | 11 | 35 |
| 6202 | 8169 | 11 | 35 |
| 6203 | 7320 | 11 | 34 |
| 6204 | 6980 | 11 | 31 |
| 6205 | 7123 | 11 | 30 |
| 6206 | 7559 | 304 | 325 |
| 6207 | 6950 | 43 | 62 |
| 6207 | 6987 | 43 | 62 |
| 6207 | 7858 | 11 | 30 |
| 6208 | 7493 | 11 | 33 |
| 6209 | 8240 | 203 | 222 |
| 6210 | 7011 | 11 | 34 |
| 6211 | 7982 | 37 | 57 |
| 6212 | 6758 | 11 | 30 |
| 6212 | 8304 | 11 | 30 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 6213 | 6777 | 45 | 68 |
| 6214 | 7052 | 40 | 59 |
| 6215 | 7137 | 46 | 68 |
| 6215 | 7139 | 47 | 69 |
| 6216 | 7382 | 11 | 30 |
| 6217 | 6997 | 33 | 52 |
| 6218 | 7267 | 11 | 31 |
| 6218 | 7387 | 51 | 71 |
| 6218 | 7419 | 51 | 71 |
| 6218 | 7518 | 11 | 31 |
| 6218 | 7527 | 51 | 71 |
| 6218 | 7795 | 11 | 31 |
| 6218 | 7908 | 51 | 71 |
| 6218 | 7998 | 51 | 71 |
| 6218 | 8114 | 11 | 31 |
| 6218 | 8184 | 51 | 71 |
| 6218 | 8335 | 11 | 31 |
| 6219 | 8201 | 11 | 34 |
| 6220 | 7621 | 11 | 34 |
| 6221 | 7098 | 11 | 31 |
| 6222 | 7847 | 47 | 68 |
| 6223 | 7896 | 33 | 53 |
| 6224 | 8051 | 11 | 34 |
| 6225 | 8231 | 49 | 72 |
| 6226 | 8036 | 10 | 33 |
| 6227 | 7448 | 41 | 64 |
| 6228 | 7990 | 1 | 24 |
| 6229 | 7684 | 137 | 160 |
| 6230 | 6737 | 11 | 34 |
| 6230 | 7155 | 11 | 34 |
| 6231 | 7473 | 11 | 34 |
| 6232 | 7024 | 44 | 63 |
| 6232 | 8010 | 43 | 62 |
| 6232 | 8329 | 44 | 63 |
| 6233 | 6908 | 41 | 60 |
| 6234 | 8274 | 40 | 63 |
| 6235 | 8136 | 11 | 30 |
| 6236 | 6726 | 137 | 160 |
| 6237 | 8110 | 11 | 34 |
| 6238 | 7884 | 38 | 59 |
| 6239 | 7995 | 11 | 30 |
| 6240 | 8000 | 46 | 69 |
| 6241 | 7751 | 11 | 34 |
| 6242 | 6702 | 11 | 30 |
| 6242 | 8331 | 11 | 30 |
| 6242 | 8397 | 11 | 30 |
| 6243 | 7054 | 75 | 95 |
| 6243 | 7346 | 75 | 95 |
| 6244 | 7050 | 11 | 34 |
| 6245 | 6855 | 71 | 90 |
| 6245 | 8370 | 71 | 90 |
| 6246 | 7900 | 84 | 106 |
| 6247 | 6846 | 112 | 135 |
| 6248 | 7579 | 47 | 68 |
| 6248 | 7734 | 47 | 68 |
| 6249 | 7278 | 128 | 148 |
| 6250 | 7146 | 11 | 30 |
| 6251 | 7708 | 38 | 58 |
| 6252 | 7313 | 47 | 70 |
| 6253 | 6699 | 11 | 34 |
| 6254 | 7199 | 72 | 93 |
| 6255 | 6868 | 49 | 69 |
| 6255 | 7362 | 49 | 69 |
| 6255 | 7604 | 49 | 69 |
| 6256 | 7977 | 39 | 62 |
| 6257 | 8302 | 11 | 31 |
| 6258 | 8196 | 11 | 31 |
| 6259 | 7108 | 11 | 34 |
| 6260 | 8243 | 236 | 259 |
| 6261 | 7284 | 11 | 32 |
| 6261 | 7746 | 11 | 32 |
| 6262 | 7349 | 38 | 58 |
| 6262 | 7402 | 11 | 31 |
| 6263 | 7261 | 33 | 55 |
| 6263 | 7629 | 34 | 56 |
| 6263 | 8309 | 33 | 55 |
| 6264 | 7189 | 11 | 34 |
| 6265 | 6899 | 11 | 34 |
| 6266 | 6889 | 33 | 52 |
| 6267 | 6937 | 11 | 35 |
| 6268 | 7455 | 11 | 31 |
| 6269 | 6796 | 11 | 31 |
| 6269 | 7656 | 11 | 31 |
| 6270 | 6897 | 78 | 102 |
| 6271 | 7102 | 35 | 55 |
| 6271 | 8197 | 35 | 55 |
| 6272 | 6825 | 86 | 109 |
| 6272 | 7090 | 86 | 109 |
| 6273 | 7961 | 53 | 75 |
| 6274 | 8044 | 54 | 74 |
| 6275 | 7077 | 34 | 55 |
| 6276 | 7203 | 95 | 116 |
| 6277 | 7478 | 71 | 91 |
| 6278 | 7494 | 177 | 200 |
| 6278 | 7999 | 11 | 34 |
| 6279 | 7870 | 11 | 34 |
| 6280 | 7877 | 11 | 34 |
| 6281 | 7505 | 11 | 34 |
| 6281 | 7533 | 11 | 34 |
| 6281 | 7534 | 11 | 34 |
| 6282 | 7325 | 82 | 103 |
| 6283 | 7694 | 190 | 209 |
| 6284 | 6994 | 31 | 51 |
| 6284 | 8061 | 31 | 51 |
| 6285 | 6887 | 48 | 70 |
| 6286 | 7456 | 141 | 164 |
| 6287 | 7489 | 46 | 67 |
| 6288 | 7846 | 51 | 72 |
| 6289 | 7659 | 11 | 34 |
| 6290 | 7405 | 47 | 70 |
| 6290 | 7955 | 47 | 70 |
| 6290 | 7960 | 47 | 70 |
| 6291 | 7651 | 36 | 55 |
| 6291 | 7904 | 61 | 80 |
| 6292 | 8168 | 52 | 73 |
| 6293 | 7743 | 11 | 30 |
| 6294 | 7519 | 11 | 32 |
| 6295 | 7238 | 11 | 30 |
| 6295 | 7385 | 11 | 30 |
| 6295 | 7903 | 11 | 30 |
| 6296 | 7159 | 11 | 30 |
| 6297 | 7214 | 11 | 31 |
| 6298 | 8297 | 42 | 62 |
| 6299 | 7886 | 44 | 63 |
| 6300 | 6936 | 170 | 189 |
| 6301 | 8118 | 134 | 156 |
| 6302 | 8177 | 376 | 397 |
| 6303 | 7776 | 11 | 34 |
| 6304 | 7081 | 40 | 61 |
| 6305 | 7348 | 42 | 65 |
| 6306 | 7586 | 59 | 82 |
| 6307 | 6963 | 112 | 132 |
| 6308 | 6805 | 11 | 35 |
| 6308 | 7257 | 11 | 35 |
| 6309 | 7332 | 83 | 102 |
| 6310 | 7825 | 237 | 260 |
| 6311 | 7333 | 11 | 34 |
| 6311 | 7334 | 11 | 34 |
| 6312 | 6802 | 11 | 35 |
| 6312 | 6925 | 11 | 35 |
| 6312 | 7080 | 11 | 35 |
| 6312 | 7592 | 11 | 35 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 6312 | 7596 | 11 | 35 |
| 6312 | 7600 | 11 | 35 |
| 6312 | 7639 | 11 | 35 |
| 6312 | 7699 | 11 | 35 |
| 6312 | 7702 | 11 | 35 |
| 6312 | 7733 | 11 | 35 |
| 6312 | 7842 | 11 | 35 |
| 6312 | 7923 | 11 | 35 |
| 6312 | 8081 | 11 | 35 |
| 6312 | 8093 | 11 | 35 |
| 6312 | 8183 | 11 | 35 |
| 6313 | 6808 | 11 | 31 |
| 6313 | 6828 | 11 | 31 |
| 6314 | 7065 | 11 | 32 |
| 6314 | 7066 | 11 | 32 |
| 6314 | 7067 | 11 | 32 |
| 6314 | 8388 | 11 | 32 |
| 6315 | 7425 | 213 | 234 |
| 6316 | 7509 | 11 | 34 |
| 6317 | 7416 | 11 | 30 |
| 6318 | 7788 | 92 | 111 |
| 6319 | 6891 | 34 | 54 |
| 6319 | 7169 | 151 | 171 |
| 6320 | 6753 | 79 | 99 |
| 6321 | 7250 | 31 | 51 |
| 6322 | 6806 | 52 | 75 |
| 6323 | 8319 | 305 | 325 |
| 6324 | 7365 | 55 | 75 |
| 6325 | 7131 | 11 | 34 |
| 6326 | 7764 | 38 | 57 |
| 6327 | 6922 | 11 | 30 |
| 6328 | 8018 | 141 | 160 |
| 6329 | 7742 | 98 | 117 |
| 6330 | 7187 | 11 | 31 |
| 6331 | 6969 | 70 | 93 |
| 6332 | 7391 | 62 | 85 |
| 6333 | 8402 | 236 | 258 |
| 6334 | 7898 | 37 | 60 |
| 6335 | 7426 | 11 | 32 |
| 6336 | 7366 | 217 | 236 |
| 6337 | 6888 | 11 | 34 |
| 6338 | 7486 | 189 | 211 |
| 6339 | 6953 | 11 | 32 |
| 6339 | 7925 | 11 | 32 |
| 6340 | 8165 | 11 | 32 |
| 6341 | 6839 | 11 | 33 |
| 6342 | 7079 | 242 | 262 |
| 6343 | 7289 | 11 | 31 |
| 6343 | 7852 | 11 | 31 |
| 6344 | 7750 | 11 | 31 |
| 6345 | 7657 | 10 | 30 |
| 6345 | 8251 | 11 | 31 |
| 6346 | 7107 | 11 | 33 |
| 6347 | 7180 | 240 | 262 |
| 6347 | 8219 | 236 | 258 |
| 6348 | 7800 | 11 | 30 |
| 6349 | 8288 | 218 | 237 |
| 6350 | 6954 | 11 | 30 |
| 6351 | 6985 | 43 | 66 |
| 6352 | 7624 | 48 | 68 |
| 6353 | 7269 | 11 | 31 |
| 6354 | 7007 | 11 | 33 |
| 6355 | 6961 | 208 | 228 |
| 6355 | 8265 | 208 | 228 |
| 6356 | 6691 | 11 | 34 |
| 6357 | 7315 | 11 | 31 |
| 6358 | 6751 | 196 | 215 |
| 6359 | 6759 | 11 | 31 |
| 6360 | 8206 | 200 | 222 |
| 6360 | 8351 | 200 | 222 |
| 6361 | 7609 | 11 | 31 |
| 6362 | 7492 | 11 | 32 |
| 6363 | 8371 | 350 | 374 |
| 6364 | 6927 | 116 | 135 |
| 6365 | 7104 | 230 | 251 |
| 6366 | 7255 | 11 | 31 |
| 6367 | 7126 | 64 | 83 |
| 6368 | 7980 | 11 | 33 |
| 6369 | 7602 | 11 | 32 |
| 6370 | 7854 | 11 | 33 |
| 6371 | 8157 | 11 | 31 |
| 6372 | 7570 | 136 | 156 |
| 6373 | 7343 | 52 | 71 |
| 6374 | 8002 | 11 | 30 |
| 6374 | 8022 | 11 | 30 |
| 6375 | 6746 | 43 | 63 |
| 6375 | 7004 | 43 | 63 |
| 6375 | 7157 | 11 | 31 |
| 6375 | 7384 | 43 | 63 |
| 6375 | 7939 | 43 | 63 |
| 6375 | 8374 | 11 | 31 |
| 6376 | 7987 | 11 | 32 |
| 6377 | 7471 | 11 | 33 |
| 6377 | 7480 | 52 | 74 |
| 6377 | 7689 | 51 | 73 |
| 6378 | 7111 | 11 | 34 |
| 6379 | 7097 | 167 | 187 |
| 6379 | 7662 | 11 | 31 |
| 6380 | 7701 | 11 | 30 |
| 6381 | 7974 | 95 | 118 |
| 6382 | 7062 | 62 | 85 |
| 6383 | 8220 | 69 | 91 |
| 6384 | 7347 | 40 | 60 |
| 6384 | 8223 | 40 | 60 |
| 6385 | 7113 | 40 | 64 |
| 6385 | 7164 | 40 | 64 |
| 6385 | 7729 | 11 | 35 |
| 6386 | 6982 | 58 | 78 |
| 6387 | 7083 | 65 | 89 |
| 6387 | 7946 | 70 | 94 |
| 6387 | 8316 | 71 | 95 |
| 6388 | 7645 | 11 | 34 |
| 6389 | 6896 | 11 | 35 |
| 6390 | 7071 | 35 | 55 |
| 6390 | 7084 | 35 | 55 |
| 6391 | 6801 | 48 | 72 |
| 6392 | 7722 | 11 | 30 |
| 6393 | 7582 | 219 | 242 |
| 6394 | 7172 | 240 | 262 |
| 6395 | 8405 | 11 | 34 |
| 6396 | 7949 | 65 | 87 |
| 6397 | 8401 | 82 | 103 |
| 6398 | 8097 | 37 | 59 |
| 6399 | 6701 | 47 | 70 |
| 6400 | 7075 | 11 | 32 |
| 6401 | 7298 | 11 | 34 |
| 6402 | 8059 | 35 | 56 |
| 6403 | 7301 | 11 | 30 |
| 6403 | 8256 | 11 | 30 |
| 6404 | 7120 | 30 | 50 |
| 6405 | 7258 | 11 | 33 |
| 6406 | 7263 | 11 | 31 |
| 6407 | 8003 | 11 | 34 |
| 6408 | 6876 | 11 | 31 |
| 6409 | 6914 | 11 | 31 |
| 6409 | 7938 | 11 | 31 |
| 6410 | 6779 | 32 | 52 |
| 6410 | 7364 | 32 | 52 |
| 6411 | 7043 | 11 | 32 |
| 6411 | 7797 | 11 | 32 |
| 6412 | 6883 | 11 | 30 |
| 6413 | 6733 | 46 | 68 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 6414 | 7467 | 81 | 101 |
| 6415 | 7422 | 11 | 31 |
| 6415 | 7766 | 11 | 31 |
| 6416 | 7148 | 34 | 53 |
| 6417 | 7661 | 11 | 33 |
| 6418 | 6757 | 11 | 31 |
| 6418 | 7468 | 11 | 31 |
| 6419 | 6834 | 37 | 56 |
| 6420 | 6851 | 11 | 35 |
| 6420 | 6971 | 11 | 35 |
| 6420 | 7311 | 11 | 35 |
| 6420 | 7374 | 11 | 35 |
| 6420 | 7626 | 11 | 35 |
| 6420 | 7784 | 11 | 35 |
| 6420 | 7799 | 11 | 35 |
| 6420 | 8313 | 11 | 35 |
| 6420 | 8338 | 11 | 35 |
| 6421 | 7017 | 215 | 238 |
| 6422 | 7053 | 125 | 148 |
| 6422 | 7185 | 11 | 34 |
| 6423 | 8325 | 11 | 30 |
| 6424 | 7757 | 11 | 30 |
| 6425 | 7211 | 32 | 52 |
| 6426 | 7976 | 389 | 412 |
| 6427 | 8037 | 49 | 73 |
| 6428 | 7916 | 11 | 30 |
| 6429 | 8342 | 33 | 54 |
| 6430 | 7531 | 11 | 31 |
| 6431 | 7830 | 3 | 25 |
| 6432 | 7411 | 133 | 155 |
| 6433 | 6965 | 45 | 64 |
| 6433 | 7449 | 46 | 65 |
| 6433 | 7562 | 45 | 64 |
| 6433 | 8033 | 11 | 30 |
| 6434 | 7791 | 155 | 176 |
| 6435 | 7516 | 134 | 157 |
| 6436 | 7389 | 69 | 89 |
| 6437 | 8334 | 76 | 96 |
| 6438 | 7147 | 11 | 30 |
| 6438 | 7147 | 54 | 73 |
| 6438 | 8269 | 11 | 30 |
| 6439 | 7272 | 11 | 30 |
| 6439 | 8271 | 11 | 30 |
| 6440 | 8227 | 52 | 75 |
| 6441 | 7636 | 11 | 34 |
| 6442 | 7593 | 11 | 34 |
| 6442 | 7593 | 67 | 90 |
| 6442 | 8381 | 11 | 34 |
| 6442 | 8381 | 67 | 90 |
| 6443 | 7818 | 46 | 69 |
| 6443 | 8077 | 44 | 67 |
| 6444 | 7676 | 11 | 34 |
| 6444 | 7808 | 11 | 34 |
| 6445 | 7420 | 11 | 31 |
| 6446 | 6814 | 138 | 157 |
| 6447 | 6728 | 202 | 222 |
| 6447 | 7368 | 201 | 221 |
| 6448 | 7535 | 11 | 34 |
| 6449 | 6822 | 1 | 24 |
| 6449 | 7513 | 11 | 34 |
| 6450 | 8249 | 47 | 70 |
| 6451 | 7056 | 11 | 34 |
| 6452 | 7309 | 98 | 119 |
| 6453 | 7299 | 32 | 51 |
| 6453 | 7623 | 26 | 45 |
| 6454 | 8104 | 71 | 93 |
| 6455 | 7291 | 51 | 72 |
| 6455 | 7292 | 51 | 72 |
| 6456 | 7658 | 31 | 50 |
| 6457 | 7099 | 11 | 34 |
| 6457 | 8132 | 11 | 34 |
| 6457 | 8139 | 11 | 34 |
| 6458 | 8258 | 11 | 30 |
| 6459 | 6841 | 60 | 84 |
| 6460 | 6901 | 51 | 72 |
| 6461 | 8082 | 11 | 30 |
| 6462 | 7640 | 11 | 34 |
| 6463 | 7091 | 11 | 31 |
| 6464 | 8070 | 11 | 32 |
| 6465 | 7329 | 62 | 81 |
| 6465 | 7574 | 62 | 81 |
| 6465 | 7716 | 62 | 81 |
| 6465 | 7935 | 62 | 81 |
| 6465 | 8317 | 62 | 81 |
| 6465 | 8353 | 62 | 81 |
| 6465 | 8369 | 62 | 81 |
| 6466 | 7597 | 70 | 90 |
| 6467 | 7437 | 221 | 244 |
| 6467 | 7541 | 75 | 98 |
| 6468 | 6874 | 11 | 30 |
| 6468 | 6945 | 11 | 30 |
| 6468 | 7153 | 11 | 30 |
| 6469 | 7803 | 192 | 213 |
| 6470 | 7940 | 11 | 34 |
| 6470 | 7940 | 67 | 90 |
| 6471 | 6727 | 11 | 32 |
| 6471 | 6913 | 11 | 32 |
| 6472 | 7432 | 2 | 23 |
| 6473 | 7345 | 11 | 31 |
| 6474 | 7703 | 62 | 85 |
| 6475 | 7969 | 30 | 49 |
| 6476 | 7130 | 35 | 57 |
| 6477 | 7162 | 251 | 272 |
| 6478 | 7201 | 74 | 98 |
| 6478 | 7413 | 11 | 35 |
| 6478 | 7421 | 74 | 98 |
| 6478 | 7452 | 74 | 98 |
| 6478 | 7567 | 74 | 98 |
| 6478 | 7963 | 74 | 98 |
| 6479 | 7952 | 11 | 30 |
| 6480 | 7128 | 68 | 92 |
| 6481 | 7610 | 11 | 34 |
| 6482 | 8121 | 11 | 32 |
| 6483 | 7506 | 11 | 32 |
| 6483 | 7787 | 11 | 32 |
| 6483 | 7901 | 11 | 32 |
| 6484 | 8318 | 42 | 63 |
| 6484 | 8346 | 42 | 63 |
| 6485 | 7372 | 11 | 34 |
| 6486 | 7369 | 11 | 35 |
| 6487 | 7805 | 87 | 106 |
| 6488 | 6915 | 36 | 59 |
| 6489 | 7444 | 60 | 82 |
| 6490 | 6857 | 11 | 34 |
| 6490 | 7376 | 11 | 34 |
| 6490 | 8181 | 11 | 34 |
| 6491 | 6783 | 11 | 32 |
| 6491 | 7429 | 11 | 32 |
| 6491 | 7889 | 10 | 31 |
| 6491 | 8167 | 11 | 32 |
| 6492 | 7589 | 196 | 215 |
| 6493 | 7911 | 62 | 83 |
| 6494 | 7231 | 11 | 31 |
| 6495 | 7371 | 11 | 34 |
| 6496 | 6956 | 11 | 34 |
| 6496 | 8007 | 11 | 34 |
| 6497 | 8207 | 11 | 33 |
| 6498 | 7006 | 11 | 34 |
| 6499 | 7341 | 189 | 209 |
| 6500 | 7682 | 45 | 69 |
| 6501 | 7674 | 11 | 35 |
| 6501 | 7712 | 11 | 35 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 6502 | 7008 | 11 | 33 |
| 6503 | 7465 | 170 | 191 |
| 6504 | 7022 | 11 | 30 |
| 6505 | 6920 | 47 | 66 |
| 6505 | 8311 | 47 | 66 |
| 6506 | 7304 | 60 | 79 |
| 6507 | 6785 | 92 | 111 |
| 6507 | 8105 | 29 | 48 |
| 6507 | 8134 | 28 | 47 |
| 6508 | 7542 | 71 | 94 |
| 6509 | 6714 | 41 | 64 |
| 6509 | 7894 | 41 | 64 |
| 6509 | 7959 | 42 | 65 |
| 6510 | 7761 | 186 | 209 |
| 6511 | 7603 | 250 | 273 |
| 6512 | 7254 | 11 | 30 |
| 6513 | 7497 | 240 | 262 |
| 6514 | 7445 | 41 | 60 |
| 6515 | 7200 | 169 | 189 |
| 6515 | 7280 | 169 | 189 |
| 6515 | 7649 | 169 | 189 |
| 6516 | 6973 | 11 | 32 |
| 6516 | 7327 | 11 | 32 |
| 6516 | 7957 | 11 | 32 |
| 6517 | 8014 | 41 | 63 |
| 6518 | 7942 | 81 | 104 |
| 6519 | 7186 | 11 | 30 |
| 6520 | 7464 | 61 | 84 |
| 6521 | 7687 | 11 | 32 |
| 6522 | 6988 | 11 | 30 |
| 6523 | 6843 | 11 | 30 |
| 6524 | 7013 | 11 | 32 |
| 6525 | 6844 | 11 | 32 |
| 6525 | 8188 | 11 | 32 |
| 6525 | 8320 | 11 | 32 |
| 6526 | 7328 | 143 | 164 |
| 6527 | 6799 | 11 | 32 |
| 6528 | 7271 | 11 | 32 |
| 6529 | 7242 | 11 | 32 |
| 6530 | 8138 | 11 | 34 |
| 6531 | 6742 | 11 | 30 |
| 6532 | 7399 | 11 | 31 |
| 6533 | 7607 | 176 | 195 |
| 6534 | 7171 | 3 | 22 |
| 6535 | 7029 | 41 | 62 |
| 6535 | 7176 | 41 | 62 |
| 6535 | 7195 | 41 | 62 |
| 6535 | 7196 | 11 | 32 |
| 6535 | 8101 | 108 | 129 |
| 6536 | 7424 | 11 | 31 |
| 6537 | 6811 | 11 | 34 |
| 6538 | 7917 | 11 | 32 |
| 6539 | 7039 | 11 | 32 |
| 6539 | 7244 | 11 | 32 |
| 6539 | 7647 | 11 | 32 |
| 6540 | 8324 | 174 | 197 |
| 6541 | 6933 | 11 | 34 |
| 6542 | 6704 | 11 | 33 |
| 6542 | 6773 | 11 | 33 |
| 6542 | 7160 | 11 | 33 |
| 6542 | 7970 | 11 | 33 |
| 6543 | 6946 | 11 | 31 |
| 6544 | 7229 | 11 | 30 |
| 6544 | 8361 | 11 | 30 |
| 6545 | 7151 | 11 | 32 |
| 6546 | 7260 | 3 | 24 |
| 6547 | 7561 | 11 | 32 |
| 6548 | 8190 | 11 | 31 |
| 6548 | 8218 | 11 | 31 |
| 6549 | 8072 | 11 | 34 |
| 6550 | 7563 | 34 | 57 |
| 6551 | 8226 | 11 | 31 |
| 6552 | 6747 | 11 | 34 |
| 6553 | 7827 | 11 | 30 |
| 6554 | 6871 | 86 | 107 |
| 6554 | 7783 | 86 | 107 |
| 6555 | 7598 | 11 | 34 |
| 6556 | 7941 | 9 | 29 |
| 6556 | 8060 | 9 | 29 |
| 6557 | 7479 | 8 | 30 |
| 6558 | 7861 | 11 | 34 |
| 6559 | 7876 | 120 | 143 |
| 6560 | 7282 | 90 | 112 |
| 6560 | 7283 | 185 | 207 |
| 6561 | 6979 | 11 | 34 |
| 6561 | 7219 | 11 | 34 |
| 6562 | 7215 | 35 | 58 |
| 6563 | 6695 | 11 | 34 |
| 6563 | 6743 | 57 | 80 |
| 6563 | 6835 | 11 | 34 |
| 6563 | 7070 | 57 | 80 |
| 6563 | 7453 | 11 | 34 |
| 6563 | 7724 | 11 | 34 |
| 6563 | 7740 | 11 | 34 |
| 6563 | 7741 | 11 | 34 |
| 6563 | 7824 | 11 | 34 |
| 6563 | 8086 | 57 | 80 |
| 6563 | 8140 | 57 | 80 |
| 6563 | 8321 | 11 | 34 |
| 6564 | 6706 | 11 | 30 |
| 6565 | 6755 | 101 | 122 |
| 6565 | 6797 | 100 | 121 |
| 6565 | 7725 | 101 | 122 |
| 6565 | 8191 | 101 | 122 |
| 6566 | 7002 | 11 | 35 |
| 6567 | 8280 | 11 | 34 |
| 6568 | 7212 | 61 | 80 |
| 6569 | 7023 | 11 | 31 |
| 6569 | 7693 | 11 | 31 |
| 6569 | 7994 | 11 | 31 |
| 6569 | 8160 | 11 | 31 |
| 6569 | 8161 | 11 | 31 |
| 6570 | 8323 | 11 | 32 |
| 6571 | 8322 | 84 | 107 |
| 6572 | 7307 | 11 | 34 |
| 6573 | 7796 | 11 | 34 |
| 6574 | 7683 | 11 | 34 |
| 6575 | 6803 | 195 | 215 |
| 6576 | 7967 | 11 | 33 |
| 6577 | 7557 | 55 | 78 |
| 6578 | 7403 | 2 | 23 |
| 6579 | 6996 | 11 | 34 |
| 6579 | 7415 | 46 | 69 |
| 6579 | 7714 | 11 | 34 |
| 6580 | 8238 | 11 | 35 |
| 6581 | 6700 | 11 | 33 |
| 6582 | 6696 | 35 | 55 |
| 6583 | 7103 | 11 | 34 |
| 6584 | 7161 | 34 | 54 |
| 6585 | 8242 | 11 | 33 |
| 6586 | 7433 | 100 | 123 |
| 6587 | 7386 | 11 | 30 |
| 6588 | 8332 | 95 | 118 |
| 6589 | 8224 | 11 | 31 |
| 6590 | 7019 | 11 | 32 |
| 6590 | 8277 | 11 | 32 |
| 6591 | 7094 | 11 | 31 |
| 6592 | 7785 | 11 | 33 |
| 6593 | 7792 | 211 | 234 |
| 6594 | 7951 | 11 | 30 |
| 6595 | 7560 | 39 | 59 |
| 6596 | 6903 | 219 | 240 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 6597 | 6939 | 11 | 30 |
| 6598 | 6800 | 11 | 34 |
| 6599 | 8379 | 41 | 65 |
| 6600 | 6999 | 11 | 30 |
| 6600 | 7690 | 11 | 30 |
| 6601 | 6717 | 11 | 34 |
| 6601 | 7679 | 11 | 34 |
| 6602 | 7409 | 224 | 244 |
| 6603 | 8212 | 34 | 53 |
| 6604 | 7615 | 11 | 32 |
| 6604 | 7616 | 11 | 32 |
| 6604 | 7671 | 11 | 32 |
| 6604 | 7696 | 11 | 32 |
| 6605 | 6831 | 91 | 115 |
| 6605 | 8088 | 91 | 115 |
| 6606 | 8071 | 37 | 60 |
| 6607 | 6964 | 11 | 31 |
| 6608 | 8398 | 143 | 162 |
| 6609 | 8089 | 45 | 65 |
| 6610 | 8020 | 11 | 34 |
| 6611 | 8299 | 11 | 31 |
| 6612 | 6692 | 130 | 153 |
| 6612 | 6872 | 130 | 153 |
| 6613 | 6928 | 41 | 64 |
| 6614 | 7145 | 11 | 35 |
| 6615 | 7758 | 71 | 90 |
| 6616 | 7711 | 172 | 195 |
| 6617 | 8073 | 79 | 102 |
| 6618 | 6711 | 104 | 125 |
| 6619 | 6782 | 42 | 61 |
| 6620 | 7251 | 41 | 61 |
| 6621 | 7770 | 11 | 30 |
| 6622 | 7943 | 61 | 85 |
| 6623 | 7837 | 33 | 52 |
| 6624 | 6761 | 11 | 31 |
| 6625 | 8262 | 11 | 32 |
| 6626 | 7122 | 52 | 75 |
| 6627 | 6729 | 11 | 32 |
| 6627 | 7178 | 11 | 32 |
| 6628 | 7548 | 38 | 58 |
| 6629 | 7739 | 11 | 32 |
| 6629 | 8252 | 11 | 32 |
| 6630 | 8261 | 11 | 32 |
| 6630 | 8295 | 204 | 225 |
| 6631 | 7578 | 57 | 78 |
| 6632 | 7047 | 41 | 60 |
| 6632 | 7234 | 41 | 60 |
| 6632 | 7522 | 41 | 60 |
| 6633 | 7221 | 11 | 31 |
| 6634 | 7482 | 11 | 32 |
| 6634 | 8068 | 11 | 32 |
| 6635 | 8005 | 11 | 33 |
| 6636 | 8137 | 50 | 73 |
| 6637 | 6842 | 11 | 31 |
| 6638 | 6813 | 31 | 51 |
| 6638 | 7286 | 31 | 51 |
| 6638 | 8006 | 31 | 51 |
| 6639 | 6745 | 11 | 31 |
| 6639 | 7241 | 11 | 31 |
| 6639 | 7454 | 4 | 24 |
| 6640 | 7338 | 11 | 34 |
| 6641 | 7811 | 166 | 186 |
| 6642 | 8283 | 82 | 103 |
| 6643 | 6812 | 11 | 34 |
| 6644 | 8102 | 11 | 31 |
| 6645 | 6775 | 11 | 31 |
| 6646 | 7044 | 11 | 30 |
| 6647 | 6838 | 165 | 185 |
| 6648 | 6684 | 54 | 74 |
| 6649 | 7048 | 196 | 219 |
| 6650 | 7794 | 78 | 99 |
| 6651 | 8216 | 86 | 106 |
| 6652 | 8009 | 226 | 246 |
| 6653 | 6740 | 11 | 31 |
| 6653 | 7149 | 11 | 31 |
| 6653 | 8126 | 11 | 31 |
| 6653 | 8395 | 11 | 31 |
| 6654 | 7281 | 7 | 30 |
| 6655 | 7096 | 11 | 31 |
| 6655 | 7993 | 11 | 31 |
| 6656 | 7339 | 187 | 210 |
| 6657 | 6788 | 11 | 31 |
| 6657 | 6926 | 106 | 126 |
| 6657 | 7856 | 45 | 65 |
| 6657 | 8055 | 94 | 114 |
| 6658 | 8380 | 43 | 66 |
| 6659 | 6735 | 207 | 227 |
| 6659 | 7276 | 125 | 145 |
| 6659 | 7553 | 11 | 31 |
| 6660 | 6712 | 34 | 57 |
| 6661 | 7523 | 11 | 35 |
| 6662 | 8106 | 44 | 67 |
| 6663 | 6688 | 115 | 136 |
| 6664 | 7929 | 6 | 29 |
| 6665 | 6744 | 11 | 34 |
| 6666 | 8232 | 208 | 228 |
| 6667 | 8028 | 48 | 70 |
| 6668 | 7032 | 174 | 195 |
| 6669 | 8400 | 11 | 34 |
| 6670 | 8069 | 39 | 62 |
| 6671 | 7540 | 11 | 32 |
| 6672 | 7058 | 11 | 34 |
| 6673 | 8015 | 73 | 96 |
| 6674 | 6917 | 11 | 34 |
| 6675 | 6715 | 61 | 81 |
| 6675 | 6960 | 61 | 81 |
| 6675 | 7228 | 61 | 81 |
| 6676 | 6966 | 11 | 34 |
| 6677 | 7863 | 84 | 107 |
| 6678 | 7404 | 98 | 121 |
| 6678 | 7973 | 11 | 34 |
| 6678 | 8173 | 11 | 34 |
| 6679 | 7174 | 11 | 32 |
| 6680 | 8300 | 11 | 31 |
| 6681 | 7831 | 41 | 64 |
| 6682 | 8234 | 240 | 263 |
| 6683 | 8113 | 11 | 32 |
| 6683 | 8372 | 11 | 32 |
| 8409 | 8604 | 11 | 31 |
| 8409 | 8626 | 11 | 31 |
| 8410 | 8649 | 11 | 31 |
| 8411 | 8660 | 104 | 123 |
| 8412 | 8674 | 11 | 30 |
| 8413 | 8655 | 11 | 31 |
| 8414 | 8671 | 129 | 149 |
| 8415 | 8594 | 70 | 90 |
| 8415 | 8740 | 70 | 90 |
| 8416 | 8713 | 11 | 31 |
| 8417 | 8648 | 129 | 149 |
| 8418 | 8562 | 11 | 30 |
| 8418 | 8588 | 11 | 30 |
| 8418 | 8592 | 70 | 89 |
| 8419 | 8579 | 11 | 31 |
| 8420 | 8571 | 70 | 90 |
| 8420 | 8634 | 75 | 95 |
| 8421 | 8584 | 11 | 31 |
| 8422 | 8572 | 99 | 118 |
| 8422 | 8590 | 76 | 95 |
| 8423 | 8612 | 11 | 30 |
| 8424 | 8619 | 30 | 50 |
| 8425 | 8717 | 11 | 32 |
| 8426 | 8639 | 11 | 31 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 8427 | 8573 | 146 | 166 |
| 8428 | 8684 | 376 | 396 |
| 8429 | 8650 | 158 | 177 |
| 8430 | 8568 | 11 | 32 |
| 8430 | 8576 | 11 | 32 |
| 8430 | 8664 | 11 | 32 |
| 8431 | 8600 | 11 | 33 |
| 8432 | 8718 | 699 | 719 |
| 8433 | 8723 | 11 | 31 |
| 8434 | 8561 | 11 | 33 |
| 8435 | 8729 | 62 | 84 |
| 8436 | 8635 | 11 | 34 |
| 8437 | 8678 | 36 | 57 |
| 8438 | 8694 | 45 | 68 |
| 8439 | 8589 | 11 | 31 |
| 8440 | 8631 | 80 | 100 |
| 8441 | 8685 | 11 | 31 |
| 8442 | 8616 | 67 | 87 |
| 8443 | 8574 | 11 | 31 |
| 8444 | 8581 | 11 | 32 |
| 8445 | 8712 | 57 | 78 |
| 8446 | 8659 | 61 | 81 |
| 8447 | 8567 | 11 | 31 |
| 8448 | 8632 | 75 | 96 |
| 8449 | 8643 | 53 | 73 |
| 8450 | 8677 | 176 | 196 |
| 8451 | 8690 | 11 | 31 |
| 8452 | 8687 | 11 | 33 |
| 8453 | 8585 | 11 | 34 |
| 8454 | 8599 | 11 | 31 |
| 8455 | 8665 | 11 | 30 |
| 8456 | 8647 | 208 | 228 |
| 8457 | 8668 | 184 | 204 |
| 8458 | 8722 | 64 | 84 |
| 8459 | 8666 | 11 | 32 |
| 8460 | 8610 | 11 | 33 |
| 8461 | 8570 | 217 | 240 |
| 8462 | 8636 | 11 | 30 |
| 8463 | 8692 | 164 | 184 |
| 8464 | 8719 | 242 | 261 |
| 8465 | 8691 | 58 | 78 |
| 8466 | 8607 | 11 | 30 |
| 8466 | 8622 | 11 | 30 |
| 8467 | 8680 | 11 | 31 |
| 8468 | 8653 | 11 | 31 |
| 8469 | 8708 | 167 | 187 |
| 8470 | 8706 | 11 | 35 |
| 8471 | 8583 | 115 | 135 |
| 8472 | 8564 | 99 | 118 |
| 8472 | 8566 | 101 | 120 |
| 8472 | 8577 | 101 | 120 |
| 8472 | 8645 | 94 | 113 |
| 8472 | 8658 | 101 | 120 |
| 8472 | 8661 | 94 | 113 |
| 8473 | 8595 | 11 | 35 |
| 8474 | 8725 | 11 | 31 |
| 8475 | 8670 | 96 | 119 |
| 8476 | 8596 | 11 | 30 |
| 8477 | 8615 | 638 | 658 |
| 8478 | 8704 | 11 | 34 |
| 8479 | 8625 | 57 | 81 |
| 8480 | 8731 | 84 | 104 |
| 8481 | 8608 | 11 | 30 |
| 8482 | 8733 | 11 | 34 |
| 8483 | 8672 | 227 | 250 |
| 8484 | 8624 | 11 | 33 |
| 8485 | 8703 | 117 | 140 |
| 8486 | 8667 | 11 | 30 |
| 8487 | 8621 | 40 | 59 |
| 8488 | 8580 | 11 | 34 |
| 8489 | 8618 | 11 | 32 |
| 8490 | 8644 | 53 | 74 |
| 8491 | 8720 | 11 | 31 |
| 8492 | 8628 | 46 | 69 |
| 8493 | 8686 | 11 | 32 |
| 8494 | 8697 | 49 | 68 |
| 8495 | 8732 | 55 | 74 |
| 8496 | 8614 | 122 | 144 |
| 8497 | 8591 | 53 | 73 |
| 8498 | 8652 | 11 | 32 |
| 8499 | 8693 | 60 | 80 |
| 8500 | 8651 | 8 | 27 |
| 8501 | 8663 | 11 | 31 |
| 8502 | 8586 | 11 | 31 |
| 8503 | 8739 | 11 | 30 |
| 8504 | 8605 | 187 | 210 |
| 8504 | 8737 | 185 | 208 |
| 8505 | 8657 | 77 | 99 |
| 8506 | 8711 | 11 | 31 |
| 8507 | 8702 | 11 | 30 |
| 8508 | 8727 | 11 | 31 |
| 8509 | 8617 | 130 | 149 |
| 8509 | 8640 | 231 | 250 |
| 8510 | 8709 | 149 | 168 |
| 8511 | 8565 | 60 | 80 |
| 8512 | 8593 | 79 | 99 |
| 8512 | 8721 | 79 | 99 |
| 8512 | 8728 | 79 | 99 |
| 8513 | 8679 | 152 | 172 |
| 8514 | 8642 | 11 | 30 |
| 8515 | 8601 | 118 | 138 |
| 8516 | 8736 | 63 | 82 |
| 8517 | 8633 | 11 | 31 |
| 8518 | 8701 | 11 | 30 |
| 8519 | 8700 | 42 | 62 |
| 8520 | 8623 | 11 | 30 |
| 8521 | 8630 | 11 | 30 |
| 8522 | 8682 | 176 | 199 |
| 8523 | 8646 | 11 | 32 |
| 8524 | 8602 | 11 | 31 |
| 8525 | 8724 | 11 | 30 |
| 8526 | 8716 | 115 | 134 |
| 8527 | 8669 | 39 | 60 |
| 8528 | 8688 | 11 | 30 |
| 8529 | 8627 | 11 | 31 |
| 8530 | 8689 | 93 | 117 |
| 8530 | 8734 | 92 | 116 |
| 8531 | 8673 | 11 | 31 |
| 8532 | 8705 | 151 | 172 |
| 8533 | 8698 | 11 | 31 |
| 8534 | 8629 | 11 | 32 |
| 8535 | 8613 | 376 | 395 |
| 8536 | 8609 | 11 | 31 |
| 8537 | 8741 | 67 | 86 |
| 8538 | 8578 | 11 | 31 |
| 8538 | 8654 | 11 | 31 |
| 8539 | 8597 | 126 | 146 |
| 8540 | 8598 | 155 | 174 |
| 8541 | 8582 | 11 | 32 |
| 8542 | 8587 | 61 | 81 |
| 8543 | 8707 | 166 | 186 |
| 8544 | 8637 | 64 | 84 |
| 8544 | 8638 | 64 | 84 |
| 8544 | 8699 | 64 | 84 |
| 8545 | 8641 | 73 | 93 |
| 8546 | 8726 | 64 | 85 |
| 8547 | 8715 | 11 | 31 |
| 8548 | 8575 | 11 | 31 |
| 8549 | 8620 | 11 | 32 |
| 8550 | 8603 | 11 | 31 |
| 8551 | 8735 | 158 | 178 |
| 8552 | 8681 | 75 | 95 |

TABLE 6-continued

Maize and soybean miRNAs and miRNA precursors

| miRNA SEQ ID NO. | pre-miRNA SEQ ID NO. | Nucleotide position of miRNA in pre-miRNA from | to |
|---|---|---|---|
| 8553 | 8676 | 11 | 31 |
| 8553 | 8730 | 11 | 31 |
| 8554 | 8683 | 11 | 31 |
| 8555 | 8675 | 100 | 120 |
| 8556 | 8611 | 76 | 96 |
| 8556 | 8662 | 76 | 96 |
| 8556 | 8695 | 76 | 96 |
| 8556 | 8710 | 76 | 96 |
| 8557 | 8656 | 355 | 375 |
| 8558 | 8696 | 11 | 32 |
| 8558 | 8714 | 11 | 32 |
| 8559 | 8563 | 11 | 30 |
| 8559 | 8606 | 11 | 30 |
| 8559 | 8738 | 11 | 30 |
| 8560 | 8569 | 11 | 32 |

MicroRNAs and their precursors and promoters, especially those having a differential expression pattern between water-sufficient and water-insufficient (drought or water stress) conditions, are useful in engineering desirable traits (e.g., increased yield, improved germination) in crops that can experience water stress. Similar utility is found in other miRNAs (and their precursors or promoters) having expression patterns specific to other abiotic or biotic stress conditions, e.g., miRNAs having a differential expression pattern between nutrient-sufficient and nutrient-insufficient conditions, or between thermally stressed and thermally non-stressed conditions. Suitable methods include the introduction of an exogenous miRNA recognition site into a sequence, deletion or modification of an endogenous miRNA recognition site from a sequence, engineering of a native miRNA or miRNA precursor sequence in order to recognize a sequence other than the endogenous target sequence, and use of a miRNA promoter to provide a particular expression pattern.

Example 6

This example describes identification of a crop plant miRNA (miRMON18) having a specific expression pattern characterized by strong expression under nitrogen-sufficient conditions and suppression under nitrogen-deficient conditions, or strong expression under phosphate-sufficient conditions and suppression under phosphate-deficient conditions Small RNAs were cloned and putative miRNAs identified from a variety of tissues and developmental stages from rice (*Oryza sativa* cv. Nipponbare), corn (maize, *Zea mays* var. LH244), and soybean (*Glycine max* var. A3525), following techniques described above in Examples 1 and 5. Small RNA abundances were normalized between libraries and calculated as transcripts per quarter million sequences (tpq). A putative mature miRNA (small RNA number 370903, assigned the trivial name "miRMON18") with the sequence UUAGAUGACCAUCAGCAAACA was identified in rice (SEQ ID NO. 393), maize (SEQ ID NO. 3227), and soybean (SEQ ID NO. 8742) small RNA libraries. This sequence did not match known miRNAs in miRBase.

A miRMON18 precursor sequence was identified from the rice genome as (SEQ ID NO. 1763, FIG. 7B)
CCAUGAACCUGUUUUGUUGCUGGUCAUCUAGCUACCCGUGCAUGCCUGGA

GAUUGGAGAAUAAUUGACGAUGCAGCAGUCGGCUUAUUGGCUCUUGGGCA

CGCGUGGUUAGAUGACCAUCAGCAAACAAGUUCGUGAG, .

Another putative miRMON18 precursor sequence was identified from available maize genomic data as (SEQ ID NO. 3936, FIG. 7A)
CUCCGAACCUGUUUUGUUGGUGGUCAUUUAACCAUGCAUGCUUCGAUCGA

UGGAUUGGUGCAUGCAUGGAUUAUUGCAUAGUGUGAUGCAUGUGGCGCAU

CAGUGCAUGGUUAGAUGACCAUCAGCAAACAUGUUCUUGAG.

The position of the mature miRMON18 is depicted above in underlined text in these precursor sequences (SEQ ID NO. 1763 and SEQ ID NO. 3936). Each miRMON18 precursor was predicted to form a fold-back structure (FIGS. 7A and 7B), with the mature miRNA (miRMON18) located in the 3' arm of the fold-back structure, with the predicted miRNA* ("miRMON18*") located in the 5' arm; this was consistent with the much greater abundance of the mature miRMON18 relative to that of miRMON18* observed in the single corn locus MRT4577_378723C.3. A fold-back structure having the sequence (SEQ ID NO. 8743, FIG. 7C)
UGCAACCCUUGAAUGUGUUUGUUGAUUGAUAUCUACACAUGUUGAUCAUC

CUUGUGUUGAUCGAUUGGUUUAGAUGACCAUCAACAAACUCUUUCGUGGU

UUUGCA was identified in *Arabidopsis thaliana* as the precursor to a related mature miRNA with the sequence UUAGAUGAC-CAUCAACAAACU (miR827, SEQ ID NO. 8744). The mature miR827 was observed only at low abundance in *Arabidopsis thaliana*. Alignment of the two mature miRNAs shows that miR827 differs from miRMON18 by two nucleotides (FIG. 7D). This two nucleotide difference between miRMON18 and miR827 appears to be conserved between monocots and dicots, with miRMON18 identified in maize (*Zea mays*), rice (*Oryza sativa*), and sugar cane (*Saccharum officinarum*, data not shown) and miR827 identified in dicots (*Arabidopsis thaliana*).

Northern blots verified expression of the miRMON18 21-mer in at least rice (grain and seedling) and maize (kernel, leaf, and root) tissue samples from plants grown under normal (non-stressed) conditions, as depicted in FIG. 8A. MicroRNA precursors originate as polyadenylated transcripts generated by RNA polymerase II and standard transcription profiling of the maize miRMON18 precursor (SEQ ID NO. 3936, corresponding to probeset A1ZMO68928_at) further confirmed elevated expression in maize endosperm, callus, and seedling (FIG. 8B), with expression in other tissues in this sample falling below the detection cut-off threshold of 500 units.

Expression of the maize miRMON18 precursor (SEQ ID NO. 3936) was analyzed in maize tissues from plants grown under water-deficient (drought) (FIG. 9A), cold (FIG. 9B), and nitrogen-deficient conditions (FIG. 9C). Expression of the miRMON18 precursor was relatively unaffected by water conditions in root, shoot, ear, kernel, and tassel, with expression in leaf and silk increased under water-deficient conditions relative to water-sufficient conditions (FIG. 9A);

expression was also relatively unaffected by temperature (FIG. 9B). However, miRMON18 expression was highly responsive to nitrogen conditions, with about 2-fold suppression observed with nitrogen limitation (2 millimolar ammonium nitrate), relative to expression observed with sufficient nitrogen (20 millimolar ammonium nitrate) (FIG. 9C). This nitrogen-responsive expression pattern was verified by phosphor image quantification of Northern blots of small RNA samples, which showed an average 9.6-fold suppression of the mature miRMON18 21-mer over 3 time points (FIG. 10A). Thus, miRMON18 showed overall enhanced expression in maize endosperm and kernel, and strong suppression in leaves induced by nitrogen deficiency.

In another experiment, maize was grown in a hydroponic system under sufficient phosphate until the V3 stage, then phosphate deprived for up to 3 days. Leaf tissue samples were taken at 1 and 3 days after phosphate deprivation had begun. At 3 days, plants were returned to phosphate sufficiency and samples taken at 30 minutes and 6 hours after recovery. Control samples at each time point were taken from plants grown continually under phosphate sufficiency. FIG. 10B depicts the results of northern blots analyzed with a miRMON18 probe and demonstrates that, in this experiment, the maize miRMON18 mature miRNA exhibited in leaf tissue strong expression under phosphate-sufficient conditions and suppression under phosphate-deficient conditions.

Example 7

This example describes identification of genes having miRNA recognition sites (miRMON18 recognition sites) natively regulated by a crop plant miRNA (miRMON18) having an expression pattern characterized by strong expression under nitrogen-sufficient conditions and suppression under nitrogen-deficient conditions, or strong expression under phosphate-sufficient conditions and suppression under phosphate-deficient conditions.

Putative targets for the mature miRMON18 (UUA-GAUGACCAUCAGCAAACA, SEQ ID NO. 393, SEQ ID NO. 3227, or SEQ ID NO. 8742) were identified and included a clade of genes in the SPX ("SYG1/Pho81/XPR1") domain family. The SPX domain has been assigned the protein family/domain identifier Pfam PF03105, and is a hydrophobic domain found in the N-terminus of several proteins, typically including a stretch of about 180 residues with three smaller sub-domains of 35-47 amino acids; see, e.g., the SPX entry for the Pfam database currently curated at the Janelia Farms Research Campus of the Howard Hughes Medical Institute, publicly available at pfam.janelia.org/family?acc=PF03105.

The majority of proteins in the SPX domain family include other conserved domains in their C-terminus. For example, several proteins in the SPX domain family also include in their C-terminus an EXS ("ERD1, XPR1, and SYG1") domain, Pfam PF03124, which is possibly involved in protein sorting; see, e.g., pfam.janelia.org/family?acc=PF03124. Other SPX proteins include a conserved VTC (vacuolar transporter chaperone 2) domain, Pfam PF09359; see, e.g., pfam.janelia.org/family?acc=PF09359. Several SPX proteins include a conserved MFS_1 or MFS ("major facilitator superfamily") domain, Pfam PF07690, which is involved in transporting small solutes such as small sugars and inorganic salts in response to chemiosmotic ion gradients; see pfam.janelia.org/family?acc=PF07690. The SPX domain is likely to be a transcription factor, and may function as a dimerization domain.

SPX proteins include those encoded by the PHO genes, which are involved in the loading of inorganic phosphate into the xylem of roots; see, e, g., Wang et al. (2004) *Plant Physiol.*, 135:400-411, who have described identification of several PHO1 homologues, conservation of the SPX domain within these proteins, and the PHO1 promoter's predominant expression in the vascular tissues of roots, leaves, stems, or flowers as well as in some nonvascular tissues. Proteins in the SPX domain family are possibly involved in G-protein associated signal transduction (and thus are possibly sensors of inorganic phosphate); see Ticconi and Abel (2004) *Trends Plant Sci.*, 9:548-555. The PHO1 genes include both the SPX domain and an EXS domain. Members of the PHO clade also include a RING domain (At1g02860 and At2g38920), or an MFS domain (At4g22990, At4g11810, and At1g63010); see Wang et al. (2004) *Plant Physiol.*, 135:400-411, especially FIG. 3 and FIG. 6d.

Recently, a gene named NLA was reported to be required for adaptation to low nitrogen availability in *Arabidopsis thaliana*; see Peng et al. (2007) *Plant Cell*, 50:320-337. NLA ("AtNLA", locus At1g02860), assigned UniProtKB/Swiss-Prot accession number Q2V4F9, has the sequence of MRT3702_101115C, SEQ ID NO. 8745; annotation of the NLA protein is publicly available at beta.uniprot.org/uniprot/Q2V4F9 and at pfam.janelia.org/protein?id=Q94C80_ARATH. The *Arabidopsis* NLA gene having the sequence of SEQ ID NO. 8745 contains an SPX domain, an MFS 1 domain, and a RING domain, and includes a miR827 recognition site (target) sequence TGTTTGTTGATGGTCATCTAA (SEQ ID NO. 8746) located at nucleotide positions 135 through 155, which was validated as a target for the *Arabidopsis* miR827. The NLA encodes a C3HC4-type RING-finger ubiquitin ligase (AT1G02860.1, SEQ ID NO. 8747); mutating this gene disrupts the adaptability of *Arabidopsis* to nitrogen limitation.

Ten additional clones of the AtNLA gene were sequenced. Clones 1, 4, and 5 contained a partial AtNLA sequence (SEQ ID NO. 8748). Clone 2 contained an AtNLA sequence lacking the SPX domain (SEQ ID NO. 8749). Clone 3 contained an AtNLA sequence lacking the RING domain (SEQ ID NO. 8750). Clone 6 contained a genomic AtNLA fragment (SEQ ID NO. 8751) with a disrupted miR827 recognition site (target sequence) located at nucleotide positions 2142-2162. Clone 7 contained another AtNLA sequence (At1g63010, SEQ ID NO. 8752). Clone 8 contained another genomic AtNLA fragment (At1g63010, SEQ ID NO. 8753) with a disrupted miR827 recognition site (target sequence) located at nucleotide positions 2142-2162. Clone 9 contained another AtNLA sequence (At1g63010, SEQ ID NO. 8754) lacking the SPX domain. Clone 10 contained an AtNLA sequence (At1g63010, SEQ ID NO. 8755) lacking the MFS domain.

A number of "virtual" cDNAs were assembled from maize genomic and cDNA sequences, describing independent genes targeted by miRMON18. The first of these novel miRMON18 targets ("SPX_MFS_117961287", derived from BAC at GI:117961287) had the sequence of SEQ ID NO. 8756 and included an ATG start codon at nucleotide positions 326-328 and a TGA stop codon at nucleotide positions 2414-2416; the longest open reading frame (translation frame=2) encoded by SEQ ID NO. 8756 had the amino acid sequence of SEQ ID NO. 8757. An alternatively spliced version of this first novel miRMON18 target gene is SEQ ID NO. 8758 ("SPX_MFS_117961287_2"), which includes an ATG start codon at nucleotide positions 87-89 and a TGA stop codon at nucleotide positions 1137-1139; the longest open reading frame (translation frame=3) encoded by SEQ ID NO. 8758 had the amino acid sequence of SEQ ID NO. 8759.

The second of these novel miRMON18 targets had the sequence of SEQ ID NO. 8760 ("SPX_MFS2", derived from BAC at GI:118200525) and included an ATG start codon at nucleotide positions 201-203 and a TGA stop codon at nucleotide positions 2295-2297; the longest open reading frame (translation frame=3) encoded by SEQ ID NO. 8760 had the amino acid sequence of SEQ ID NO. 8761. An alternatively spliced version of this second novel miRMON18 target gene is SEQ ID NO. 8762 ("SPX_MFS_117961287_2"), which includes an ATG start codon at nucleotide positions 145-147 and a TGA stop codon at nucleotide positions 1189-1191; the longest open reading frame (translation frame=1) encoded by SEQ ID NO. 8762 had the amino acid sequence of SEQ ID NO. 8763.

A third novel miRMON18 target included stitched cDNA sequences from EST data and had the sequence of SEQ ID NO. 8764 (derived from BAC at GI: 126116193) and included two possible ATG start codons at nucleotide positions 217-219 and 1034-1036 and a TGA stop codon at nucleotide positions 2093-2095. Two proteins were predicted from the two possible open reading frames by homology; the first protein (predicted with a frame shift of 1) contained 625 amino acids and had the sequence of SEQ ID NO. 8765, and the second protein contained 353 amino acids and had the sequence of SEQ ID NO. 8766.

The peptides encoded by these novel maize miRMON18 target genes were aligned using ClustalW (version 1.82); the resulting multiple sequence alignment is depicted in FIG. 11, and shows the maize SPX domain (indicated by underlined sequence, where present) and the maize MFS domain (indicated by sequence in bold text).

Additional cloning work from BAC115312385 confirmed the sequence of the first miRMON18 target ("SPX_MFS_117961287", SEQ ID NO. 8756) and yielded the genomic SPX_MFS2 sequence SEQ ID NO. 8767 in which was further identified leader sequence (indicated by italicized text), 5' introns (indicated by underlined text), exons (indicated by upper-case text), and the miRMON18 recognition site (located at nucleotides 2628-2648 of SEQ ID NO. 8767 and indicated by bold upper-case text):

```
                                                                        (SEQ ID NO. 8767)
gttacaaggcaatattttgtagaataaaatcttaaaggaaactcaactccacgaattggtcacttgcattaaatcatattgtgggtctcttttagttgca tcttaagatggcggcaacaagatttcaagcacttttatctagtgaccgcaatgcactggagataaataagaatccaaatattatttttgataaccttga cactatttaaatcttcttataagtgacgaagtagtttgatcaacaataaaaacgtatagatttcaacatttttgcgattgtaggatatatgttagcaaata ttttaagcaaaataatattttatctataatctctatatggattattctagattttggggaccctatataaaattagctatgagtattaacacttgataatct tgcctagaatgtcttcgatttctggtctaccactacacctaactgagtttaaccctgcaataaataattaatctcgtgaaatcatttggagattttgactca atttaaataggtagctactgtgtagttaggttgaaccaggacaccaggtgtaacacgagtcacatatgcatgcatgtgtattgactcaatcggccgg cgcacgctatgatggtgctagaaaatgttttatacggctgtgaaaggtgtaacctgtgctgtgtcgcaaacaatatattgtttaacttttgtttggccttg aactcctgggggcaaacataagatataaaagatcgatatgcctttcatgattccgtcataatctcgaccgtaattaaggcccgctctatataaaccttt aaagcaaattgttagtcatataataatttattagttggattgatgcaacaaataacaactatttatttaagattaactaacttctcagttaaatttagtcact aactattagttttagaggtttggaacatgttataagaacctaaccggtctctcaacgttacaaaagctatcatatttgaaccccgtcatcggagcgc acacgttttattttgttctgttcatgtctatgctgagatactaaaattttgtgcacaagactacaaggacgagagcacctaatgaggtattaatcggttat tcaaattccgtaagagttgggggtattggaagagattattagaattttttgacctgttaagatttaaacccacttaatttcttgcaacacatactgcaggt cctcagatagcgaggcgcagtcgcgcagaccgcagagcgccgaatcgtgagaaggatcagaagtgcttgttacttccgtacgggttagagcat ctccaacaacgtgacctataaaaatgccctataatttgaaaatgagtatatttatagaatttagggcaccaacaaaacaccccgctccaacagtaa agccccaaatctagattataggggcagcccactacggtgtagtatatttgagtcacttgagagggtgccctatagtttttttgacaaaattttatgaaatg gagcactgttggagtagttttcctgtgtagagccctatatttcaatttgaggcactagtttgaggcattgttggagatgctcttacaaatacacggaa catatttgggttcagcaacagggacggacggacggcgcgccgtgttctacagacttgccgtcgctgcttctgcatctgttcgaaaaccgtaaccc ccgtgcaccgctggtcagtagtcgtcgtttcgtttcgtttcgtttcgtcgcggcgatcttcgaaccgatgaagcgtggcacttggctggttggtggt ggtacgccgggccagaaggtgacctgcctcgatccgaataccatgcatcgatctgtgcacgtgcctgttctcttcctactccgattaccgatagtc cgggccgggaaaaagagcgcgaagccagatctgaccactagggtctgtttggttggtttctctcgccaacctggctgtgtgagccaggatcac tggagcctggctctgaagatacgaccaatctgctcgtatctggtgagcctggcccaaggtgctttaaggatcgtgcgagtctggattcaaatctac atgcagacaaccaaacacagagctcgcacgcgcatagcttggctcatagcaaccaaacagcagctacccgcatcccgcgacgcaagcacgc gcagatgcaggcaaccaaacagacccccaggtgatccaggtcgtcgaatgttccacgcgaaccgcagccgcgagtgccgtctccggctccgc cacaggtagagctcagagcagaaaatgctccagccacctgtctctcttcttcctccttcctgccctgcacgcggctataagtacccaccgccatct cactttgcccagcagcacggcagtagctgcgccattgcacgcctccggccggcggctgcttgtcttgctgcttctgccgcacatccgtgatccgt
```

-continued acgtcgtcacctcaccactcacgcacaagcacaaagagcgttaatttcttgctggagattctattctatttctatggcgtgtccctgatcgaatcctaa
atcctaaacctctgtggtgcactgcagggcagaaggtgcttcgttcgttgcaggcctggcgccacgccgtaccgtgcaagcg**CGTTTGC
TGATGTTCATCTAA***ttactgtataataatatctccgggcgaaagagctagcaatcgtcggcggggaggagggctcgattg*
*ctgctcaa*<u>ggtgagttgtaattccttggctctggatttccctatctgttggctgttcatggatcatccaatggatggatggcgctccctgttctctacac</u>
<u>ctgcgtgctcttcttccctcgcctcgccggggtcttgtgtcagttactgtatctccctgttgattttaaaatctaagaagcaacaacaaaagatgattca</u>
<u>aaaaaatattcaaatttgaaggaccacaatgcgtgtgctactgctagctatgctaccattagagcatgccttcactgcattcttcttcttttgttacgagt</u>
<u>gcttaatctcatggctcgctcccttaattcttgctaccattagagcatcttcaatactttctaaaaaaaaccacttgacaaactaatgaaatcagttggta</u>
<u>aactaataagtttcacgagtgactaaaaaaagataggagctagcttctagtcctagataatgctcttatgagctttccttgtccagttgtcccaactc</u>
<u>ccaacgaacaaaaaaaaaaggtaagaaaacacatttggcctttcttcttttttcttttcaactcaaaacgatcgctcagttacaaaaaaaaagaga</u>
<u>gcttgcaattgcgagcgagataccaccgttacagggaaaaaaagacaagttgttcaagttctctactagcttcctagcgcttccgtgtcgttctag</u>
<u>atgagcttctctagcaaaggacaataatttggttgccacgtcagatgtcgactcagtgtcatttgctaccagctggcttatcaacttgggagattattg</u>
<u>ctcgcacctggacccggtgtccagtcaattattaatgatgttgatccatcttcgtatttttatcttggcaagaaactgttagtattaagttactgtcacctt</u>
<u>tggaagctgaatctcccctcgaagatatcagtatgggcatatagccatccgttcttatacacagctatttacgtctattttacaattttatatcttcgtctt</u>
<u>cctcttttacacctacattcgaaccatctatttagagctttcaatgtgcaattcgtctttggtcattgtcaacatgaaccgtccagtgataatgctttgatg</u>
<u>ctgactaagaagtacggtctccggttcttaaatatttattgtctaatatttattttaaaataaaacatgataaataaaaagaacggagtgagtagaat</u>
<u>acattgtgagctgttgttggtttgttgcacattctttacttgtttttttttacgaacatttgttgcaagcatcagcaaagccgtataaacttgtgcagctcta</u>
<u>gatagcgattttttttaaacaaaaccttaatattagattttggagcattgatttagaaagctgagcaactccaatgggagaggtgttttattttctcgtccat</u>
<u>ccacatccgccgttggcccgttgtttcttttctacccgcgcctgtgggcccaaccgtccggtcaaccgaccagcgtttcctgttccaccgtacgtc</u>
<u>gtcgt</u>*tctcgttcggtcgtttttcgttcccctacctccagtccagtcccaggtccgagccggaccttgatcgccgcgtgcctcggcgcaaggaa
tgggccttcggtcttaccccttgcacgcgccgccggcatcaggagacgtctctgtgtgcttcgccgtgccttcagccgtagccggcgccgcat
cagcgtgctccagagaggaccgcagcttccagcacgtgtccctgacaccgccccacactggattgggaagggcgctgacccacgcac*
<u>ctgcccgctggccagtgttggaaggtttgggaaatgagatgttgattttaagctgacttttgagggttttagcttacagcttttaaatcaatcttcgac</u>
<u>caacggtttgaaattccgtgtttagagttgaattactcgattcagaagtttaagtttctctaatttaagctaaagggagaagagatggagcgcctggct</u>
<u>tgagttggccgcacgcagctgggaagaaggatctgaaaacactgtcgtccatgtattgattcacttaaacatttgtccgtatctattatttttaatttttttt</u>
<u>ataatctacggtcacaagatatgcctgtgttgtttgtgaatagaaaacactgaacaatgattgtgagtcaacagctatcattatttgtgtttggttgtgc</u>
<u>gagggtatactaatgtctaatgattggctaaaccttagtcttacatcgctgtctttccttgcgctgtagggcaaggcaaccaccaattgggtaaaagc</u>
<u>atataagcaggcttaccgatcaataaatataaaaaagggtagctttcaagaagtctgcttatgtaataccattattttccttttttttacctcgaaggagt</u>
<u>gataatcaccaaaatagcattatattgtcatcatacggctgcactatctttttcttctgtaacatgccgtctaattattatcttc</u>*agtttcagactcagttat
ttgaaacatcaag*ATGGTTAATTTCGAAAGAAATTGATGGCTGATCAAGTGGACGAATGGAA
AGGGtatgacttttcttttggtacttatgaaatcatctattttatcttatcagggcaaatgttctttattttcatatatgcccactccactagtccactag
gatacattagaacaccataccgtagttatcaccatatcacagtccttactatcattatctggttaattttataattaaattaaacaaaatctagcagttatc
gaattgataggttgcactacaataatgaagtcacttcccgctaatgcaagctaatgtcactttgtttaacggtttatcagaaatcttatcagcttttggt
cttttccatttctagatactacatcaattacaagaaatcttatcagcttttggtcttcatttctAGATACTACATCAATTACAAGC
TGATGAAGAAAATGTTAAAGCAATATGTCCAACAAACCCAACATGATGAGAAAGATCG
CGAACAAGTTCTTAAAGACTTTTCAAGGTTTCTTGATGAccaggtatacaaagaaagatttcccttgaaatg
atcataatatatgattttgagcatcatctatcctgtcagtagtcacttgtatccttgtaaggaacagaacagtgtcatgcgacaagcttaatagtcttagt
gaattgggatcattttttcttagttgtgagctaaaatacacatgtatttcttcgttCCAGATTGAAAGGATTGTGCTTTTCTG
CTACAACAACAAGGCCATCTTGCCAGTAGGATTGAGAAATTGGCAGAAAAACGCACTG
CTCTTCTGGAAGAGTATGACATATCACAAGTTTATCAGCTGCATGATGCATACAGGGA
AGTCGGGCTTGATCTCATAAAGCTTCTCCGCTTTGTTGATGTGAATGCTACTGGTATAC
GCAAGATACTAAAGAAATTTGATAAACGCTTTGGCTACAAGTTCACTGATTATTATGTC

```
ACCACTCGTGCAAATCATCCTTATTCTCAGCTTCAGCAAGTATTTAAGCAAGTGGtaattttc atgcattttgcattttcctttcttgatgtgtgaagtaattcccagtacctattatttatcatggactcatacggatgcaggGAATTGTAGCTG

TTGTAGGTGCATTATCGCGCAACCTTGAATATCTGCAGCATCATGAAGGAAGCTTTGTA

TCCATCTATGATCGTCCAGCAGTTACCTTGAaggtattctattttcactattccattctcatttcagaaattctgctattga atttataaatgaaaaccttgaaaggtgctcttcttacctcggaactgcatcaattatatttccacatgaagtagggtgtgacatgacactttttttgttgtt atattcAGGACCCTATTATAGACCAAGTAAACCATGCAGTACAGAAACTCACGCATGCCAC

GAATTTTATGCAATTCTTGGGACAGCACGCGCTTATTGTCCAGGAAGATGCAGAAAGC

GAGTCGGAGGATCTTGTTGGTGATCAGAGCTACCATTTCATGTCCCTGGTGCTTAATCT

AGTGAACACATTCCTTTACATGGTGAATACATATATCATTGTGCCGACTGCAGATGACT

ATGCAGTAAGCCTTGGGGCTGCTGCAACTGTATGTGGTATAATTATTGGATCGATGGCA

GTCGCCCAAGTATTCTCCTCAGTCTACTTCAGTGCCTGGTCAAATAAGTCCTACTTCAA

ACCTCTTGTGTTCAGTAGCATTATGCTGTTTCTTGGAAACCTACTGTATGCATTGGCATA

TGATCTGAATTCACTAATAGTTCTCCTGACTGGACGACTGCTATGTGGGTatgcaattttctcaatt cactctatctcacttgatttacgttccacttttgtatgctagcattgatctgggtgaaaattactagtatgacaaatgcaggttgaggatccttaagctga gggcaatattctagaatatttatattgctgaatagaaaacaaaatggaaactgtatatcttacaaggagataaaggattttaaatctcgagactggcat taaaatatatgcttttctatttcttttatagaacttaactagttatccctacctcccttgggctagtaatttgtctatattgtttaaggttcttgatttt ctgacggtgcatctgtgatcgagctgccagcatgtaatgtgcaggtTAGGTTCTGCAAGAGCAGTGAACCGTCGCTATAT

CAGTGACTGTGTGCCTCTCAAGATGAGGCTACAAGCCTCTGCCGGGTTCGTTAGTGCTA

GCGCTCTTGGCATGGCATGTGGCCCTGCTCTTGCTGGTTTTCTCCAGATTAAATTCAAG

ATATACTCGCTCAGTTTTAATCAGAGCACATTGCCTGGATGGGTCATGTGCATTTCTTG

GCTTATTTACTTATTGTGGTTGTGGCTTACATTCAAGGAACCAGAACACTTCACTAAAA

CTCTGGTCAATGAACAGCCGTCAGAATCTGGtaagctaacaatacactgaaatggcaacatgttttgtttgaattcat gaatatgctcgaatcaaaccttattgtacaatcaggatgtgtatgcttatcattcttaggaacttttctgagatgtttatttccttattatgaaaataggCC

GCCAAGGAAATTCTAACTTGGAGGCAGGTCTAGCTGAACCATTGCTTCAAGGTATAGA

ACGAAGGCAGGATGAGAACTCAGAAGTTAATGATGATACTGAAGTAGAGTCAGAAAG

CTCTCATGAACCAGCAACATCAATTGCTTCAGCATACAGATTGCTAACTCCATCTGTGA

AGGtttccttcccccctcccttcccaattatcgattttctttgtcttgttcttggttcaaacgtttgaaagaaagaagctcacaatctacataggggttcttt tgtaaataaagttagataaattaactatataatataataaaactgcatctttaaatagtaatgggtaaatacattccagttactagtaggtacatctgcat gtcatacaagcaaacataacggacacgccatgtaaaagaaactaggccaacctaggagaaactaggttgcatttattattatattattattaagatg aaaataggcacccaaatttaccttgacaaggacttgaacctaggtggtctgggtttacgagcacacccttgaccaagtgagctagctcagttccct tgacacaccagccagatgaaaagttgcatgtgcagctaccccttttttccacgcccttttcatcttccaatctttgttggagctaccttctcatgtattcat atctttaaaaaatggttgtttgtcAGGCCCAGCTACTGATATACTTCATGCTCAAGTACGCAATGGAAA

TACTACTATCAGAATCGAGCGTTGTCACCACATACTATTTTAGCTGGTCTACAAGTGCT

GTGGCTATCTTTCTAGCGATTCTTGGATTAACGGTTCTTCCAGTAAATGCCATTGTTGGA

AGCTACGTTACAAATTTATTCGAGGATAGGtaagctttgtactcttacaaaacatactacatgaaacttttatattctcta gacattgttttctcttaaactgagacatgattcacaaaataagaacttgctctatcatttgcaggCAAATTTTGTTGGCATCTGA

AGTCATGGTTCTCATCGGTATAATCATGAGCTTTTGTTTCACACCTCACTACTCCATCCC

GCAATATGTTCTTTCAGCTTTCATCACATTTGTATTTGCTGAGGTGCTTGAaggtatgtatgtttat atacattaatggtttgagacagcgaaacctaaatcaatcatacgctgctgatttatcagccactcaacttctaacctcgagctatgcAGGAGT

GAATCTGTCCTTGCTCTCACGAGTAATGTCATCGAGGCTTTCCCGAGGGACCTACAATG
```

-continued

```
GTGGACTCCTTTCGACAGAGGCCGGGACGTTGGCCCGTGTAGTTGCAGATGCCACGAT

TACTGCAGCCGGTTATCTCGGCACGGACCTCCTTCTGAATGTCACTCTTCTCCCATCCCT

TGTGATTTGCATAGTCTCCATCGCAGCAGCACTCTACACTTACAACAATCTCTATTGAag ctattgttgctgtacaagtgtacaacaatgttcctaagctaaaatgttcctgcccacaacgggtttgtatatctgttcaagcatggtttgtaaacattttgat caagtttgtatgcaaaatttcttgtatttagtgcatttatgtaaagattcatcctgtaaagaattataaactatgagacgctattgccatttatgatcattt atgtttatcttttttagccttatgttatttgaatttgtctaatcaatgccatcttccatcacgagcacatcattgacatattactgatggatagacctttttg ggacgtgagatgctaaaggcacaacctatatagctgaaaatttctaacatatttatcaataataccaagatgcctttgttgtttatcaattgcacattattt caacgtaaatgcaattttgttaaatatgtcatggtgtcgagcctactgcttacccagcatgttgaattgctgccttaagcagaaacatcgaaaaacctg cgtagattccacgatccaacaatcctctccgttcattttttagttccatatgaaaggaccgattacgtctgaaagaagagtttcattagacaatctattt cttttaactaatgcctctagttttcaaaacctatgcaataaataggtgtaactatagttttgactaagggttgtaatctctttgtaaaatatttatgcaatc tcgatttcaaatctatccactagcctaacaactaataagataaaacatcaaccaagatacataatataaatacgggagcttaaatacgatatacatat aaactcttattgatgactccattgtttttatcgagataccaagaaagacgcaagtttctccctagtcctcattggagcccagtccgcgcgagtaccaa gctctcggtcaggtaacattgtggatagcctaggttttttgccacacacaagtgggctttagtgtagcctcttctaaatgctctctatcaaaggtggt ccaggaaaagattcaaaatggggccctagcagtagtagtattactactaacaacaataatgataaataagtaaatgctcaatgtgcataaaattgat ctaagaagtacttgtaaactcatgtaatgttgtaaacttatttgcttatttctttatgttcttttctcacatccgaacagattccttctagaggacatgattgt aagttaaaaaataaaatagaacactaattaaatcaaagctatcgctacttgctgagttacaaaattattaaatctatttataaaatactaccaattatgtc gtacttccaaattatcaaacaattgaatagattacaaaataatatttaatcaatagattacaaaatacctactacaaattcacaaaacaatttgtctagttt agtaattattcaaactatagttgtacatagtaattaatttggctttggtttagaccctcggccttggtgaacgacgaacaacgaggtatcctatgtgtag tcatgtatgatgcgtctaggatgtagatgcagtggccagtggcaatcctcagtcttcacgaatcaggatgaacatatggagggtggggcctcgcg gaatagggggactagggta.
```

TIGR transcript databases were searched for SPX:MFS domain coding sequences for SPX genes. Identification of such genes supports the existence of a conserved regulatory pathway in higher plants. Putative miRMON18 target sites were found by searching for a conserved sequence complementary to miRMON18 in the 5' untranslated region upstream of the start codon. A putative mirMON18 target (TA40434_29760) was identified in grape (*Vitis vinifera*) with the sequence of SEQ ID NO. 8768, with the miRMON18 recognition site located at nucleotides 323-343 of SEQ ID NO. 8768. Similarly, a miRMON18 target (TA5852_4236) was identified in lettuce (*Lactuca sativa*) as having the sequence, SEQ ID NO. 8769, with the miRMON18 recognition site located at nucleotides 64-84 of SEQ ID NO. 8769.

Figure 12:
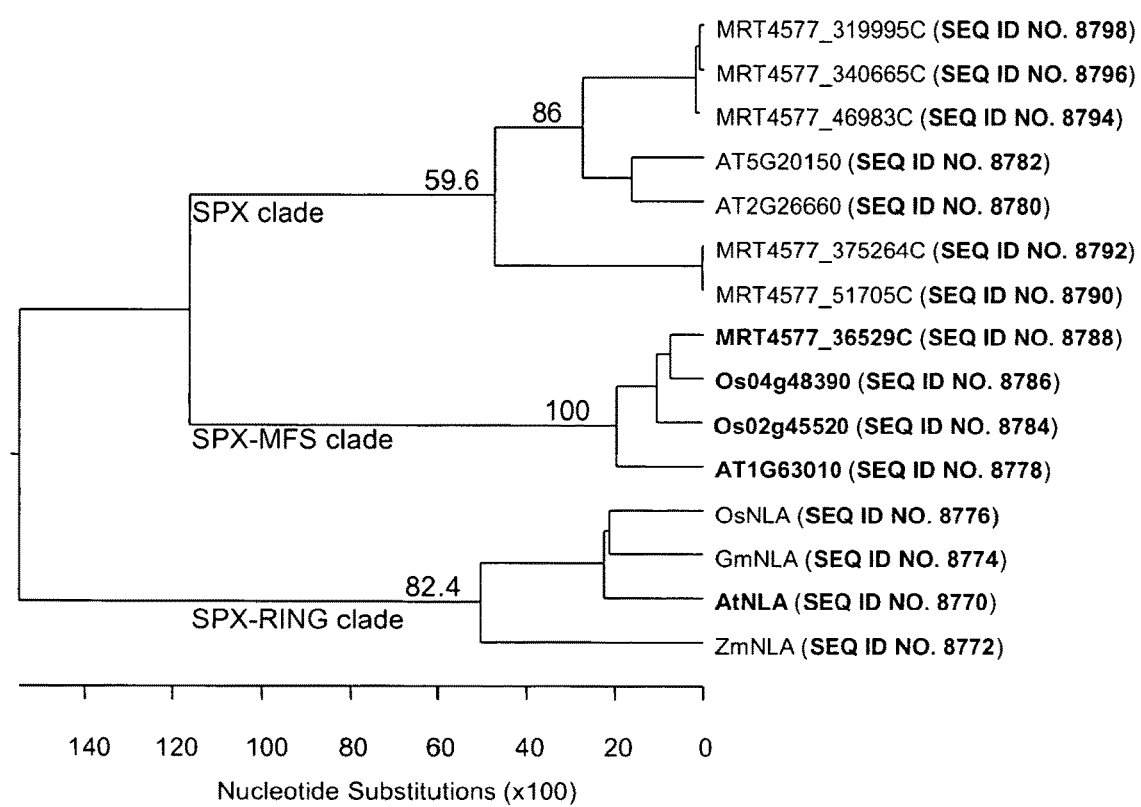
FIG. 12 depicts a phylogenetic tree constructed for the identified SPX genes, as described in Example 7; genes containing a predicted miRMON18 recognition site (in genes from species other than *Arabidopsis thaliana*) or a predicted miR827 recognition site (in genes from *Arabidopsis thaliana*) that has been experimentally validated are indicated in bold text.

Orthologous SPX-domain-containing genes including NLA-like genes were identified in various species including maize, rice, and soybean. Where sequence was available, putative miRMON18 or miR827 target sequences (recognition sites) were identified in the 5'UTR. FIG. 12 depicts the phylogenetic tree constructed for the identified SPX genes using amino acid sequences aligned by ClustalW, with bootstrap values determined using 10000 iterations; genes containing a predicted miRMON18 recognition site (in genes from species other than *Arabidopsis thaliana*) or a predicted miR827 recognition site (in genes from *Arabidopsis thaliana*) that has been experimentally validated are indicated in bold text. In addition to the *Arabidopsis thaliana* NLA gene AtNLA containing the SPX and RING domains (MRT3702_101115C, At1g02860, SEQ ID NO. 8770, which includes a miR827 recognition site at nucleotides 135-155, and encodes the protein with the sequence of SEQ ID NO. 8771), the genes included in the phylogenic tree are the maize NLA-like gene ZmNLA (SEQ ID NO. 8772, encoding the protein with the sequence of SEQ ID NO. 8773), the soybean NLA-like gene GmNLA (SEQ ID NO. 8774, encoding the protein with the sequence of SEQ ID NO. 8775), the rice NLA-like gene OsNLA (SEQ ID NO. 8776, encoding the protein with the sequence of SEQ ID NO. 8777); the *Arabidopsis* sequences At1g63010 (SEQ ID NO. 8778, which includes a miR827 recognition site at nucleotides 153-173, and encodes the protein with the sequence of SEQ ID NO. 8779), AT2g26660 (SEQ ID NO. 8780, encoding the protein with the sequence of SEQ ID NO. 8781), and AT5g20150 (SEQ ID NO. 8782, encoding the protein with the sequence of SEQ ID NO. 8783); the rice sequences Os02g45520 (SEQ ID NO. 8784, which includes a miRMON18 recognition site at nucleotides 395-415, and encodes the protein with the sequence of SEQ ID NO. 8785) and Os04g48390 (SEQ ID NO. 8786, which includes a miRMON18 recognition site at nucleotides 334-354, and encodes the protein with the sequence of SEQ ID NO. 8787); and the maize sequences MRT4577_36529C (SEQ ID NO. 8788, which includes a miRMON18 recognition site at nucleotides 1660-1680, and encodes the protein with the sequence of SEQ ID NO. 8789), MRT4577_51705C (SEQ ID NO. 8790, encoding the protein with the sequence of SEQ ID NO. 8791), MRT4577_375264C (SEQ ID NO. 8792, encoding the protein with the sequence of SEQ ID NO. 8793), MRT4577_46983C (SEQ ID NO. 8794, encoding the protein with the sequence of SEQ ID NO. 8795), MRT4577_340665C (SEQ ID NO. 8796, encoding the protein with the sequence of SEQ ID NO. 8797), and MRT4577_319995C (SEQ ID NO. 8798, encoding the protein with the sequence of SEQ ID NO. 8799).

Several kilobases of sequence were available upstream of the maize and rice NLA-like coding sequence, within which a miRMON18 target site was not identified from preliminary sequencing efforts. Based on expression profiling data it appears that ZmNLA (SEQ ID NO. 8772) RNA level does not respond to nitrogen availability. In contrast, the SPX-MFS domain clade (SEQ ID NO. 8788, SEQ ID NO. 8786, SEQ ID NO. 8784, and SEQ ID NO. 8778) shown in FIG. 12 is suppressed under sufficient nitrogen in maize and Arabidopsis and is predicted to be regulated by miRMON18; sequences in this clade contain an experimentally validated miRMON18 (or miR827) recognition site. The SPX clade shown at the top of the tree (SEQ ID NO. 8798, SEQ ID NO. 8796, SEQ ID NO. 8794, SEQ ID NO. 8782, SEQ ID NO. 8780, SEQ ID NO. 8792, and SEQ ID NO. 8790) (FIG. 12) contains only an identifiable SPX domain, is suppressed by limiting nitrogen, and is also predicted to be regulated by miRMON18. In maize, the TxP data corresponding to genes in clade 1 (SEQ ID NO. 8798, SEQ ID NO. 8796, SEQ ID NO. 8794, SEQ ID NO. 8792, and SEQ ID NO. 8780) were correlated to miRMON18 precursor expression; expression of both the miRMON18 precursor and of clade 1 genes was upregulated under conditions of nitrogen sufficiency. Genes in the SPX-MFS clade 2 (SEQ ID NO. 8788, SEQ ID NO. 8786, SEQ ID NO. 8784, and SEQ ID NO. 8778) are directly suppressed by miRMON18, whereas clade 1 genes lack a direct target, suggesting that miRMON18 may indirectly regulate clade 1 gene expression through suppression of clade 2 genes.

Example 8

This example describes identification of a crop plant miRNA (miRMON18) promoter having an expression pattern characterized by strong expression under nitrogen-sufficient conditions and suppression under nitrogen-deficient conditions, or strong expression under phosphate-sufficient conditions and suppression under phosphate-deficient conditions Further characterization of the maize miRMON18 gene involved BLAST matching of a miRMON18 precursor (SEQ ID NO. 3936) to cDNA libraries and microarray elements, and inverse PCR cloning of a miRMON18 genomic sequence (SEQ ID NO. 8800) from maize (Zea mays var. LH244) using inverse PCR primers based on a cDNA sequence (SEQ ID NO. 8801) from clone LIB5025-018-A1-XP1-B6. This miRMON18 genomic sequence (SEQ ID NO. 8800) had the annotated sequence depicted in FIG. 13, where the miRMON18 transcript is given in upper-case text at nucleotides 2173-2788 of SEQ ID NO. 8800. This genomic sequence also included a miRMON18 promoter element in lower-case text at nucleotides 211-2172 of SEQ ID NO. 8800, a leader element in lower-case text at nucleotides 2173-2308 of SEQ ID NO. 8800, a canonical TATA box (ending 25 nucleotides upstream of the transcription start site) in underlined lower-case text at nucleotides 2144-2147 of SEQ ID NO. 8800, the mature miRMON18 as underlined upper-case text at nucleotides 2419-2439 of SEQ ID NO. 8800, and the miRMON18* as underlined upper-case text at nucleotides 2322-2341 of SEQ ID NO. 8800.

To verify the expression pattern of the miRMON18 promoter, two recombinant DNA constructs (SEQ ID NO. 8802 and SEQ ID NO. 8803) were constructed in a binary vector that included a rice actin 1 promoter driving neomycin phosphotransferase II (nptII) as a selectable marker. The construct (SEQ ID NO. 8802) in plasmid pMON111971 included a miRMON18 promoter (SEQ ID NO. 8804) and a miRMON18 leader sequence (SEQ ID NO. 8805) driving expression of a GUS gene (SEQ ID NO. 8806) followed by a NOS terminator sequence (SEQ ID NO. 8807). The construct (SEQ ID NO. 8803) in plasmid pMON111967 contained a DnaK intron (SEQ ID NO. 8808) and also included a miRMON18 promoter (SEQ ID NO. 8804), a miRMON18 leader sequence (SEQ ID NO. 8805), a GUS gene (SEQ ID NO. 8806) followed by a NOS terminator sequence (SEQ ID NO. 8807). The vectors are transformed into maize using Agrobacterium-mediated transformation and antibiotic selection using standard techniques as described under the heading "Making and Using Non-natural Transgenic Plant Cells and Non-natural Transgenic Plants". Strong miRMON18-promoter-driven expression of GUS is observed in transformed maize leaves under nitrogen-sufficient and phosphate-sufficient conditions. GUS expression is suppressed in the transformed maize leaves under nitrogen-deficient or phosphate-deficient conditions.

Alternative miRMON18 promoter sequence useful for driving expression of a transgene with the expression pattern of the native miRMON18 gene (i.e., strong expression under nitrogen-sufficient conditions and suppression under nitrogen-deficient conditions, or strong expression under phosphate-sufficient conditions and suppression under phosphate-deficient conditions) include the promoter having the sequence of nucleotides 211-2172 of SEQ ID NO. 8800; a fragment of at least about 50, at least about 100, at least about 150, at least about 200, at least about 300, at least about 400, or at least 500 contiguous nucleotides having at least 85%, at least 90%, at least 95%, or at least 98% identity to nucleotides 211-2172 of SEQ ID NO. 8800, wherein the fragment has promoter activity in at least one plant tissue that is characterized by strong expression under nitrogen-sufficient conditions and suppression under nitrogen-deficient conditions or strong expression under phosphate-sufficient conditions and suppression under phosphate-deficient conditions; and a fragment of at least about 50, at least about 100, at least about 150, at least about 200, at least about 300, at least about 400, or at least 500 contiguous nucleotides having at least 85%, at least 90%, at least 95%, or at least 98% identity to SEQ ID NO. 8804, wherein the fragment has promoter activity in at least one plant tissue that is characterized by strong expression under nitrogen-sufficient conditions and suppression under nitrogen-deficient conditions or strong expression under phosphate-sufficient conditions and suppression under phosphate-deficient conditions. Identification of alternative promoter sequences is confirmed by routine techniques, such as verification of a TATA box within the promoter sequence and validation of promoter activity in at least one plant tissue (e.g., by testing a recombinant DNA construct including the promoter driving expression of a reporter gene such as GUS or luciferase in either transient expression experiments or in stably transformed plants).

Example 9

This example describes identification of recognition sites of a crop plant miRNA (miRMON18) having an expression pattern characterized by strong expression under nitrogen-sufficient conditions and suppression under nitrogen-deficient conditions, or strong expression under phosphate-sufficient conditions and suppression under phosphate-deficient conditions. Also disclosed are methods of use of the miRNA, the miRNA promoter, and a miRNA recognition site. Non-limiting examples including a method of providing a non-natural transgenic crop plant having improved yield under nitrogen or phosphate deficiency by expressing in the transgenic crop plant a recombinant DNA construct including a miRMON18-unresponsive transgene, and a method of providing a non-natural transgenic crop plant having improved yield under nitrogen or phosphate deficiency by expressing in the transgenic crop plant a recombinant DNA construct including a miRMON18 recognition site that has been added to the sequence of a normally miRMON18-unresponsive gene.

Figure 14:
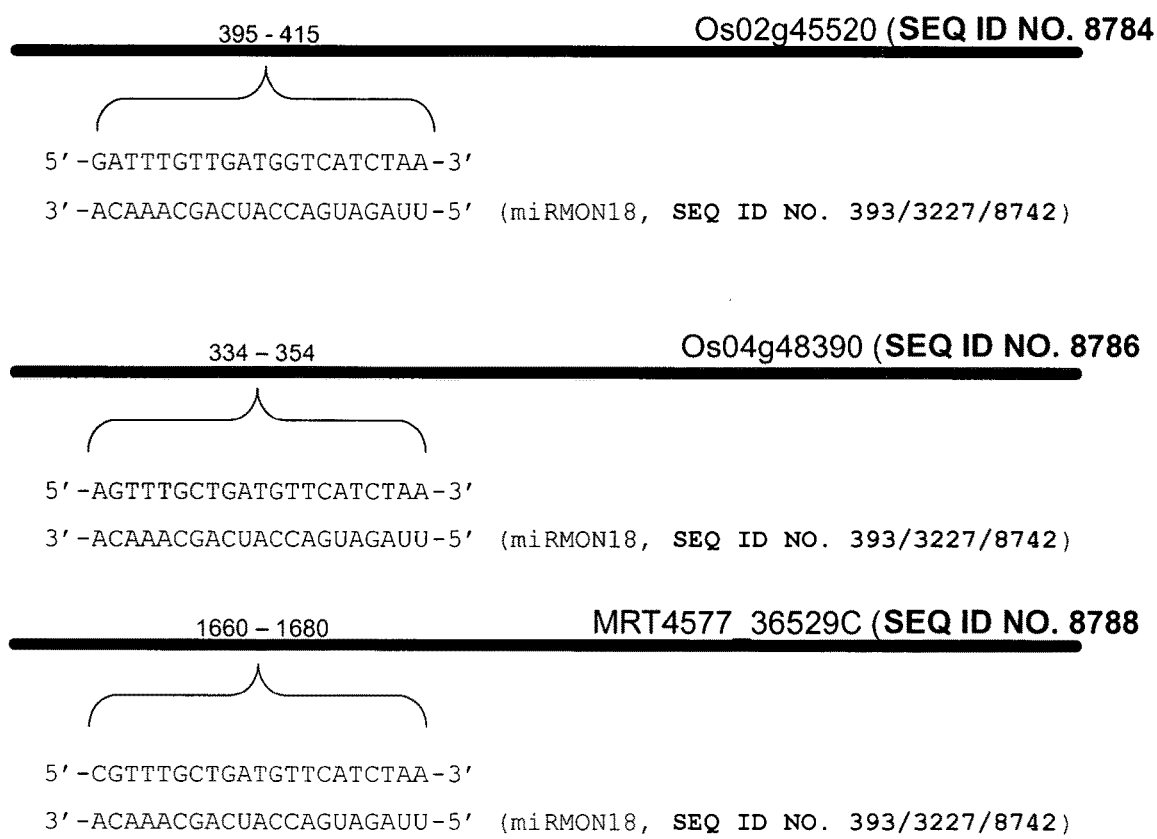
FIG. 14 depicts the predicted cleavage by miRMON18 of the rice sequences Os02g45520 (SEQ ID NO. 8784) and Os04g48390 (SEQ ID NO. 8786) and the maize sequence MRT4577_36529C (SEQ ID NO. 8788), as described in Example 9.

Prediction of a recognition site is achieved using methods known in the art, such as sequence complementarity rules as described by Zhang (2005) *Nucleic Acids Res.,* 33:W701-704 and by Rhoades et al. (2002) *Cell,* 110:513-520. One non-limiting method to experimentally validate predicted miRNA recognition sites is the technique known as RNA ligase-mediated rapid amplification of cDNA 5' ends ("5' RLM-RACE"), which identifies miRNA cleavage patterns; see, for example, Kasschau et al. (2003) *Dev. Cell,* 4:205-217, and Llave et al. (2002) *Science,* 297:2053-2056. This approach relies on ligation of an RNA adapter molecule to the 5' end of the cleavage site and is dependent on the 5' phosphate left by RNase III enzymes including Ago1. The resulting PCR products are sequenced and the relative number of clones which align to the predicted miRNA cleavage site between nucleotides 10 and 11 relative to the miRNA 5' end provide an estimate of miRNA activity. FIG. 14 depicts the predicted cleavage by miRMON18 of the rice sequences Os02g45520 (SEQ ID NO. 8784) and Os04g48390 (SEQ ID NO. 8786) and the maize sequence MRT4577_36529C (SEQ ID NO. 8788). Results from 5' RLM-RACE assays were used to confirm cleavage of the predicted miRMON18 recognition sites (target sites) in the rice sequences Os02g45520 (SEQ ID NO. 8784) and Os04g48390 (SEQ ID NO. 8786), for which 3 of 24 clones and 13 of 16 clones, respectively, were sequenced and found to have the predicted cleavage pattern (between nucleotides 10 and 11 relative to the miRMON18 5' end). 5'-RACE experiments also partially validated the miRMON18 recognition site in the maize SPX_MFS2 sequence SEQ ID NO. 8767 (data not shown).

Another non-limiting method to experimentally validate predicted miRNA recognition sites is to examine expression levels of the putative target, e.g., by transcription profiling experiments. The expression level of a true target of a miRNA would be predicted to be high when the miRNA is not expressed, and low when the miRNA is expressed. Thus, a miRMON18 target would be predicted to have higher expression when miRMON18 is not expressed (i.e., under nitrogen-deficient or phosphate-deficient conditions), and low expression when miRMON18 is expressed (i.e., under nitrogen-sufficient and phosphate-sufficient conditions). FIG. 15B depicts expression profiles of the maize sequence MRT4577_36529C (SEQ ID NO. 8788), which contains a predicted miRMON18 recognition site. MRT4577_36529C (SEQ ID NO. 8788) was unaffected by water availability or temperature (with no large differences in transcript levels seen between water sufficient or drought conditions or between cold or normal temperatures; data not shown), but exhibited higher expression levels under nitrogen-deficient conditions than under nitrogen-sufficient conditions, i.e., an expression pattern opposite to that of miRMON18 as shown in FIG. 15A (also see FIG. 9 and FIG. 10), indicating that MRT4577_36529C (SEQ ID NO. 8788) is indeed regulated by miRMON18.

These data verify that miRMON18 regulates conserved SPX-domain-containing genes. Expression of miRMON18 is suppressed during nitrogen deficiency or phosphate-deficiency, allowing the endogenous miRMON18-regulated genes to be expressed under these conditions. Manipulating the expression of either the mature miRMON18 miRNA or of miRMON18 targets (genes including at least on miRMON18 recognition site) is useful in altering a plant's response to nitrogen deficiency or phosphate deficiency.

One aspect of this invention includes a method of providing a non-natural transgenic crop plant having improved yield under nitrogen or phosphate deficiency by expressing in the transgenic crop plant a miRMON18-unresponsive transgene. One embodiment is expressing in a non-natural transgenic crop plant a recombinant DNA construct comprising a synthetic miRMON18-unresponsive transgene sequence, wherein the synthetic miRMON18-unresponsive transgene sequence is: (a) derived from a natively miRMON18-responsive sequence by deletion or modification of all native miRMON18 miRNA recognition sites within the natively miRMON18-responsive sequence (that is to say, eliminating or changing nucleotides of the natively miRMON18-responsive sequence that are recognized by a mature miRMON18 miRNA having the sequence of SEQ ID NO. 393, SEQ ID NO. 3227, or SEQ ID NO. 8742 or by a mature miRMON18 miRNA derived from a miRMON18 precursor sequence selected from SEQ ID NO. 1763, SEQ ID NO. 3936, and SEQ ID NO. 8800), and (b) is not recognized by a mature miRMON18 miRNA. In a non-limiting example, the miRMON18 recognition site in any of the conserved SPX-domain-containing genes depicted in FIG. 12 is deleted or modified such that the modified SPX gene is not recognized and bound by an endogenous mature miRMON18 (SEQ ID NO. 393, SEQ ID NO. 3227, or SEQ ID NO. 8742) and is thereby decoupled from miRMON18 regulation and thus from the influence of nitrogen or phosphate deficiency. In a non-limiting specific example, the maize gene MRT4577_36529C (SEQ ID NO. 8788) can be decoupled from miRMON18 regulation and thus from the influence of nitrogen or phosphate deficiency by expression of a modified MRT4577_36529C gene wherein the miRMON18 recognition site in its 5' untranslated region (nucleotides 1660-1680 of SEQ ID NO. 8788) has been deleted or modified such that the modified MRT4577_36529C gene is not recognized and bound by a mature miRMON18 (SEQ ID NO. 393, SEQ ID NO. 3227, or SEQ ID NO. 8742). The modified miRMON18-unresponsive MRT4577_36529C is expressed using constitutive or tissue-specific promoters in maize, increasing nutrient uptake and utilization under nitrogen-sufficient and phosphate-sufficient conditions and resulting in improved yield under normal conditions and preferably also under nitrogen-deficient or phosphate-deficient conditions.

Alternatively, the miRMON18 recognition site is engineered into normally miRMON18-unresponsive genes that are to be suppressed under nitrogen-sufficient conditions and expressed during nitrogen-deficient conditions; this is a useful approach, e.g., with a nitrogen-transport gene that gives increased performance or yield when expressed under nitrogen- or phosphate-limiting conditions, but provides no benefit when expressed under non-limiting conditions.

Example 10

Additional non-limiting examples of methods and recombinant DNA constructs useful in improving nitrogen or phosphate utilization based on manipulating miRMON18 or SPX gene expression are described below.

(A) Modulation of SPX Gene Expression to Improve Nitrogen Utilization Under Limiting Conditions.

In this embodiment, a SPX-domain-containing gene engineered to lack a miRMON18 recognition site (or in *Arabidopsis thaliana*, a miR827 recognition site) in the 5' UTR is expressed in plants. Decoupling the SPX gene from endogenous miRMON18 (or in *Arabidopsis thaliana*, miR827) regulation provides adaptation to nutrient availability under nitrogen- or phosphate-sufficient conditions, and result in increased yield. One desirable result of increasing expression of the SPX-MFS clade (SEQ ID NO. 8788, SEQ ID NO. 8786, SEQ ID NO. 8784, and SEQ ID NO. 8778) (FIG. 12) is the increase of protein content in at least one plant tissue (such as leaf, stalk, root, or seed) during nitrogen- or phosphate-sufficient conditions through increasing nutrient availability in sink tissues. Several vectors (see Table 7) are evaluated in *Arabidopsis thaliana* to model the function of SPX genes.

The predicted phenotype of upregulating AtNLA (At1g02860, containing an SPX-RING domain, SEQ ID NO. 8745) in a plant is constitutive adaptation to low nitrogen or low phosphate conditions and improvement of overall transport and utilization of nutrients by the plant; a similar phenotype is predicted for upregulating the related genes in the SPX-RING clade (SEQ ID NO. 8772, SEQ ID NO. 8770, SEQ ID NO. 8774, and SEQ ID NO. 8776) (FIG. 12). Vector numbers 1 through 5 are chimeric transcripts including non-targeted 5' and 3' untranslated regions and the coding region of AtNLA (SEQ ID NO. 8745); vector number 6 includes a genomic AtNLA (SEQ ID NO. 8745) fragment including the sequence from the endogenous AtNLA promoter through the termination sequence (to prevent ectopic expression) but where the native miR827 recognition site has been deleted or modified to prevent recognition by a mature miR827.

The predicted phenotype of upregulating SPX-MFS clade genes (SEQ ID NO. 8788, SEQ ID NO. 8786, SEQ ID NO. 8784, and SEQ ID NO. 8778) (FIG. 12) is increased nutrient (especially nitrogen and/or phosphate) transport, particularly from source to sink tissues, resulting in increased yield. Vector numbers 7, 9, and 10 are chimeric transcripts including non-targeted 5' and 3' untranslated regions and the coding region of At1g63010 (SEQ ID NO. 8778); vector number 8 includes a genomic At1g63010 (SEQ ID NO. 8778) fragment including the sequence from the endogenous At1g63010 promoter through the termination sequence (to prevent ectopic expression) but where the native miR827 recognition site has been deleted or modified to prevent recognition by a mature miR827; vector number 11 is a chimeric transcript including non-targeted 5' and 3' untranslated regions and the coding region of Os04g48390 (SEQ ID NO. 8786); vector number 12 includes a genomic Os04g48390 (SEQ ID NO. 8786) fragment including the sequence from the endogenous Os04g48390 promoter through the termination sequence (to prevent ectopic expression) but where the native miRMON18 recognition site has been deleted or modified to prevent recognition by a mature miRMON18 (or in *Arabidopsis thaliana*, by a mature miR827).

The effects of upregulating genes from the SPX clade of unclassified function but predicted to be repressed by low nitrogen availability is evaluated by expression of MRT4577_319995C (SEQ ID NO. 8798) with vectors 13-15 (Table 7).

Similar expression experiments are conducted in maize. Vectors (Table 7) including genes with a conserved SPX domain (see FIG. 12) are constructed and transformed into maize. Vector variants include a vector including the SPX gene's genomic sequence and vectors including the SPX gene's cloned cDNA driven by the native promoter. In non-limiting examples, vectors 16-18 use the coding sequence from MRT4577_36529C (SEQ ID NO. 8788), and have a disrupted miRMON18 recognition site, permitting expression of the transgene under sufficient nitrogen only where the native promoter is expressed. A third construct to express only the MFS domain from MRT4577_36529C (SEQ ID NO. 8788), which represents a native alternatively spliced isoform lacking SPX, will also be made and tested for nitrogen assimilation in maize.

TABLE 7

| Vector No. | Construct* | Predicted expression pattern |
|---|---|---|
| 1 | 35S: AtNLA | constitutive |
| 2 | 35S: AtNLA lacking SPX domain | constitutive |
| 3 | 35S: AtNLA lacking RING domain | constitutive |
| 4 | FDA/PPDK: AtNLA | leaf-specific |
| 5 | RCc3: AtNLA | root-specific |
| 6 | AtNLA promoter: AtNLA with disrupted miR827 recognition site | native AtNLA expression |
| 7 | 35S: At1g63010 | constitutive |
| 8 | At1g63010 promoter: At1g63010 with disrupted miR827 recognition site | native At1g63010 expression |
| 9 | 35S: At1g63010 lacking SPX domain | constitutive |
| 10 | 35S: At1g63010 lacking MFS domain | constitutive |
| 11 | 35S: Os04g48390 | constitutive |
| 12 | Os04g48390 promoter: Os04g48390 with disrupted miRMON18 recognition site | |
| 13 | 35S: MRT4577_319995C | constitutive |
| 14 | FDA/PPDK: MRT4577_319995C | leaf-specific |
| 15 | RCc3: MRT4577_319995C | root-specific |
| 16 | Promoter ZmSPXMFS: ZmSPXMFS cDNA: Terminator ZmSPXMFS | |
| 17 | Promoter ZmSPXMFS: ZmSPXMFS gDNA: Terminator ZmSPXMFS | |
| 18 | Promoter ZmSPXMFS: ZmMFS cDNA: Terminator ZmSPXMFS | |

*35S, cauliflower mosaic virus (CaMV) 35S promoter; FDA, fructose bisphosphate aldolase promoter (bundle sheath promoter); PPDK, pyruvate orthophosphate dikinase promoter (mesophyll cell promoter); RCc3, promoter of rice RCc3 gene (root specific promoter)

(B) Gene Expression Under Sufficient Nitrogen Utilizing a MIRMON18 Promoter.

In this embodiment, a miRMON18 promoter is utilized to eliminate undesirable phenotypes (off-types) resulting from expression of transgenes under limiting nitrogen. For example, when nitrogen is not limiting the expression of asparagine synthetase gives a desirable high-protein phenotype. Under limiting nitrogen, overexpression of asparagine synthetase causes a yield reduction. Expression of asparagine synthetase driven by the MIRMON18 promoter gives a high-protein phenotype under sufficient nitrogen availability, yet under limiting nitrogen the transgene is turned off preventing the yield penalty. Vectors are constructed including the maize miRMON18 promoter (SEQ ID NO. 8804), maize miRMON18 leader sequence (SEQ ID NO. 8805), and a miRMON18 foldback structure fused to an asparagine synthetase gene. Non-limiting examples of an asparagine synthetase gene include a soybean (*Glycine max*) asparagine synthetase (SEQ ID NO. 8809), a *Galdieria sulphuraria* asparagine synthetase (SEQ ID NO. 8810), and a maize (*Zea mays*) asparagine synthetase (SEQ ID NO. 8811). These vectors are transformed into maize, and yield and protein quality are evaluated in the resulting transgenic maize plants under limiting and sufficient nitrogen.

(C) Gene Suppression under Limiting Nitrogen Utilizing a miRMON18 Recognition Site Sequence. A non-limiting example of this embodiment is a recombinant DNA construct including a transgene transcription unit and an exogenous miRMON18 recognition site, wherein expression of the recombinant DNA construct in a plant results in expression of the transgene when the mature miRMON18 miRNA is not expressed. The 5'UTR of SPX-domain-containing genes of higher plants confers suppression of the mRNA under sufficient nitrogen through regulation by an endogenous mature miRMON18 or miR827. In a non-limiting embodiment of this invention the 5'UTR of an SPX gene regulated by miRMON18 or miR827, such as, but not limited to, AtNLA (SEQ ID NO. 8770), At1g63010 (SEQ ID NO. 8778), Os02g45520 (SEQ ID NO. 8784), Os04g48390 (SEQ ID NO. 8786), and MRT4577_36529C (SEQ ID NO. 8788), is incorporated in the leader sequence of a transgene expression cassette. This results in suppression of the transgene under sufficient nitrogen, regardless of promoter sequence utilized, to eliminate off-types associated with unregulated transgene expression. In a preferred embodiment, the conserved 4-nucleotide sequence AUG(G/U) present at the cleavage site in the miRMON18 or miR827 recognition site is changed to GUGG to prevent unintended initiation while preserving base-pairing to the mature miRNA. Alternatively, synthetic miRMON18 or miR827 recognition sites are incorporated into non-translated regions, or within the coding region without changing the protein function, to confer suppression under sufficient nitrogen.

In another example, the 5' UTR of Os04g48390 (SEQ ID NO. 8786) is fused to GUS driven by a constitutive promoter; one version containing the endogenous rice sequence with AUG present at the miRMON18 cleavage site, and another version wherein the AUG at the miRMON18 cleavage site has been modified to GUG are constructed. A third construct, with tandem (two or more) synthetic miRMON18 recognition sites introduced into the 3' UTR is also evaluated. These vectors are evaluated in transformed maize plants grown under varying nutrient (nitrogen or phosphate) conditions and various tissues assayed for GUS expression.

Figure 16:
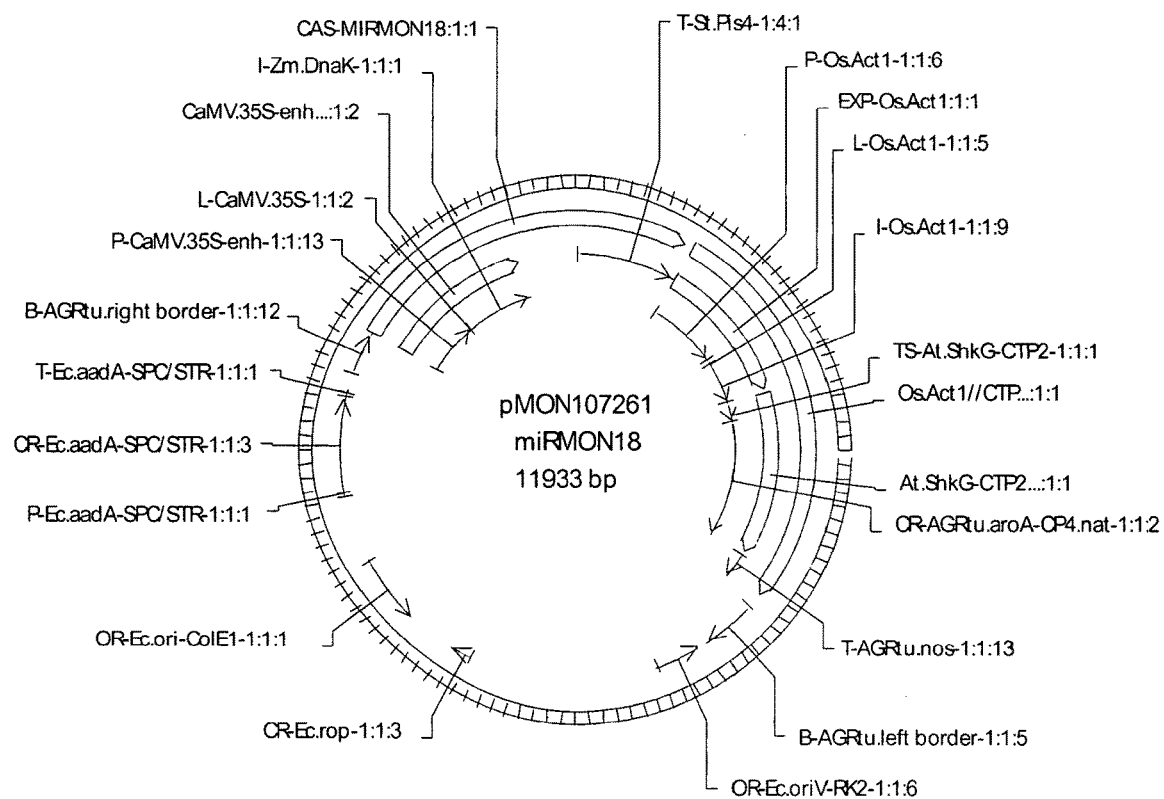
FIG. 16 depicts the vector pMON107261, which includes a CaMV 35S promoter driving expression of the maize miRMON18 transcript (e.g., nucleotides 2173-2788 of SEQ ID NO. 8800), as described in Example 10.

(D) Ectopic Expression of MIRMON18 to Limit SPX Gene Expression. In this embodiment, miRMON18 (or in *Arabidopsis*, miR827) expression is driven by a constitutive or tissue-specific promoter, resulting in suppression of all miRMON18-regulated (or miR827-regulated) genes such as the conserved SPX genes. One non-limiting example includes the vector pMON107261 (FIG. 16), which includes a CaMV 35S promoter driving expression of the maize miRMON18 transcript (e.g., nucleotides 2173-2788 of SEQ ID NO. 8800). Phenotypes of transgenic maize and *Arabidopsis* plants transformed with this vector are evaluated and plants exhibiting improved traits such as increased yield under nitrogen- or phosphate-limited conditions are selected.

Example 11

This example describes a recombinant DNA construct that is transcribed to an RNA transcript including at least one miRNA decoy sequence that is recognized and bound by an endogenous mature miRNA but not cleaved. In one preferred embodiment of this invention, the endogenous mature miRNA is one that is responsive to nutrient stress—e.g., a mature miRNA with expression that is either upregulated or downregulated by conditions of nutrient deficiency, relative to expression under nutrient sufficiency. More specifically, this example describes miRNA decoy sequences for mature miRNAs (miR827, miRMON18, and miR399) that are responsive to nutrient stress.

Examples 6-10 describe two miRNAs, miR827 (SEQ ID NO. 8744) and miRMON18 (SEQ ID NO. 393, SEQ ID NO. 3227, or SEQ ID NO. 8742) that exhibit an expression pattern characterized by regulation of the miRNA by nutrient stress (for example, suppression of the miRNA under conditions of nitrogen deficiency, phosphate deficiency, or both nitrogen and phosphate deficiency). Another miRNA, miR399, identified in *Arabidopsis thaliana*, has the sequence UGCCAAAGGAGAGUUGCCCUG (SEQ ID NO. 8812); an identical miRNA was identified by small RNA sequencing in maize (SEQ ID NO. 8813) rice (SEQ ID NO. 8814), and soybean (SEQ ID NO. 8815).

The maize miR399 gene was found to be responsive to nitrogen availability. Maize miR399 precursors were identified from proprietary cDNA datasets and included a Zm-miR399 cDNA sequence (MRT4577_22484C.8) having the sequence of SEQ ID NO. 8816, which contained a Zm-miR399 precursor (SEQ ID NO. 8817) at nucleotides 71-175 of SEQ ID NO. 8816, and another Zm-miR399 cDNA sequence (MRT4577_22487C.6) having the sequence of SEQ ID NO. 8818, which contained a Zm-miR399 precursor (SEQ ID NO. 8819) at nucleotides 136-330 of SEQ ID NO. 8818. The fold-back structures of the maize miR399 precursors are depicted in FIG. 17A; FIG. 17B depicts results of transcriptional profiling experiments with probe A1ZM033468_at corresponding to MRT4577_22487C.6 (SEQ ID NO. 8818), which demonstrate that the Zm-miR399 pri-miRNA (SEQ ID NO. 8817) is suppressed under nitrogen-deficient conditions (black bars) and is expressed under nitrogen-sufficient conditions (white bars).

In *Arabidopsis thaliana*, miR399 has been reported to be responsive to inorganic phosphate availability and to suppress a clade of genes including the *Arabidopsis thaliana* PHO2 gene (At2g33770, encoding an E2 conjugase) and putative PHO2 orthologues from various plants. Inorganic phosphate deprivation induces expression of miR399; overexpression of miR399 in phosphate-replete conditions represses PHO2 expression and leads to high leaf phosphate concentrations. See Fujii et al. (2005) *Curr. Biol.*, 15: 2038-2043; Chiou et al. (2006) *Plant Cell*, 18:412-421; Aung et al. (2006) *Plant Physiol.* 141:1000-1011; and Bari et al. (2006) *Plant Physiol.*, 141:988-999.

A conserved 23-nucleotide motif found in the *Arabidopsis thaliana* IPS 1 transcript and other members of the Mt4-TPSI family of genes was reported to have a sequence complementary to miR399 except for a mismatched loop corresponding to positions 10 and 11 in the mature miR399, which prevents cleavage of the miR399:IPS1 duplex; see Franco-Zorrilla et al. (2007) *Nature Genetics*, 39:1033-1037. A similar non-cleavable sequence that also contains mismatches corresponding to positions 10 and 11 in the mature miRNA has been reported for miR390; see Axtell et al. (2006) *Cell*, 127:565-577.

Rules were developed for predicting an endogenous "microRNA decoy sequence", i.e., a sequence that can be recognized and bound by an endogenous mature miRNA resulting in base-pairing between the miRNA decoy sequence and the endogenous mature miRNA, thereby forming a cleavage-resistant RNA duplex that is not cleaved because of the presence of mismatches between the miRNA decoy sequence and the mature miRNA. In general, these rules define (1) mismatches that are required, and (2) mismatches that are permitted but not required. Mismatches include canonical mismatches (e.g., G-A, C-U, C-A) as well as G::U wobble pairs and indels (nucleotide insertions or deletions).

Required mismatches include: (a) at least 1 mismatch between the miRNA decoy sequence and the endogenous mature miRNA at positions 9, 10, or 11 of the endogenous mature miRNA, or alternatively, (b) 1, 2, 3, 4, or 5 insertions (i.e., extra nucleotides) at a position in the miRNA decoy sequence corresponding to positions 9, 10, or 11 of the endogenous mature miRNA. In preferred embodiments, there exists either (a) at least 1 mismatch between the miRNA decoy sequence and the endogenous mature miRNA at positions 10 and/or 11 of the endogenous mature miRNA, or (b) at least 1 insertion at a position in the miRNA decoy sequence corresponding to positions 10 and/or 11 of the endogenous mature miRNA.

Mismatches that are permitted, but not required, include: (a) 0, 1, or 2 mismatches between the miRNA decoy sequence and the endogenous mature miRNA at positions 1, 2, 3, 4, 5, 6, 7, 8, and 9 of the endogenous mature miRNA, and (b) 0, 1, 2, or 3 mismatches between the miRNA decoy sequence and the endogenous mature miRNA at positions 12 through the last position of the endogenous mature miRNA (i.e., at position 21 of a 21-nucleotide mature miRNA), wherein each of the mismatches at positions 12 through the last position of the endogenous mature miRNA is adjacent to at least one complementary base-pair (i.e., so that there is not more than 2 contiguous mismatches at positions 12 through the last position of the endogenous mature miRNA). In preferred embodiments, there exist no mismatches (i.e., there are all complementary base-pairs) at positions 1, 2, 3, 4, 5, 6, 7, and 8 of the endogenous mature miRNA.

These rules were employed to identify from proprietary cDNA datasets a number of maize sequences or soybean sequences containing endogenous miRNA decoy sequences. Table 8 provides maize (*Zea mays*) endogenous miRNA decoy sequences for miRMON18 (SEQ ID NO. 393, SEQ ID NO. 3227, or SEQ ID NO. 8742); mismatches in the miRNA decoy sequence are indicated by underlined text in the alignment between the miRNA and the miRNA decoy sequence.

TABLE 8

| SEQ ID NO. | miRMON18 decoy sequence | maize cDNA identifier and SEQ ID NO. (nucleotide position of encoded miRNA decoy sequence in cDNA) | Alignment between miRMON18 given in 3' to 5' direction (above) and miRNA decoy sequence given in 5' to 3' direction (below) |
|---|---|---|---|
| 8820 | AGGUUGCUGAUGAAGUCAUCUAA | MRT4577_321885C.1 (SEQ ID NO. 8821) (182-204) | ACAAACGACUAC--CAGUAGAUU AGGUUGCUGAUGAAGUCAUCUAA |
| 8822 | UCUUUGCAGAGUGUCAUCUAA | MRT4577_531852C.2 (SEQ ID NO. 8823) (198-218) | ACAAACGACUACCAGUAGAUU UCUUUGCAGAGUGUCAUCUAA |
| 8824 | UGUUUGAUAGAGAUCAUCUAA | MRT4577_606578C.1 (SEQ ID NO. 8825) (65-85) | ACAAACGACUACCAGUAGAUU UGUUUGAUAGAGAUCAUCUAA |

Table 9 provides maize (*Zea mays*) endogenous miRNA decoy sequences for miR399 (SEQ ID NO. 8812, SEQ ID NO. 8813, SEQ ID NO. 8814, or SEQ ID NO. 8815); mismatches in the miRNA decoy sequence are indicated by underlined text in the alignment between the miRNA and the miRNA decoy sequence.

TABLE 9

| SEQ ID NO. | miR399 decoy sequence | maize cDNA identifier and SEQ ID NO. (nucleotide position of encoded miRNA decoy sequence in cDNA) | Alignment between miR399 given in 3' to 5' direction (above) and miRNA decoy sequence given in 5' to 3' direction (below) |
|---|---|---|---|
| 8826 | UAGGGCAACUUGUAUCCUUUGGCA | MRT4577_47862C.7 (SEQ ID NO. 8827) (699-722) | GUCCCGUUGAG---AGGAAACCGU UAGGGCAACUUGUAUCCUUUGGCA |
| 8828 | CAGGGCAAGUUGAAUCCUUUGGCA | MRT4577_36567C.8 (SEQ ID NO. 8829) (746-769) | GUCCCGUUGAG---AGGAAACCGU CAGGGCAAGUUGAAUCCUUUGGCA |
| 8830 | UAGGGCAACUUGUAUCCUUUGGCA | MRT4577_521786C.1 (SEQ ID NO. 8831) (156-179) | GUCCCGUUGAG---AGGAAACCGU UAGGGCAACUUGUAUCCUUUGGCA |
| 8832 | UAGGGCACCUUGUCUCCUUUGGCA | MRT4577_135578C.1 (SEQ ID NO. 8833) (185-208) | GUCCCGUUGU---GAGGAAACCGU UAGGGCACCUUGUCUCCUUUGGCA |

Figure 18:
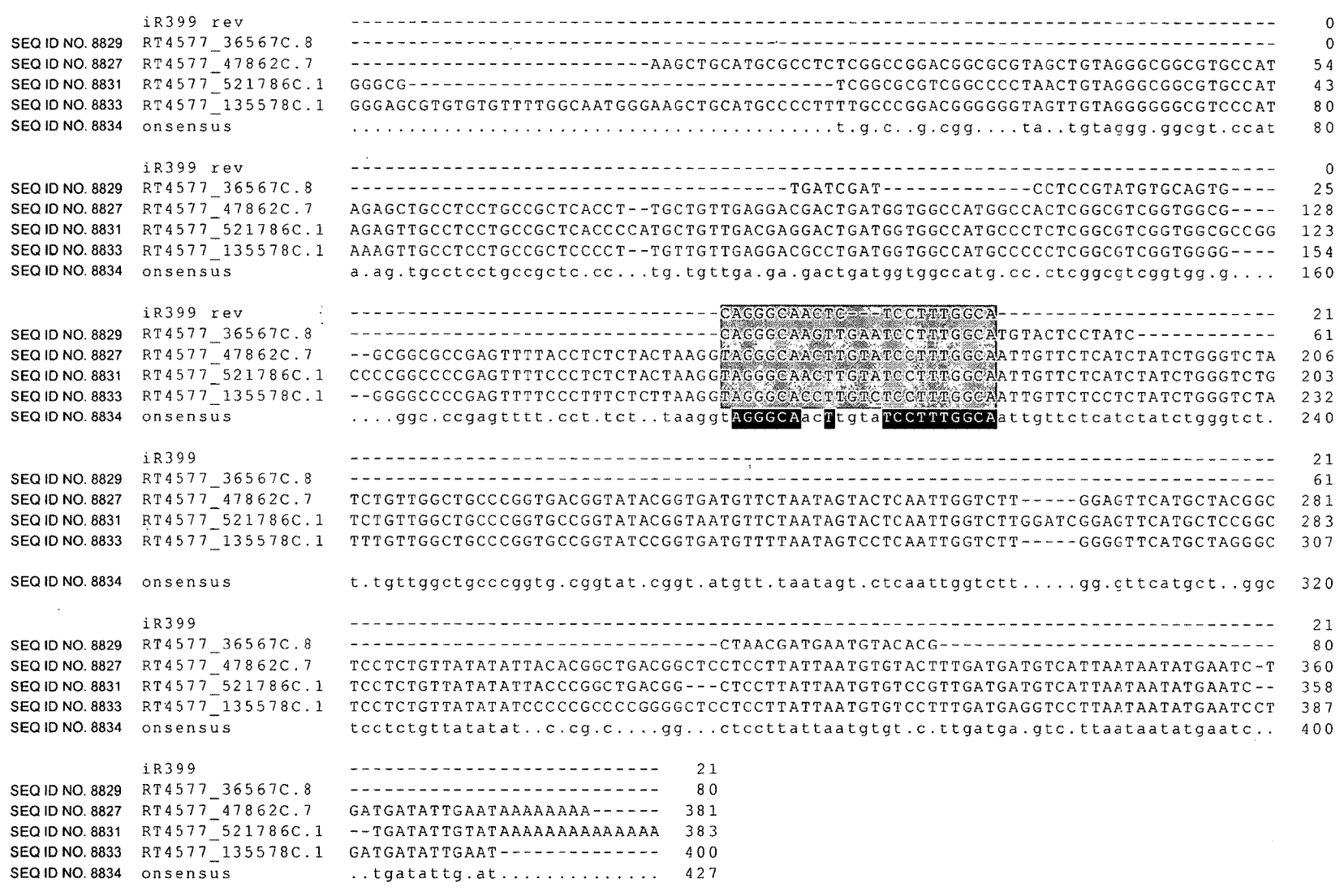

MicroRNA miR399 decoy sequences were identified in the minus strand of two cDNA sequences (SEQ ID NO. 8831 and SEQ ID NO. 8833). A six-frame translation analysis of the cDNA sequences provided in Table 9 did not reveal any long open reading frames, and BLAST searches of these same sequences did not identify any protein in public databases, indicating that these genes are likely non-coding sequences. Alignment of the maize cDNA sequences of the miR399 decoy sequences is depicted in FIG. 18 with the consensus sequence given as SEQ ID NO. 8834, and reveals at least two groups of genes containing miR399 decoy sequences: the first group contains closely related genes MRT4577_47862C.7 (SEQ ID NO. 8827), MRT4577_521786C.1 (SEQ ID NO. 8831), and MRT4577_135578C.1 (SEQ ID NO. 8833), and the second group contains MRT4577_36567C.8 (SEQ ID NO. 8829). There was only a 1-nucleotide difference between the miRNA decoy sequence in the first group of maize genes containing a miR399 decoy sequence (SEQ ID NO. 8827, SEQ ID NO. 8831, and SEQ ID NO. 8833) and the *Arabidopsis thaliana* IPS1 (AT3G09922.1) miR399 "mimic" site reported by Franco-Zorrilla et al. (2007) *Nature Genetics*, 39:1033-1037; the conserved G at position 12 of SEQ ID NO. 8826, SEQ ID NO. 8830, and SEQ ID NO. 8832 is replaced by a C in the *Arabidopsis* miR399 "mimic" site. However, homology between the maize genes (SEQ ID NO. 8827, SEQ ID NO. 8831, and SEQ ID NO. 8833) and the *Arabidopsis thaliana* IPS1 (AT3G09922.1) gene was limited to the miRNA decoy sequence site.

Table 10 provides soybean (*Glycine max*) endogenous miRNA decoy sequences for miR399 (SEQ ID NO. 8812, SEQ ID NO. 8813, SEQ ID NO. 8814, or SEQ ID NO. 8815); mismatches in the miRNA decoy sequence are indicated by underlined text in the alignment between the miRNA and the miRNA decoy sequence. Transcription profiling data was used to compare expression of endogenous miRNA decoy cDNA sequences and the corresponding miRNA precursors; the probeset included A1GM035741_at (corresponding to SEQ ID NO. 8836), A1GM069937_at (corresponding to SEQ ID NO. 8838), A1GM074873_at (corresponding to SEQ ID NO. 8840), A1GM031412_at (corresponding to SEQ ID NO. 8842), and A1GM053788_at (corresponding to SEQ ID NO. 8844).

Transcription profiling experiments were used to compare expression of maize endogenous miR399 decoy cDNA sequences and the corresponding maize miR399 precursors under different nitrogen conditions. Group 1 miR399 decoy gene MRT4577_47862C.7 (SEQ ID NO. 8827) exhibited about a two-fold down-regulation under nitrogen-deficient conditions in maize leaf (FIG. 19A); group 2 miR399 decoy gene MRT4577_36567C.8 (SEQ ID NO. 8829) exhibited an even more dramatic down-regulation of at least ten-fold or greater under nitrogen-deficient conditions in maize leaf (FIG. 19B). These results were verified by northern blots measuring expression of the mature miR399 (FIG. 19C) and of the miR399 decoy sequence MRT4577_47862C.7 (SEQ ID NO. 8827) (FIG. 19D). The northern blots were made with 5 micrograms per lane of total RNA from V6 leaf from maize grown under low (2 millimolar) or high (20 millimolar) nitrogen, and the same blot probed for the mature 21-nucleotide miR399 (FIG. 19C) and the miR399 decoy sequence MRT4577_47862C.7 (SEQ ID NO. 8827) (FIG. 19D, with major band at about 600 bp). Higher expression levels of the maize miR399 decoy sequences during nitrogen sufficiency mirror the higher expression levels of the maize miR399 precursors during nitrogen sufficiency (FIG. 17B).

Similar transcription profiling experiments were used to compare expression of maize endogenous miR399 decoy cDNA sequences and the corresponding maize miR399 precursors under different temperature conditions. Group 2 miR399 decoy gene MRT4577_36567C.8 (SEQ ID NO. 8829) exhibited at least ten-fold or greater higher expression during nitrogen-sufficient conditions in maize leaf, especially during daylight hours (FIG. 20A). This same gene exhibited at least a two-fold down-regulation in root (FIG. 20B) and in shoot (FIG. 20C) after extended exposure to cold.

The expression of the endogenous miR399 decoy cDNA sequences were also compared in different tissues in both maize and soybean. FIG. 21A depicts expression levels of the group 1 maize miR399 decoy sequence SEQ ID NO. 8827 (MRT4577_47862C, represented by probes A1ZMO05814_at and A1ZMO05813_s_at), and the group 2 maize miR399 decoy sequence SEQ ID NO. 8829

TABLE 10

| SEQ ID NO. | miR399 decoy sequence | maize cDNA identifier and SEQ ID NO. (nucleotide position of encoded miRNA decoy sequence in cDNA) | Alignment between miR399 given in 3' to 5' direction (above) and miRNA decoy sequence given in 5' to 3' direction (below) |
|---|---|---|---|
| 8835 | UAGGGCAACUUCGAUCCUUUGGCA | MRT3847_238967C.1 (SEQ ID NO. 8836) (390-413) | GUCCCGUUAAG---AGGAAACCGU uagggcaacuucgauccuuuggca |
| 8837 | UAGGGCAACUUCUAUCCUUUGGCA | MRT3847_241832C.1 (SEQ ID NO. 8838) (393-416) | GUCCCGUUAAG---AGGAAACCGU uagggcaacuucuauccuuuggca |
| 8839 | AAGGGCAACUUCAAUCCUUUGGCA | MRT3847_336885C.1 (SEQ ID NO. 8840) (96-119) | GUCCCGUUAAG---AGGAAACCGU aagggcaacuucaauccuuuggca |
| 8841 | AAGGGCAACUUCCAUCCUUUGGCA | MRT3847_217257C.2 (SEQ ID NO. 8842) (179-202) | GUCCCGUUAAG---AGGAAACCGU aagggcaacuuccauccuuuggca |
| 8843 | AAGGGCAACUUCCAUCCUUUGGCA | MRT3847_236871C.3 (SEQ ID NO. 8844) (238-261) | GUCCCGUUAAG---AGGAAACCGU aagggcaacuuccauccuuuggca |

(MRT4577_36567C, represented by probe A1ZM048024_at), as well as of the maize pri-miR399 sequence SEQ ID NO. 8818 (MRT4577_22487C.6 represented by probe A1ZM033468_at). FIG. 21B depicts expression levels of the soybean miR399 decoy sequences SEQ ID NO. 8842 (MRT3847_217257C.2, represented by probe A1GM031412_at), SEQ ID NO. 8844 (MRT3847_236871C.2, represented by probe A1GM053788_at), SEQ ID NO. 8836 (MRT3847_238967C.1, represented by probe A1GM035741_at), and SEQ ID NO. 8838 (MRT3847_241832C.1, represented by probe A1GM069937_at).

These data confirm a novel nitrogen-responsive expression pattern in crop plants including maize and soybean for both the mature miR399 (and the miR399 precursors) as well as for the endogenous miR399 decoy sequences. Various utilities of the miR399 include overexpression of the mature miR399 (e.g., by overexpression of a pri-miR399 sequence), expression of an engineered miR399 designed to suppress a gene other than one natively targeted by a native mature miR399, expression of a transgene (coding or non-coding sequence or both) under control of the miR399 promoter, expression of a transgene in which a miR399 recognition site has been added or removed, overexpression of a miR399 decoy sequence, and suppression of an endogenous miR399 decoy sequence.

Table 11 provides soybean (*Glycine max*) and maize (*Zea mays*) endogenous miRNA decoy sequences for miR319, UUGGACUGAAAGGAGCUCCU (SEQ ID NO. 8845), which has been identified in a number of plant species including *Arabidopsis thaliana, Oryza sativa, Zea mays*, and *Glycine max* (see publicly available examples at miRBase, microrna.sanger.ac.uk/cgi-bin/sequences/query.pl?terms=miR319); mismatches in the miRNA decoy sequence are indicated by underlined text in the alignment between the miRNA and the miRNA decoy sequence. FIG. 22A depicts transcription profiling data in various soybean tissues of the soybean endogenous miR319 decoy SEQ ID NO. 8847 (MRT3847_41831C.6, represented by probe A1GM001017_at); FIG. 22B depicts transcription profiling data in various maize tissues of the maize endogenous miR319 decoy SEQ ID NO. 8849 (MRT4577_577703C.1, represented by probe A1ZMO12886_s_at).

Among the target genes regulated by miR319 are the TCP genes involved in leaf development and MYB genes involved in flower development. One embodiment of this invention is altering a plant's leaf or floral architecture or developmental pattern by suppressing transcription of an endogenous mature miR319 in a transgenic plant, or to alter endogenous miR319 activity by overexpressing a miR319 decoy sequence in a transgenic plant.

In yet another example, miR398b (SEQ ID NO. 8850) has been shown to regulate expression of CSD1 and CSD2 (copper/zinc superoxide dismutase); see Sunkar et al. (2006) *Plant Cell*, 18:2051-2065. Superoxide dismutase aids in the scavenging of reactive oxygen species (ROS) by converting $O_2$ to $H_2O_2$ and minimizes potential damage caused by superoxide or by superoxide-derived ROS. miR398 is slightly down regulated by oxidative stress and strongly downregulated by Cu availability; see Yamasaki et al. (2007) *J. Biol. Chem.*, 282:16369-16378. One embodiment of this invention includes expressing an chimeric transcript including miR398b decoy sequences (e.g., SEQ ID NOS. 8851-8852) under the control of an oxidative stress-inducible promoter, resulting in further suppression of the activity of miR398b and increased CSD1 and CSD2 accumulation and stress protection under stress conditions.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

TABLE 11

| SEQ ID NO. | miR319 decoy sequence | cDNA identifier and SEQ ID NO. (nucleotide position of encoded miRNA decoy sequence in cDNA) | Alignment between miR319 given in 3' to 5' direction (above) and miRNA decoy sequence given in 5' to 3' direction (below) |
|---|---|---|---|
| 8846 | GGGAGUUUCUACCUCCAGUCCAA | MRT3847_41831C.6 (SEQ ID NO. 8847) (545-567) | UCCUCGAGGA---AAGUCAGGUU gggag<u>u</u>uucua<u>cc</u>u<u>c</u>caguccaa |
| 8848 | GGGAGCGCCAAUCAGUCCAA | MRT4577_577703C.1 (SEQ ID NO. 8849) (751-770) | UCCUCGAGGAAAGUCAGGUU gggagc<u>g</u>cc<u>aa</u>ucaguccaa |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10435686B2). An electronic copy of the "Sequence Listing" will also be available from the USPTO upon request and payment of the fee set forth in 37 CFR 1.19(b)(3).

What is claimed is:

1. A recombinant DNA construct comprising a synthetic miRMON18-unresponsive transgene sequence, wherein said synthetic miRMON18-unresponsive transgene sequence is derived by modifying an SPX-domain-containing sequence that comprises at least one native miRMON18 miRNA recognition site, wherein said modification of said SPX-domain-containing sequence is selected from the group consisting of:
   (i) all native miRMON18 miRNA recognition sites within said SPX-domain-containing sequence have been deleted; and
   (ii) all native miRMON18 miRNA recognition sites within said SPX-domain-containing sequence have been modified, wherein said modification of said native miRMON18 miRNA recognition sites comprises mismatches corresponding to positions 10 and 11 of a mature miRMON18 miRNA, wherein said mismatches result in prevention of recognition and cleavage by said mature miRNA;
   wherein said SPX-domain-containing sequence encodes a plant SPX-domain-containing protein,
   wherein said native miRMON18 miRNA recognition sites are recognized by a mature miRMON18 miRNA having the sequence of SEQ ID NO:393,
   wherein said SPX-domain-containing sequence exhibits higher expression under nitrogen-deficient conditions than under nitrogen-sufficient conditions, and
   wherein said synthetic miRMON18-unresponsive transgene sequence is not recognized and cleaved by said mature miRMON18 miRNA having the sequence of SEQ ID NO:393, thus the expression of said synthetic miRMON18-unresponsive transgene sequence is decoupled from miRMON18 regulation and improves nitrogen utilization.

2. The recombinant DNA construct of claim 1, wherein said plant SPX-domain-containing protein comprises in its C-terminus an EXS, VTC, or MFS domain.

3. A non-natural transgenic plant cell comprising a recombinant DNA construct of claim 1.

4. A non-natural transgenic plant comprising a regenerated plant prepared from the non-natural transgenic plant cell of claim 3, or a progeny plant of a regenerated plant prepared from the non-natural transgenic plant cell of claim 3, wherein said non-natural transgenic plant has improved yield under nitrogen deficiency, relative to a plant lacking said recombinant DNA construct.

5. A method of providing a transgenic crop plant having improved yield under nitrogen deficiency, comprising expressing in said transgenic crop plant the recombinant DNA construct of claim 1,
   wherein said plant SPX-domain-containing protein comprises in its C-terminus an MFS or a RING domain, and
   wherein said transgenic crop plant has improved yield under nitrogen deficiency relative to a crop plant lacking said recombinant DNA construct.

6. The recombinant DNA construct of claim 1, wherein said SPX-domain-containing sequence comprises a nucleotide sequence selected from:
   (i) SEQ ID NOs: 8756, 8760, and 8764; and
   (ii) nucleotide sequences encoding amino acid sequences selected from SEQ ID NOs: 8757, 8761, 8765, wherein said nucleotide sequences encode an SPX domain and comprise at least one native miRMON18 miRNA recognition site that is recognized by a mature miRMON18 miRNA having the sequence of SEQ ID NO:393.

7. The recombinant DNA construct of claim 1, wherein said SPX-domain-containing sequence comprises a nucleotide sequence selected from:
   (i) SEQ ID NOs: 8770, 8772, 8774, and 8776; and
   (ii) nucleotide sequences encoding amino acid sequences selected from SEQ ID NOs: 8771, 8773, 8775, and 8777, wherein said nucleotide sequences encode an SPX domain and comprise at least one native miRMON18 miRNA recognition site that is recognized by a mature miRMON18 miRNA having the sequence of SEQ ID NO:393.

8. The recombinant DNA construct of claim 1, wherein said SPX-domain-containing sequence comprises a nucleotide sequence selected from:
   (i) SEQ ID NOs: 8778, 8784, 8786, and 8788; and
   (ii) nucleotide sequences encoding amino acid sequences selected from SEQ ID NOs: 8779, 8785, 8787, and 8789, wherein said nucleotide sequences encode an SPX domain and comprise at least one native miRMON18 miRNA recognition site that is recognized by a mature miRMON18 miRNA having the sequence of SEQ ID NO:393.

9. The method of claim 5, wherein said SPX-domain-containing sequence comprises a nucleotide sequence selected from:
   (i) SEQ ID NOs: 8756, 8760, and 8764; and
   (ii) nucleotide sequences encoding amino acid sequences selected from SEQ ID NOs: 8757, 8761, and 8765, wherein said nucleotide sequences encode an SPX domain and comprise at least one native miRMON18 miRNA recognition site that is recognized by a mature miRMON18 miRNA having the sequence of SEQ ID NO:393.

10. The method of claim 5, wherein said SPX-domain-containing sequence comprises a nucleotide sequence selected from:
    (i) SEQ ID NOs: 8770, 8772, 8774, and 8776; and
    (ii) nucleotide sequences encoding amino acid sequences selected from SEQ ID NOs: 8771, 8773, 8775, and 8777, wherein said nucleotide sequences encode an SPX domain and comprise at least one native miRMON18 miRNA recognition site that is recognized by a mature miRMON18 miRNA having the sequence of SEQ ID NO:393.

11. The method of claim 5, wherein said SPX-domain-containing sequence comprises a nucleotide sequence selected from:
(i) SEQ ID NOs: 8778, 8784, 8786, and 8788; and
(ii) nucleotide sequences encoding amino acid sequences selected from SEQ ID NOs: 8779, 8785, 8787, and 8789, wherein said nucleotide sequences encode an SPX domain and comprise at least one native miRMON18 miRNA recognition site that is recognized by a mature miRMON18 miRNA having the sequence of SEQ ID NO:393.

* * * * *